(12) United States Patent
Damude

(10) Patent No.: US 8,377,673 B2
(45) Date of Patent: Feb. 19, 2013

(54) DELTA-9 ELONGASES AND THEIR USE IN MAKING POLYUNSATURATED FATTY ACIDS

(75) Inventor: Howard G. Damude, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/347,938

(22) Filed: Jan. 11, 2012

(65) Prior Publication Data

US 2012/0100595 A1 Apr. 26, 2012

Related U.S. Application Data

(62) Division of application No. 12/102,979, filed on Apr. 15, 2008, now Pat. No. 8,119,860.

(60) Provisional application No. 60/911,925, filed on Apr. 16, 2007.

(51) Int. Cl.
*C12N 9/10* (2006.01)
(52) U.S. Cl. .................................................. 435/193
(58) Field of Classification Search .................. None
See application file for complete search history.

(56) References Cited

U.S. PATENT DOCUMENTS

| | | | |
|---|---|---|---|
| 7,256,033 B2 | 8/2007 | Damude et al. | |
| 7,550,286 B2 | 6/2009 | Damude et al. | |
| 7,588,931 B2 | 9/2009 | Damude et al. | |
| 7,645,604 B2 | 1/2010 | Damude et al. | |
| 7,932,077 B2 | 4/2011 | Damude et al. | |
| 8,119,860 B2 * | 2/2012 | Damude et al. | 800/298 |
| 2007/0118929 A1 | 5/2007 | Damude et al. | |
| 2008/0155705 A1 | 6/2008 | Zank et al. | |

FOREIGN PATENT DOCUMENTS

| | | |
|---|---|---|
| WO | WO 02077213 | 10/2002 |
| WO | WO 2004057001 | 7/2004 |
| WO | WO 2004071467 | 8/2004 |
| WO | WO 2004101753 | 11/2004 |
| WO | WO 2004101757 | 11/2004 |
| WO | WO 2005083093 | 9/2005 |
| WO | WO 2006052870 | 5/2006 |
| WO | WO 2006052871 | 5/2006 |
| WO | WO 2006055322 | 5/2006 |
| WO | WO 2007061742 | 5/2007 |
| WO | WO 2007061845 | 5/2007 |

OTHER PUBLICATIONS

Fourgoux-Nicol et al, Plant Mol Biol 40: 857-872, 1999.
Qi et al., Identification of a cDNA encoding a novel C18-Delta 9 polyunsaturated fatty acid-specific elongating activity from the docosahexaenoic acid (DHA)-producing microalga, isochrysis galbana, FEES letter, vol. 510, pp. 159-165, 2002.
National Center for Biotechnology Information General Identifier No. 17226123, Qi et al., Identification of a cDNA encoding a novel C18-Delta (9) polyunsaturated fatty acid-specific elongating activity from the docosahexaenoic acid (DHA)-producing microalga, *Isochrysis galbana*, Genbank Accession No. AAL37626, 2006.
National Center for Biotechnology Information General Identifier No. 17226122, Qi et al., Identification of a cDNA encoding a novel C18-Delta (9) polyunsaturated fatty acid-specific elongating activity from the docosahexaenoic acid (DHA)-producing microalga, *Isochrysis galbana*, Accession No. AF390174, 2006.
Sequence alignment of SEQ ID No. 13 and AGD17259, Damude et al, run date Oct. 6, 2010.
U.S. Appl. No. 12/102,979, Requirement Restriction Election, mailed Aug. 25, 2010.
U.S. Appl. No. 12/102,979, Non-Final Rejection, mailed Nov. 18, 2010.
U.S. Appl. No. 12/102,979, Final Rejection, mailed Jul. 19, 2011.
U.S. Appl. No. 12/102,979, Notice Allowance Fees Due, mailed Oct. 20, 2011.

* cited by examiner

*Primary Examiner* — Manjunath Rao
*Assistant Examiner* — William W Moore

(57) ABSTRACT

Isolated nucleic acid fragments and recombinant constructs comprising such fragments encoding delta-9 elongases along with a method of making long-chain polyunsaturated fatty acids (PUFAs) and using these delta-9 elongases in plants.

4 Claims, 15 Drawing Sheets

FIG. 5

| Event | Fatty acid composition (wt.%) | | | | | | | | | | delta-9 %Elong | Ave. delta-9 %Elong |
|---|---|---|---|---|---|---|---|---|---|---|---|---|
| | 16:0 | 16:1 | 18:0 | 18:1 | LA | 20:0 | 20:1 (11) | EDA | 22:0 | 24:0 | 24:1 | | |
| pY173-1 | 16.7 | 14.5 | 4.1 | 46.5 | 12.5 | 0.2 | 0.2 | 3.6 | 0.2 | 1.4 | 0.1 | 22.2 | 22.7 |
| pY173-2 | 16.6 | 14.2 | 4.1 | 46.8 | 12.4 | 0.2 | 0.2 | 3.7 | 0.2 | 1.5 | 0.1 | 22.7 | |
| pY173-3 | 16.5 | 14.0 | 4.2 | 47.1 | 12.3 | 0.2 | 0.2 | 3.7 | 0.2 | 1.5 | 0.2 | 23.2 | |
| pY174-1 | 16.9 | 14.3 | 4.2 | 46.8 | 12.5 | 0.2 | 0.2 | 3.2 | 0.2 | 1.4 | 0.1 | 20.5 | 21.1 |
| pY174-2 | 17.0 | 14.1 | 4.3 | 47.4 | 11.8 | 0.2 | 0.2 | 3.3 | 0.2 | 1.4 | 0.1 | 21.6 | |
| pY174-3 | 17.0 | 14.2 | 4.3 | 47.2 | 11.9 | 0.2 | 0.2 | 3.2 | 0.2 | 1.4 | 0.2 | 21.2 | |

EaD9E (same as EaD9Elo1) (SEQ ID NO:11)
EaD9ES (SEQ ID NO:40)

| Event | Fatty acid composition (wt %) | | | | | | | delta-9 %Elong | LA %Elong | ALA %Elong | Ratio (LA/ALA) %Elong |
|---|---|---|---|---|---|---|---|---|---|---|---|
| | 16:0 | 18:0 | 18:1 | LA | ALA | EDA | ERA | | | | |
| 2129-2-2-1 | 15.4 | 5.8 | 11.0 | 32.1 | 8.2 | 21.8 | 5.9 | 40.6 | 40.3 | 41.8 | 1.0 |
| 2129-2-2-2 | 14.9 | 3.8 | 15.5 | 28.3 | 6.2 | 24.8 | 6.5 | 47.6 | 46.7 | 51.2 | 0.9 |
| 2129-2-2-3 | 15.1 | 4.8 | 13.9 | 26.5 | 7.2 | 25.5 | 7.3 | 49.4 | 49.1 | 50.4 | 1.0 |
| 2129-2-2-4 | 17.3 | 8.0 | 9.6 | 25.1 | 8.5 | 23.3 | 8.2 | 48.4 | 48.2 | 49.2 | 1.0 |
| 2129-2-2-5 | 15.2 | 4.1 | 10.5 | 25.2 | 7.5 | 27.6 | 9.9 | 53.3 | 52.2 | 56.8 | 0.9 |
| Avg. | 15.6 | 5.2 | 12.1 | 27.4 | 7.5 | 24.6 | 7.6 | 47.9 | 47.3 | 49.9 | 0.9 |
| 2129-2-5-1 | 12.8 | 4.5 | 10.9 | 31.9 | 5.8 | 28.6 | 5.5 | 47.6 | 47.3 | 48.8 | 1.0 |
| 2129-2-5-2 | 18.5 | 3.7 | 3.6 | 34.0 | 13.7 | 20.6 | 6.0 | 35.8 | 37.7 | 30.4 | 1.2 |
| 2129-2-5-3 | 13.3 | 4.3 | 8.2 | 35.8 | 6.0 | 27.5 | 4.9 | 43.8 | 43.5 | 45.2 | 1.0 |
| 2129-2-5-4 | 13.4 | 5.2 | 8.5 | 38.0 | 6.5 | 22.9 | 4.4 | 38.0 | 37.6 | 40.0 | 0.9 |
| 2129-2-5-5 | 12.8 | 5.3 | 11.5 | 31.9 | 6.3 | 27.6 | 4.6 | 45.7 | 46.4 | 42.1 | 1.1 |
| Avg. | 14.2 | 4.6 | 8.8 | 34.3 | 7.7 | 25.4 | 5.1 | 42.1 | 42.5 | 41.3 | 1.0 |
| 2129-2-6-1 | 13.4 | 3.4 | 10.3 | 33.8 | 6.2 | 28.1 | 4.9 | 45.2 | 45.4 | 44.0 | 1.0 |
| 2129-2-6-2 | 13.3 | 4.2 | 12.8 | 31.1 | 3.8 | 30.5 | 4.3 | 55.0 | 49.5 | 53.3 | 0.9 |
| 2129-2-6-3 | 14.8 | 4.7 | 12.7 | 30.7 | 5.4 | 27.1 | 4.7 | 46.9 | 46.9 | 46.8 | 1.0 |
| 2129-2-6-4 | 14.4 | 4.0 | 11.3 | 34.9 | 6.5 | 26.3 | 3.6 | 41.1 | 42.1 | 35.3 | 1.2 |
| 2129-2-6-5 | 18.1 | 4.7 | 12.5 | 29.7 | 7.9 | 22.4 | 4.7 | 41.8 | 43.0 | 37.5 | 1.1 |
| Avg. | 14.8 | 4.2 | 11.9 | 32.0 | 6.0 | 28.7 | 4.4 | 46.0 | 45.4 | 43.4 | 1.1 |
| 2129-6-1-1 | 13.4 | 2.9 | 14.9 | 27.4 | 10.6 | 22.9 | 7.8 | 44.5 | 45.4 | 41.8 | 1.1 |
| 2129-6-1-2 | 12.3 | 3.3 | 19.1 | 25.1 | 7.3 | 26.0 | 6.9 | 55.4 | 50.9 | 48.5 | 1.1 |
| 2129-6-1-3 | 12.3 | 3.2 | 16.8 | 26.8 | 7.3 | 26.9 | 6.7 | 49.6 | 50.1 | 47.7 | 1.1 |
| 2129-6-1-4 | 14.0 | 3.3 | 13.2 | 33.0 | 13.2 | 17.5 | 5.9 | 33.5 | 34.6 | 30.7 | 1.1 |
| 2129-6-1-5 | 12.8 | 3.0 | 16.8 | 27.5 | 9.9 | 23.2 | 7.0 | 44.7 | 45.7 | 41.5 | 1.1 |
| Avg. | 12.9 | 3.1 | 16.1 | 28.0 | 9.7 | 23.3 | 6.8 | 44.5 | 45.3 | 42.0 | 1.1 |
| 2129-6-3-1 | 13.1 | 3.8 | 16.7 | 26.7 | 9.2 | 24.0 | 7.5 | 47.6 | 48.3 | 45.0 | 1.1 |
| 2129-6-3-2 | 13.3 | 3.8 | 13.8 | 27.1 | 10.0 | 24.0 | 8.1 | 46.3 | 47.0 | 44.5 | 1.1 |
| 2129-6-3-3 | 13.4 | 3.9 | 17.3 | 27.4 | 10.6 | 20.4 | 7.0 | 41.9 | 42.7 | 39.6 | 1.1 |
| 2129-6-3-4 | 13.3 | 3.2 | 16.4 | 29.3 | 9.8 | 21.7 | 6.2 | 41.7 | 42.6 | 38.8 | 1.1 |
| 2129-6-3-5 | 14.1 | 3.8 | 16.8 | 29.4 | 9.7 | 20.9 | 5.3 | 40.2 | 41.6 | 35.3 | 1.2 |
| Avg. | 13.5 | 3.8 | 16.2 | 27.8 | 9.9 | 22.2 | 6.8 | 43.5 | 44.4 | 40.6 | 1.1 |

FIG. 11

| | Fatty acid composition (wt.%) | | | | | | | | | C18 % delta-9 elong | C20 % delta-8 desat |
|---|---|---|---|---|---|---|---|---|---|---|---|
| Event | 16:0 | 18:0 | 18:1 | LA | ALA | EDA | DGLA | ERA | ETA | | |
| 2131-2-9-1 | 15.4 | 4.0 | 19.9 | 27.7 | 6.8 | 8.8 | 13.4 | 0.8 | 3.0 | 42.7 | 63.7 |
| 2131-2-9-2 | 17.0 | 3.6 | 10.5 | 29.9 | 10.9 | 7.7 | 15.1 | 1.4 | 3.5 | 40.4 | 67.1 |
| 2131-2-9-3 | 16.8 | 3.7 | 9.4 | 26.2 | 9.2 | 8.7 | 19.6 | 1.4 | 4.5 | 49.0 | 70.5 |
| 2131-2-9-4 | 16.2 | 3.7 | 14.7 | 29.2 | 8.8 | 8.0 | 14.8 | 0.9 | 3.3 | 41.4 | 66.9 |
| 2131-2-9-5 | 16.9 | 3.8 | 12.5 | 27.9 | 9.5 | 8.9 | 14.8 | 1.3 | 3.5 | 43.4 | 64.4 |
| Avg. | 16.5 | 3.8 | 13.4 | 28.2 | 9.0 | 8.3 | 15.5 | 1.2 | 3.6 | 43.4 | 66.5 |
| | | | | | | | | | | | |
| 2131-2-15-1 | 16.0 | 3.9 | 13.3 | 29.1 | 7.4 | 8.6 | 16.0 | 1.0 | 4.1 | 44.9 | 67.5 |
| 2131-2-15-2 | 16.4 | 3.4 | 10.3 | 27.3 | 6.6 | 11.6 | 20.6 | 1.4 | 4.1 | 53.4 | 65.5 |
| 2131-2-15-3 | 16.9 | 3.8 | 13.7 | 28.6 | 8.2 | 8.9 | 14.7 | 1.0 | 3.6 | 43.3 | 64.9 |
| 2131-2-15-4 | 17.3 | 3.2 | 6.6 | 22.2 | 10.3 | 6.8 | 24.1 | 1.7 | 7.3 | 54.9 | 79.3 |
| 2131-2-15-5 | 14.6 | 3.7 | 11.0 | 26.0 | 6.0 | 8.9 | 22.3 | 1.6 | 5.2 | 54.2 | 72.4 |
| Avg. | 16.0 | 3.6 | 11.0 | 26.6 | 7.5 | 8.9 | 19.5 | 1.3 | 4.8 | 50.2 | 69.9 |
| | | | | | | | | | | | |
| 2131-2-22-1 | 18.2 | 4.7 | 6.5 | 17.5 | 4.8 | 15.1 | 24.7 | 3.0 | 6.2 | 68.7 | 63.0 |
| 2131-2-22-2 | 17.3 | 4.9 | 7.0 | 24.2 | 9.7 | 12.5 | 16.4 | 2.8 | 4.4 | 51.5 | 58.0 |
| 2131-2-22-3 | 17.3 | 5.1 | 9.5 | 20.7 | 6.5 | 14.6 | 18.7 | 2.4 | 4.3 | 59.5 | 57.5 |
| 2131-2-22-4 | 18.7 | 5.2 | 7.4 | 18.5 | 6.4 | 12.3 | 23.9 | 2.0 | 5.6 | 64.8 | 67.4 |
| 2131-2-22-5 | 18.4 | 5.0 | 8.6 | 18.0 | 5.6 | 11.1 | 24.3 | 2.0 | 5.8 | 64.8 | 69.6 |
| Avg. | 17.6 | 5.0 | 7.8 | 19.6 | 6.4 | 13.1 | 21.6 | 2.4 | 5.3 | 61.9 | 63.1 |
| | | | | | | | | | | | |
| 2131-2-24-1 | 17.0 | 4.0 | 5.3 | 19.3 | 6.1 | 11.6 | 21.6 | 3.7 | 8.0 | 62.1 | 65.9 |
| 2131-2-24-2 | 17.4 | 4.1 | 6.4 | 19.8 | 5.8 | 9.0 | 26.8 | 2.0 | 7.6 | 63.9 | 75.8 |
| 2131-2-24-3 | 16.0 | 4.2 | 6.3 | 23.0 | 6.6 | 16.8 | 17.6 | 3.8 | 4.8 | 58.2 | 52.0 |
| 2131-2-24-4 | 18.0 | 5.9 | 8.4 | 17.2 | 5.6 | 7.9 | 26.4 | 1.7 | 7.8 | 65.7 | 78.0 |
| 2131-2-24-5 | 18.1 | 4.8 | 7.3 | 18.0 | 5.9 | 8.1 | 26.5 | 2.1 | 8.0 | 66.2 | 77.1 |
| Avg. | 17.3 | 4.6 | 6.7 | 19.5 | 6.4 | 10.7 | 23.8 | 2.6 | 7.2 | 63.2 | 69.8 |
| | | | | | | | | | | | |
| 2131-6-14-1 | 17.5 | 4.1 | 17.3 | 21.0 | 7.6 | 8.1 | 17.4 | 1.1 | 5.0 | 52.4 | 70.9 |
| 2131-6-14-2 | 17.5 | 4.7 | 16.4 | 26.4 | 8.5 | 8.3 | 13.1 | 1.2 | 3.1 | 42.4 | 63.2 |
| 2131-6-14-3 | 17.2 | 3.2 | 12.3 | 22.4 | 8.1 | 10.2 | 18.1 | 1.7 | 5.4 | 52.9 | 66.5 |
| 2131-6-14-4 | 18.1 | 3.6 | 10.9 | 24.6 | 9.1 | 7.7 | 19.6 | 1.0 | 4.8 | 49.7 | 73.6 |
| 2131-6-14-5 | 16.6 | 3.8 | 13.6 | 26.3 | 8.9 | 8.1 | 17.0 | 1.0 | 4.4 | 46.5 | 70.1 |
| Avg. | 17.4 | 3.9 | 14.1 | 24.1 | 8.7 | 8.5 | 17.1 | 1.2 | 4.5 | 48.8 | 68.8 |

| Event | Fatty acid composition (wt. %) | | | | | | | | | delta-9 %Elong |
|---|---|---|---|---|---|---|---|---|---|---|
| | 16:0 | 18:0 | 18:1 | LA | ALA | 20:0 | 20:1 (11) | EDA | ERA | |
| ff1191-1 | 7.8 | 2.6 | 22.8 | 41.8 | 1.6 | 0.9 | 1.8 | 19.1 | 1.3 | 32.0 |
| ff1191-2 | 7.8 | 3.2 | 27.2 | 44.0 | 0.5 | 0.7 | 1.3 | 14.5 | 0.6 | 25.4 |
| ff1191-3 | 8.2 | 2.8 | 19.8 | 36.4 | 0.6 | 0.7 | 2.1 | 27.9 | 1.1 | 44.0 |
| ff1191-4 | 7.6 | 2.8 | 21.1 | 41.6 | 1.3 | 0.8 | 2.2 | 21.3 | 0.9 | 34.1 |
| ff1191-5 | 8.5 | 2.9 | 18.5 | 41.2 | 1.1 | 0.9 | 1.9 | 23.6 | 1.0 | 38.8 |
| ff1191-6 | 7.8 | 3.1 | 17.8 | 37.0 | 0.8 | 0.8 | 2.0 | 29.2 | 1.2 | 44.5 |
| ff1191-7 | 8.5 | 2.6 | 19.9 | 34.4 | 0.8 | 0.7 | 2.4 | 29.4 | 1.2 | 46.7 |
| ff1191-8 | 8.1 | 2.4 | 18.4 | 36.7 | 0.4 | 0.5 | 2.0 | 30.3 | 1.2 | 45.9 |
| ff1191-9 | 7.6 | 2.6 | 21.8 | 41.9 | 0.5 | 0.7 | 1.8 | 22.0 | 0.8 | 35.0 |
| ff1191-10 | 7.9 | 2.5 | 20.3 | 36.2 | 0.5 | 0.8 | 2.1 | 28.6 | 1.0 | 44.7 |
| ff1191-11 | 8.2 | 2.8 | 19.3 | 37.6 | 0.6 | 0.8 | 2.2 | 27.2 | 1.1 | 42.6 |
| ff1191-12 | 8.6 | 3.4 | 21.9 | 40.4 | 1.1 | 0.8 | 1.3 | 21.9 | 1.0 | 35.8 |
| ff1191-13 | 8.6 | 3.0 | 30.6 | 55.0 | 1.2 | 0.9 | 0.9 | 0.2 | 0.0 | 0.4 |
| ff1191-14 | 8.9 | 3.0 | 17.2 | 39.3 | 0.9 | 0.8 | 1.3 | 26.5 | 1.2 | 40.6 |
| ff1191-15 | 15.9 | 0.0 | 20.5 | 41.4 | 0.6 | 0.0 | 0.0 | 22.3 | 0.0 | 35.0 |
| ff1191-16 | 9.0 | 2.9 | 18.0 | 32.6 | 0.8 | 0.8 | 1.7 | 32.9 | 1.6 | 50.9 |
| ff1191-17 | 8.7 | 3.2 | 17.2 | 37.9 | 1.0 | 1.0 | 1.5 | 27.8 | 1.3 | 42.8 |
| ff1191-18 | 8.0 | 2.8 | 21.2 | 41.1 | 0.5 | 0.7 | 1.5 | 23.1 | 0.9 | 36.6 |

SEQUENCE LISTING

<160> NUMBER OF SEQ ID NOS: 42

<210> SEQ ID NO 1
<211> LENGTH: 1129
<212> TYPE: DNA
<213> ORGANISM: Euglena anabaena

<400> SEQUENCE: 1

```
tttttttcgg tctaaaatgg aagcagccaa agaattggtt tccatcgtcc aagaggagct      60
ccccaaggtg gactatgccc agctttggca ggatgccagc agctgtgagg tcctttacct     120
ctcggtggca ttcgtggcga tcaagttcat gctgcgccca ctggacctga agcgccaggc     180
caccttgaag aagctgttca cagcatacaa cttcctcatg tcgatctatt cctttggctc     240
cttcctggcc atggcctatg ccctatcagt aactggcatc ctctccggcg actgtgagac     300
ggcgttcaac aacgatgtgt tcaggatcac aactcagctg ttctacctca gcaagttcgt     360
agagtacatc gactccttct accttcccct tatggacaag ccactgtcgt tccttcagtt     420
cttccatcat ttgggggccc ccattgacat gtggctattc tacaaatacc gcaacgaagg     480
agtctggatc tttgtcctgt tgaatgggtt cattcactgg atcatgtacg gttactattg     540
gacgcggctc atcaagctga acttccccat gcccaagaac ctgatcacct ccatgcagat     600
catccagttc aatgtcgggt tctacatcgt ctggaagtac cgcaatgtgc catgctaccg     660
ccaggatggg atgcgcatgt ttgcctggat cttcaactac tggtatgtcg ggacggtctt     720
gctgctgttc ctcaactttt acgtgcagac gtacatccgg aagccgagga agaaccgagg     780
gaagaaggag taggccacat ggcgcctgcg ctggaggaaa cggtacgctc ggatggtgca     840
ctgcacttgc actccgccgt ttctagcctc ccctcgctct aaccactgcg gcatgcctgc     900
ttgaggcgtg acgttgcctc gtatgataca gtttacaccc ttcccacagc ccacggagct     960
ggtgactgtt tccagcgtct gcagatcatt gatctggtgc aatgtgcaca gaccaagccc    1020
ctctaacgtc ttgcggtgta ccgctcgaca ctcactgcaa gagacagatg gctgagcatg    1080
ttatagcccc ttacattcta cccttcgtcc caacctgacc gtcacattc               1129
```

<210> SEQ ID NO 2
<211> LENGTH: 1145
<212> TYPE: DNA
<213> ORGANISM: Euglena anabaena

<400> SEQUENCE: 2

```
atttttttc ggtctaaaat ggaagcagcc aaagaattgg tttccatcgt ccaagaggag      60
ctccccaagg tggactatgc ccagctttgg caggacgcca gcagctgtga ggtcctttac     120
ctctcggtgg cattcgtggc gatcaagttc atgctgcgcc cactggacct gaagcgccag     180
```

```
gccaccttga agaagctgtt cacagcatac aacttcctca tgtcgatcta ttcctttggc      240
tccttcctgg ccatggccta tgccctatca gtaactggca tcctctccgg cgactgtgag      300
acagcgttca acaacgatgt gttcaggatc acaactcagc tgttctacct cagcaagttc      360
gtagagtaca tcgactcctt ctaccttccc cttatggaca agccactgtc gttccttcag      420
ttcttccatc atttgggggc tcccattgac atgtggctat tctacaaata ccgcaacgaa      480
ggagtctgga tctttgtcct gttgaatggg ttcattcact ggatcatgta cggttactac      540
tggacgcggc tcatcaagct gaacttcccc atgcccaaga acctgatcac ctccatgcag      600
atcatccagt tcaatgtcgg gttctacatc gtctggaagt accgcaatgt gccatgctac      660
cgccaggatg ggatgcgcat gtttgcctgg atcttcaact actggtacgt cgggacggtc      720
ttgctgctgt tcctcaactt ttacgtgcag acgtacatcc ggaagccgag gaagaaccaa      780
gggaagaagg agtaggccac atggcgcctg cgctggagga acggtacgc tcggatggtg      840 cactgcactt gcactccgcc gcttctagcc tcccctcgct ctaacctctg cgacatgcct      900
gcttgaggcg tgacgttgcc tcgtgcgata cagtttacac ccttcccatg gcccacggag      960
caggtgactg tctccagcgt ctgcaattct gatcattggt ctggtgcaat gtgcgcagac      1020
caagcccctc taacgtcttg cggtgtaccg ctcgacactc actgcacgag acagatggct      1080
gagcatgtta tagcccctga cattctaccc ttcgtcctta cctgaccgtc acattcatgc      1140
ttacc                                                                  1145

<210> SEQ ID NO 3
<211> LENGTH: 774
<212> TYPE: DNA
<213> ORGANISM: Euglena gracilis

<400> SEQUENCE: 3
atggaggtgg tgaatgaaat agtctcaatt gggcaggaag ttttacccaa agttgattat       60
gcccaactct ggagtgatgc cagtcactgt gaggtgcttt acttgtccat cgcatttgtc      120
atcttgaagt tcactcttgg ccccccttggt ccaaaaggtc agtctcgtat gaagtttgtt     180
ttcaccaatt acaaccttct catgtccatt tattcgttgg gatcattcct ctcaatggca      240
tatgccatgt acaccatcgg tgttatgtct gacaactgcg agaaggcttt tgacaacaac      300
gtcttcagga tcaccacgca gttgttctat ttgagcaagt tcctggagta tattgactcc      360
ttctatttgc cactgatggg caagcctctg acctggttgc aattcttcca tcatttgggg      420
gcaccgatgg atatgtggct gttctataat taccgaaatg aagctgtttg gattttttgtg    480 ctgttgaatg gtttcatcca ctggatcatg tacggttatt attggaccag attgatcaag      540
ctgaagttcc ccatgccaaa atccctgatt acatcaatgc agatcattca attcaatgtt      600
ggtttctaca ttgtctggaa gtacaggaac attccctgtt atcgccaaga tgggatgagg      660
atgtttggct ggttcttcaa ttacttttat gttggcacag tcttgtgttt gttcttgaat      720
ttctatgtgc aaacgtatat cgtcaggaag cacaagggag ccaaaaagat tcag           774

<210> SEQ ID NO 4
<211> LENGTH: 30
<212> TYPE: DNA
<213> ORGANISM: Artificial Sequence
<220> FEATURE:
<223> OTHER INFORMATION: sense oligonucleotide oEugEL1-1

<400> SEQUENCE: 4
agcggccgca ccatggaggt ggtgaatgaa                                        30
```

<210> SEQ ID NO 5
<211> LENGTH: 30
<212> TYPE: DNA
<213> ORGANISM: Artificial Sequence
<220> FEATURE:
<223> OTHER INFORMATION: sense oligonucleotide oEugEL1-2

<400> SEQUENCE: 5
tgcggccgct cactgaatct ttttggctcc                               30

<210> SEQ ID NO 6
<211> LENGTH: 4311
<212> TYPE: DNA
<213> ORGANISM: Artificial Sequence
<220> FEATURE:
<223> OTHER INFORMATION: plasmid pKR906

<400> SEQUENCE: 6

| | |
|---|---|
| agcggccgca ccatggaggt ggtgaatgaa atagtctcaa ttgggcagga agttttaccc | 60 |
| aaagttgatt atgcccaact ctggagtgat gccagtcact gtgaggtgct ttacttgtcc | 120 |
| atcgcatttg tcatcttgaa gttcactctt ggccccttg gtccaaaagg tcagtctcgt | 180 |
| atgaagtttg ttttcaccaa ttacaacctt ctcatgtcca tttattcgtt gggatcattc | 240 |
| ctctcaatgg catatgccat gtacaccatc ggtgttatgt ctgacaactg cgagaaggct | 300 |
| tttgacaaca acgtcttcag gatcaccacg cagttgttct atttgagcaa gttcctggag | 360 |
| tatattgact ccttctattt gccactgatg ggcaagcctc tgacctggtt gcaattcttc | 420 |
| catcatttgg gggcaccgat ggatatgtgg ctgttctata attaccgaaa tgaagctgtt | 480 |
| tggatttttg tgctgttgaa tggtttcatc cactggatca tgtacggtta ttattggacc | 540 |
| agattgatca agctgaagtt ccccatgcca aaatccctga ttacatcaat gcagatcatt | 600 |
| caattcaatg ttggtttcta cattgtctgg aagtacagga acattccctg ttatcgccaa | 660 |
| gatgggatga ggatgtttgg ctggttcttc aattactttt atgttggcac agtcttgtgt | 720 |
| ttgttcttga atttctatgt gcaaacgtat atcgtcagga agcacaaggg agccaaaaag | 780 |
| attcagtgag cggccgcacc tgaattccag cacactggcg gccgttacta gtggatccga | 840 |
| gctcggtacc aagcttgatg catagcttga gtattctaac gcgtcaccta atagcttgg | 900 |
| cgtaatcatg gtcatagctg tttcctgtgt gaaattgtta tccgctcaca attccacaca | 960 |
| acatacgagc cggaagcata aagtgtaaag cctggggtgc ctaatgagtg agctaactca | 1020 |
| cattaattgc gttgcgctca ctgcccgctt tccagtcggg aaacctgtcg tgccagctgc | 1080 |
| attaatgaat cggccaacgc gcggggagag gcggtttgcg tattgggcgc tcttccgctt | 1140 |
| cctcgctcac tgactcgctg cgctcggtcg ttcggctgcg gcgagcggta tcagctcact | 1200 |
| caaaggcggt aatacggtta tccacagaat caggggataa cgcaggaaag aacatgtgag | 1260 |
| caaaaggcca gcaaaagccc aggaaccgta aaaaggccgc gttgctggcg ttttccata | 1320 |
| ggctccgccc cctgacgag catcacaaaa atcgacgctc aagtcagagg tggcgaaacc | 1380 |
| cgacaggact ataaagatac caggcgtttc ccctggaag ctccctcgtg cgctctcctg | 1440 |
| ttccgaccct gccgcttacc ggatacctgt ccgcctttct cccttcggga agcgtggcgc | 1500 |
| tttctcatag ctcacgctgt aggtatctca gttcggtgta ggtcgttcgc tccaagctgg | 1560 |
| gctgtgtgca cgaaccccc gttcagcccg accgctgcgc cttatccggt aactatcgtc | 1620 |
| ttgagtccaa cccggtaaga cacgacttat cgccactggc agcagccact ggtaacagga | 1680 |
| ttagcagagc gaggtatgta ggcggtgcta cagagttctt gaagtggtgg cctaactacg | 1740 |

```
gctacactag aaggacagta tttggtatct gcgctctgct gaagccagtt accttcggaa    1800
aaagagttgg tagctcttga tccggcaaac aaaccaccgc tggtagcggt ggttttttg    1860 tttgcaagca gcagattacg cgcagaaaaa aaggatctca agaagatcct ttgatctttt    1920
ctacggggtc tgacgctcag tggaacgaaa actcacgtta agggattttg gtcatgagat    1980
tatcaaaaag gatcttcacc tagatccttt taaattaaaa atgaagtttt agcacgtgtc    2040
agtcctgctc ctcggccacg aagtgcacgc agttgccggc cgggtcgcgc agggcgaact    2100
cccgccccca cggctgctcg ccgatctcgg tcatggccgg cccggaggcg tcccggaagt    2160
tcgtggacac gacctccgac cactcggcgt acagctcgtc caggccgcgc acccacaccc    2220
aggccagggt gttgtccggc accacctggt cctggaccgc gctgatgaac agggtcacgt    2280
cgtcccggac cacaccggcg aagtcgtcct ccacgaagtc ccgggagaac ccgagccggt    2340
cggtccagaa ctcgaccgct ccggcgacgt cgcgcgcgt gagcaccgga acggcactgg    2400
tcaacttggc catggtggcc ctcctcacgt gctattattg aagcatttat cagggttatt    2460
gtctcatgag cggatacata tttgaatgta tttagaaaaa taaacaaata ggggttccgc    2520
gcacatttcc ccgaaaagtg ccacctgtat gcggtgtgaa ataccgcaca gatgcgtaag    2580
gagaaaatac cgcatcagga aattgtaagc gttaataatt cagaagaact cgtcaagaag    2640
gcgatagaag gcgatgcgct gcgaatcggg agcggcgata ccgtaaagca cgaggaagcg    2700
gtcagcccat tcgccgccaa gctcttcagc aatatcacgg gtagccaacg ctatgtcctg    2760
atagcggtcc gccacaccca gccggccaca gtcgatgaat ccagaaaagc ggccattttc    2820
caccatgata ttcggcaagc aggcatcgcc atgggtcacg acgagatcct cgccgtcggg    2880
catgctcgcc ttgagcctgg cgaacagttc ggctggcgcg agcccctgat gctcttcgtc    2940
cagatcatcc tgatcgacaa gaccggcttc catccgagta cgtgctcgct cgatgcgatg    3000
tttcgcttgg tggtcgaatg ggcaggtagc cggatcaagc gtatgcagcc gccgcattgc    3060
atcagccatg atggatactt tctcggcagg agcaaggtga gatgacagga gatcctgccc    3120
cggcacttcg cccaatagca gccagtccct tcccgcttca gtgacaacgt cgagcacagc    3180
tgcgcaagga acgcccgtcg tggccagcca cgatagccgc gctgcctcgt cttgcagttc    3240
attcagggca ccggacaggt cggtcttgac aaaaagaacc gggcgcccct gcgctgacag    3300
ccggaacacg gcggcatcag agcagccgat tgtctgttgt gcccagtcat agccgaatag    3360
cctctccacc caagcggccg gagaacctgc gtgcaatcca tcttgttcaa tcatgcgaaa    3420
cgatcctcat cctgtctctt gatcagagct tgatccctg cgccatcaga tccttggcgg    3480
cgagaaagcc atccagttta ctttgcaggg cttcccaacc ttaccagagg gcgccccagc    3540
tggcaattcc ggttcgcttg ctgtccataa aaccgcccag tctagctatc gccatgtaag    3600
cccactgcaa gctacctgct ttctctttgc gcttgcgttt tcccttgtcc agatagccca    3660
gtagctgaca ttcatccggg gtcagcaccg tttctgcgga ctggctttct acgtgaaaag    3720
gatctaggtg aagatccttt ttgataatct catgcctgac atttatattc cccagaacat    3780
caggttaatg gcgtttttga tgtcattttc gcggtggctg agatcagcca cttcttcccc    3840
gataacggag accggcacac tggccatatc ggtggtcatc atgcgccagc tttcatcccc    3900
gatatgcacc accgggtaaa gttcacggga actttatct gacagcagac gtgcactggc    3960 caggggggatc accatccgtc gccccggcgt gtcaataata tcactctgta catccacaaa    4020
cagacgataa cggctctctc ttttataggt gtaaacctta aactgccgta cgtataggct    4080
gcgcaactgt tgggaagggc gatcggtgcg ggcctcttcg ctattacgcc agctggcgaa    4140
```

```
aggggggatgt gctgcaaggc gattaagttg ggtaacgcca gggttttccc agtcacgacg    4200
ttgtaaaacg acggccagtg aattgtaata cgactcacta tagggcgaat tgggccctct    4260
agatgcatgc tcgagcggcc gccagtgtga tggatatctg cagaattcag g             4311

<210> SEQ ID NO 7
<211> LENGTH: 18
<212> TYPE: DNA
<213> ORGANISM: Artificial Sequence
<220> FEATURE:
<223> OTHER INFORMATION: M13F universal primer

<400> SEQUENCE: 7
tgtaaaacga cggccagt                                                  18

<210> SEQ ID NO 8
<211> LENGTH: 22
<212> TYPE: DNA
<213> ORGANISM: Artificial Sequence
<220> FEATURE:
<223> OTHER INFORMATION: primer M13-28Rev

<400> SEQUENCE: 8
gtaatacgac tcactatagg gc                                             22

<210> SEQ ID NO 9
<211> LENGTH: 3668
<212> TYPE: DNA
<213> ORGANISM: Artificial Sequence
<220> FEATURE:
<223> OTHER INFORMATION: plasmid pLF121-1
<220> FEATURE:
<221> NAME/KEY: misc_feature
<222> LOCATION: (3616)..(3655)
<223> OTHER INFORMATION: n is a, c, g, or t

<400> SEQUENCE: 9
gtacaaagtt ggcattataa gaaagcattg cttatcaatt tgttgcaacg aacaggtcac    60
tatcagtcaa aataaaatca ttatttgcca tccagctgat atccctata gtgagtcgta    120 ttacatggtc atagctgttt cctggcagct ctggcccgtg tctcaaaatc tctgatgtta   180
cattgcacaa gataaaaata tatcatcatg ttagaaaaac tcatcgagca tcaaatgaaa   240 ctgcaatttta ttcatatcag gattatcaat accatatttt tgaaaagcc gtttctgtaa   300 tgaaggagaa aactcaccga ggcagttcca taggatggca agatcctggt atcggtctgc   360
gattccgact cgtccaacat caatacaacc tattaattc ccctcgtcaa aaataaggtt   420
atcaagtgag aaatcaccat gagtgacgac tgaatccggt gagaatggca aaagcttatg   480
catttctttc cagacttgtt caacaggcca gccattacgc tcgtcatcaa aatcactcgc   540
atcaaccaaa ccgttattca ttcgtgattg cgcctgagcg agacgaaata cgcgatcgct   600
gttaaaagga caattacaaa caggaatcga atgcaaccgg cgcaggaaca ctgccagcgc   660
atcaacaata ttttcacctg aatcaggata ttcttctaat acctggaatg ctgttttccc   720
ggggatcgca gtggtgagta accatgcatc atcaggagta cggataaaat gcttgatggt   780
cggaagaggc ataaattccg tcagccagtt tagtctgacc atctcatctg taacatcatt   840
ggcaacgcta cctttgccat gtttcagaaa caactctggc gcatcgggct tcccatacaa   900
tcgatagatt gtcgcacctg attgcccgac attatcgcga gcccatttat acccatataa   960
atcagcatcc atgttggaat ttaatcgcgg cctcgagcaa gacgtttccc gttgaatatg   1020
gctcatagat cttttctcca tcactgatag ggagtggtaa aataactcca tcaatgatag   1080
```

```
agtgtcaaca acatgaccaa aatcccttaa cgtgagttac gcgtattaat tgcgttgcgc   1140
tcactgcccg ctttccagtc gggaaacctg tcgtgccagc tgcattaatg aatcggccaa   1200
cgcgcgggga gaggcggttt gcgtattggg cgctcttccg cttcctcgct cactgactcg   1260
ctgcgctcgg tcgttcggct gcggcgagcg gtatcagctc actcaaaggc ggtaatacgg   1320
ttatccacag aatcagggga taacgcagga agaacatgt gagcaaaagg ccagcaaaag   1380
gccaggaacc gtaaaaaggc cgcgttgctg gcgtttttcc ataggctccg ccccctgac   1440
gagcatcaca aaaatcgacg ctcaagtcag aggtggcgaa acccgacagg actataaaga   1500
taccaggcgt ttccccctgg aagctccctc gtgcgctctc ctgttccgac cctgccgctt   1560
accggatacc tgtccgcctt tctcccttcg ggaagcgtgg cgctttctca atgctcacgc   1620
tgtaggtatc tcagttcggt gtaggtcgtt cgctccaagc tgggctgtgt gcacgaaccc   1680
cccgttcagc ccgaccgctg cgccttatcc ggtaactatc gtcttgagtc caacccggta   1740
agacacgact tatcgccact ggcagcagcc actggtaaca ggattagcag agcgaggtat   1800
gtaggcggtg ctacagagtt cttgaagtgg tggcctaact acggttacac tagaagaaca   1860
gtatttggta tctgcgctct gctgaagcca gttaccttcg gaaaaagagt tggtagctct   1920
tgatccggca aacaaaccac cgctggtagc ggtggttttt ttgtttgcaa gcagcagatt   1980
acgcgcagaa aaaaggatc tcaagaagat cctttgatct tttctacggg gtctgacgct   2040
cagggaacga cgcgtaccgc tagccaggaa gagtttgtag aaacgcaaaa aggccatccg   2100
tcaggatggc cttctgctta gtttgatgcc tggcagttta tggcgggcgt cctgcccgcc   2160
accctccggg ccgttgcttc acaacgttca aatccgctcc cggcggattt gtcctactca   2220
ggagagcgtt caccgacaaa caacagataa aacgaaaggc ccagtcttcc gactgagcct   2280
ttcgttttat ttgatgcctg gcagttccct actctcgcgt taacgctagc atggatgttt   2340
tcccagtcac gacgttgtaa aacgacggcc agtcttaagc tcgggcccca aataatgatt   2400
ttattttgac tgatagtgac ctgttcgttg caacaaattg atgagcaatg cttttttata   2460
atgccaactt tgtacaaaaa agttggtttt tttcggtcta aaatggaagc agccaaagaa   2520
ttggttttcca tcgtccaaga ggagctcccc aaggtggact atgcccagct ttggcaggat   2580
gccagcagct gtgaggtcct ttacctctcg gtggcattcg tggcgatcaa gttcatgctg   2640
cgcccactgg acctgaagcg ccaggccacc ttgaagaagc tgttcacagc atacaacttc   2700
ctcatgtcga tctattcctt tggctccttc ctggccatgg cctatgccct atcagtaact   2760
ggcatcctct ccggcgactg tgagacggcg ttcaacaacg atgtgttcag gatcacaact   2820
cagctgttct acctcagcaa gttcgtagag tacatcgact ccttctacct tccccttatg   2880
gacaagccac tgtcgttcct tcagttcttc catcatttgg gggcccccat tgacatgtgg   2940
ctattctaca aataccgcaa cgaaggagtc tggatctttg tcctgttgaa tgggttcatt   3000
cactggatca tgtacggtta ctattggacg cggctcatca agctgaactt ccccatgccc   3060
aagaacctga tcacctccat gcagatcatc cagttcaatg tcgggttcta catcgtctgg   3120
aagtaccgca atgtgccatg ctaccgccag gatgggatgc gcatgtttgc ctggatcttc   3180
aactactggt atgtcgggac ggtcttgctg ctgttcctca acttttacgt gcagacgtac   3240
atccggaagc cgaggaagaa ccgagggaag aaggagtagg ccacatggcg cctgcgctgg   3300
aggaaacggt acgctcggat ggtgcactgc acttgcactc cgccgtttct agcctcccct   3360
cgctctaacc actgcggcat gcctgcttga ggcgtgacgt tgcctcgtat gatacagttt   3420
acacccttcc cacagcccac ggagctggtg actgtttcca gcgtctgcag atcattgatc   3480
```

| | | |
|---|---|---|
| tggtgcaatg tgcacagacc aagcccctct aacgtcttgc ggtgtaccgc tcgacactca | 3540 |
| ctgcaagaga cagatggctg agcatgttat agccccttac attctaccct tcgtcccaac | 3600 |
| ctgaccgtca cattcnnnnn nnnnnnnnnn nnnnnnnnnn nnnnnaccca | 3660 |
| actttctt | 3668 |

```
<210> SEQ ID NO 10
<211> LENGTH: 3684
<212> TYPE: DNA
<213> ORGANISM: Artificial Sequence
<220> FEATURE:
<223> OTHER INFORMATION: plasmid pLF121-2
<220> FEATURE:
<221> NAME/KEY: misc_feature
<222> LOCATION: (3632)..(3671)
<223> OTHER INFORMATION: n is a, c, g, or t

<400> SEQUENCE: 10
```

| | | |
|---|---|---|
| gtacaaagtt ggcattataa gaaagcattg cttatcaatt tgttgcaacg aacaggtcac | 60 |
| tatcagtcaa aataaaatca ttatttgcca tccagctgat atcccctata gtgagtcgta | 120 |
| ttacatggtc atagctgttt cctggcagct ctggcccgtg tctcaaaatc tctgatgtta | 180 |
| cattgcacaa gataaaaata tatcatcatg ttagaaaaac tcatcgagca tcaaatgaaa | 240 |
| ctgcaattta ttcatatcag gattatcaat accatatttt tgaaaaagcc gtttctgtaa | 300 |
| tgaaggagaa aactcaccga ggcagttcca taggatggca agatcctggt atcggtctgc | 360 |
| gattccgact cgtccaacat caatacaacc tattaatttc ccctcgtcaa aaataaggtt | 420 |
| atcaagtgag aaatcaccat gagtgacgac tgaatccggt gagaatggca aaagcttatg | 480 |
| catttctttc cagacttgtt caacaggcca gccattacgc tcgtcatcaa atcactcgc | 540 |
| atcaaccaaa ccgttattca ttcgtgattg cgcctgagcg agacgaaata cgcgatcgct | 600 |
| gttaaaagga caattacaaa caggaatcga atgcaaccgg cgcaggaaca ctgccagcgc | 660 |
| atcaacaata ttttcacctg aatcaggata ttcttctaat acctggaatg ctgttttccc | 720 |
| ggggatcgca gtggtgagta accatgcatc atcaggagta cggataaaat gcttgatggt | 780 |
| cggaagaggc ataaattccg tcagccagtt tagtctgacc atctcatctg taacatcatt | 840 |
| ggcaacgcta cctttgccat gtttcagaaa caactctggc gcatcgggct tcccatacaa | 900 |
| tcgatagatt gtcgcacctg attgcccgac attatcgcga gcccatttat acccatataa | 960 |
| atcagcatcc atgttggaat ttaatcgcgg cctcgagcaa gacgtttccc gttgaatatg | 1020 |
| gctcatagat cttttctcca tcactgatag ggagtggtaa aataactcca tcaatgatag | 1080 |
| agtgtcaaca acatgaccaa aatccctttaa cgtgagttac gcgtattaat tgcgttgcgc | 1140 |
| tcactgcccg ctttccagtc gggaaacctg tcgtgccagc tgcattaatg aatcggccaa | 1200 |
| cgcgcgggga gaggcggttt gcgtattggg cgctcttccg cttcctcgct cactgactcg | 1260 |
| ctgcgctcgg tcgttcggct gcggcgagcg gtatcagctc actcaaaggc ggtaatacgg | 1320 |
| ttatccacag aatcagggga taacgcagga aagaacatgt gagcaaaagg ccagcaaaag | 1380 |
| gccaggaacc gtaaaaaggc cgcgttgctg gcgtttttcc ataggctccg ccccccctgac | 1440 |
| gagcatcaca aaaatcgacg ctcaagtcag aggtggcgaa acccgacagg actataaaga | 1500 |
| taccaggcgt ttccccctgg aagctccctc gtgcgctctc ctgttccgac cctgccgctt | 1560 |
| accggatacc tgtccgcctt tctcccttcg ggaagcgtgg cgctttctca atgctcacgc | 1620 |
| tgtaggtatc tcagttcggt gtaggtcgtt cgctccaagc tgggctgtgt gcacgaaccc | 1680 |
| cccgttcagc ccgaccgctg cgccttatcc ggtaactatc gtcttgagtc aacccggta | 1740 |

```
agacacgact tatcgccact ggcagcagcc actggtaaca ggattagcag agcgaggtat     1800
gtaggcggtg ctacagagtt cttgaagtgg tggcctaact acggttacac tagaagaaca     1860
gtatttggta tctgcgctct gctgaagcca gttaccttcg gaaaaagagt tggtagctct     1920
tgatccggca aacaaaccac cgctggtagc ggtggttttt ttgtttgcaa gcagcagatt     1980
acgcgcagaa aaaaggatc tcaagaagat cctttgatct tttctacggg gtctgacgct       2040
cagggaacga cgcgtaccgc tagccaggaa gagtttgtag aaacgcaaaa aggccatccg     2100
tcaggatggc cttctgctta gtttgatgcc tggcagttta tggcgggcgt cctgcccgcc     2160
accctccggg ccgttgcttc acaacgttca atccgctcc cggcggattt gtcctactca       2220
ggagagcgtt caccgacaaa caacagataa acgaaaggc ccagtcttcc gactgagcct        2280
ttcgttttat ttgatgcctg gcagttccct actctcgcgt taacgctagc atggatgttt     2340
tcccagtcac gacgttgtaa aacgacggcc agtcttaagc tcgggcccca aataatgatt     2400
ttattttgac tgatagtgac ctgttcgttg caacaaattg atgagcaatg cttttttata     2460
atgccaactt tgtacaaaaa agttggattt ttttcggtc taaaatggaa gcagccaaag       2520
aattggtttc catcgtccaa gaggagctcc ccaaggtgga ctatgcccag ctttggcagg     2580
acgccagcag ctgtgaggtc ctttacctct cggtggcatt cgtggcgatc aagttcatgc     2640
tgcgcccact ggacctgaag cgccaggcca ccttgaagaa gctgttcaca gcatacaact     2700
tcctcatgtc gatctattcc tttggctcct tcctggccat ggcctatgcc ctatcagtaa     2760
ctggcatcct ctccggcgac tgtgagacag cgttcaacaa cgatgtgttc aggatcacaa     2820
ctcagctgtt ctacctcagc aagttcgtag agtacatcga ctccttctac cttcccctta     2880
tggacaagcc actgtcgttc cttcagttct tccatcattt gggggctccc attgacatgt     2940
ggctattcta caaataccgc aacgaaggag tctggatctt tgtcctgttg aatgggttca     3000
ttcactggat catgtacggt tactactgga cgcggctcat caagctgaac ttccccatgc     3060
ccaagaacct gatcacctcc atgcagatca tccagttcaa tgtcgggttc tacatcgtct     3120
ggaagtaccg caatgtgcca tgctaccgcc aggatgggat gcgcatgttt gcctggatct     3180
tcaactactg gtacgtcggg acggtcttgc tgctgttcct caacttttac gtgcagacgt     3240
acatccggaa gccgaggaag aaccaaggga agaaggagta ggccacatgg cgcctgcgct     3300
ggaggaaacg gtacgctcgg atggtgcact gcacttgcac tccgccgctt ctagcctccc     3360
ctcgctctaa cctctgcgac atgcctgctt gaggcgtgac gttgcctcgt gcgatacagt     3420
ttacacccTT cccatggccc acggagcagg tgactgtctc cagcgtctgc aattctgatc     3480
attggtctgg tgcaatgtgc gcagaccaag cccctctaac gtcttgcggt gtaccgctcg     3540
acactcactg cacgagacag atggctgagc atgttatagc ccctgacatt ctacccttcg     3600
tccttacctg accgtcacat tcatgcttac cnnnnnnnnn nnnnnnnnnn nnnnnnnnnn     3660
nnnnnnnnnn nacccaactt tctt                                             3684
```

<210> SEQ ID NO 11
<211> LENGTH: 774
<212> TYPE: DNA
<213> ORGANISM: Euglena anabaena

<400> SEQUENCE: 11

```
atggaagcag ccaaagaatt ggtttccatc gtccaagagg agctccccaa ggtggactat       60
gcccagcttt ggcaggatgc cagcagctgt gaggtccttt acctctcggt ggcattcgtg     120
gcgatcaagt tcatgctgcg cccactggac ctgaagcgcc aggccacctt gaagaagctg     180
```

```
ttcacagcat acaacttcct catgtcgatc tattcctttg gctccttcct ggccatggcc    240
tatgccctat cagtaactgg catcctctcc ggcgactgtg agacggcgtt caacaacgat    300
gtgttcagga tcacaactca gctgttctac ctcagcaagt tcgtagagta catcgactcc    360
ttctaccttc cccttatgga caagccactg tcgttccttc agttcttcca tcatttgggg    420
gcccccattg acatgtggct attctacaaa taccgcaacg aaggagtctg gatctttgtc    480
ctgttgaatg ggttcattca ctggatcatg tacggttact attggacgcg gctcatcaag    540
ctgaacttcc ccatgcccaa gaacctgatc acctccatgc agatcatcca gttcaatgtc    600
gggttctaca tcgtctggaa gtaccgcaat gtgccatgct accgccagga tgggatgcgc    660
atgtttgcct ggatcttcaa ctactggtat gtcgggacgg tcttgctgct gttcctcaac    720
ttttacgtgc agacgtacat ccggaagccg aggaagaacc gagggaagaa ggag          774
```

<210> SEQ ID NO 12
<211> LENGTH: 774
<212> TYPE: DNA
<213> ORGANISM: Euglena anabaena

<400> SEQUENCE: 12

```
atggaagcag ccaaagaatt ggtttccatc gtccaagagg agctccccaa ggtggactat     60
gcccagcttt ggcaggacgc cagcagctgt gaggtccttt acctctcggt ggcattcgtg    120
gcgatcaagt tcatgctgcg cccactggac ctgaagcgcc aggccacctt gaagaagctg    180
ttcacagcat acaacttcct catgtcgatc tattcctttg gctccttcct ggccatggcc    240
tatgccctat cagtaactgg catcctctcc ggcgactgtg agacagcgtt caacaacgat    300
gtgttcagga tcacaactca gctgttctac ctcagcaagt tcgtagagta catcgactcc    360
ttctaccttc cccttatgga caagccactg tcgttccttc agttcttcca tcatttgggg    420
gctcccattg acatgtggct attctacaaa taccgcaacg aaggagtctg gatctttgtc    480
ctgttgaatg ggttcattca ctggatcatg tacggttact actggacgcg gctcatcaag    540
ctgaacttcc ccatgcccaa gaacctgatc acctccatgc agatcatcca gttcaatgtc    600
gggttctaca tcgtctggaa gtaccgcaat gtgccatgct accgccagga tgggatgcgc    660
atgtttgcct ggatcttcaa ctactggtac gtcgggacgg tcttgctgct gttcctcaac    720
ttttacgtgc agacgtacat ccggaagccg aggaagaacc aagggaagaa ggag          774
```

<210> SEQ ID NO 13
<211> LENGTH: 258
<212> TYPE: PRT
<213> ORGANISM: Euglena anabaena

<400> SEQUENCE: 13

```
Met Glu Ala Ala Lys Glu Leu Val Ser Ile Val Gln Glu Glu Leu Pro
1               5                   10                  15

Lys Val Asp Tyr Ala Gln Leu Trp Gln Asp Ala Ser Ser Cys Glu Val
            20                  25                  30

Leu Tyr Leu Ser Val Ala Phe Val Ala Ile Lys Phe Met Leu Arg Pro
        35                  40                  45

Leu Asp Leu Lys Arg Gln Ala Thr Leu Lys Lys Leu Phe Thr Ala Tyr
    50                  55                  60

Asn Phe Leu Met Ser Ile Tyr Ser Phe Gly Ser Phe Leu Ala Met Ala
65                  70                  75                  80

Tyr Ala Leu Ser Val Thr Gly Ile Leu Ser Gly Asp Cys Glu Thr Ala
                85                  90                  95
```

```
Phe Asn Asn Asp Val Phe Arg Ile Thr Thr Gln Leu Phe Tyr Leu Ser
            100                 105                 110

Lys Phe Val Glu Tyr Ile Asp Ser Phe Tyr Leu Pro Leu Met Asp Lys
        115                 120                 125

Pro Leu Ser Phe Leu Gln Phe Phe His His Leu Gly Ala Pro Ile Asp
        130                 135                 140

Met Trp Leu Phe Tyr Lys Tyr Arg Asn Glu Gly Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Asn Phe Pro Met Pro Lys Asn Leu Ile Thr Ser
            180                 185                 190

Met Gln Ile Ile Gln Phe Asn Val Gly Phe Tyr Ile Val Trp Lys Tyr
        195                 200                 205

Arg Asn Val Pro Cys Tyr Arg Gln Asp Gly Met Arg Met Phe Ala Trp
        210                 215                 220

Ile Phe Asn Tyr Trp Tyr Val Gly Thr Val Leu Leu Phe Leu Asn
225                 230                 235                 240

Phe Tyr Val Gln Thr Tyr Ile Arg Lys Pro Arg Lys Asn Arg Gly Lys
                245                 250                 255

Lys Glu

<210> SEQ ID NO 14
<211> LENGTH: 258
<212> TYPE: PRT
<213> ORGANISM: Euglena anabaena

<400> SEQUENCE: 14

Met Glu Ala Ala Lys Glu Leu Val Ser Ile Val Gln Glu Glu Leu Pro
1               5                   10                  15

Lys Val Asp Tyr Ala Gln Leu Trp Gln Asp Ala Ser Ser Cys Glu Val
            20                  25                  30

Leu Tyr Leu Ser Val Ala Phe Val Ala Ile Lys Phe Met Leu Arg Pro
        35                  40                  45

Leu Asp Leu Lys Arg Gln Ala Thr Leu Lys Lys Leu Phe Thr Ala Tyr
    50                  55                  60

Asn Phe Leu Met Ser Ile Tyr Ser Phe Gly Ser Phe Leu Ala Met Ala
65                  70                  75                  80

Tyr Ala Leu Ser Val Thr Gly Ile Leu Ser Gly Asp Cys Glu Thr Ala
                85                  90                  95

Phe Asn Asn Asp Val Phe Arg Ile Thr Thr Gln Leu Phe Tyr Leu Ser
            100                 105                 110

Lys Phe Val Glu Tyr Ile Asp Ser Phe Tyr Leu Pro Leu Met Asp Lys
        115                 120                 125

Pro Leu Ser Phe Leu Gln Phe Phe His His Leu Gly Ala Pro Ile Asp
        130                 135                 140

Met Trp Leu Phe Tyr Lys Tyr Arg Asn Glu Gly Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Asn Phe Pro Met Pro Lys Asn Leu Ile Thr Ser
            180                 185                 190

Met Gln Ile Ile Gln Phe Asn Val Gly Phe Tyr Ile Val Trp Lys Tyr
        195                 200                 205
```

```
Arg Asn Val Pro Cys Tyr Arg Gln Asp Gly Met Arg Met Phe Ala Trp
        210                 215                 220

Ile Phe Asn Tyr Trp Tyr Val Gly Thr Val Leu Leu Leu Phe Leu Asn
225                 230                 235                 240

Phe Tyr Val Gln Thr Tyr Ile Arg Lys Pro Arg Lys Asn Gln Gly Lys
                245                 250                 255

Lys Glu

<210> SEQ ID NO 15
<211> LENGTH: 263
<212> TYPE: PRT
<213> ORGANISM: Isochrysis galbana

<400> SEQUENCE: 15

Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro
            20                  25                  30

Leu Leu Arg Asn Ser Gly Leu Val Asp Glu Lys Lys Gly Ala Tyr Arg
        35                  40                  45

Thr Ser Met Ile Trp Tyr Asn Val Leu Leu Ala Leu Phe Ser Ala Leu
50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110

Ala Phe Tyr Tyr Ser Lys Tyr Val Glu Tyr Leu Asp Thr Ala Trp Leu
        115                 120                 125

Val Leu Lys Gly Lys Arg Val Ser Phe Leu Gln Ala Phe His His Phe
130                 135                 140

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Gly Phe Leu Leu
        195                 200                 205

Val Trp Asp Tyr Ile Asn Val Pro Cys Phe Asn Ser Asp Lys Gly Lys
210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Leu Ala Thr Lys Lys Ser
                245                 250                 255

Ala Lys Ala Gly Lys Gln Leu
            260

<210> SEQ ID NO 16
<211> LENGTH: 258
<212> TYPE: PRT
<213> ORGANISM: Euglena gracilis

<400> SEQUENCE: 16

Met Glu Val Val Asn Glu Ile Val Ser Ile Gly Gln Glu Val Leu Pro
1               5                   10                  15
```

| | | | | | | | | | | | |
|---|---|---|---|---|---|---|---|---|---|---|---|
|Lys|Val|Asp|Tyr|Ala|Gln|Leu|Trp|Ser|Asp|Ala|Ser|His|Cys|Glu|Val|
| | |20| | | |25| | | |30| |

Leu Tyr Leu Ser Ile Ala Phe Val Ile Leu Lys Phe Thr Leu Gly Pro
       35              40             45

Leu Gly Pro Lys Gly Gln Ser Arg Met Lys Phe Val Phe Thr Asn Tyr
 50              55              60

Asn Leu Leu Met Ser Ile Tyr Ser Leu Gly Ser Phe Leu Ser Met Ala
65              70              75              80

Tyr Ala Met Tyr Thr Ile Gly Val Met Ser Asp Asn Cys Glu Lys Ala
       85              90              95

Phe Asp Asn Asn Val Phe Arg Ile Thr Thr Gln Leu Phe Tyr Leu Ser
       100             105            110

Lys Phe Leu Glu Tyr Ile Asp Ser Phe Tyr Leu Pro Leu Met Gly Lys
       115             120            125

Pro Leu Thr Trp Leu Gln Phe Phe His His Leu Gly Ala Pro Met Asp
   130               135              140

Met Trp Leu Phe Tyr Asn Tyr Arg Asn Glu Ala Val Trp Ile Phe Val
145             150              155             160

Leu Leu Asn Gly Phe Ile His Trp Ile Met Tyr Gly Tyr Tyr Trp Thr
       165             170            175

Arg Leu Ile Lys Leu Lys Phe Pro Met Pro Lys Ser Leu Ile Thr Ser
       180             185            190

Met Gln Ile Ile Gln Phe Asn Val Gly Phe Tyr Ile Val Trp Lys Tyr
       195             200            205

Arg Asn Ile Pro Cys Tyr Arg Gln Asp Gly Met Arg Met Phe Gly Trp
   210               215              220

Phe Phe Asn Tyr Phe Tyr Val Gly Thr Val Leu Cys Leu Phe Leu Asn
225             230              235             240

Phe Tyr Val Gln Thr Tyr Ile Val Arg Lys His Lys Gly Ala Lys Lys
       245             250            255

Ile Gln

```
<210> SEQ ID NO 17
<211> LENGTH: 9472
<212> TYPE: DNA
<213> ORGANISM: Artificial Sequence
<220> FEATURE:
<223> OTHER INFORMATION: plasmid pDMW263

<400> SEQUENCE: 17
catggcatgg atggtacgtc ctgtagaaac cccaacccgt gaaatcaaaa aactcgacgg      60
cctgtgggca ttcagtctgg atcgcgaaaa ctgtggaatt gatcagcgtt ggtgggaaag     120
cgcgttacaa gaaagccggg caattgctgt gccaggcagt tttaacgatc agttcgccga     180
tgcagatatt cgtaattatg cgggcaacgt ctggtatcag cgcgaagtct ttataccgaa     240
aggttgggca ggccagcgta tcgtgctgcg tttcgatgcg gtcactcatt acggcaaagt     300
gtgggtcaat aatcaggaag tgatggagca tcagggcggc tatacgccat ttgaagccga     360
tgtcacgccg tatgttattg ccgggaaaag tgtacgtatc accgtttgtg tgaacaacga     420
actgaactgg cagactatcc cgccgggaat ggtgattacc gacgaaaacg caagaaaaa     480 gcagtcttac ttccatgatt tctttaacta tgccgggatc catcgcagcg taatgctcta     540
caccacgccg aacacctggg tggacgatat caccgtggtg acgcatgtcg cgcaagactg     600
taaccacgcg tctgttgact ggcaggtggt ggccaatggt gatgtcagcg ttgaactgcg     660
```

```
tgatgcggat caacaggtgg ttgcaactgg acaaggcact agcgggactt tgcaagtggt      720
gaatccgcac ctctggcaac cgggtgaagg ttatctctat gaactgtgcg tcacagccaa      780
aagccagaca gagtgtgata tctacccgct tcgcgtcggc atccggtcag tggcagtgaa      840
gggcgaacag ttcctgatta accacaaacc gttctacttt actggctttg gtcgtcatga      900
agatgcggac ttacgtggca aaggattcga taacgtgctg atggtgcacg accacgcatt      960
aatggactgg attggggcca actcctaccg taccctcgcat tacccttacg ctgaagagat     1020
gctcgactgg gcagatgaac atggcatcgt ggtgattgat gaaactgctg ctgtcggctt     1080
taacctctct ttaggcattg gtttcgaagc gggcaacaag ccgaaagaac tgtacagcga     1140
agaggcagtc aacggggaaa ctcagcaagc gcacttacag gcgattaaag agctgatagc     1200
gcgtgacaaa aaccacccaa gcgtggtgat gtggagtatt gccaacgaac cggatacccg     1260
tccgcaagtg cacgggaata tttcgccact ggcggaagca acgcgtaaac tcgacccgac     1320
gcgtccgatc acctgcgtca atgtaatgtt ctgcgacgct cacaccgata ccatcagcga     1380
tctctttgat gtgctgtgcc tgaaccgtta ttacggatgg tatgtccaaa gcggcgattt     1440
ggaaacggca gagaaggtac tggaaaaaga acttctggcc tggcaggaga aactgcatca     1500
gccgattatc atcaccgaat acggcgtgga tacgttagcc gggctgcact caatgtacac     1560
cgacatgtgg agtgaagagt atcagtgtgc atggctggat atgtatcacc gcgtctttga     1620
tcgcgtcagc gccgtcgtcg gtgaacaggt atggaatttc gccgattttg cgacctcgca     1680
aggcatattg cgcgttggcg gtaacaagaa agggatcttc actcgcgacc gcaaaccgaa     1740
gtcggcggct tttctgctgc aaaaacgctg gactggcatg aacttcggtg aaaaaccgca     1800
gcagggaggc aaacaatgat taattaacta gagcggccgc caccgcggcc cgagattccg     1860
gcctcttcgg ccgccaagcg acccgggtgg acgtctagag gtacctagca attaacagat     1920
agtttgccgg tgataattct cttaacctcc cacactcctt tgacataacg atttatgtaa     1980
cgaaactgaa atttgaccag atattgtgtc cgcggtggag ctccagcttt tgttcccttt     2040
agtgagggtt aatttcgagc ttggcgtaat catggtcata gctgtttcct gtgtgaaatt     2100
gttatccgct cacaattcca cacaacatac gagccggaag cataaagtgt aaagcctggg     2160
gtgcctaatg agtgagctaa ctcacattaa ttgcgttgcg ctcactgccc gctttccagt     2220
cgggaaacct gtcgtgccag ctgcattaat gaatcggcca acgcgcgggg agaggcggtt     2280
tgcgtattgg gcgctcttcc gcttcctcgc tcactgactc gctgcgctcg tcgttcggc     2340 tgcggcgagc ggtatcagct cactcaaagg cggtaatacg ttatccaca gaatcagggg     2400 ataacgcagg aaagaacatg tgagcaaaag gccagcaaaa ggccaggaac cgtaaaaagg     2460
ccgcgttgct ggcgtttttc cataggctcc gcccccctga cgagcatcac aaaaatcgac     2520
gctcaagtca gaggtggcga aacccgacag gactataaag ataccaggcg tttcccctg     2580 gaagctccct cgtgcgctct cctgttccga ccctgccgct taccggatac ctgtccgcct     2640 ttctccttc gggaagcgtg cgctttctc atagctcacg ctgtaggtat ctcagttcgg     2700
tgtaggtcgt tcgctccaag ctgggctgtg tgcacgaacc ccccgttcag cccgaccgct     2760
gcgccttatc cggtaactat cgtcttgagt ccaacccggt aagacacgac ttatcgccac     2820
tggcagcagc cactggtaac aggattagca gagcgaggta tgtaggcggt gctacagagt     2880
tcttgaagtg gtggcctaac tacggctaca ctagaaggac agtatttggt atctgcgctc     2940
tgctgaagcc agttaccttc ggaaaaagag ttggtagctc ttgatccggc aaacaaacca     3000
ccgctggtag cggtggtttt tttgtttgca agcagcagat tacgcgcaga aaaaaggat     3060
```

```
ctcaagaaga tcctttgatc ttttctacgg ggtctgacgc tcagtggaac gaaaactcac    3120
gttaagggat tttggtcatg agattatcaa aaaggatctt cacctagatc cttttaaatt    3180
aaaaatgaag ttttaaatca atctaaagta tatatgagta aacttggtct gacagttacc    3240
aatgcttaat cagtgaggca cctatctcag cgatctgtct atttcgttca tccatagttg    3300
cctgactccc cgtcgtgtag ataactacga tacgggaggg cttaccatct ggccccagtg    3360
ctgcaatgat accgcgagac ccacgctcac cggctccaga tttatcagca ataaaccagc    3420
cagccggaag ggccgagcgc agaagtggtc ctgcaacttt atccgcctcc atccagtcta    3480
ttaattgttg ccgggaagct agagtaagta gttcgccagt taatagtttg cgcaacgttg    3540
ttgccattgc tacaggcatc gtggtgtcac gctcgtcgtt tggtatggct tcattcagct    3600
ccggttccca acgatcaagg cgagttacat gatcccccat gttgtgcaaa aaagcggtta    3660
gctccttcgg tcctccgatc gttgtcagaa gtaagttggc cgcagtgtta tcactcatgg    3720
ttatggcagc actgcataat tctcttactg tcatgccatc cgtaagatgc ttttctgtga    3780
ctggtgagta ctcaaccaag tcattctgag aatagtgtat gcggcgaccg agttgctctt    3840
gcccggcgtc aatacgggat aataccgcgc cacatagcag aactttaaaa gtgctcatca    3900
ttggaaaacg ttcttcgggg cgaaaactct caaggatctt accgctgttg agatccagtt    3960
cgatgtaacc cactcgtgca cccaactgat cttcagcatc ttttactttc accagcgttt    4020
ctgggtgagc aaaaacagga aggcaaaatg ccgcaaaaaa gggaataagg gcgacacgga    4080
aatgttgaat actcatactc ttcctttttc aatattattg aagcatttat cagggttatt    4140
gtctcatgag cggatacata tttgaatgta tttagaaaaa taaacaaata ggggttccgc    4200
gcacatttcc ccgaaaagtg ccacctgacg cgccctgtag cggcgcatta agcgcggcgg    4260
gtgtggtggt tacgcgcagc gtgaccgcta cacttgccag cgccctagcg cccgctcctt    4320
tcgctttctt cccttccttt ctcgccacgt tcgccggctt tccccgtcaa gctctaaatc    4380
gggggctccc tttagggttc cgatttagtg ctttacggca cctcgacccc aaaaaacttg    4440
attagggtga tggttcacgt agtgggccat cgccctgata acggtttttt cgccctttga    4500
cgttggagtc cacgttcttt aatagtggac tcttgttcca aactggaaca acactcaacc    4560
ctatctcggt ctattctttt gatttataag ggattttgcc gatttcggcc tattggttaa    4620
aaaatgagct gatttaacaa aaatttaacg cgaattttaa caaaatatta acgcttacaa    4680
tttccattcg ccattcaggc tgcgcaactg ttgggaaggg cgatcggtgc gggcctcttc    4740
gctattacgc cagctggcga aagggggatg tgctgcaagg cgattaagtt gggtaacgcc    4800
agggttttcc cagtcacgac gttgtaaaac gacggccagt gaattgtaat acgactcact    4860
atagggcgaa ttgggtaccg gccccccct cgaggtcgat ggtgtcgata agcttgatat    4920
cgaattcatg tcacacaaac cgatcttcgc ctcaaggaaa cctaattcta catccgagag    4980
actgccgaga tccagtctac actgattaat tttcgggcca ataatttaaa aaaatcgtgt    5040
tatataatat tatatgtatt atatatatac atcatgatga tactgacagt catgtcccat    5100
tgctaaatag acagactcca tctgccgcct ccaactgatg ttctcaatat ttaaggggtc    5160
atctcgcatt gtttaataat aaacagactc catctaccgc ctccaaatga tgttctcaaa    5220
atatattgta tgaacttatt tttattactt agtattatta gacaacttac ttgctttatg    5280
aaaaacactt cctatttagg aaacaattta taatggcagt tcgttcattt aacaatttat    5340
gtagaataaa tgttataaat gcgtatggga aatcttaaat atggatagca taaatgatat    5400
ctgcattgcc taattcgaaa tcaacagcaa cgaaaaaaat cccttgtaca acataaatag    5460
```

```
tcatcgagaa atatcaacta tcaaagaaca gctattcaca cgttactatt gagattatta   5520
ttggacgaga atcacacact caactgtctt tctctcttct agaaatacag gtacaagtat   5580
gtactattct cattgttcat acttctagtc atttcatccc acatattcct tggatttctc   5640
tccaatgaat gacattctat cttgcaaatt caacaattat aataagatat accaaagtag   5700
cggtatagtg gcaatcaaaa agcttctctg gtgtgcttct cgtatttatt tttattctaa   5760
tgatccatta aaggtatata tttatttctt gttatataat cctttgttt attacatggg    5820 ctggatacat aaaggtattt tgatttaatt ttttgcttaa attcaatccc ccctcgttca   5880
gtgtcaactg taatggtagg aaattaccat acttttgaag aagcaaaaaa aatgaaagaa   5940 aaaaaaatc gtatttccag gttagacgtt ccgcagaatc tagaatgcgg tatgcggtac     6000
attgttcttc gaacgtaaaa gttgcgctcc ctgagatatt gtacatttt gcttttacaa    6060 gtacaagtac atcgtacaac tatgtactac tgttgatgca tccacaacag tttgttttgt    6120 tttttttgt ttttttttt tctaatgatt cattaccgct atgtatacct acttgtactt      6180
gtagtaagcc gggttattgg cgttcaatta atcatagact tatgaatctg cacggtgtgc    6240
gctgcgagtt acttttagct tatgcatgct acttgggtgt aatattggga tctgttcgga   6300
aatcaacgga tgctcaaccg atttcgacag taataatttg aatcgaatcg gagcctaaaa   6360
tgaacccgag tatatctcat aaaattctcg gtgagaggtc tgtgactgtc agtacaaggt   6420
gccttcatta tgccctcaac cttaccatac ctcactgaat gtagtgtacc tctaaaaatg    6480
aaatacagtg ccaaaagcca aggcactgag ctcgtctaac ggacttgata tacaaccaat    6540
taaaacaaat gaaagaaat acagttcttt gtatcatttg taacaattac cctgtacaaa    6600
ctaaggtatt gaaatcccac aatattccca aagtccaccc cttttccaaat tgtcatgcct    6660 acaactcata taccaagcac taacctacca aacaccacta aaacccaca aaatatatct     6720 taccgaatat acagtaacaa gctaccacca cactcgttgg gtgcagtcgc cagcttaaag    6780
atatctatcc acatcagcca caactcccct cctttaataa accgactaca cccttggcta    6840
ttgaggttat gagtgaatat actgtagaca agacactttc aagaagactg tttccaaaac   6900
gtaccactgt cctccactac aaacacaccc aatctgcttc ttctagtcaa ggttgctaca   6960
ccggtaaatt ataaatcatc atttcattag cagggcaggg ccctttttat agagtcttat    7020
acactagcgg accctgccgg tagaccaacc cgcaggcgcg tcagtttgct ccttccatca   7080
atgcgtcgta gaaacgactt actccttctt gagcagctcc ttgaccttgt tggcaacaag   7140
tctccgacct cggaggtgga ggaagagcct ccgatatcgg cggtagtgat accagcctcg   7200
acggactcct tgacggcagc ctcaacagcg tcaccggcgg gcttcatgtt aagagagaac    7260
ttgagcatca tggcggcaga cagaatggtg gcaatgggt tgaccttctg cttgccgaga    7320 tcggggggcag atccgtgaca gggctcgtac agaccgaacg cctcgttggt gtcgggcaga    7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatgcggc cgagtcgatc agctggtggt tgagctcgag ctgggggaat    7560
tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagatacctc cgacgagctc tcggacaatg    7800
atgaagtcgg tgccctcaac gtttcggatg ggggagagat cggcgagctt gggcgacagc    7860
```

```
agctggcagg gtcgcaggtt ggcgtacagg ttcaggtcct ttcgcagctt gaggagaccc      7920
tgctcgggtc gcacgtcggt tcgtccgtcg ggagtggtcc atacggtgtt ggcagcgcct      7980
ccgacagcac cgagcataat agagtcagcc tttcggcaga tgtcgagagt agcgtcggtg      8040
atgggctcgc cctccttctc aatggcagct cctccaatga gtcggtcctc aaacacaaac      8100
tcggtgccgg aggcctcagc aacagacttg agcaccttga cggcctcggc aatcacctcg      8160
gggccacaga agtcgccgcc gagaagaaca atcttcttgg agtcagtctt ggtcttctta      8220
gtttcgggtt ccattgtgga tgtgtgtggt tgtatgtgtg atgtggtgtg tggagtgaaa      8280
atctgtggct ggcaaacgct cttgtatata tacgcacttt tgcccgtgct atgtggaaga      8340
ctaaacctcc gaagattgtg actcaggtag tgcggtatcg gctagggacc caaaccttgt      8400
cgatgccgat agcgctatcg aacgtacccc agcggccgg gagtatgtcg gaggggacat       8460
acgagatcgt caagggtttg tggccaactg gtaaataaat gatgtcgacg tttaaacagt      8520
gtacgcagat ctactataga ggaacattta aattgccccg gagaagacgg ccaggccgcc      8580
tagatgacaa attcaacaac tcacagctga ctttctgcca ttgccactag ggggggcct       8640 ttttatatgg ccaagccaag ctctccacgt cggttgggct gcaccaaca ataaatgggt       8700 aggttgcac caacaaaggg atgggatggg gggtagaaga tacgaggata acgggctca        8760 atggcacaaa taagaacgaa tactgccatt aagactcgtg atccagcgac tgacaccatt      8820
gcatcatcta agggcctcaa aactacctcg gaactgctgc gctgatctgg acaccacaga      8880
ggttccgagc actttaggtt gcaccaaatg tcccaccagg tgcaggcaga aaacgctgga      8940
acagcgtgta cagtttgtct taacaaaaag tgagggcgct gaggtcgagc agggtggtgt      9000
gacttgttat agcctttaga gctgcgaaag cgcgtatgga tttggctcat caggccagat      9060
tgagggtctg tggacacatg tcatgttagt gtacttcaat cgcccctgg atatagcccc       9120 gacaataggc cgtggcctca ttttttgcc ttccgcacat ttccattgct cgatacccac       9180
accttgcttc tcctgcactt gccaaccta atactggttt acattgacca acatcttaca       9240 agcgggggc ttgtctaggg tatatataaa cagtggctct cccaatcggt tgccagtctc       9300 tttttcctt tctttcccca cagattcgaa atctaaacta cacatcacag aattccgagc      9360
cgtgagtatc cacgacaaga tcagtgtcga gacgacgcgt tttgtgtaat gacacaatcc      9420
gaaagtcgct agcaacacac actctctaca caaactaacc cagctctggt ac            9472
```

<210> SEQ ID NO 18
<211> LENGTH: 7879
<212> TYPE: DNA
<213> ORGANISM: Artificial Sequence
<220> FEATURE:
<223> OTHER INFORMATION: plasmid pDMW237

<400> SEQUENCE: 18

```
ggccgcaagt gtggatgggg aagtgagtgc ccggttctgt gtgcacaatt ggcaatccaa       60
gatggatgga ttcaacacag ggatatagcg agctacgtgg tggtgcgagg atatagcaac      120
ggatatttat gtttgacact tgagaatgta cgatacaagc actgtccaag tacaatacta      180
aacatactgt acatactcat actcgtaccc gggcaacggt ttcacttgag tgcagtggct      240
agtgctctta ctcgtacagt gtgcaatact gcgtatcata gtctttgatg tatatcgtat      300
tcattcatgt tagttgcgta cgagccggaa gcataaagtg taaagcctgg ggtgcctaat      360
gagtgagcta actcacatta attgcgttgc gctcactgcc cgctttccag tcggaaacc       420 tgtcgtgcca gctgcattaa tgaatcggcc aacgcgcggg gagaggcggt ttgcgtattg      480
```

```
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt cgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgcctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct tccccgtcca agctctaaat cgggggctcc   2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
```

```
gccattcagg ctgcgcaact gttgggaagg gcgatcggtg cgggcctctt cgctattacg    2940
ccagctggcg aaaggggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaaggggt catctcgcat    3360
tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg gctggataca    4020
taaaggtatt ttgatttaat tttttgctta aattcaatcc cccctcgttc agtgtcaact    4080
gtaatggtag gaaattacca tacttttgaa gaagcaaaaa aaatgaaaga aaaaaaaaat    4140
cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg tttttttttg    4320
tttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tacttttagc ttatgcatgc tacttgggtg taatattggg atctgttcgg aaatcaacgg    4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc caccccgggg    4980
gtcagaataa gccagtcctc agagtcgccc ttaggtcggt tctgggcaat gaagccaacc    5040
acaaactcgg ggtcggatcg ggcaagctca atggtctgct tggagtactc gccagtggcc    5100
agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
```

```
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa gcggacttg tggacgttag ctcgagcttc gtaggagggc     5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgactcag gcgacgacgg aattcctgca gcccatctgc    6060
agaattcagg agagaccggg ttggcggcgt atttgtgtcc caaaaaacag ccccaattgc    6120
cccggagaag acggccaggc cgcctagatg acaaattcaa caactcacag ctgactttct    6180
gccattgcca ctaggggggg gcctttttat atggccaagc caagctctcc acgtcggttg    6240
ggctgcaccc aacaataaat gggtagggtt gcaccaacaa agggatggga tgggggtag     6300
aagatacgag gataacgggg ctcaatggca caaataagaa cgaatactgc cattaagact    6360
cgtgatccag cgactgacac cattgcatca tctaagggcc tcaaaactac ctcggaactg    6420
ctgcgctgat ctggacacca cagaggttcc gagcacttta ggttgcacca aatgtcccac    6480
caggtgcagg cagaaaacgc tggaacagcg tgtacagttt gtcttaacaa aaagtgaggg    6540
cgctgaggtc gagcagggtg gtgtgacttg ttatagcctt tagagctgcg aaagcgcgta    6600
tggatttggc tcatcaggcc agattgaggg tctgtggaca catgtcatgt tagtgtactt    6660
caatcgcccc ctggatatag ccccgacaat aggccgtggc ctcatttttt tgccttccgc    6720
acatttccat tgctcggtac ccacaccttg cttctcctgc acttgccaac cttaatactg    6780
gtttacattg accaacatct tacaagcggg gggcttgtct agggtatata taaacagtgg    6840
ctctcccaat cggttgccag tctcttttt cctttctttc cccacagatt cgaaatctaa     6900
actacacatc acacaatgcc tgttactgac gtccttaagc gaaagtccgg tgtcatcgtc    6960
ggcgacgatg tccgagccgt gagtatccac gacaagatca gtgtcgagac gacgcgtttt    7020
gtgtaatgac acaatccgaa agtcgctagc aacacacact ctctacacaa actaacccag    7080
ctctccatgg ctctggccaa cgacgctggc gagcgaatct gggctgccgt caccgatccc    7140
gaaatcctca ttggcacctt ctcctacctg ctcctgaagc ctctcctgcg aaactctggt    7200
ctcgtggacg agaagaaagg agcctaccga acctccatga tctggtacaa cgtcctcctg    7260
gctctcttct ctgccctgtc cttctacgtg actgccaccg ctctcggctg ggactacggt    7320
actgagccct ggctgcgaag acagaccggt gatactcccc agcctctctt tcagtgtccc    7380
tctcctgtct gggactccaa gctgttcacc tggactgcca aggccttcta ctattctaag    7440
tacgtggagt acctcgacac cgcttggctg gtcctcaagg gcaagcgagt gtcctttctg    7500
caggccttcc atcactttgg agctccctgg gacgtctacc tcggcattcg actgcacaac    7560
gagggtgtgt ggatcttcat gttctttaac tcgttcattc acaccatcat gtacacctac    7620
tatggactga ctgccgctgg ctacaagttc aaggccaagc ctctgatcac tgccatgcag    7680
```

```
atttgccagt tcgtcggtgg ctttctcctg gtctgggact acatcaacgt tccctgcttc    7740
aactctgaca agggcaagct gttctcctgg gcttcaact acgcctacgt cggatctgtc    7800
tttctcctgt tctgtcactt cttttaccag acaacctgg ccaccaagaa atccgctaag    7860
gctggtaagc agctttagc                                                 7879

<210> SEQ ID NO 19
<211> LENGTH: 7783
<212> TYPE: DNA
<213> ORGANISM: Artificial Sequence
<220> FEATURE:
<223> OTHER INFORMATION: plasmid pY115

<400> SEQUENCE: 19
catggctctg ccaacgacg ctggcgagcg aatctgggct gccgtcaccg atcccgaaat      60
cctcattggc accttctcct acctgctcct gaagcctctc ctgcgaaact ctggtctcgt    120
ggacgagaag aaaggagcct accgaacctc catgatctgg tacaacgtcc tcctggctct    180
cttctctgcc ctgtccttct acgtgactgc caccgctctc ggctgggact acggtactgg    240
agcctggctg cgaagacaga ccggtgatac tccccagcct ctctttcagt gtccctctcc    300
tgtctgggac tccaagctgt tcacctggac tgccaaggcc ttctactatt ctaagtacgt    360
ggagtacctc gacaccgctt ggctggtcct caagggcaag cgagtgtcct ttctgcaggc    420
cttccatcac tttggagctc cctgggacgt ctacctcggc attcgactgc acaacgaggg    480
tgtgtggatc ttcatgttct ttaactcgtt cattcacacc atcatgtaca cctactatgg    540
actgactgcc gctggctaca agttcaaggc caagcctctg atcactgcca tgcagatttg    600
ccagttcgtc ggtggctttc tcctggtctg ggactacatc aacgttccct gcttcaactc    660
tgacaagggc aagctgttct cctgggcttt caactacgcc tacgtcggat ctgtctttct    720
cctgttctgt cacttctttt accaggacaa cctggccacc aagaaatccg ctaaggctgg    780
taagcagctt tagcggccgc aagtgtggat ggggaagtga gtgcccggtt ctgtgtgcac    840
aattggcaat ccaagatgga tggattcaac acagggatat agcgagctac gtggtggtgc    900
gaggatatag caacggatat ttatgtttga cacttgagaa tgtacgatac aagcactgtc    960
caagtacaat actaaacata ctgtacatat tcatactcgt acccgggcaa cggtttcact    1020
tgagtgcagt ggctagtgct cttactcgta cagtgtgcaa tactgcgtat catagtcttt    1080
gatgtatatc gtattcattc atgttagttg cgtacgagcc ggaagcataa agtgtaaagc    1140
ctggggtgcc taatgagtga gctaactcac attaattgcg ttgcgctcac tgcccgcttt    1200
ccagtcggga aacctgtcgt gccagctgca ttaatgaatc ggccaacgcg cggggagagg    1260
cggtttgcgt attgggcgct cttccgcttc ctcgctcact gactcgctgc gctcggtcgt    1320
tcggctgcgg cgagcggtat cagctcactc aaaggcggta atacggttat ccacagaatc    1380
aggggataac gcaggaaaga acatgtgagc aaaaggccag caaaaggcca ggaaccgtaa    1440
aaaggccgcg ttgctggcgt ttttccatag gctccgcccc cctgacgagc atcacaaaaa    1500
tcgacgctca agtcagaggt ggcgaaaccc gacaggacta taaagatacc aggcgtttcc    1560
ccctggaagc tccctcgtgc gctctcctgt tccgaccctg ccgcttaccg gatacctgtc    1620
cgcctttctc ccttcgggaa gcgtggcgct ttctcatagc tcacgctgta ggtatctcag    1680
ttcggtgtag gtcgttcgct ccaagctggg ctgtgtgcac gaaccccccg ttcagcccga    1740
ccgctgcgcc ttatccggta actatcgtct gagtccaacc cggtaagac acgacttatc    1800 gccactggca gcagccactg gtaacaggat tagcagagcg aggtatgtag gcggtgctac    1860
```

```
agagttcttg aagtggtggc ctaactacgg ctacactaga aggacagtat tggtatctg    1920
cgctctgctg aagccagtta ccttcggaaa aagagttggt agctcttgat ccggcaaaca    1980
aaccaccgct ggtagcggtg gttttttttgt ttgcaagcag cagattacgc gcagaaaaaa    2040
aggatctcaa gaagatcctt tgatcttttc tacggggtct gacgctcagt ggaacgaaaa    2100
ctcacgttaa gggattttgg tcatgagatt atcaaaaagg atcttcacct agatcctttt    2160
aaattaaaaa tgaagtttta aatcaatcta agtatatat gagtaaactt ggtctgacag    2220
ttaccaatgc ttaatcagtg aggcacctat ctcagcgatc tgtctatttc gttcatccat    2280
agttgcctga ctccccgtcg tgtagataac tacgatacgg gagggcttac catctggccc    2340
cagtgctgca atgataccgc gagacccacg ctcaccggct ccagatttat cagcaataaa    2400
ccagccagcc ggaagggccg agcgcagaag tggtcctgca actttatccg cctccatcca    2460
gtctattaat tgttgccggg aagctagagt aagtagttcg ccagttaata gtttgcgcaa    2520
cgttgttgcc attgctacag gcatcgtggt gtcacgctcg tcgtttggta tggcttcatt    2580
cagctccggt tcccaacgat caaggcgagt tacatgatcc cccatgttgt gcaaaaaagc    2640
ggttagctcc ttcggtcctc cgatcgttgt cagaagtaag ttggccgcag tgttatcact    2700
catggttatg gcagcactgc ataattctct tactgtcatg ccatccgtaa gatgcttttc    2760
tgtgactggt gagtactcaa ccaagtcatt ctgagaatag tgtatgcggc gaccgagttg    2820
ctcttgcccg gcgtcaatac gggataatac cgcgccacat agcagaactt taaaagtgct    2880
catcattgga aaacgttctt cggggcgaaa actctcaagg atcttaccgc tgttgagatc    2940
cagttcgatg taacccactc gtgcacccaa ctgatcttca gcatctttta ctttcaccag    3000
cgtttctggg tgagcaaaaa caggaaggca aaatgccgca aaaaagggaa taagggcgac    3060
acggaaatgt tgaatactca tactcttcct ttttcaatat tattgaagca tttatcaggg    3120
ttattgtctc atgagcggat acatatttga atgtatttag aaaaataaac aaataggggt    3180
tccgcgcaca tttccccgaa aagtgccacc tgacgcgccc tgtagcggcg cattaagcgc    3240
ggcgggtgtg gtggttacgc gcagcgtgac cgctacactt gccagcgccc tagcgcccgc    3300
tcctttcgct ttcttccctt cctttctcgc cacgttcgcc ggctttcccc gtcaagctct    3360
aaatcggggg ctccctttag ggttccgatt tagtgcttta cggcacctcg accccaaaaa    3420
acttgattag ggtgatggtt cacgtagtgg gccatcgccc tgatagacgg ttttcgccc    3480
tttgacgttg gagtccacgt tctttaatag tggactcttg ttccaaactg gaacaacact    3540
caaccctatc tcggtctatt cttttgattt ataaggggatt ttgccgattt cggcctattg    3600
gttaaaaaat gagctgattt aacaaaaatt taacgcgaat tttaacaaaa tattaacgct    3660
tacaatttcc attcgccatt caggctgcgc aactgttggg aagggcgatc ggtgcgggcc    3720
tcttcgctat tacgccagct ggcgaaaggg ggatgtgctg caaggcgatt aagttgggta    3780
acgccagggt tttcccagtc acgacgttgt aaaacgacgg ccagtgaatt gtaatacgac    3840
tcactatagg gcgaattggg tacccggggcc cccctcgagg tcgatggtgt cgataagctt    3900
gatatcgaat tcatgtcaca caaaccgatc ttcgcctcaa ggaaacctaa ttctacatcc    3960
gagagactgc cgagatccag tctacactga ttaattttcg ggccaataat ttaaaaaaat    4020
cgtgttatat aatattatat gtattatata tatacatcat gatgatactg acagtcatgt    4080
cccattgcta aatagacaga ctccatctgc cgcctccaac tgatgttctc aatatttaag    4140
gggtcatctc gcattgttta ataataaaca gactccatct accgcctcca aatgatgttc    4200
tcaaaatata ttgtatgaac ttattttat tacttagtat tattagacaa cttacttgct    4260
```

```
ttatgaaaaa cacttcctat ttaggaaaca atttataatg gcagttcgtt catttaacaa    4320
tttatgtaga ataaatgtta taaatgcgta tgggaaatct taaatatgga tagcataaat    4380
gatatctgca ttgcctaatt cgaaatcaac agcaacgaaa aaaatcccctt gtacaacata   4440 aatagtcatc gagaaatatc aactatcaaa gaacagctat tcacacgtta ctattgagat    4500
tattattgga cgagaatcac acactcaact gtctttctct cttctagaaa tacaggtaca    4560
agtatgtact attctcattg ttcatacttc tagtcatttc atcccacata ttccttggat    4620
ttctctccaa tgaatgacat tctatcttgc aaattcaaca attataataa gatataccaa    4680
agtagcggta tagtggcaat caaaaagctt ctctggtgtg cttctcgtat ttattttat    4740 tctaatgatc cattaaaggt atatatttat ttcttgttat ataatccttt tgtttattac    4800
atgggctgga tacataaagg tattttgatt taatttttg cttaaattca atccccctc     4860 gttcagtgtc aactgtaatg gtaggaaatt accatacttt tgaagaagca aaaaaatga    4920 aagaaaaaaa aaatcgtatt tccaggttag acgttccgca gaatctagaa tgcggtatgc    4980
ggtacattgt tcttcgaacg taaaagttgc gctccctgag atattgtaca ttttgctt     5040 tacaagtaca agtacatcgt acaactatgt actactgttg atgcatccac aacagtttgt    5100
tttgtttttt tttgtttttt tttttctaa tgattcatta ccgctatgta tacctacttg     5160
tacttgtagt aagccgggtt attggcgttc aattaatcat agacttatga atctgcacgg    5220
tgtgcgctgc gagttacttt tagcttatgc atgctacttg ggtgtaatat tgggatctgt    5280
tcggaaatca acggatgctc aatcgatttc gacagtaatt aattaagtca tacacaagtc   5340
agctttcttc gagcctcata taagtataag tagttcaacg tattagcact gtacccagca    5400
tctccgtatc gagaaacaca acaacatgcc ccattggaca gatcatgcgg atacacaggt    5460
tgtgcagtat catacatact cgatcagaca ggtcgtctga ccatcataca agctgaacaa    5520
gcgctccata cttgcacgct ctctatatac acagttaaat tacatatcca tagtctaacc    5580
tctaacagtt aatcttctgg taagcctccc agccagcctt ctggtatcgc ttggcctcct    5640
caataggatc tcggttctgg ccgtacagac ctcggccgac aattatgata tccgttccgg    5700
tagacatgac atcctcaaca gttcggtact gctgtccgag agcgtctccc ttgtcgtcaa    5760
gacccacccc gggggtcaga ataagccagt cctcagagtc gcccttaggt cggttctggg    5820
caatgaagcc aaccacaaac tcggggtcgg atcgggcaag ctcaatggtc tgcttggagt    5880
actcgccagt ggccagagag ccccttgcaag acagctcggc cagcatgagc agacctctgg   5940
ccagcttctc gttgggagag gggactagga actccttgta ctgggagttc tcgtagtcag    6000
agacgtcctc cttcttctgt tcagagacag tttcctcggc accagctcgc aggccagcaa    6060
tgattccggt tccgggtaca ccgtgggcgt tggtgatatc ggaccactcg gcgattcggt    6120
gacaccggta ctggtgcttg acagtgttgc caatatctgc gaactttctg tcctcgaaca    6180
ggaagaaacc gtgcttaaga gcaagttcct tgaggggag cacagtgccg gcgtaggtga    6240
agtcgtcaat gatgtcgata tgggttttga tcatgcacac ataaggtccg accttatcgg    6300
caagctcaat gagctccttg gtggtggtaa catccagaga agcacacagg ttggttttct    6360
tggctgccac gagcttgagc actcgagcgg caaaggcgga cttgtggacg ttagctcgag    6420
cttcgtagga gggcattttg gtggtgaaga ggagactgaa ataaatttag tctgcagaac    6480
tttttatcgg aaccttatct ggggcagtga agtatatgtt atggtaatag ttacgagtta    6540
gttgaactta tagatagact ggactatacg gctatcggtc caaattagaa agaacgtcaa    6600
tggctctctg ggcgtcgcct ttgccgacaa aaatgtgatc atgatgaaag ccagcaatga    6660
```

-continued

```
cgttgcagct gatattgttg tcggccaacc gcgccgaaaa cgcagctgtc agacccacag      6720
cctccaacga agaatgtatc gtcaaagtga tccaagcaca ctcatagttg gagtcgtact      6780
ccaaaggcgg caatgacgag tcagacagat actcgtcgac gtttaaacag tgtacgcaga      6840
tctactatag aggaacattt aaattgcccc ggagaagacg gccaggccgc ctagatgaca      6900
aattcaacaa ctcacagctg actttctgcc attgccacta gggggggggcc ttttatatg      6960 gccaagccaa gctctccacg tcggttgggc tgcacccaac aataaatggg tagggttgca      7020
ccaacaaagg gatgggatgg ggggtagaag atacgaggat aacgggctc aatggcacaa       7080 ataagaacga atactgccat taagactcgt gatccagcga ctgacaccat tgcatcatct      7140
aagggcctca aaactacctc ggaactgctg cgctgatctg gacaccacag aggttccgag      7200
cactttaggt tgcaccaaat gtcccaccag gtgcaggcag aaaacgctgg aacagcgtgt      7260
acagtttgtc ttaacaaaaa gtgagggcgc tgaggtcgag cagggtggtg tgacttgtta      7320
tagcctttag agctgcgaaa gcgcgtatgg atttggctca tcaggccaga ttgagggtct      7380
gtggacacat gtcatgttag tgtacttcaa tcgcccctg gatatagccc cgacaatagg       7440
ccgtggcctc attttttgc cttccgcaca tttccattgc tcgatacca caccttgctt        7500 ctcctgcact tgccaacctt aatactggtt tacattgacc aacatcttac aagcgggggg      7560
cttgtctagg gtatatataa acagtggctc tcccaatcgg ttgccagtct cttttttcct     7620
ttctttcccc acagattcga aatctaaact acacatcaca gaattccgag ccgtgagtat      7680
ccacgacaag atcagtgtcg agacgacgcg ttttgtgtaa tgacacaatc cgaaagtcgc      7740
tagcaacaca cactctctac acaaactaac ccagctctgg tac                       7783
```

```
<210> SEQ ID NO 20
<211> LENGTH: 19
<212> TYPE: DNA
<213> ORGANISM: Artificial Sequence
<220> FEATURE:
<223> OTHER INFORMATION: primer oYFBA1

<400> SEQUENCE: 20
acgcagatct actatagag                                                    19

<210> SEQ ID NO 21
<211> LENGTH: 27
<212> TYPE: DNA
<213> ORGANISM: Artificial Sequence
<220> FEATURE:
<223> OTHER INFORMATION: primer oYFBA1-6

<400> SEQUENCE: 21
agcggccgct ggtaccagag ctgggtt                                           27

<210> SEQ ID NO 22
<211> LENGTH: 6992
<212> TYPE: DNA
<213> ORGANISM: Artificial Sequence
<220> FEATURE:
<223> OTHER INFORMATION: plasmid pY158

<400> SEQUENCE: 22
ggccgcaagt gtggatgggg aagtgagtgc ccggttctgt gtgcacaatt ggcaatccaa       60
gatggatgga ttcaacacag ggatatagcg agctacgtgg tggtgcgagg atatagcaac      120
ggatatttat gtttgacact tgagaatgta cgatacaagc actgtccaag tacaatacta      180
aacatactgt acatactcat actcgtaccc ggcaacggtt tcacttgagt gcagtggcta      240
```

```
gtgctcttac tcgtacagtg tgcaatactg cgtatcatag tctttgatgt atatcgtatt    300
cattcatgtt agttgcgtac gagccggaag cataaagtgt aaagcctggg gtgcctaatg    360
agtgagctaa ctcacattaa ttgcgttgcg ctcactgccc gctttccagt cgggaaacct    420
gtcgtgccag ctgcattaat gaatcggcca acgcgcgggg agaggcggtt tgcgtattgg    480
gcgctcttcc gcttcctcgc tcactgactc gctgcgctcg tcgttcggc tgcggcgagc      540 ggtatcagct cactcaaagg cggtaatacg gttatccaca gaatcagggg ataacgcagg    600
aaagaacatg tgagcaaaag gccagcaaaa ggccaggaac cgtaaaaagg ccgcgttgct    660 ggcgttttc cataggctcc gcccccctga cgagcatcac aaaaatcgac gctcaagtca      720
gaggtggcga acccgacag gactataaag ataccaggcg tttccccctg gaagctccct      780
cgtgcgctct cctgttccga ccctgccgct taccggatac ctgtccgcct ttctcccttc    840
gggaagcgtg gcgctttctc atagctcacg ctgtaggtat ctcagttcgg tgtaggtcgt    900
tcgctccaag ctgggctgtg tgcacgaacc ccccgttcag cccgaccgct gcgccttatc    960
cggtaactat cgtcttgagt ccaacccggt aagacacgac ttatcgccac tggcagcagc    1020
cactggtaac aggattagca gagcgaggta tgtaggcggt gctacagagt tcttgaagtg    1080
gtggcctaac tacggctaca ctagaaggac agtatttggt atctgcgctc tgctgaagcc    1140
agttaccttc ggaaaaagag ttggtagctc ttgatccggc aaacaaacca ccgctggtag    1200
cggtggtttt tttgtttgca agcagcagat tacgcgcaga aaaaaggat ctcaagaaga      1260 tcctttgatc ttttctacgg ggtctgacgc tcagtggaac gaaaactcac gttaagggat    1320
tttggtcatg agattatcaa aaaggatctt cacctagatc cttttaaatt aaaaatgaag    1380
ttttaaatca atctaaagta tatatgagta aacttggtct gacagttacc aatgcttaat    1440
cagtgaggca cctatctcag cgatctgtct atttcgttca tccatagttg cctgactccc    1500
cgtcgtgtag ataactacga tacgggaggg cttaccatct ggccccagtg ctgcaatgat    1560
accgcgagac ccacgctcac cggctccaga tttatcagca ataaaccagc cagccggaag    1620
ggccgagcgc agaagtggtc ctgcaacttt atccgcctcc atccagtcta ttaattgttg    1680
ccgggaagct agagtaagta gttcgccagt taatagtttg cgcaacgttg ttgccattgc    1740
tacaggcatc gtggtgtcac gctcgtcgtt tggtatggct tcattcagct ccggttccca    1800
acgatcaagg cgagttacat gatccccat gttgtgcaaa aaagcggtta gctccttcgg    1860
tcctccgatc gttgtcagaa gtaagttggc cgcagtgtta tcactcatgg ttatggcagc    1920
actgcataat tctcttactg tcatgccatc cgtaagatgc ttttctgtga ctggtgagta    1980
ctcaaccaag tcattctgag aatagtgtat gcggcgaccg agttgctctt gcccggcgtc    2040
aatacgggat aataccgcgc cacatagcag aactttaaaa gtgctcatca ttggaaaacg    2100
ttcttcgggg cgaaaactct caaggatctt accgctgttg agatccagtt cgatgtaacc    2160
cactcgtgca cccaactgat cttcagcatc ttttactttc accagcgttt ctgggtgagc    2220
aaaaacagga aggcaaaatg ccgcaaaaaa gggaataagg gcgacacgga aatgttgaat    2280
actcatactc ttccttttc aatattattg aagcatttat cagggttatt gtctcatgag    2340
cggatacata tttgaatgta tttagaaaaa taaacaaata ggggttccgc gcacatttcc    2400
ccgaaaagtg ccacctgacg cgccctgtag cggcgcatta agcgcggcgg gtgtggtggt    2460
tacgcgcagc gtgaccgcta cacttgccag cgccctagcg cccgctcctt tcgctttctt    2520
cccttccttt ctcgccacgt tcgccggctt tccccgtcaa gctctaaatc gggggctccc    2580
tttagggttc cgatttagtg ctttacggca cctcgacccc aaaaaacttg attagggtga    2640
```

```
tggttcacgt agtgggccat cgccctgata gacggttttt cgccctttga cgttggagtc    2700
cacgttcttt aatagtggac tcttgttcca aactggaaca acactcaacc ctatctcggt    2760
ctattctttt gatttataag ggattttgcc gatttcggcc tattggttaa aaaatgagct    2820
gatttaacaa aaatttaacg cgaatttaaa caaaatatta acgcttacaa tttccattcg    2880
ccattcaggc tgcgcaactg ttgggaaggg cgatcggtgc gggcctcttc gctattacgc    2940
cagctggcga aggggggatg tgctgcaagg cgattaagtt gggtaacgcc agggttttcc    3000
cagtcacgac gttgtaaaac gacggccagt gaattgtaat acgactcact atagggcgaa    3060
ttgggtaccg gccccccct cgaggtcgat ggtgtcgata agcttgatat cgaattcatg    3120
tcacacaaac cgatcttcgc ctcaaggaaa cctaattcta catccgagag actgccgaga    3180
tccagtctac actgattaat tttcgggcca ataatttaaa aaaatcgtgt tatataatat    3240
tatatgtatt atatatatac atcatgatga tactgacagt catgtcccat tgctaaatag    3300
acagactcca tctgccgcct ccaactgatg ttctcaatat ttaaggggtc atctcgcatt    3360
gtttaataat aaacagactc catctaccgc ctccaaatga tgttctcaaa atatattgta    3420
tgaacttatt tttattactt agtattatta gacaacttac ttgctttatg aaaaacactt    3480
cctatttagg aaacaattta taatggcagt tcgttcattt aacaatttat gtagaataaa    3540
tgttataaat gcgtatggga aatcttaaat atggatagca taaatgatat ctgcattgcc    3600
taattcgaaa tcaacagcaa cgaaaaaaat cccttgtaca acataaatag tcatcgagaa    3660
atatcaacta tcaaagaaca gctattcaca cgttactatt gagattatta ttggacgaga    3720
atcacacact caactgtctt tctctcttct agaaatacag gtacaagtat gtactattct    3780
cattgttcat acttctagtc atttcatccc acatattcct tggatttctc tccaatgaat    3840
gacattctat cttgcaaatt caacaattat aataagatat accaaagtag cggtatagtg    3900
gcaatcaaaa agcttctctg gtgtgcttct cgtatttatt tttattctaa tgatccatta    3960
aaggtatata tttatttctt gttatataat ccttttgttt attacatggg ctggatacat    4020
aaaggtattt tgatttaatt ttttgcttaa attcaatccc ccctcgttca gtgtcaactg    4080
taatggtagg aaattaccat acttttgaag aagcaaaaaa aatgaaagaa aaaaaaaatc    4140
gtatttccag gttagacgtt ccgcagaatc tagaatgcgg tatgcggtac attgttcttc    4200
gaacgtaaaa gttgcgctcc ctgagatatt gtacattttt gcttttacaa gtacaagtac    4260
atcgtacaac tatgtactac tgttgatgca tccacaacag tttgtttttgt ttttttttgt    4320
tttttttttt tctaatgatt cattaccgct atgtatacct acttgtactt gtagtaagcc    4380
gggttattgg cgttcaatta atcatagact tatgaatctg cacggtgtgc gctgcgagtt    4440
actttttagct tatgcatgct acttgggtgt aatattggga tctgttcgga aatcaacgga    4500
tgctcaatcg atttcgacag taattaatta agtcatacac aagtcagctt tcttcgagcc    4560
tcatataagt ataagtagtt caacgtatta gcactgtacc cagcatctcc gtatcgagaa    4620
acacaacaac atgccccatt ggacagatca tgcggataca caggttgtgc agtatcatac    4680
atactcgatc agacaggtcg tctgaccatc atacaagctg aacaagcgct ccatacttgc    4740
acgctctcta tatacacagt taaattacat atccatagtc taacctctaa cagttaatct    4800
tctggtaagc ctcccagcca gccttctggt atcgcttggc ctcctcaata ggatctcggt    4860
tctggccgta cagacctcgg ccgacaatta tgatatccgt tccggtagac atgacatcct    4920
caacagttcg gtactgctgt ccgagagcgt ctcccttgtc gtcaagaccc accccggggg    4980
tcagaataag ccagtcctca gagtcgccct taggtcggtt ctgggcaatg aagccaacca    5040
```

```
caaactcggg gtcggatcgg gcaagctcaa tggtctgctt ggagtactcg ccagtggcca    5100
gagagcccct gcaagacagc tcggccagca tgagcagacc tctggccagc ttctcgttgg    5160
gagaggggac taggaactcc ttgtactggg agttctcgta gtcagagacg tcctccttct    5220
tctgttcaga gacagtttcc tcggcaccag ctcgcaggcc agcaatgatt ccggttccgg    5280
gtacaccgtg ggcgttggtg atatcggacc actcggcgat tcggtgacac cggtactggt    5340
gcttgacagt gttgccaata tctgcgaact ttctgtcctc gaacaggaag aaaccgtgct    5400
taagagcaag ttccttgagg gggagcacag tgccggcgta ggtgaagtcg tcaatgatgt    5460
cgatatgggt tttgatcatg cacacataag gtccgacctt atcggcaagc tcaatgagct    5520
ccttggtggt ggtaacatcc agagaagcac acaggttggt tttcttggct gccacgagct    5580
tgagcactcg agcggcaaag gcggacttgt ggacgttagc tcgagcttcg taggagggca    5640
ttttggtggt gaagaggaga ctgaaataaa tttagtctgc agaactttt atcggaacct    5700
tatctgggc agtgaagtat atgttatggt aatagttacg agttagttga acttatagat    5760
agactggact atacggctat cggtccaaat tagaaagaac gtcaatggct ctctgggcgt    5820
cgcctttgcc gacaaaaatg tgatcatgat gaaagccagc aatgacgttg cagctgatat    5880
tgttgtcggc caaccgcgcc gaaaacgcag ctgtcagacc cacagcctcc aacgaagaat    5940
gtatcgtcaa agtgatccaa gcacactcat agttggagtc gtactccaaa ggcggcaatg    6000
acgagtcaga cagatactcg tcgacgttta acagtgtac gcagatctac tatagaggaa    6060
catttaaatt gccccggaga agacggccag gccgcctaga tgacaaattc aacaactcac    6120
agctgacttt ctgccattgc cactaggggg gggccttttt atatggccaa gccaagctct    6180
ccacgtcggt tgggctgcac ccaacaataa atgggtaggg ttgcaccaac aaagggatgg    6240
gatgggggt agaagatacg aggataacgg ggctcaatgg cacaaataag aacgaatact    6300
gccattaaga ctcgtgatcc agcgactgac accattgcat catctaaggg cctcaaaact    6360
acctcggaac tgctgcgctg atctggacac cacagaggtt ccgagcactt taggttgcac    6420
caaatgtccc accaggtgca ggcagaaaac gctggaacag cgtgtacagt ttgtcttagc    6480
aaaaagtgaa ggcgctgagg tcgagcaggg tggtgtgact tgttatagcc tttagagctg    6540
cgaaagcgcg tatggatttg gctcatcagg ccagattgag ggtctgtgga cacatgtcat    6600
gttagtgtac ttcaatcgcc ccctggatat agccccgaca ataggccgtg gcctcatttt    6660
tttgccttcc gcacatttcc attgctcgat acccacacct tgcttctcct gcacttgcca    6720
accttaatac tggtttacat tgaccaacat cttacaagcg gggggcttgt ctagggtata    6780
tataaacagt ggctctccca atcggttgcc agtctctttt ttcctttctt tccccacaga    6840
ttcgaaatct aaactacaca tcacagaatt ccgagccgtg agtatccacg acaagatcag    6900
tgtcgagacg acgcgttttg tgtaatgaca caatccgaaa gtcgctagca acacacactc    6960
tctacacaaa ctaacccagc tctggtacca gc                                  6992

<210> SEQ ID NO 23
<211> LENGTH: 8707
<212> TYPE: DNA
<213> ORGANISM: Artificial Sequence
<220> FEATURE:
<223> OTHER INFORMATION: plasmid pY159

<400> SEQUENCE: 23
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
```

```
ggatatttat gtttgacact tgagaatgta cgatacaagc actgtccaag tacaatacta    180
aacatactgt acatactcat actcgtaccc ggcaacggtt tcacttgagt gcagtggcta    240
gtgctcttac tcgtacagtg tgcaatactg cgtatcatag tctttgatgt atatcgtatt    300
cattcatgtt agttgcgtac gagccggaag cataaagtgt aaagcctggg gtgcctaatg    360
agtgagctaa ctcacattaa ttgcgttgcg ctcactgccc gctttccagt cgggaaacct    420
gtcgtgccag ctgcattaat gaatcggcca acgcgcgggg agaggcggtt tgcgtattgg    480
gcgctcttcc gcttcctcgc tcactgactc gctgcgctcg gtcgttcggc tgcggcgagc    540
ggtatcagct cactcaaagg cggtaatacg gttatccaca gaatcagggg ataacgcagg    600
aaagaacatg tgagcaaaag gccagcaaaa ggccaggaac cgtaaaaagg ccgcgttgct    660 ggcgttttc cataggctcc gccccctga cgagcatcac aaaaatcgac gctcaagtca    720
gaggtggcga aacccgacag gactataaag ataccaggcg tttccccctg gaagctccct    780
cgtgcgctct cctgttccga ccctgccgct taccggatac ctgtccgcct ttctcccttc    840
gggaagcgtg gcgctttctc atagctcacg ctgtaggtat ctcagttcgg tgtaggtcgt    900
tcgctccaag ctgggctgtg tgcacgaacc ccccgttcag cccgaccgct gcgccttatc    960
cggtaactat cgtcttgagt ccaacccggt aagacacgac ttatcgccac tggcagcagc    1020
cactggtaac aggattagca gagcgaggta tgtaggcggt gctacagagt tcttgaagtg    1080
gtggcctaac tacggctaca ctagaaggac agtatttggt atctgcgctc tgctgaagcc    1140
agttaccttc ggaaaaagag ttggtagctc ttgatccggc aaacaaacca ccgctggtag    1200
cggtggtttt tttgtttgca agcagcagat tacgcgcaga aaaaaaggat ctcaagaaga    1260
tcctttgatc ttttctacgg ggtctgacgc tcagtggaac gaaaactcac gttaagggat    1320
tttggtcatg agattatcaa aaaggatctt cacctagatc cttttaaatt aaaaatgaag    1380
ttttaaatca atctaaagta tatatgagta aacttggtct gacagttacc aatgcttaat    1440
cagtgaggca cctatctcag cgatctgtct atttcgttca tccatagttg cctgactccc    1500
cgtcgtgtag ataactacga tacgggaggg cttaccatct ggccccagtg ctgcaatgat    1560
accgcgagac ccacgctcac cggctccaga tttatcagca ataaaccagc cagccggaag    1620
ggccgagcgc agaagtggtc ctgcaacttt atccgcctcc atccagtcta ttaattgttg    1680
ccgggaagct agagtaagta gttcgccagt taatagtttg cgcaacgttg ttgccattgc    1740
tacaggcatc gtggtgtcac gctcgtcgtt tggtatggct tcattcagct ccggttccca    1800
acgatcaagg cgagttacat gatccccat gttgtgcaaa aaagcggtta gctccttcgg    1860
tcctccgatc gttgtcagaa gtaagttggc cgcagtgtta tcactcatgg ttatggcagc    1920
actgcataat tctcttactg tcatgccatc cgtaagatgc ttttctgtga ctggtgagta    1980
ctcaaccaag tcattctgag aatagtgtat gcggcgaccg agttgctctt gcccggcgtc    2040
aatacgggat aataccgcgc cacatagcag aactttaaaa gtgctcatca ttggaaaacg    2100
ttcttcgggg cgaaaactct caaggatctt accgctgttg agatccagtt cgatgtaacc    2160
cactcgtgca cccaactgat cttcagcatc ttttactttc accagcgttt ctgggtgagc    2220
aaaaacagga aggcaaaatg ccgcaaaaaa gggaataagg gcgacacgga aatgttgaat    2280
actcatactc ttcctttttc aatattattg aagcatttat cagggttatt gtctcatgag    2340
cggatacata tttgaatgta tttagaaaaa taaacaaata ggggttccgc gcacatttcc    2400
ccgaaaagtg ccacctgacg cgccctgtag cggcgcatta agcgcggcgg gtgtggtggt    2460
tacgcgcagc gtgaccgcta cacttgccag cgccctagcg cccgctcctt tcgctttctt    2520
```

```
cccttcctttt ctcgccacgt tcgccggctt tccccgtcaa gctctaaatc gggggctccc    2580
tttagggttc cgattagtg ctttacggca cctcgacccc aaaaaacttg attagggtga      2640
tggttcacgt agtgggccat cgccctgata acggttttt cgcccttga cgttggagtc       2700 cacgttcttt aatagtggac tcttgttcca aactggaaca acactcaacc ctatctcggt     2760
ctattctttt gatttataag ggattttgcc gatttcggcc tattggttaa aaaatgagct     2820
gatttaacaa aaatttaacg cgaattttaa caaaatatta acgcttacaa tttccattcg     2880
ccattcaggc tgcgcaactg ttgggaaggg cgatcggtgc gggcctcttc gctattacgc     2940
cagctggcga aagggggatg tgctgcaagg cgattaagtt gggtaacgcc agggttttcc     3000
cagtcacgac gttgtaaaac gacggccagt gaattgtaat acgactcact atagggcgaa     3060
ttgggtaccg ggccccccct cgaggtcgat ggtgtcgata agcttgatat cgaattcatg     3120
tcacacaaac cgatcttcgc ctcaaggaaa cctaattcta catccgagag actgccgaga     3180
tccagtctac actgattaat tttcgggcca ataatttaaaa aaatcgtgt tatataaat      3240 tatatgtatt atatatatac atcatgatga tactgacagt catgtcccat tgctaaatag    3300
acagactcca tctgccgcct ccaactgatg ttctcaatat ttaaggggtc atctcgcatt    3360
gtttaataat aaacagactc catctaccgc ctccaaatga tgttctcaaa atatattgta    3420
tgaacttatt tttattactt agtattatta gacaactta ttgctttatg aaaaacactt     3480
cctatttagg aaacaattta taatggcagt tcgttcattt aacaatttat gtagaataaa    3540
tgttataaat gcgtatggga aatcttaaat atggatagca taaatgatat ctgcattgcc    3600
taattcgaaa tcaacagcaa cgaaaaaaat cccttgtaca acataaaatag tcatcgagaa   3660 atatcaacta tcaaagaaca gctattcaca cgttactatt gagattatta ttggacgaga   3720
atcacacact caactgtctt tctctcttct agaaatacag gtacaagtat gtactattct    3780
cattgttcat acttctagtc atttcatccc acatattcct tggatttctc tccaatgaat    3840
gacattctat cttgcaaatt caacaattat aataagatat accaaagtag cggtatagtg    3900
gcaatcaaaa agcttctctg gtgtgcttct cgtatttatt tttattctaa tgatccatta    3960
aaggtatata tttatttctt gttatataat ccttttgttt attacatggg ctggatacat    4020
aaaggtattt tgatttaatt ttttgcttaa attcaatccc ccctcgttca gtgtcaactg    4080
taatggtagg aaaattaccat acttttgaag aagcaaaaaa aatgaaagaa aaaaaaatc    4140 gtatttccag gttagacgtt ccgcagaatc tagaatgcgg tatgcggtac attgttcttc    4200
gaacgtaaaa gttgcgctcc ctgagatatt gtacattttt gcttttacaa gtacaagtac   4260
atcgtacaac tatgtactac tgttgatgca tccacaacag tttgtttttgt ttttttttgt  4320 ttttttttt tctaatgatt cattaccgct atgtatacct acttgtactt gtagtaagcc    4380
gggttattgg cgttcaatta atcatagact tatgaatctg cacggtgtgc gctgcgagtt   4440
acttttagct tatgcatgct acttgggtgt aatattggga tctgttcgga aatcaacgga   4500
tgctcaatcg atttcgacag taattaatta agtcatacac aagtcagctt cttcgagcc    4560 tcatataagt ataagtagtt caacgtatta gcactgtacc cagcatctcc gtatcgagaa   4620
acacaacaac atgccccatt ggacagatca tgcggataca caggttgtgc agtatcatac   4680
atactcgatc agacaggtcg tctgaccatc atacaagctg aacaagcgct ccatacttgc   4740
acgctctcta tatacacagt taaattacat atccatagtc taacctctaa cagttaatct   4800
tctggtaagc ctcccagcca gccttctggt atcgcttggc ctcctcaata ggatctcggt   4860
tctggccgta cagacctcgg ccgacaatta tgatatccgt tccggtagac atgacatcct   4920
```

```
caacagttcg gtactgctgt ccgagagcgt ctcccttgtc gtcaagaccc accccggggg    4980
tcagaataag ccagtcctca gagtcgccct taggtcggtt ctgggcaatg aagccaacca    5040
caaactcggg gtcggatcgg gcaagctcaa tggtctgctt ggagtactcg ccagtggcca    5100
gagagcccct tgcaagacagc tcggccagca tgagcagacc tctggccagc ttctcgttgg    5160
gagaggggac taggaactcc ttgtactggg agttctcgta gtcagagacg tcctccttct    5220
tctgttcaga gacagtttcc tcggcaccag ctcgcaggcc agcaatgatt ccggttccgg    5280
gtacaccgtg ggcgttggtg atatcggacc actcggcgat tcggtgacac cggtactggt    5340
gcttgacagt gttgccaata tctgcgaact ttctgtcctc gaacaggaag aaaccgtgct    5400
taagagcaag ttccttgagg gggagcacag tgccggcgta ggtgaagtcg tcaatgatgt    5460
cgatatgggt tttgatcatg cacacataag gtccgacctt atcggcaagc tcaatgagct    5520
ccttggtggt ggtaacatcc agagaagcac acaggttggt tttcttggct gccacgagct    5580
tgagcactcg agcggcaaag gcggacttgt ggacgttagc tcgagcttcg taggagggca    5640
ttttggtggt gaagaggaga ctgaaataaa tttagtctgc agaactttt atcggaacct    5700 tatctggggc agtgaagtat atgttatggt aatagttacg agttagttga acttatagat    5760
agactggact atacggctat cggtccaaat tagaaagaac gtcaatggct ctctgggcgt    5820
cgcctttgcc gacaaaaatg tgatcatgat gaaagccagc aatgacgttg cagctgatat    5880
tgttgtcggc caaccgcgcc gaaaacgcag ctgtcagacc cacagcctcc aacgaagaat    5940
gtatcgtcaa agtgatccaa gcacactcat agttggagtc gtactccaaa ggcggcaatg    6000
acgagtcaga cagatactcg tcgacgttta acagtgtac gcagatctac tatagaggaa    6060
catttaaatt gccccggaga agacggccag gccgcctaga tgacaaattc aacaactcac    6120
agctgacttt ctgccattgc cactagggg gggccttttt atatggccaa gccagctct     6180 ccacgtcggt tgggctgcac ccaacaataa atgggtaggg ttgcaccaac aaagggatgg    6240 gatgggggt agaagatacg aggataacgg ggctcaatgg cacaaataag aacgaatact    6300
gccattaaga ctcgtgatcc agcgactgac accattgcat catctaaggg cctcaaaact    6360
acctcggaac tgctgcgctg atctggacac cacagaggtt ccgagcactt taggttgcac    6420
caaatgtccc accaggtgca ggcagaaaac gctggaacag cgtgtacagt ttgtcttagc    6480
aaaaagtgaa ggcgctgagg tcgagcaggg tggtgtgact tgttatagcc tttagagctg    6540
cgaaagcgcg tatggatttg gctcatcagg ccagattgag ggtctgtgga cacatgtcat    6600
gttagtgtac ttcaatcgcc ccctggatat agccccgaca ataggccgtg gcctcatttt    6660
tttgccttcc gcacatttcc attgctcgat acccacacct tgcttctcct gcacttgcca    6720
accttaatac tggtttacat tgaccaacat cttacaagcg gggggcttgt ctagggtata    6780
tataaacagt ggctctccca atcggttgcc agtctctttt ttccttctt tccccacaga    6840 ttcgaaatct aaactacaca tcacagaatt ccgagccgtg agtatccacg acaagatcag    6900
tgtcgagacg acgcgttttg tgtaatgaca caatccgaaa gtcgctagca acacacactc    6960
tctacacaaa ctaacccagc tctggtacca gcggccatca caagtttgta caaaaaagct    7020
gaacgagaaa cgtaaaatga tataaatatc aatatattaa attagatttt gcataaaaaa    7080
cagactacat aatactgtaa aacacaacat atccagtcat attggcggcc gcattaggca    7140
ccccaggctt tacactttat gcttccggct cgtataatgt gtggattttg agttaggatc    7200
cgtcgagatt ttcaggagct aaggaagcta aatggagaa aaaatcact ggatatacca     7260 ccgttgatat atcccaatgg catcgtaaag aacattttga ggcatttcag tcagttgctc    7320
```

```
aatgtaccta taaccagacc gttcagctgg atattacggc cttttttaaag accgtaaaga   7380
aaaataagca caagttttat ccggccttta ttcacattct tgcccgcctg atgaatgctc   7440
atccggaatt ccgtatggca atgaaagacg gtgagctggt gatatgggat agtgttcacc   7500
cttgttacac cgttttccat gagcaaactg aaacgttttc atcgctctgg agtgaatacc   7560
acgacgattt ccggcagttt ctacacatat attcgcaaga tgtggcgtgt tacggtgaaa   7620
acctggccta tttccctaaa gggtttattg agaatatgtt tttcgtctca gccaatccct   7680
gggtgagttt caccagtttt gatttaaacg tggccaatat ggacaacttc ttcgccccg    7740
tttcaccat gggcaaatat tatacgcaag gcgacaaggt gctgatgccg ctggcgattc    7800
aggttcatca tgccgtttgt gatggcttcc atgtcggcag aatgcttaat gaattacaac   7860
agtactgcga tgagtggcag ggcggggcgt aaacgcgtgg atccggctta ctaaaagcca   7920
gataacagta tgcgtatttg cgcgctgatt tttgcggtat aagaatatat actgatatgt   7980
atacccgaag tatgtcaaaa agaggtatgc tatgaagcag cgtattacag tgacagttga   8040
cagcgacagc tatcagttgc tcaaggcata tatgatgtca atatctccgg tctggtaagc   8100
acaaccatgc agaatgaagc ccgtcgtctg cgtgccgaac gctggaaagc ggaaaatcag   8160
gaagggatgg ctgaggtcgc ccggtttatt gaaatgaacg gctcttttgc tgacgagaac   8220
aggggctggt gaaatgcagt ttaaggttta cacctataaa agagagagcc gttatcgtct   8280
gtttgtggat gtacagagtg atattattga cacgcccggg cgacggatgg tgatcccect   8340
ggccagtgca cgtctgctgt cagataaagt ctcccgtgaa ctttaccegg tggtgcatat   8400
cggggatgaa agctggcgca tgatgaccac cgatatggcc agtgtgccgg tctccgttat   8460
cggggaagaa gtggctgatc tcagccaccg cgaaaatgac atcaaaaacg ccattaacct   8520
gatgttctgg ggaatataaa tgtcaggctc ccttatacac agccagtctg caggtcgacc   8580
atagtgactg gatatgttgt gttttacagc attatgtagt ctgttttta tgcaaaatct    8640
aatttaatat attgatattt atatcatttt acgtttctcg ttcagctttc ttgtacaaag   8700
tggtgat                                                             8707

<210> SEQ ID NO 24
<211> LENGTH: 8219
<212> TYPE: DNA
<213> ORGANISM: Artificial Sequence
<220> FEATURE:
<223> OTHER INFORMATION: plasmid pY173
<220> FEATURE:
<221> NAME/KEY: misc_feature
<222> LOCATION: (8170)..(8209)
<223> OTHER INFORMATION: n is a, c, g, or t

<400> SEQUENCE: 24
cttgtacaaa gtggtgatgg ccgcaagtgt ggatggggaa gtgagtgccc ggttctgtgt     60
gcacaattgg caatccaaga tggatggatt caacacaggg atatagcgag ctacgtggtg    120
gtgcgaggat atagcaacgg atatttatgt tgacacttga gaatgtacg atacaagcac     180
tgtccaagta caatactaaa catactgtac atactcatac tcgtacccgg caacggtttc    240
acttgagtgc agtggctagt gctcttactc gtacagtgtg caatactgcg tatcatagtc    300
tttgatgtat atcgtattca ttcatgttag ttgcgtacga gccggaagca taaagtgtaa    360
agcctggggt gcctaatgag tgagctaact cacattaatt gcgttgcgct cactgcccgc    420
tttccagtcg ggaaacctgt cgtgccagct gcattaatga atcggccaac gcgcggggag    480
aggcggtttg cgtattgggc gctcttccgc ttcctcgctc actgactcgc tgcgctcggt    540
```

```
cgttcggctg cggcgagcgg tatcagctca ctcaaaggcg gtaatacggt tatccacaga    600 atcagggat  aacgcaggaa agaacatgtg agcaaaaggc cagcaaaagg ccaggaaccg    660
taaaaaggcc gcgttgctgg cgttttttcca taggctccgc cccctgacg agcatcacaa    720 aaatcgacgc tcaagtcaga ggtggcgaaa cccgacagga ctataaagat accaggcgtt    780
tccccctgga agctccctcg tgcgctctcc tgttccgacc ctgccgctta ccggatacct    840
gtccgccttt ctcccttcgg gaagcgtggc gctttctcat agctcacgct gtaggtatct    900
cagttcggtg taggtcgttc gctccaagct gggctgtgtg cacgaacccc ccgttcagcc    960
cgaccgctgc gccttatccg gtaactatcg tcttgagtcc aacccggtaa gacacgactt   1020
atcgccactg gcagcagcca ctggtaacag gattagcaga gcgaggtatg taggcggtgc   1080
tacagagttc ttgaagtggt ggcctaacta cggctacact agaaggacag tatttggtat   1140
ctgcgctctg ctgaagccag ttaccttcgg aaaaagagtt ggtagctctt gatccggcaa   1200
acaaaccacc gctggtagcg gtggttttt  tgtttgcaag cagcagatta cgcgcagaaa   1260
aaaaggatct caagaagatc ctttgatctt ttctacgggg tctgacgctc agtggaacga   1320
aaactcacgt taagggattt tggtcatgag attatcaaaa aggatcttca cctagatcct   1380
tttaaattaa aaatgaagtt ttaaatcaat ctaaagtata tatgagtaaa cttggtctga   1440
cagttaccaa tgcttaatca gtgaggcacc tatctcagcg atctgtctat ttcgttcatc   1500
catagttgcc tgactccccg tcgtgtagat aactacgata cgggagggct taccatctgg   1560
ccccagtgct gcaatgatac cgcgagaccc acgctcaccg gctccagatt tatcagcaat   1620
aaaccagcca gccggaaggg ccgagcgcag aagtggtcct gcaactttat ccgcctccat   1680
ccagtctatt aattgttgcc gggaagctag agtaagtagt tcgccagtta atagtttgcg   1740
caacgttgtt gccattgcta caggcatcgt ggtgtcacgc tcgtcgtttg gtatggcttc   1800
attcagctcc ggttcccaac gatcaaggcg agttacatga tcccccatgt tgtgcaaaaa   1860
agcggttagc tccttcggtc ctccgatcgt tgtcagaagt aagttggccg cagtgttatc   1920
actcatggtt atggcagcac tgcataattc tcttactgtc atgccatccg taagatgctt   1980
ttctgtgact ggtgagtact caaccaagtc attctgagaa tagtgtatgc ggcgaccgag   2040
ttgctcttgc ccggcgtcaa tacgggataa taccgcgcca catagcagaa ctttaaaagt   2100
gctcatcatt ggaaaacgtt cttcggggcg aaaactctca aggatcttac cgctgttgag   2160
atccagttcg atgtaaccca ctcgtgcacc caactgatct tcagcatctt ttactttcac   2220
cagcgtttct gggtgagcaa aaacaggaag gcaaaatgcc gcaaaaaagg gaataagggc   2280
gacacggaaa tgttgaatac tcatactctt cctttttcaa tattattgaa gcatttatca   2340
gggttattgt ctcatgagcg gatacatatt tgaatgtatt tagaaaaata aacaaatagg   2400
ggttccgcgc acatttcccc gaaaagtgcc acctgacgcg ccctgtagcg gcgcattaag   2460
cgcggcgggt gtggtggtta cgcgcagcgt gaccgctaca cttgccagcg ccctagcgcc   2520 cgctccttc  gctttcttcc cttcctttct cgccacgttc gccggctttc cccgtcaagc   2580
tctaaatcgg gggctccctt tagggttccg atttagtgct ttacggcacc tcgaccccaa   2640
aaaacttgat tagggtgatg gttcacgtag tgggccatcg ccctgataga cggtttttcg   2700
ccctttgacg ttggagtcca cgttctttaa tagtggactc ttgttccaaa ctggaacaac   2760
actcaaccct atctcggtct attctttga  tttataaggg attttgccga tttcggccta   2820
ttggttaaaa aatgagctga tttaacaaaa atttaacgcg aattttaaca aaatattaac   2880
gcttacaatt tccattcgcc attcaggctg cgcaactgtt gggaagggcg atcggtgcgg   2940
```

```
gcctcttcgc tattacgcca gctggcgaaa gggggatgtg ctgcaaggcg attaagttgg    3000
gtaacgccag ggttttccca gtcacgacgt tgtaaaacga cggccagtga attgtaatac    3060
gactcactat agggcgaatt gggtaccggg ccccccctcg aggtcgatgg tgtcgataag    3120
cttgatatcg aattcatgtc acacaaaccg atcttcgcct caaggaaacc taattctaca    3180
tccgagagac tgccgagatc cagtctacac tgattaattt tcgggccaat aatttaaaaa    3240
aatcgtgtta tataatatta tatgtattat atatatacat catgatgata ctgacagtca    3300
tgtcccattg ctaaatagac agactccatc tgccgcctcc aactgatgtt ctcaatattt    3360
aaggggtcat ctcgcattgt ttaataataa acagactcca tctaccgcct ccaaatgatg    3420
ttctcaaaat atattgtatg aacttatttt tattacttag tattattaga caacttactt    3480
gctttatgaa aaacacttcc tatttaggaa acaatttata atggcagttc gttcatttaa    3540
caatttatgt agaataaatg ttataaatgc gtatgggaaa tcttaaatat ggatagcata    3600
aatgatatct gcattgccta attcgaaatc aacagcaacg aaaaaaatcc cttgtacaac    3660
ataaatagtc atcgagaaat atcaactatc aaagaacagc tattcacacg ttactattga    3720
gattattatt ggacgagaat cacacactca actgtctttc tctcttctag aaatacaggt    3780
acaagtatgt actattctca ttgttcatac ttctagtcat ttcatcccac atattccttg    3840
gatttctctc caatgaatga cattctatct tgcaaattca acaattataa taagatatac    3900
caaagtagcg gtatagtggc aatcaaaaag cttctctggt gtgcttctcg tatttatttt    3960
tattctaatg atccattaaa ggtatatatt tatttcttgt tatataatcc ttttgtttat    4020
tacatgggct ggatacataa aggtattttg atttaatttt ttgcttaaat tcaatccccc    4080
ctcgttcagt gtcaactgta atggtaggaa attaccatac ttttgaagaa gcaaaaaaaa    4140
tgaaagaaaa aaaaaatcgt atttccaggt tagacgttcc gcagaatcta gaatgcggta    4200
tgcggtacat tgttcttcga acgtaaaagt tgcgctccct gagatattgt acattttgc    4260 ttttacaagt acaagtacat cgtacaacta tgtactactg ttgatgcatc cacaacagtt    4320
tgttttgttt ttttttgttt ttttttttc taatgattca ttaccgctat gtataccctac    4380 ttgtacttgt agtaagccgg gttattggcg ttcaattaat catagactta tgaatctgca    4440
cggtgtgcgc tgcgagttac ttttagctta tgcatgctac ttgggtgtaa tattgggatc    4500
tgttcggaaa tcaacggatg ctcaatcgat ttcgacagta attaattaag tcatacacaa    4560
gtcagctttc ttcgagcctc atataagtat aagtagttca acgtattagc actgtaccca    4620
gcatctccgt atcgagaaac acaacaacat gccccattgg acagatcatg cggatacaca    4680
ggttgtgcag tatcatacat actcgatcag acaggtcgtc tgaccatcat acaagctgaa    4740
caagcgctcc atacttgcac gctctctata tacacagtta aattacatat ccatagtcta    4800
acctctaaca gttaatcttc tggtaagcct cccagccagc cttctggtat cgcttggcct    4860
cctcaatagg atctcggttc tggccgtaca gacctcggcc gacaattatg atatccgttc    4920
cggtagacat gacatcctca acagttcggt actgctgtcc gagagcgtct cccttgtcgt    4980
caagacccac cccgggggtc agaataagcc agtcctcaga gtcgccctta ggtcggttct    5040
gggcaatgaa gccaaccaca aactcggggt cggatcgggc aagctcaatg gtctgcttgg    5100
agtactcgcc agtggccaga gagcccttgc aagacagctc ggccagcatg agcagacctc    5160
tggccagctt ctcgttggga gagggactag gaactccttg tactgggagt tctcgtagt    5220 cagagacgtc ctccttcttc tgttcagaga cagtttcctc ggcaccagct cgcaggccag    5280
caatgattcc ggttccgggt acaccgtggg cgttggtgat atcggaccac tcggcgattc    5340
```

```
ggtgacaccg gtactggtgc ttgacagtgt tgccaatatc tgcgaactttc tgtcctcga    5400
acaggaagaa accgtgctta agagcaagtt ccttgagggg gagcacagtg ccggcgtagg    5460
tgaagtcgtc aatgatgtcg atatgggttt tgatcatgca cacataaggt ccgaccttat    5520
cggcaagctc aatgagctcc ttggtggtgg taacatccag agaagcacac aggttggttt    5580
tcttggctgc cacgagcttg agcactcgag cggcaaggc ggacttgtgg acgttagctc     5640
gagcttcgta ggagggcatt ttggtggtga agaggagact gaaataaatt tagtctgcag    5700
aactttttat cggaacctta tctggggcag tgaagtatat gttatggtaa tagttacgag    5760
ttagttgaac ttatagatag actggactat acggctatcg gtccaaatta gaaagaacgt    5820
caatggctct ctgggcgtcg cctttgccga caaaaatgtg atcatgatga aagccagcaa    5880
tgacgttgca gctgatattg ttgtcggcca accgcgccga aaacgcagct gtcagaccca    5940
cagcctccaa cgaagaatgt atcgtcaaag tgatccaagc acactcatag ttggagtcgt    6000
actccaaagg cggcaatgac gagtcagaca gatactcgtc gacgtttaaa cagtgtacgc    6060
agatctacta tagaggaaca tttaaattgc cccggagaag acggccaggc cgcctagatg    6120
acaaattcaa caactcacag ctgactttct gccattgcca ctagggggg gccttttat     6180
atggccaagc caagctctcc acgtcggttg ggctgcaccc aacaataaat gggtagggtt    6240
gcaccaacaa agggatggga tgggggtag aagatacgag gataacgggg ctcaatggca    6300
caaataagaa cgaatactgc cattaagact cgtgatccag cgactgacac cattgcatca    6360
tctaagggcc tcaaaactac ctcggaactg ctgcgctgat ctggacacca cagaggttcc    6420
gagcactta ggttgcacca aatgtcccac caggtgcagg cagaaaacgc tggaacagcg     6480
tgtacagttt gtcttagcaa aaagtgaagg cgctgaggtc gagcagggtg gtgtgacttg    6540
ttatagcctt tagagctgcg aaagcgcgta tggatttggc tcatcaggcc agattgaggg    6600
tctgtggaca catgtcatgt tagtgtactt caatcgcccc ctggatatag ccccgacaat    6660
aggccgtggc ctcattttt tgccttccgc acatttccat tgctcgatac ccacaccttg    6720
cttctcctgc acttgccaac cttaatactg gtttacattg accaacatct tacaagcggg    6780
gggcttgtct agggtatata taaacagtgg ctctcccaat cggttgccag tctctttttt    6840
cctttctttc cccacagatt cgaaatctaa actacacatc acagaattcc gagccgtgag    6900
tatccacgac aagatcagtg tcgagacgac gcgttttgtg taatgacaca atccgaaagt    6960
cgctagcaac acacactctc tacacaaact aacccagctc tggtaccagc ggccatcaca    7020
agtttgtaca aaaagttgg tttttttcgg tctaaaatgg aagcagccaa agaattggtt     7080
tccatcgtcc aagaggagct ccccaaggtg gactatgccc agctttggca ggatgccagc    7140
agctgtgagg tcctttacct ctcggtggca ttcgtggcga tcaagttcat gctgcgccca    7200
ctggacctga agcgccaggc caccttgaag aagctgttca cagcatacaa cttcctcatg    7260
tcgatctatt cctttggctc cttcctggcc atggcctatg ccctatcagt aactggcatc    7320
ctctccggcg actgtgagac ggcgttcaac aacgatgtgt tcaggatcac aactcagctg    7380
ttctacctca gcaagttcgt agagtacatc gactccttct accttcccct tatgacaag    7440
ccactgtcgt tccttcagtt cttccatcat ttgggggccc ccattgacat gtggctattc    7500
tacaaatacc gcaacgaagg agtctggatc tttgtcctgt tgaatgggtt cattcactgg    7560
atcatgtacg gttactattg gacgcggctc atcaagctga acttccccat gcccaagaac    7620
ctgatcacct ccatgcagat catccagttc aatgtcgggt tctacatcgt ctggaagtac    7680
cgcaatgtgc catgctaccg ccaggatggg atgcgcatgt tgcctggat cttcaactac    7740
```

-continued

```
tggtatgtcg ggacggtctt gctgctgttc ctcaactttt acgtgcagac gtacatccgg      7800
aagccgagga agaaccgagg gaagaaggag taggccacat ggcgcctgcg ctggaggaaa      7860
cggtacgctc ggatggtgca ctgcacttgc actccgccgt ttctagcctc ccctcgctct     7920
aaccactgcg gcatgcctgc ttgaggcgtg acgttgcctc gtatgataca gtttacaccc     7980
ttcccacagc ccacggagct ggtgactgtt ccagcgtct gcagatcatt gatctggtgc      8040
aatgtgcaca gaccaagccc ctctaacgtc ttgcggtgta ccgctcgaca ctcactgcaa     8100
gagacagatg gctgagcatg ttatagcccc ttacattcta cccttcgtcc caacctgacc     8160
gtcacattcn nnnnnnnnnn nnnnnnnnnn nnnnnnnnnn nnnnnnnnna cccaacttt      8219
```

<210> SEQ ID NO 25
<211> LENGTH: 8235
<212> TYPE: DNA
<213> ORGANISM: Artificial Sequence
<220> FEATURE:
<223> OTHER INFORMATION: plasmid pY174
<220> FEATURE:
<221> NAME/KEY: misc_feature
<222> LOCATION: (8186)..(8225)
<223> OTHER INFORMATION: n is a, c, g, or t

<400> SEQUENCE: 25

```
cttgtacaaa gtggtgatgg ccgcaagtgt ggatggggaa gtgagtgccc ggttctgtgt       60
gcacaattgg caatccaaga tggatggatt caacacaggg atatagcgag ctacgtggtg      120
gtgcgaggat atagcaacgg atatttatgt ttgacacttg agaatgtacg atacaagcac      180
tgtccaagta caatactaaa catactgtac atactcatac tcgtacccgg caacggtttc      240
acttgagtgc agtggctagt gctcttactc gtacagtgtg caatactgcg tatcatagtc      300
tttgatgtat atcgtattca ttcatgttag ttgcgtacga gccggaagca taaagtgtaa      360 agcctgggt gcctaatgag tgagctaact cacattaatt gcgttgcgct cactgcccgc       420
tttccagtcg ggaaacctgt cgtgccagct gcattaatga atcggccaac gcgcggggag     480
aggcggtttg cgtattgggc gctcttccgc ttcctcgctc actgactcgc tgcgctcggt      540
cgttcggctg cggcgagcgg tatcagctca ctcaaaggcg gtaatacggt tatccacaga      600
atcaggggat aacgcaggaa agaacatgtg agcaaaaggc cagcaaaagg ccaggaaccg      660
taaaaaggcc gcgttgctgg cgttttttcca taggctccgc cccctgacg agcatcacaa       720 aaatcgacgc tcaagtcaga ggtggcgaaa cccgacagga ctataaagat accaggcgtt      780
tccccctgga agctccctcg tgcgctctcc tgttccgacc ctgccgctta ccggatacct     840
gtccgccttt ctcccttcgg gaagcgtggc gctttctcat agctcacgct gtaggtatct     900
cagttcggtg taggtcgttc gctccaagct gggctgtgtg cacgaacccc ccgttcagcc     960
cgaccgctgc gccttatccg gtaactatcg tcttgagtcc aacccggtaa gacacgactt     1020
atcgccactg gcagcagcca ctggtaacag gattagcaga gcgaggtatg taggcggtgc     1080
tacagagttc ttgaagtggt ggcctaacta cggctacact agaaggacag tatttggtat     1140
ctgcgctctg ctgaagccag ttaccttcgg aaaaagagtt ggtagctctt gatccggcaa     1200
acaaaccacc gctggtagcg gtggtttttt tgtttgcaag cagcagatta cgcgcagaaa     1260
aaaaggatct caagaagatc ctttgatctt ttctacgggg tctgacgctc agtggaacga     1320
aaactcacgt taagggattt tggtcatgag attatcaaaa aggatcttca cctagatcct     1380
tttaaattaa aaatgaagtt ttaaatcaat ctaaagtata tatgagtaaa cttggtctga     1440
cagttaccaa tgcttaatca gtgaggcacc tatctcagcg atctgtctat ttcgttcatc     1500
```

```
catagttgcc tgactcccog tcgtgtagat aactacgata cgggagggct taccatctgg    1560
ccccagtgct gcaatgatac cgcgagaccc acgctcaccg gctccagatt tatcagcaat    1620
aaaccagcca gccggaaggg ccgagcgcag aagtggtcct gcaactttat ccgcctccat    1680
ccagtctatt aattgttgcc gggaagctag agtaagtagt tcgccagtta atagtttgcg    1740
caacgttgtt gccattgcta caggcatcgt ggtgtcacgc tcgtcgtttg gtatggcttc    1800
attcagctcc ggttcccaac gatcaaggcg agttacatga tcccccatgt tgtgcaaaaa    1860
agcggttagc tccttcggtc ctccgatcgt tgtcagaagt aagttggccg cagtgttatc    1920
actcatggtt atggcagcac tgcataattc tcttactgtc atgccatccg taagatgctt    1980
ttctgtgact ggtgagtact caaccaagtc attctgagaa tagtgtatgc ggcgaccgag    2040
ttgctcttgc ccggcgtcaa tacgggataa taccgcgcca catagcagaa ctttaaaagt    2100
gctcatcatt ggaaaacgtt cttcggggcg aaaactctca aggatcttac cgctgttgag    2160
atccagttcg atgtaaccca ctcgtgcacc caactgatct tcagcatctt ttactttcac    2220
cagcgtttct gggtgagcaa aaacaggaag gcaaaatgcc gcaaaaaagg gaataagggc    2280
gacacggaaa tgttgaatac tcatactctt ccttttcaa tattattgaa gcatttatca    2340
gggttattgt ctcatgagcg gatacatatt tgaatgtatt tagaaaaata aacaaatagg    2400
ggttccgcgc acatttcccc gaaaagtgcc acctgacgcg ccctgtagcg gcgcattaag    2460
cgcggcgggt gtggtggtta cgcgcagcgt gaccgctaca cttgccagcg ccctagcgcc    2520
cgctcctttc gctttcttcc cttcctttct cgccacgttc gccggctttc cccgtcaagc    2580
tctaaatcgg gggctccctt tagggttccg atttagtgct ttacggcacc tcgaccccaa    2640
aaaacttgat tagggtgatg gttcacgtag tgggccatcg ccctgataga cggtttttcg    2700
ccctttgacg ttggagtcca cgttctttaa tagtggactc ttgttccaaa ctggaacaac    2760
actcaaccct atctcggtct attcttttga tttataaggg attttgccga tttcggccta    2820
ttggttaaaa aatgagctga tttaacaaaa atttaacgcg aattttaaca aaatattaac    2880
gcttacaatt tccattcgcc attcaggctg cgcaactgtt gggaagggcg atcggtgcgg    2940
gcctcttcgc tattacgcca gctggcgaaa ggggatgtg ctgcaaggcg attaagttgg    3000
gtaacgccag ggttttccca gtcacgacgt tgtaaaacga cggccagtga attgtaatac    3060
gactcactat agggcgaatt gggtaccggg ccccccctcg aggtcgatgg tgtcgataag    3120
cttgatatcg aattcatgtc acacaaaccg atcttcgcct caaggaaacc taattctaca    3180
tccgagagac tgccgagatc cagtctcac tgattaattt tcgggccaat aatttaaaaa    3240
aatcgtgtta tataatatta tatgtattat atatatacat catgatgata ctgacagtca    3300
tgtcccattg ctaaatagac agactccatc tgccgcctcc aactgatgtt ctcaatattt    3360
aaggggtcat ctcgcattgt ttaataataa acagactcca tctaccgcct ccaaatgatg    3420
ttctcaaaat atattgtatg aacttatttt tattacttag tattattaga caacttactt    3480
gctttatgaa aaacacttcc tatttaggaa acaatttata atggcagttc gttcatttaa    3540
caatttatgt agaataaatg ttataaatgc gtatgggaaa tcttaaatat ggatagcata    3600
aatgatatct gcattgccta attcgaaatc aacagcaacg aaaaaaatcc cttgtacaac    3660
ataaatagtc atcgagaaat atcaactatc aagaacagc tattcacacg ttactattga    3720
gattattatt ggacgagaat cacacactca actgtctttc tctcttctag aaatacaggt    3780
acaagtatgt actattctca ttgttcatac ttcagtcat ttcatcccac atattccttg    3840
gatttctctc caatgaatga cattctatct tgcaaattca acaattataa taagatatac    3900
```

```
caaagtagcg gtatagtggc aatcaaaaag cttctctggt gtgcttctcg tatttatttt    3960
tattctaatg atccattaaa ggtatatatt tatttcttgt tatataatcc ttttgtttat    4020
tacatgggct ggatacataa aggtatttg atttaattt ttgcttaaat tcaatcccc      4080 ctcgttcagt gtcaactgta atggtaggaa attaccatac ttttgaagaa gcaaaaaaaa    4140
tgaaagaaaa aaaaaatcgt atttccaggt tagacgttcc gcagaatcta gaatgcggta    4200
tgcggtacat tgttcttcga acgtaaaagt tgcgctccct gagatattgt acattttgc    4260 ttttacaagt acaagtacat cgtacaacta tgtactactg ttgatgcatc cacaacagtt    4320
tgttttgttt ttttttgttt ttttttttc taatgattca ttaccgctat gtatacctac     4380
ttgtacttgt agtaagccgg gttattggcg ttcaattaat catagactta tgaatctgca    4440
cggtgtgcgc tgcagttac ttttagctta tgcatgctac ttgggtgtaa tattgggatc     4500
tgttcggaaa tcaacggatg ctcaatcgat ttcgacagta attaattaag tcatacacaa    4560
gtcagctttc ttcgagcctc atataagtat aagtagttca acgtattagc actgtaccca    4620
gcatctccgt atcgagaaac acaacaacat gccccattgg acagatcatg cggatacaca    4680
ggttgtgcag tatcatacat actcgatcag acaggtcgtc tgaccatcat acaagctgaa    4740
caagcgctcc atacttgcac gctctctata tacacagtta aattacatat ccatagtcta    4800
acctctaaca gttaatcttc tggtaagcct cccagccagc cttctggtat cgcttggcct    4860
cctcaatagg atctcggttc tggccgtaca gacctcggcc gacaattatg atatccgttc    4920
cggtagacat gacatcctca acagttcggt actgctgtcc gagagcgtct cccttgtcgt    4980
caagacccac cccggggtc agaataagcc agtcctcaga gtcgcccta ggtcggttct      5040 gggcaatgaa gccaaccaca aactcggggt cggatcgggc aagctcaatg gtctgcttgg    5100
agtactcgcc agtggccaga gagcccttgc aagacagctc ggccagcatg agcagacctc    5160
tggccagctt ctcgttggga gaggggacta ggaactcctt gtactgggag ttctcgtagt    5220
cagagacgtc ctccttcttc tgttcagaga cagtttcctc ggcaccagct cgcaggccag    5280
caatgattcc ggttccgggt acaccgtggg cgttggtgat atcggaccac tcggcgattc    5340
ggtgacaccg gtactggtgc ttgacagtgt tgccaatatc tgcgaacttt ctgtcctcga    5400
acaggaagaa accgtgctta agagcaagtt ccttgagggg gagcacagtg ccggcgtagg    5460
tgaagtcgtc aatgatgtcg atatgggttt tgatcatgca cacataaggt ccgaccttat    5520
cggcaagctc aatgagctcc ttggtggtgg taacatccag agaagcacac aggttggttt    5580
tcttggctgc cacgagcttg agcactcgag cggcaaaggc ggacttgtgg acgttagctc    5640
gagcttcgta ggagggcatt ttggtggtga agaggagact gaaataaatt tagtctgcag    5700
aactttttat cggaacctta tctggggcag tgaagtatat gttatggtaa tagttacgag    5760
ttagttgaac ttatagatag actggactat acggctatcg gtccaaatta gaaagaacgt    5820
caatggctct ctgggcgtcg cctttgccga caaaaatgtg atcatgatga aagccagcaa    5880
tgacgttgca gctgatattg ttgtcggcca accgcgccga aaacgcagct gtcagaccca    5940
cagcctccaa cgaagaatgt atcgtcaaag tgatccaagc acactcatag ttggagtcgt    6000
actccaaagg cggcaatgac gagtcagaca gatactcgtc gacgtttaaa cagtgtacgc    6060
agatctacta tagaggaaca tttaaattgc cccggagaag acggccaggc cgcctagatg    6120
acaaattcaa caactcacag ctgactttct gccattgcca ctagggggg gccttttat     6180 atggccaagc caagctctcc acgtcggttg ggctgcaccc aacaataaat gggtagggtt    6240
gcaccaacaa agggatggga tgggggtag aagatacgag gataacgggg ctcaatggca    6300
```

```
caaataagaa cgaatactgc cattaagact cgtgatccag cgactgacac cattgcatca    6360
tctaagggcc tcaaaactac ctcggaactg ctgcgctgat ctggacacca cagaggttcc    6420
gagcacttta ggttgcacca aatgtcccac caggtgcagg cagaaaacgc tggaacagcg    6480
tgtacagttt gtcttagcaa aaagtgaagg cgctgaggtc gagcagggtg gtgtgacttg    6540
ttatagcctt tagagctgcg aaagcgcgta tggatttggc tcatcaggcc agattgaggg    6600
tctgtggaca catgtcatgt tagtgtactt caatcgcccc ctggatatag ccccgacaat    6660
aggccgtggc ctcattttt tgccttccgc acatttccat tgctcgatac ccacaccttg     6720
cttctcctgc acttgccaac cttaatactg gtttacattg accaacatct tacaagcggg    6780
gggcttgtct agggtatata taaacagtgg ctctcccaat cggttgccag tctcttttt    6840 cctttctttc cccacagatt cgaaatctaa actacacatc acagaattcc gagccgtgag    6900
tatccacgac aagatcagtg tcgagacgac gcgttttgtg taatgacaca atccgaaagt    6960
cgctagcaac acacactctc tacacaaact aacccagctc tggtaccagc ggccatcaca    7020
agtttgtaca aaaaagttgg atttttttc ggtctaaaat ggaagcagcc aaagaattgg     7080
tttccatcgt ccaagaggag ctccccaagg tggactatgc ccagctttgg caggacgcca    7140
gcagctgtga ggtcctttac ctctcggtgg cattcgtggc gatcaagttc atgctgcgcc    7200
cactggacct gaagcgccag gccaccttga agaagctgtt cacagcatac aacttcctca    7260
tgtcgatcta ttcctttggc tccttcctgg ccatggccta tgccctatca gtaactggca    7320
tcctctccgg cgactgtgag acagcgttca caacgatgt gttcaggatc acaactcagc     7380
tgttctacct cagcaagttc gtagagtaca tcgactcctt ctaccttccc cttatggaca    7440
agccactgtc gttccttcag ttcttccatc atttggggc tcccattgac atgtggctat     7500
tctacaaata ccgcaacgaa ggagtctgga tctttgtcct gttgaatggg ttcattcact    7560
ggatcatgta cggttactac tggacgcggc tcatcaagct gaacttcccc atgcccaaga    7620
acctgatcac ctccatgcag atcatccagt tcaatgtcgg gttctacatc gtctggaagt    7680
accgcaatgt gccatgctac cgccaggatg ggatgcgcat gtttgcctgg atcttcaact    7740
actggtacgt cgggacggtc ttgctgctgt tcctcaactt ttacgtgcag acgtacatcc    7800
ggaagccgag gaagaaccaa gggaagaagg agtaggccac atggcgcctg cgctggagga    7860
aacggtacgc tcggatggtg cactgcactt gcactccgcc gcttctagcc tcccctcgct    7920
ctaacctctg cgacatgcct gcttgaggcg tgacgttgcc tcgtgcgata cagtttacac    7980
ccttcccatg gcccacggag caggtgactg tctccagcgt ctgcaattct gatcattggt    8040
ctggtgcaat gtgcgcagac caagcccctc taacgtcttg cggtgtaccg ctcgacactc    8100
actgcacgag acagatggct gagcatgtta tagcccctga cattctaccc ttcgtcctta    8160
cctgaccgtc acattcatgc ttaccnnnnn nnnnnnnnnn nnnnnnnnnn nnnnnnnnnn    8220
nnnnnaccca acttt                                                    8235

<210> SEQ ID NO 26
<211> LENGTH: 33
<212> TYPE: DNA
<213> ORGANISM: Artificial Sequence
<220> FEATURE:
<223> OTHER INFORMATION: primer oEAd9e11-1

<400> SEQUENCE: 26
agcggccgca ccatggaagc agccaaagaa ttg                                  33

<210> SEQ ID NO 27
```

```
<211> LENGTH: 26
<212> TYPE: DNA
<213> ORGANISM: Artificial Sequence
<220> FEATURE:
<223> OTHER INFORMATION: oEAd9el1-2

<400> SEQUENCE: 27
tgcggccgct actccttctt ccctcg                                          26

<210> SEQ ID NO 28
<211> LENGTH: 4310
<212> TYPE: DNA
<213> ORGANISM: Artificial Sequence
<220> FEATURE:
<223> OTHER INFORMATION: plasmid pKR1137

<400> SEQUENCE: 28
aattccagca cactggcggc cgttactagt ggatccgagc tcggtaccaa gcttgatgca      60
tagcttgagt attctaacgc gtcacctaaa tagcttggcg taatcatggt catagctgtt     120
tcctgtgtga aattgttatc cgctcacaat tccacacaac atacgagccg aagcataaa     180 gtgtaaagcc tggggtgcct aatgagtgag ctaactcaca ttaattgcgt tgcgctcact     240
gcccgctttc cagtcgggaa acctgtcgtg ccagctgcat taatgaatcg gccaacgcgc     300
ggggagaggc ggtttgcgta ttgggcgctc ttccgcttcc tcgctcactg actcgctgcg     360
ctcggtcgtt cggctgcggc gagcggtatc agctcactca aaggcggtaa tacggttatc     420
cacagaatca ggggataacg caggaaagaa catgtgagca aaaggccagc aaaagcccag     480
gaaccgtaaa aaggccgcgt tgctggcgtt tttccatagg ctccgccccc ctgacgagca     540
tcacaaaaat cgacgctcaa gtcagaggtg gcgaaacccg acaggactat aaagatacca     600
ggcgtttccc cctggaagct ccctcgtgcg ctctcctgtt ccgaccctgc cgcttaccgg     660
atacctgtcc gcctttctcc cttcgggaag cgtggcgctt tctcatagct cacgctgtag     720
gtatctcagt tcggtgtagg tcgttcgctc caagctgggc tgtgtgcacg aaccccccgt     780
tcagcccgac cgctgcgcct tatccggtaa ctatcgtctt gagtccaacc cggtaagaca     840
cgacttatcg ccactggcag cagccactgg taacaggatt agcagagcga ggtatgtagg     900
cggtgctaca gagttcttga agtggtggcc taactacggc tacactagaa ggacagtatt     960
tggtatctgc gctctgctga agccagttac cttcggaaaa agagttggta gctcttgatc    1020
cggcaaacaa accaccgctg gtagcggtgg tttttttgtt tgcaagcagc agattacgcg    1080
cagaaaaaaa ggatctcaag aagatccttt gatcttttct acggggtctg acgctcagtg    1140
gaacgaaaac tcacgttaag ggattttggt catgagatta tcaaaaagga tcttcaccta    1200
gatcctttta aattaaaaat gaagttttag cacgtgtcag tcctgctcct cggccacgaa    1260
gtgcacgcag ttgccggccg ggtcgcgcag ggcgaactcc cgcccccacg gctgctcgcc    1320
gatctcggtc atggccggcc cggaggcgtc ccggaagttc gtggacacga cctccgacca    1380
ctcggcgtac agctcgtcca ggccgcgcac ccacacccag gccagggtgt tgtccggcac    1440
cacctggtcc tggaccgcgc tgatgaacag ggtcacgtcg tcccgaccca caccggcgaa    1500
gtcgtcctcc acgaagtccc gggagaaccc gagccggtcg gtccagaact cgaccgctcc    1560
ggcgacgtcg cgcgcggtga gcaccggaac ggcactggtc aacttggcca tggtggccct    1620
cctcacgtgc tattattgaa gcatttatca gggttattgt ctcatgagcg gatacatatt    1680
tgaatgtatt tagaaaaata aacaaatagg ggttccgcgc acatttcccc gaaaagtgcc    1740
acctgtatgc ggtgtgaaat accgcacaga tgcgtaagga gaaaataccg catcaggaaa    1800
```

```
ttgtaagcgt taataattca gaagaactcg tcaagaaggc gatagaaggc gatgcgctgc    1860
gaatcgggag cggcgatacc gtaaagcacg aggaagcggt cagcccattc gccgccaagc    1920
tcttcagcaa tatcacgggt agccaacgct atgtcctgat agcggtccgc cacacccagc    1980
cggccacagt cgatgaatcc agaaaagcgg ccattttcca ccatgatatt cggcaagcag    2040
gcatcgccat gggtcacgac gagatcctcg ccgtcgggca tgctcgcctt gagcctggcg    2100
aacagttcgg ctgcgcgag cccctgatgc tcttcgtcca gatcatcctg atcgacaaga    2160
ccggcttcca tccgagtacg tgctcgctcg atgcgatgtt tcgcttggtg gtcgaatggg    2220
caggtagccg gatcaagcgt atgcagccgc cgcattgcat cagccatgat ggatactttc    2280
tcggcaggag caaggtgaga tgacaggaga tcctgccccg gcacttcgcc caatagcagc    2340
cagtcccttc ccgcttcagt gacaacgtcg agcacagctg cgcaaggaac gcccgtcgtg    2400
gccagccacg atagccgcgc tgcctcgtct tgcagttcat tcagggcacc ggacaggtcg    2460
gtcttgacaa aaagaaccgg cgccccctgc gctgacagcc ggaacacggc ggcatcagag    2520
cagccgattg tctgttgtgc ccagtcatag ccgaatagcc tctccaccca gcggccgga    2580 gaacctgcgt gcaatccatc ttgttcaatc atgcgaaacg atcctcatcc tgtctcttga    2640
tcagagcttg atcccctgcg ccatcagatc cttggcggcg agaaagccat ccagtttact    2700
ttgcagggct tcccaacctt accagagggc gccccagctg gcaattccgg ttcgcttgct    2760
gtccataaaa ccgcccagtc tagctatcgc catgtaagcc cactgcaagc tacctgcttt    2820
ctctttgcgc ttgcgttttc ccttgtccag atagcccagt agctgacatt catccggggt    2880
cagcaccgtt tctgcggact ggcttttctac gtgaaaagga tctaggtgaa gatccttttt    2940
gataatctca tgcctgacat ttatattccc cagaacatca ggttaatggc gttttttgatg    3000 tcattttcgc ggtggctgag atcagccact tcttccccga taacggagac cggcacactg    3060
gccatatcgg tggtcatcat gcgccagctt tcatccccga tatgcaccac cgggtaaagt    3120
tcacgggaga ctttatctga cagcagacgt gcactggcca gggggatcac catccgtcgc    3180
cccggcgtgt caataatatc actctgtaca tccacaaaca gacgataacg gctctctctt    3240
ttataggtgt aaaaccttaaa ctgccgtacg tataggctgc gcaactgttg ggaagggcga    3300
tcggtgcggg cctcttcgct attacgccag ctggcgaaag ggggatgtgc tgcaaggcga    3360
ttaagttggg taacgccagg gttttcccag tcacgacgtt gtaaaacgac ggccagtgaa    3420
ttgtaatacg actcactata gggcgaattg ggccctctag atgcatgctc gagcggccgc    3480
cagtgtgatg gatatctgca gaattcagga gcggccgcac catggaagca gccaaagaat    3540
tggtttccat cgtccaagag gagctcccca aggtggacta tgcccagctt tggcaggatg    3600
ccagcagctg tgaggtcctt tacctctcgg tggcattcgt ggcgatcaag ttcatgctgc    3660
gcccactgga cctgaagcgc caggccacct tgaagaagct gttcacagca tacaacttcc    3720
tcatgtcgat ctattccttt ggctccttcc tggccatggc ctatgcccta tcagtaactg    3780
gcatcctctc cggcgactgt gagacggcgt tcaacaacga tgtgttcagg atcacaactc    3840
agctgttcta cctcagcaag ttcgtagagt acatcgactc cttctaccct cccctttatgg    3900 acaagccact gtcgttcctt cagttcttcc atcatttggg ggcccccatt gacatgtggc    3960
tattctacaa ataccgcaac gaaggagtct ggatctttgt cctgttgaat gggttcattc    4020
actggatcat gtacggttac tattggacgc ggctcatcaa gctgaacttc cccatgccca    4080
agaacctgat cacctccatg cagatcatcc agttcaatgt cgggttctac atcgtctgga    4140
agtaccgcaa tgtgccatgc taccgccagg atgggatgcg catgtttgcc tggatcttca    4200
```

| | | |
|---|---|---|
| actactggta tgtcgggacg gtcttgctgc tgttcctcaa cttttacgtg cagacgtaca | 4260 |
| tccggaagcc gaggaagaac cgagggaaga aggagtagcg gccgcacctg | 4310 |

<210> SEQ ID NO 29
<211> LENGTH: 7085
<212> TYPE: DNA
<213> ORGANISM: Artificial Sequence
<220> FEATURE:
<223> OTHER INFORMATION: plasmid pKR72

<400> SEQUENCE: 29

| | |
|---|---|
| gtacggatcc gtcgacggcg cgcccgatca tccggatata gttcctcctt tcagcaaaaa | 60 |
| acccctcaag acccgtttag aggccccaag gggttatgct agttattgct cagcggtggc | 120 |
| agcagccaac tcagcttcct ttcgggcttt gttagcagcc ggatcgatcc aagctgtacc | 180 |
| tcactattcc tttgccctcg gacgagtgct ggggcgtcgg tttccactat cggcgagtac | 240 |
| ttctacacag ccatcggtcc agacggccgc gcttctgcgg gcgatttgtg tacgcccgac | 300 |
| agtcccggct ccggatcgga cgattgcgtc gcatcgaccc tgcgcccaag ctgcatcatc | 360 |
| gaaattgccg tcaaccaagc tctgatagag ttggtcaaga ccaatgcgga gcatatacgc | 420 |
| ccggagccgc ggcgatcctg caagctccgg atgcctccgc tcgaagtagc gcgtctgctg | 480 |
| ctccatacaa gccaaccacg gcctccagaa gaagatgttg gcgacctcgt attgggaatc | 540 |
| cccgaacatc gcctcgctcc agtcaatgac cgctgttatg cggccattgt ccgtcaggac | 600 |
| attgttggag ccgaaatccg cgtgcacgag gtgccggact tcgggcagt cctcggccca | 660 |
| aagcatcagc tcatcgagag cctgcgcgac ggacgcactg acggtgtcgt ccatcacagt | 720 |
| ttgccagtga tacacatggg gatcagcaat cgcgcatatg aaatcacgcc atgtagtgta | 780 |
| ttgaccgatt ccttgcggtc cgaatgggcc gaacccgctc gtctggctaa gatcggccgc | 840 |
| agcgatcgca tccatagcct ccgcgaccgg ctgcagaaca gcgggcagtt cggtttcagg | 900 |
| caggtcttgc aacgtgacac cctgtgcacg gcgggagatg caataggtca ggctctcgct | 960 |
| gaattcccca atgtcaagca cttccggaat cgggagcgcg gccgatgcaa agtgccgata | 1020 |
| aacataacga tctttgtaga aaccatcggc gcagctattt acccgcagga catatccacg | 1080 |
| ccctcctaca tcgaagctga aagcacgaga ttcttcgccc tccgagagct gcatcaggtc | 1140 |
| ggagacgctg tcgaactttt cgatcagaaa cttctcgaca gacgtcgcgg tgagttcagg | 1200 |
| cttttccatg gtatatctc cttcttaaag ttaaacaaaa ttatttctag agggaaaccg | 1260 |
| ttgtggtctc cctatagtga gtcgtattaa tttcgcggga tcgagatcga tccaattcca | 1320 |
| atcccacaaa aatctgagct aacagcaca gttgctcctc tcagagcaga atcgggtatt | 1380 |
| caacaccctc atatcaacta ctacgttgtg tataacggtc cacatgccgg tatatacgat | 1440 |
| gactggggtt gtacaaaggc ggcaacaaac ggcgttcccg gagttgcaca agaaatttt | 1500 |
| gccactatta cagaggcaag agcagcagct gacgcgtaca caacaagtca gcaaacagac | 1560 |
| aggttgaact tcatccccaa aggagaagct caactcaagc ccaagagctt tgctaaggcc | 1620 |
| ctaacaagcc caccaaagca aaagcccac tggctcacgc taggaaccaa aaggcccagc | 1680 |
| agtgatccag ccccaaaaga gatctccttt gccccggaga ttacaatgga cgatttcctc | 1740 |
| tatctttacg atctaggaag gaagttcgaa ggtgaaggtg acgacactat gttcaccact | 1800 |
| gataatgaga aggttagcct cttcaatttc agaaagaatg ctgacccaca gatggttaga | 1860 |
| gaggcctacg cagcaggtct catcaagacg atctacccga gtaacaatct ccaggagatc | 1920 |
| aaataccttc ccaagaaggt taagatgca gtcaaaagat tcaggactaa ttgcatcaag | 1980 |

```
aacacagaga aagacatatt tctcaagatc agaagtacta ttccagtatg gacgattcaa    2040
ggcttgcttc ataaaccaag gcaagtaata gagattggag tctctaaaaa ggtagttcct    2100
actgaatcta aggccatgca tggagtctaa gattcaaatc gaggatctaa cagaactcgc    2160
cgtgaagact ggcgaacagt tcatacagag tcttttacga ctcaatgaca agaagaaaat    2220
cttcgtcaac atggtggagc acgacactct ggtctactcc aaaaatgtca agatacagt     2280 ctcagaagac caaagggcta ttgagacttt tcaacaaagg ataatttcgg gaaacctcct    2340
cggattccat tgcccagcta tctgtcactt catcgaaagg acagtagaaa aggaaggtgg    2400
ctcctacaaa tgccatcatt gcgataaagg aaaggctatc attcaagatg cctctgccga    2460
cagtggtccc aaagatggac ccccacccac gaggagcatc gtggaaaaag aagacgttcc    2520
aaccacgtct tcaaagcaag tggattgatg tgacatctcc actgacgtaa gggatgacgc    2580
acaatcccac tatccttcgc aagacccttc ctctatataa ggaagttcat ttcatttgga    2640
gaggacacgc tcgagctcat ttctctatta cttcagccat aacaaaagaa ctcttttctc    2700
ttcttattaa accatgaaaa agcctgaact caccgcgacg tctgtcgaga gtttctgat    2760 cgaaaagttc gacagcgtct ccgacctgat gcagctctcg gagggcgaag aatctcgtgc    2820
tttcagcttc gatgtaggag ggcgtggata tgtcctgcgg gtaaatagct gcgccgatgg    2880
tttctacaaa gatcgttatg tttatcggca cttttgcatcg gccgcgctcc cgattccgga    2940
agtgcttgac attggggaat tcagcgagag cctgacctat tgcatctccc gccgtgcaca    3000
gggtgtcacg ttgcaagacc tgcctgaaac cgaactgccc gctgttctgc agccggtcgc    3060
ggaggccatg gatgcgatcg ctgcggccga tcttagccag acgagcgggt tcggcccatt    3120
cggaccgcaa ggaatcggtc aatacactac atggcgtgat ttcatatgcg cgattgctga    3180
tccccatgtg tatcactggc aaactgtgat ggacgacacc gtcagtgcgt ccgtcgcgca    3240
ggctctcgat gagctgatgc tttgggccga ggactgcccc gaagtccggc acctcgtgca    3300
cgcggatttc ggctccaaca atgtcctgac ggacaatggc cgcataacag cggtcattga    3360
ctggagcgag gcgatgttcg gggattccca atacgaggtc gccaacatct tcttctggag    3420
gccgtggttg gcttgtatgg agcagcagac gcgctacttc gagcggaggc atccggagct    3480
tgcaggatcg ccgcggctcc gggcgtatat gctccgcatt ggtcttgacc aactctatca    3540
gagcttggtt gacggcaatt tcgatgatgc agcttgggcg cagggtcgat gcgacgcaat    3600
cgtccgatcc ggagccggga ctgtcgggcg tacacaaatc gcccgcagaa gcgcggccgt    3660
ctggaccgat ggctgtgtag aagtactcgc cgatagtgga aaccgacgcc ccagcactcg    3720
tccgagggca aaggaatagt gaggtaccta agaaggagt gcgtcgaagc agatcgttca    3780
aacatttggc aataaagttt cttaagattg aatcctgttg ccggtcttgc gatgattatc    3840
atataatttc tgttgaatta cgttaagcat gtaataatta acatgtaatg catgacgtta    3900
tttatgagat gggttttat gattagagtc ccgcaattat acatttaata cgcgatagaa    3960
aacaaaatat agcgcgcaaa ctaggataaa ttatcgcgcg cggtgtcatc tatgttacta    4020
gatcgatgtc gaatcgatca acctgcatta atgaatcggc caacgcgcgg ggagaggcgg    4080
tttgcgtatt gggcgctctt ccgcttcctc gctcactgac tcgctgcgct cggtcgttcg    4140
gctgcggcga gcggtatcag ctcactcaaa ggcggtaata cggttatcca cagaatcagg    4200
ggataacgca ggaaagaaca tgtgagcaaa aggccagcaa aaggccagga accgtaaaaa    4260
ggccgcgttg ctggcgtttt tccataggct ccgcccccct gacgagcatc acaaaaatcg    4320
acgctcaagt cagaggtggc gaaacccgac aggactataa agataccagg cgtttccccc    4380
```

| | |
|---|---|
| tggaagctcc ctcgtgcgct ctcctgttcc gaccctgccg cttaccggat acctgtccgc | 4440 |
| ctttctccct tcgggaagcg tggcgctttc tcaatgctca cgctgtaggt atctcagttc | 4500 |
| ggtgtaggtc gttcgctcca agctgggctg tgtgcacgaa ccccccgttc agcccgaccg | 4560 |
| ctgcgcctta tccggtaact atcgtcttga gtccaacccg gtaagacacg acttatcgcc | 4620 |
| actggcagca gccactggta acaggattag cagagcgagg tatgtaggcg gtgctacaga | 4680 |
| gttcttgaag tggtggccta actacggcta cactagaagg acagtatttg gtatctgcgc | 4740 |
| tctgctgaag ccagttacct tcggaaaaag agttggtagc tcttgatccg gcaaacaaac | 4800 |
| caccgctggt agcggtggtt ttttgtttg caagcagcag attacgcgca gaaaaaaagg | 4860 |
| atctcaagaa gatcctttga tcttttctac ggggtctgac gctcagtgga acgaaaactc | 4920 |
| acgttaaggg attttggtca tgacattaac ctataaaaat aggcgtatca cgaggccctt | 4980 |
| tcgtctcgcg cgtttcggtg atgacggtga aaacctctga cacatgcagc tcccggagac | 5040 |
| ggtcacagct tgtctgtaag cggatgccgg gagcagacaa gcccgtcagg gcgcgtcagc | 5100 |
| gggtgttggc gggtgtcggg gctggcttaa ctatgcggca tcagagcaga ttgtactgag | 5160 |
| agtgcaccat atggacatat tgtcgttaga acgcggctac aattaataca taaccttatg | 5220 |
| tatcatacac atacgattta ggtgacacta tagaacggcg cgccaagctt gttgaaacat | 5280 |
| ccctgaagtg tctcatttta ttttatttat tctttgctga taaaaaaata aaataaaaga | 5340 |
| agctaagcac acggtcaacc attgctctac tgctaaaagg gttatgtgta gtgttttact | 5400 |
| gcataaatta tgcagcaaac aagacaactc aaattaaaaa atttcctttg cttgtttttt | 5460 |
| tgttgtctct gacttgactt tcttgtggaa gttggttgta taaggattgg gacaccattg | 5520 |
| tccttcttaa tttaatttta ttctttgctg ataaaaaaaa aaatttcata tagtgttaaa | 5580 |
| taataatttg ttaaataacc aaaaagtcaa atatgtttac tctcgtttaa ataattgaga | 5640 |
| ttcgtccagc aaggctaaac gattgtatag atttatgaca atatttactt ttttatagat | 5700 |
| aaatgttata ttataataaa tttatataca tatattatat gttatttatt attattttaa | 5760 |
| atccttcaat atttatcaa accaactcat aatttttttt ttatctgtaa gaagcaataa | 5820 |
| aattaaatag acccacttta aggatgatcc aacctttata cagagtaaga gagttcaaat | 5880 |
| agtacccttt catatacata tcaactaaaa tattagaaat atcatggatc aaaccttata | 5940 |
| aagacattaa ataagtggat aagtataata tataaatggg tagtatataa tatataaatg | 6000 |
| gatacaaact tctctctttta taattgttat gtctccttaa catcctaata taatacataa | 6060 |
| gtgggtaata tataatatat aaatggagac aaacttcttc cattataatt gttatgtctt | 6120 |
| cttaacactt atgtctcgtt cacaatgcta aggttagaat tgtttagaaa gtcttatagt | 6180 |
| acacatttgt ttttgtacta tttgaagcat tccataagcc gtcacgattc agatgattta | 6240 |
| taataataag aggaaattta tcatagaaca ataaggtgca tagatagagt gttaatatat | 6300 |
| cataacatcc tttgtttatt catagaagaa gtgagatgga gctcagttat tatactgtta | 6360 |
| catggtcgga tacaatattc catgctctcc atgagctctt acacctacat gcatttttagt | 6420 |
| tcatacttgc ggccgcagta tatcttaaat tctttaatac ggtgtactag gatattgaac | 6480 |
| tggttcttga tgatgaaaac ctgggccgag attgcagcta tttatagtca taggtcttgt | 6540 |
| taacatgcat ggacatttgg ccacggggtg gcatgcagtt tgacgggtgt tgaaataaac | 6600 |
| aaaaatgagg tggcggaaga gaatacgagt ttgaggttgg gttagaaaca acaaatgtga | 6660 |
| gggctcatga tgggttgagt tggtgaatgt tttgggctgc tcgattgaca cctttgtgag | 6720 |
| tacgtgttgt tgtgcatggc ttttgggggtc cagttttttt ttcttgacgc ggcgatcctg | 6780 |

-continued

```
atcagctagt ggataagtga tgtccactgt gtgtgattgc gttttttgttt gaattttatg    6840 aacttagaca ttgctatgca aaggatactc tcattgtgtt ttgtcttctt ttgttccttg    6900 gcttttttctt atgatccaag agactagtca gtgttgtggc attcgagact accaagatta    6960
attatgatgg gggaaggata agtaactgat tagtacggac tgttaccaaa ttaattaata    7020
agcggcaaat gaagggcatg gatcaaaagc ttggatctcc tgcaggatct ggccggccgg    7080
atctc                                                                7085
```

<210> SEQ ID NO 30
<211> LENGTH: 7872
<212> TYPE: DNA
<213> ORGANISM: Artificial Sequence
<220> FEATURE:
<223> OTHER INFORMATION: plasmid pKR1140

<400> SEQUENCE: 30

```
ggccgcaagt atgaactaaa atgcatgtag gtgtaagagc tcatggagag catggaatat     60
tgtatccgac catgtaacag tataataact gagctccatc tcacttcttc tatgaataaa    120
caaaggatgt tatgatatat taacactcta tctatgcacc ttattgttct atgataaatt    180
tcctcttatt attataaatc atctgaatcg tgacggctta tggaatgctt caaatagtac    240
aaaaacaaat gtgtactata agactttcta aacaattcta accttagcat tgtgaacgag    300
acataagtgt taagaagaca taacaattat aatggaagaa gtttgtctcc atttatatat    360
tatatattac ccacttatgt attatattag gatgttaagg agacataaca attataaaga    420
gagaagtttg tatccattta tatattatat actacccatt tatatattat acttatccac    480
ttatttaatg tctttataag gtttgatcca tgatatttct aatattttag ttgatatgta    540
tatgaaaggg tactatttga actctcttac tctgtataaa ggttggatca tccttaaagt    600
gggtctattt aattttattg cttcttacag ataaaaaaaa aattatgagt tggtttgata    660
aaatattgaa ggatttaaaa taataataaa taacatataa tatatgtata taaatttatt    720
ataatataac atttatctat aaaaaagtaa atattgtcat aaatctatac aatcgtttag    780
ccttgctgga cgaatctcaa ttatttaaac gagagtaaac atatttgact ttttggttat    840
ttaacaaatt attatttaac actatatgaa attttttttt ttatcagcaa agaataaaat    900
taaattaaga aggacaatgg tgtcccaatc cttatacaac caacttccac aagaaagtca    960
agtcagagac aacaaaaaaa caagcaaagg aaatttttta atttgagttg tcttgtttgc   1020
tgcataattt atgcagtaaa acactacaca taacccttt  agcagtagag caatggttga   1080
ccgtgtgctt agcttctttt atttttatttt tttatcagca aagaataaat aaaataaaat   1140
gagacacttc agggatgttt caacaagctt ggcgcgccgt tctatagtgt cacctaaatc   1200
gtatgtgtat gatacataag gttatgtatt aattgtagcc gcgttctaac gacaatatgt   1260
ccatatggtg cactctcagt acaatctgct ctgatgccgc atagttaagc cagccccgac   1320
acccgccaac acccgctgac gcgccctgac gggcttgtct gctcccggca tccgcttaca   1380
gacaagctgt gaccgtctcc gggagctgca tgtgtcagag gttttcaccg tcatcaccga   1440
aacgcgcgag acgaaagggc ctcgtgatac gcctattttt ataggttaat gtcatgacca   1500
aaatccctta acgtgagttt tcgttccact gagcgtcaga ccccgtagaa aagatcaaag   1560
gatcttcttg agatcctttt tttctgcgcg taatctgctg cttgcaaaca aaaaaaccac   1620
cgctaccagc ggtggtttgt ttgccggatc aagagctacc aactcttttt ccgaaggtaa   1680
ctggcttcag cagagcgcag ataccaaata ctgtccttct agtgtagccg tagttaggcc   1740
```

```
accacttcaa gaactctgta gcaccgccta catacctcgc tctgctaatc ctgttaccag    1800
tggctgctgc cagtggcgat aagtcgtgtc ttaccgggtt ggactcaaga cgatagttac    1860
cggataaggc gcagcggtcg ggctgaacgg ggggttcgtg cacacagccc agcttggagc    1920
gaacgaccta caccgaactg agatacctac agcgtgagca ttgagaaagc gccacgcttc    1980
ccgaagggag aaaggcggac aggtatccgg taagcggcag ggtcggaaca ggagagcgca    2040
cgagggagct tccaggggga aacgcctggt atctttatag tcctgtcggg tttcgccacc    2100
tctgacttga gcgtcgattt tgtgatgct cgtcagggggg gcggagccta tggaaaaacg    2160
ccagcaacgc ggccttttta cggttcctgg ccttttgctg ccttttgct cacatgttct    2220 ttcctgcgtt atccctgat tctgtggata accgtattac cgccttttgag tgagctgata    2280 ccgctcgccg cagccgaacg accgagcgca gcgagtcagt gagcgaggaa gcggaagagc    2340
gcccaatacg caaaccgcct ctccccgcgc gttggccgat tcattaatgc aggttgatcg    2400
attcgacatc gatctagtaa catagatgac accgcgcgcg ataatttatc ctagtttgcg    2460
cgctatattt tgttttctat cgcgtattaa atgtataatt gcgggactct aatcataaaa    2520
acccatctca taaataacgt catgcattac atgttaatta ttacatgctt aacgtaattc    2580
aacagaaatt atatgataat catcgcaaga ccggcaacag gattcaatct aagaaacttt    2640
tattgccaaa tgtttgaacg atctgcttcg acgcactcct tctttaggta cctcactatt    2700
cctttgccct cggacgagtg ctggggcgtc ggtttccact atcggcgagt acttctacac    2760
agccatcggt ccagacggcc gcgcttctgc gggcgatttg tgtacgcccg acagtcccgg    2820
ctccggatcg gacgattgcg tcgcatcgac cctgcgccca agctgcatca tcgaaattgc    2880
cgtcaaccaa gctctgatag agttggtcaa gaccaatgcg gagcatatac gcccggagcc    2940
gcggcgatcc tgcaagctcc ggatgcctcc gctcgaagta gcgcgtctgc tgctccatac    3000
aagccaacca cggcctccag aagaagatgt tggcgacctc gtattgggaa tccccgaaca    3060
tcgcctcgct ccagtcaatg accgctgtta tgcggccatt gtccgtcagg acattgttgg    3120
agccgaaatc cgcgtgcacg aggtgccgga cttcggggca gtcctcggcc caaagcatca    3180
gctcatcgag agcctgcgcg acggacgcac tgacggtgtc gtccatcaca gtttgccagt    3240
gatacacatg gggatcagca atcgcgcata tgaaatcacg ccatgtagtg tattgaccga    3300
ttccttgcgg tccgaatggg ccgaacccgc tcgtctggct aagatcggcc gcagcgatcg    3360
catccatggc ctccgcgacc ggctgcagaa cagcgggcag ttcggtttca ggcaggtctt    3420
gcaacgtgac accctgtgca cggcgggaga tgcaataggt caggctctcg ctgaattccc    3480
caatgtcaag cacttccgga atcgggagcg cggccgatgc aaagtgccga taaacataac    3540 gatcttgta gaaaccatcg gcgcagctat ttacccgcag gacatatcca cgccctccta    3600
catcgaagct gaaagcacga gattcttcgc cctccgagag ctgcatcagg tcggagacgc    3660
tgtcgaactt ttcgatcaga aacttctcga cagacgtcgc ggtgagttca gcttttttca    3720
tggtttaata agaagagaaa agagttcttt tgttatggct gaagtaatag agaaatgagc    3780
tcgagcgtgt cctctccaaa tgaaatgaac ttccttatat agaggaaggg tcttgcgaag    3840
gatagtggga ttgtgcgtca tcccttacgt cagtggagat gtcacatcaa tccacttgct    3900
ttgaagacgg ggttggaacg tcttcttttt ccacgatgct cctcgtgggt gggggtccat    3960
ctttgggacc actgtcggca gaggcatctt gaatgatagc ctttcctttta tcgcaatgat    4020 ggcatttgta ggagccacct tccttttcta ctgtccttttc gatgaagtga cagatagctg    4080
ggcaatggaa tccgaggagg tttcccgaaa ttatcctttg ttgaaaagtc tcaatagccc    4140
```

```
tttggtcttc tgagactgta tctttgacat ttttggagta gaccagagtg tcgtgctcca    4200
ccatgttgac gaagattttc ttcttgtcat tgagtcgtaa aagactctgt atgaactgtt    4260
cgccagtctt cacggcgagt tctgttagat cctcgatttg aatcttagac tccatgcatg    4320
gccttagatt cagtaggaac tacctttta gagactccaa tctctattac ttgccttggt     4380
ttatgaagca agccttgaat cgtccatact ggaatagtac ttctgatctt gagaaatatg    4440
tctttctctg tgttcttgat gcaattagtc ctgaatcttt tgactgcatc tttaaccttc    4500
ttgggaaggt atttgatctc ctggagattg ttactcgggt agatcgtctt gatgagacct    4560
gctgcgtagg cctctctaac catctgtggg tcagcattct ttctgaaatt gaagaggcta    4620
accttctcat tatcagtggt gaacatagtg tcgtcacctt caccttcgaa cttccttcct    4680
agatcgtaaa gatagaggaa atcgtccatt gtaatctccg gggcaaagga gatctctttt    4740
ggggctggat cactgctggg cctttggtt cctagcgtga gccagtgggc ttttgctttt     4800
ggtgggcttg ttagggcctt agcaaagctc tgggcttga gttgagcttc tcctttgggg     4860
atgaagttca acctgtctgt ttgctgactt gttgtgtacg cgtcagctgc tgctcttgcc    4920
tctgtaatag tggcaaattt cttgtgtgca actccgggaa cgccgtttgt tgccgccttt    4980
gtacaacccc agtcatcgta tataccggca tgtggaccgt tatacacaac gtagtagttg    5040
atatgagggt gttgaatacc cgattctgct ctgagaggag caactgtgct gttaagctca    5100
gattttgtg ggattggaat tggatcgatc tcgatcccgc gaaattaata cgactcacta     5160
tagggagacc acaacggttt ccctctagaa ataattttgt ttaactttaa gaaggagata    5220
tacccatgga aaagcctgaa ctcaccgcga cgtctgtcga agtttctg atcgaaaagt      5280
tcgacagcgt ctccgacctg atgcagctct cggagggcga agaatctcgt gctttcagct    5340
tcgatgtagg agggcgtgga tatgtcctgc gggtaaatag ctgcgccgat ggtttctaca    5400
aagatcgtta tgtttatcgg cacttttgcat cggccgcgct cccgattccg gaagtgcttg    5460
acattgggga attcagcgag agcctgacct attgcatctc ccgccgtgca cagggtgtca    5520
cgttgcaaga cctgcctgaa accgaactgc ccgctgttct gcagccggtc gcggaggcta    5580
tggatgcgat cgctgcggcc gatcttagcc agacgagcgg gttcggccca ttcggaccgc    5640
aaggaatcgg tcaatacact acatggcgtg atttcatatg cgcgattgct gatccccatg    5700
tgtatcactg gcaaactgtg atggacgaca ccgtcagtgc gtccgtcgcg caggctctcg    5760
atgagctgat gctttgggcc gaggactgcc ccgaagtccg gcacctcgtg cacgcggatt    5820
tcggctccaa caatgtcctg acggacaatg gccgcataac agcggtcatt gactggagcg    5880
aggcgatgtt cggggattcc caatacgagg tcgccaacat cttcttctgg aggccgtggt    5940
tggcttgtat ggagcagcag acgcgctact tcgagcggag gcatccggag cttgcaggat    6000
cgccgcggct ccgggcgtat atgctccgca ttggtcttga ccaactctat cagagcttgg    6060
ttgacggcaa tttcgatgat gcagcttggg cgcagggtcg atgcgacgca atcgtccgat    6120
ccggagccgg gactgtcggg cgtacacaaa tcgcccgcag aagcgcggcc gtctggaccg    6180
atggctgtgt agaagtactc gccgatagtg gaaaccgacg ccccagcact cgtccgaggg    6240
caaaggaata gtgaggtaca gcttggatcg atccggctgc taacaaagcc cgaaaggaag    6300
ctgagttggc tgctgccacc gctgagcaat aactagcata accccttggg gcctctaaac    6360
gggtcttgag gggttttttg ctgaaaggag gaactatatc cggatgatcg gcgcgccgt     6420
cgacggatcc gtacgagatc cggcggcca gatcctgcag gagatccaag cttttgatcc     6480
atgcccttca tttgccgctt attaattaat ttggtaacag tccgtactaa tcagttactt    6540
```

| | |
|---|---|
| atccttcccc catcataatt aatcttggta gtctcgaatg ccacaacact gactagtctc | 6600 |
| ttggatcata agaaaaagcc aaggaacaaa agaagacaaa acacaatgag agtatccttt | 6660 |
| gcatagcaat gtctaagttc ataaaattca acaaaaacg caatcacaca cagtggacat | 6720 |
| cacttatcca ctagctgatc aggatcgccg cgtcaagaaa aaaaaactgg accccaaaag | 6780 |
| ccatgcacaa caacacgtac tcacaaaggt gtcaatcgag cagcccaaaa cattcaccaa | 6840 |
| ctcaacccat catgagccct cacatttgtt gtttctaacc caacctcaaa ctcgtattct | 6900 |
| cttccgccac ctcattttg tttatttcaa cacccgtcaa actgcatgcc accccgtggc | 6960 |
| caaatgtcca tgcatgttaa caagacctat gactataaat agctgcaatc tcggcccagg | 7020 |
| ttttcatcat caagaaccag ttcaatatcc tagtacaccg tattaaagaa tttaagatat | 7080 |
| actgcggccg caccatggaa gcagccaaag aattggtttc catcgtccaa gaggagctcc | 7140 |
| ccaaggtgga ctatgcccag ctttggcagg atgccagcag ctgtgaggtc ctttacctct | 7200 |
| cggtggcatt cgtggcgatc aagttcatgc tgcgcccact ggacctgaag cgccaggcca | 7260 |
| ccttgaagaa gctgttcaca gcatacaact tcctcatgtc gatctattcc tttggctcct | 7320 |
| tcctggccat ggcctatgcc ctatcagtaa ctggcatcct ctccggcgac tgtgagacgg | 7380 |
| cgttcaacaa cgatgtgttc aggatcacaa ctcagctgtt ctacctcagc aagttcgtag | 7440 |
| agtacatcga ctccttctac cttcccctta tggacaagcc actgtcgttc cttcagttct | 7500 |
| tccatcattt gggggccccc attgacatgt ggctattcta caaataccgc aacgaaggag | 7560 |
| tctggatctt tgtcctgttg aatgggttca ttcactggat catgtacggt tactattgga | 7620 |
| cgcggctcat caagctgaac ttccccatgc ccaagaacct gatcacctcc atgcagatca | 7680 |
| tccagttcaa tgtcgggttc tacatcgtct ggaagtaccg caatgtgcca tgctaccgcc | 7740 |
| aggatgggat gcgcatgttt gcctggatct tcaactactg gtatgtcggg acggtcttgc | 7800 |
| tgctgttcct caacttttac gtgcagacgt acatccggaa gccgaggaag aaccgaggga | 7860 |
| agaaggagta gc | 7872 |

<210> SEQ ID NO 31
<211> LENGTH: 1260
<212> TYPE: DNA
<213> ORGANISM: Tetruetreptia pomquetensis 1491

<400> SEQUENCE: 31

| | |
|---|---|
| atgtctccta agcggcaagc tctgccaatc acaattgatg gcgcaactta tgatgtgtct | 60 |
| gcttgggtca atcaccaccc tggaggagct gacattatcg agaactatcg caaccgcgat | 120 |
| gcgaccgatg tcttcatggt gatgcactct caagaagccg tcgccaagtt gaagagaatg | 180 |
| cctgttatgg agccttcctc tcctgacaca cctgttgcac ccaagcctaa gcgtgatgag | 240 |
| ccccaggagg atttccgcaa gttgcgggag gaattcatct ccaagggtat gttcgagacg | 300 |
| agtttccttt ggtattttta caagacttca actaccgtcg gtttgatggt cctttccatc | 360 |
| ttgatgaccg tgtacacgaa ttggtatttc accgctgctt tggttcttgg cgtgtgctac | 420 |
| caacagctag gctggttgtc ccacgactat tgccatcacc aggttttcac aaaccgcaag | 480 |
| attaacgacg ctttcggtct ctttttcggt aacgtgatgc agggatactc acagacttgg | 540 |
| tggaaggata ggcacaatgg tcaccatgcc gccaccaatg tggtcggcca tgacccagat | 600 |
| attgataacc tccccatcct ggcttggtct cccgaagatg tcaagagggc tactccttcg | 660 |
| actcggaatc tcatcaagta ccagcagtac tacttcattc ccaccattgc atcccttagg | 720 |
| ttcatctggt gcctccaatc catcggcggc gtcatgtcct acaagagcga ggagaggaac | 780 |

```
ctgtactaca agcgccagta cactaaggag gcgattggtc tggccctcca ctgggtgctc      840
aaggccactt tctattgcag tgccatgcct agctttgcca ccggtttggg atgcttcttg      900
atctccgagc tgctcggagg atttggcatt gccatcgttg tgtttctgaa tcactatcct      960
ttggacaagg ttgaggagac tgtctgggat gagcacgggt tcagcgccag ccagatccac     1020
gagacgttga acattaagcc cggccttctc accgattggg tctttggtgg tctcaactac     1080
cagattgagc accacttgtg gcccaacatg cccaggcaca acctcacggc agcttccctg     1140
gaggtgcaga agttgtgcgc caagcacaac ctgccctaca gggccccagc catcatcccc     1200
ggggttcaga aattggtcag cttcttaggc gagattgccc agctggctgc tgtccctgaa     1260
```

<210> SEQ ID NO 32
<211> LENGTH: 39
<212> TYPE: DNA
<213> ORGANISM: Artificial Sequence
<220> FEATURE:
<223> OTHER INFORMATION: SMART IV oligonucleotide

<400> SEQUENCE: 32

```
aagcagtggt atcaacgcag agtggccatt acggccggg                              39
```

<210> SEQ ID NO 33
<211> LENGTH: 37
<212> TYPE: DNA
<213> ORGANISM: Artificial Sequence
<220> FEATURE:
<223> OTHER INFORMATION: Adaptor Primer from Invitrogen 3'-RACE kit

<400> SEQUENCE: 33

```
ggccacgcgt cgactagtac ttttttttttt tttttt                                37
```

<210> SEQ ID NO 34
<211> LENGTH: 31
<212> TYPE: DNA
<213> ORGANISM: Artificial Sequence
<220> FEATURE:
<223> OTHER INFORMATION: primer TpomNot-5

<400> SEQUENCE: 34

```
gcggccgcac catgtctcct aagcggcaag c                                      31
```

<210> SEQ ID NO 35
<211> LENGTH: 27
<212> TYPE: DNA
<213> ORGANISM: Artificial Sequence
<220> FEATURE:
<223> OTHER INFORMATION: primer TpomNot-3

<400> SEQUENCE: 35

```
gcggccgctc attcagggac agcagcc                                           27
```

<210> SEQ ID NO 36
<211> LENGTH: 4300
<212> TYPE: DNA
<213> ORGANISM: Artificial Sequence
<220> FEATURE:
<223> OTHER INFORMATION: plasmid pLF114-10

<400> SEQUENCE: 36

```
taatacgact cactataggg cgaattgggc ccgacgtcgc atgctcccgg ccgccatggc        60
ggccgcggga attcgattgg cggccgcacc atgtctccta agcggcaagc tctgccaatc       120
acaattgatg gcgcaactta tgatgtgtct gcttgggtca atcaccaccc tggaggagct       180
```

```
gacattatcg agaactatcg caaccgcgat gcgaccgatg tcttcatggt gatgcactct      240
caagaagccg tcgccaagtt gaagagaatg cctgttatgg agccttcctc tcctgacaca      300
cctgttgcac ccaagcctaa gcgtgatgag ccccaggagg atttccgcaa gttgcgggag      360
gaattcatct ccaagggtat gttcgagacg agtttccttt ggtattttta caagacttca      420
actaccgtcg gtttgatggt cctttccatc ttgatgaccg tgtacacgaa ttggtatttc      480
accgctgctt tggttcttgg cgtgtgctac aacagctag gctggttgtc ccacgactat       540
tgccatcacc aggttttcac aaaccgcaag attaacgacg ctttcggtct cttttcggt      600 aacgtgatgc agggatactc acagacttgg tggaaggata ggcacaatgg tcaccatgcc      660
gccaccaatg tggtcggcca tgacccagat attgataacc tccccatcct ggcttggtct      720
cccgaagatg tcaagagggc tactccttcg actcggaatc tcatcaagta ccagcagtac      780
tacttcattc ccaccattgc atcccttagg ttcatctggt gcctccaatc catcggcggc      840
gtcatgtcct acaagagcga ggagaggaac ctgtactaca agcgccagta cactaaggag      900
gcgattggtc tggccctcca ctgggtgctc aaggccactt tctattgcag tgccatgcct      960
agctttgcca ccggtttggg atgcttcttg atctccgagc tgctcggagg atttggcatt     1020
gccatcgttg tgtttctgaa tcactatcct ttggacaagg ttgaggagac tgtctgggat     1080
gagcacgggt tcagcgccag ccagatccac gagacgttga acattaagcc cggccttctc     1140
accgattggg tctttggtgg tctcaactac cagattgagc accacttgtg gcccaacatg     1200
cccaggcaca acctcacggc agcttccctg gaggtgcaga agttgtgcgc caagcacaac     1260
ctgccctaca gggccccagc catcatcccc ggggttcaga aattggtcag cttcttaggc     1320
gagattgccc agctggctgc tgtccctgaa tgagcggccg caatcactag tgaattcgcg     1380
gccgcctgca ggtcgaccat atgggagagc tcccaacgcg ttggatgcat agcttgagta     1440
ttctatagtg tcacctaaat agcttggcgt aatcatggtc atagctgttt cctgtgtgaa     1500
attgttatcc gctcacaatt ccacacaaca tacgagccgg aagcataaag tgtaaagcct     1560
ggggtgccta atgagtgagc taactcacat taattgcgtt gcgctcactg cccgctttcc     1620
agtcgggaaa cctgtcgtgc cagctgcatt aatgaatcgg ccaacgcgcg gggagaggcg     1680
gtttgcgtat tgggcgctct tccgcttcct cgctcactga ctcgctgcgc tcggtcgttc     1740
ggctgcggcg agcggtatca gctcactcaa aggcggtaat acggttatcc acagaatcag     1800
gggataacgc aggaaagaac atgtgagcaa aaggccagca aaaggccagg aaccgtaaaa     1860
aggccgcgtt gctggcgttt ttccataggc tccgccccc tgacgagcat cacaaaaatc      1920
gacgctcaag tcagaggtgg cgaaacccga caggactata agataccag gcgtttcccc       1980 ctggaagctc cctcgtgcgc tctcctgttc cgaccctgcc gcttaccgga tacctgtccg     2040
cctttctccc ttcgggaagc gtggcgcttt ctcatagctc acgctgtagg tatctcagtt     2100
cggtgtaggt cgttcgctcc aagctgggct gtgtgcacga accccccgtt cagcccgacc     2160
gctgcgcctt atccggtaac tatcgtcttg agtccaaccc ggtaagacac gacttatcgc     2220
cactggcagc agccactggt aacaggatta gcagagcgag gtatgtaggc ggtgctacag     2280
agttcttgaa gtggtggcct aactacggct acactagaag aacagtattt ggtatctgcg     2340
ctctgctgaa gccagttacc ttcggaaaaa gagttggtag ctcttgatcc ggcaaacaaa     2400
ccaccgctgg tagcggtggt ttttttgttt gcaagcagca gattacgcgc agaaaaaaag     2460
gatctcaaga agatccttg atcttttcta cggggtctga cgctcagtgg aacgaaaact      2520
cacgttaagg gattttggtc atgagattat caaaaaggat cttcacctag atccttttaa     2580
```

| | |
|---|---|
| attaaaaatg aagttttaaa tcaatctaaa gtatatatga gtaaacttgg tctgacagtt | 2640 |
| accaatgctt aatcagtgag gcacctatct cagcgatctg tctatttcgt tcatccatag | 2700 |
| ttgcctgact ccccgtcgtg tagataacta cgatacggga gggcttacca tctggcccca | 2760 |
| gtgctgcaat gataccgcga gacccacgct caccggctcc agatttatca gcaataaacc | 2820 |
| agccagccgg aagggccgag cgcagaagtg gtcctgcaac tttatccgcc tccatccagt | 2880 |
| ctattaattg ttgccgggaa gctagagtaa gtagttcgcc agttaatagt ttgcgcaacg | 2940 |
| ttgttgccat tgctacaggc atcgtggtgt cacgctcgtc gtttggtatg gcttcattca | 3000 |
| gctccggttc ccaacgatca aggcgagtta catgatcccc catgttgtgc aaaaaagcgg | 3060 |
| ttagctcctt cggtcctccg atcgttgtca gaagtaagtt ggccgcagtg ttatcactca | 3120 |
| tggttatggc agcactgcat aattctctta ctgtcatgcc atccgtaaga tgcttttctg | 3180 |
| tgactggtga gtactcaacc aagtcattct gagaatagtg tatgcggcga ccgagttgct | 3240 |
| cttgcccggc gtcaatacgg gataataccg cgccacatag cagaacttta aaagtgctca | 3300 |
| tcattggaaa acgttcttcg ggcgaaaac tctcaaggat cttaccgctg ttgagatcca | 3360 |
| gttcgatgta acccactcgt gcacccaact gatcttcagc atcttttact ttcaccagcg | 3420 |
| tttctgggtg agcaaaaaca ggaaggcaaa atgccgcaaa aagggaata agggcgacac | 3480 |
| ggaaatgttg aatactcata ctcttccttt tcaatatta ttgaagcatt tatcagggtt | 3540 |
| attgtctcat gagcggatac atatttgaat gtatttagaa aaataaacaa ataggggttc | 3600 |
| cgcgcacatt tccccgaaaa gtgccacctg atgcggtgtg aaataccgca cagatgcgta | 3660 |
| aggagaaaat accgcatcag gaaattgtaa gcgttaatat tttgttaaaa ttcgcgttaa | 3720 |
| attttttgtta aatcagctca ttttttaacc aataggccga atcggcaaa atcccttata | 3780 |
| aatcaaaaga atagaccgag atagggttga gtgttgttcc agtttggaac aagagtccac | 3840 |
| tattaaagaa cgtggactcc aacgtcaaag ggcgaaaaac cgtctatcag ggcgatggcc | 3900 |
| cactacgtga accatcaccc taatcaagtt ttttggggtc gaggtgccgt aaagcactaa | 3960 |
| atcggaaccc taaagggagc ccccgattta gagcttgacg gggaaagccg gcgaacgtgg | 4020 |
| cgagaaagga agggaagaaa gcgaaaggag cgggcgctag ggcgctggca agtgtagcgg | 4080 |
| tcacgctgcg cgtaaccacc acacccgccg cgcttaatgc gccgctacag ggcgcgtcca | 4140 |
| ttcgccattc aggctgcgca actgttggga agggcgatcg gtgcgggcct cttcgctatt | 4200 |
| acgccagctg gcgaaagggg gatgtgctgc aaggcgatta agttgggtaa cgccagggtt | 4260 |
| ttcccagtca cgacgttgta aaacgacggc cagtgaattg | 4300 |

<210> SEQ ID NO 37
<211> LENGTH: 5252
<212> TYPE: DNA
<213> ORGANISM: Artificial Sequence
<220> FEATURE:
<223> OTHER INFORMATION: plasmid pKR457
<220> FEATURE:
<221> NAME/KEY: misc_feature
<222> LOCATION: (3872)..(3872)
<223> OTHER INFORMATION: n is a, c, g, or t

<400> SEQUENCE: 37

| | |
|---|---|
| gtacgtgggc ggatccccg ggctgcagga attcactggc cgtcgtttta caacgtcgtg | 60 |
| actgggaaaa ccctggcgtt acccaactta atcgccttgc agcacatccc cctttcgcca | 120 |
| gctggcgtaa tagcgaagag gcccgcaccg atcgcccttc ccaacagttg cgcagcctga | 180 |
| atggcgaatg gcgcctgatg cggtattttc tccttacgca tctgtgcggt atttcacacc | 240 |

```
gcatatggtg cactctcagt acaatctgct ctgatgccgc atagttaagc cagccccgac    300
acccgccaac acccgctgac gcgccctgac gggcttgtct gctcccggca tccgcttaca    360
gacaagctgt gaccgtctcc gggagctgca tgtgtcagag gttttcaccg tcatcaccga    420
aacgcgcgag acgaaagggc ctcgtgatac gcctattttt ataggttaat gtcatgataa    480
taatggtttc ttagacgtca ggtggcactt tcggggaaa tgtgcgcgga acccctattt    540
gtttattttt ctaaatacat tcaaatatgt atccgctcat gagacaataa ccctgataaa    600
tgcttcaata atattgaaaa aggaagagta tgagtattca acatttccgt gtcgccctta    660
ttcccttttt tgcggcattt tgccttcctg ttttgctca cccagaaacg ctggtgaaag    720
taaaagatgc tgaagatcag ttgggtgcac gagtgggtta catcgaactg gatctcaaca    780
gcggtaagat ccttgagagt tttcgccccg aagaacgttt tccaatgatg agcactttta    840
aagttctgct atgtggcgcg gtattatccc gtattgacgc cgggcaagag caactcggtc    900
gccgcataca ctattctcag aatgacttgg ttgagtactc accagtcaca gaaaagcatc    960
ttacggatgg catgacagta agagaattat gcagtgctgc cataaccatg agtgataaca   1020
ctgcggccaa cttacttctg acaacgatcg gaggaccgaa ggagctaacc gcttttttgc   1080
acaacatggg ggatcatgta actcgccttg atcgttggga accggagctg aatgaagcca   1140
taccaaacga cgagcgtgac accacgatgc ctgtagcaat ggcaacaacg ttgcgcaaac   1200
tattaactgg cgaactactt actctagctt cccggcaaca attaatagac tggatggagg   1260
cggataaagt tgcaggacca cttctgcgct cggcccttcc ggctggctgg tttattgctg   1320
ataaatctgg agccggtgag cgtgggtctc gcggtatcat tgcagcactg gggccagatg   1380
gtaagccctc ccgtatcgta gttatctaca cgacggggag tcaggcaact atggatgaac   1440
gaaatagaca gatcgctgag ataggtgcct cactgattaa gcattggtaa ctgtcagacc   1500
aagtttactc atatatactt tagattgatt taaaacttca ttttaatttt aaaaggatct   1560
aggtgaagat ccttttttgat aatctcatga ccaaaatccc ttaacgtgag ttttcgttcc   1620
actgagcgtc agaccccgta gaaaagatca aaggatcttc ttgagatcct ttttttctgc   1680
gcgtaatctg ctgcttgcaa acaaaaaaac caccgctacc agcggtggtt tgtttgccgg   1740
atcaagagct accaactctt tttccgaagg taactggctt cagcagagcg cagataccaa   1800
atactgtcct tctagtgtag ccgtagttag gccaccactt caagaactct gtagcaccgc   1860
ctacatacct cgctctgcta atcctgttac cagtggctgc tgccagtggc gataagtcgt   1920
gtcttaccgg gttggactca agacgatagt taccggataa ggcgcagcgg tcgggctgaa   1980
cggggggttc gtgcacacag cccagcttgg agcgaacgac ctacaccgaa ctgagatacc   2040
tacagcgtga gctatgagaa agcgccacgc ttcccgaagg gagaaaggcg gacaggtatc   2100
cggtaagcgg cagggtcgga acaggagagc gcacgaggga gcttccaggg ggaaacgcct   2160
ggtatcttta tagtcctgtc gggtttcgcc acctctgact tgagcgtcga tttttgtgat   2220
gctcgtcagg ggggcggagc ctatggaaaa acgccagcaa cgcggccttt ttacggttcc   2280
tggccttttg ctggccttt gctcacatgt tctttcctgc gttatcccct gattctgtgg   2340
ataaccgtat taccgccttt gagtgagctg ataccgctcg ccgcagccga acgaccgagc   2400
gcagcgagtc agtgagcgag gaagcggaag agcgcccaat acgcaaaccg cctctccccg   2460
cgcgttggcc gattcattaa tgcagctggc acgacaggtt cccgactgg aaagcgggca   2520
gtgagcgcaa cgcaattaat gtgagttagc tcactcatta ggcaccccag gctttacact   2580
ttatgcttcc ggctcgtatg ttgtgtggaa ttgtgagcgg ataacaattt cacacaggaa   2640
```

```
acagctatga ccatgattac gccaagcttg catgcctgca ggtcgactcg acgtacgtcc    2700
tcgaagagaa gggttaataa cacattttt aacattttta acacaaattt tagttattta    2760
aaaatttatt aaaaaattta aaataagaag aggaactctt taaataaatc taacttacaa    2820
aatttatgat ttttaataag ttttcaccaa taaaaatgt cataaaaata tgttaaaaag    2880
tatattatca atattctctt tatgataaat aaaagaaaa aaaaaataaa agttaagtga    2940
aaatgagatt gaagtgactt taggtgtgta taaatatatc aaccccgcca acaatttatt    3000
taatccaaat atattgaagt atattattcc atagccttta tttatttata tatttattat    3060
ataaaagctt tatttgttct aggttgttca tgaaatattt ttttggtttt atctccgttg    3120
taagaaaatc atgtgctttg tgtcgccact cactattgca gcttttcat gcattggtca    3180 gattgacggt tgattgtatt tttgttttt atggttttgt gttatgactt aagtcttcat    3240
ctctttatct cttcatcagg tttgatggtt acctaatatg gtccatgggt acatgcatgg    3300
ttaaattagg tggccaactt tgttgtgaac gatagaattt tttttatatt aagtaaacta    3360
tttttatatt atgaaataat aataaaaaaa atattttatc attattaaca aaatcatatt    3420
agttaatttg ttaactctat aataaaagaa atactgtaac attcacatta catggtaaca    3480
tctttccacc ctttcatttg tttttttgttt gatgacttt ttctcttgttt aaatttattt    3540 cccttctttt aaatttggaa tacattatca tcatatataa actaaaatac taaaaacagg    3600
attacacaaa tgataaataa taacacaaat atttataaat ctagctgcaa tatatttaaa    3660
ctagctatat cgatattgta aaataaaact agctgcattg atactgataa aaaaatatca    3720
tgtgctttct ggactgatga tgcagtatac ttttgacatt gcctttattt tatttttcag    3780
aaaagctttc ttagttctgg gttcttcatt atttgtttcc catctccatt gtgaattgaa    3840
tcatttgctt cgtgtcacaa atacaattta gntaggtaca tgcattggtc agattcacgg    3900
tttattatgt catgacttaa gttcatggta gtacattacc tgccacgcat gcattatatt    3960
ggttagattt gataggcaaa tttggttgtc aacaatataa atataaataa tgttttata    4020 ttacgaaata acagtgatca aaacaaacag ttttatcttt attaacaaga ttttgttttt    4080
gtttgatgac gtttttaat gtttacgctt tccccttct tttgaattta gaacactta    4140 tcatcataaa atcaaatact aaaaaaatta catatttcat aaataataac acaaatattt    4200 ttaaaaatc tgaaataata atgaacaata ttacatatta tcacgaaaat tcattaataa    4260
aaatattata taaataaaat gtaatagtag ttatatgtag gaaaaaagta ctgcacgcat    4320
aatatataca aaaagattaa aatgaactat tataaataat aacactaaat taatggtgaa    4380
tcatatcaaa ataatgaaaa agtaaataaa atttgtaatt aacttctata tgtattacac    4440
acacaaataa taaataatag taaaaaaaat tatgataaat atttaccatc tcataagata    4500
tttaaaataa tgataaaaat atagattatt ttttatgcaa ctagctagcc aaaaagagaa    4560
cacgggtata tataaaaaga gtacctttaa attctactgt acttcctta ttcctgacgt    4620 ttttatatca agtggacata cgtgaagatt ttaattatca gtctaaatat ttcattagca    4680
cttaatactt ttctgttta ttcctatcct ataagtagtc ccgattctcc caacattgct    4740
tattcacaca actaactaag aaagtcttcc atagcccccc aagcggccgc gacacaagtg    4800
tgagagtact aaataaatgc tttggttgta cgaaatcatt acactaaata aaataatcaa    4860
agcttatata tgccttccgc taaggccgaa tgcaagaaa ttggttcttt ctcgttatct    4920
tttgccactt ttactagtac gtattaatta ctacttaatc atctttgttt acggctcatt    4980
atatccggtc tagaggatcc aaggccgcga agttaaaagc aatgttgtca cttgtcgtac    5040
```

-continued

| | | | | |
|---|---|---|---|---|
| taacacatga | tgtgatagtt | tatgctagct | agctataaca | taagctgtct ctgagtgtgt | 5100 |
| tgtatattaa | taaagatcat | cactggtgaa | tggtgatcgt | gtacgtaccc tacttagtag | 5160 |
| gcaatggaag | cacttagagt | gtgctttgtg | catggccttg | cctctgtttt gagacttttg | 5220 |
| taatgttttc | gagtttaaat | ctttgccttt | gc | | 5252 |

```
<210> SEQ ID NO 38
<211> LENGTH: 6526
<212> TYPE: DNA
<213> ORGANISM: Artificial Sequence
<220> FEATURE:
<223> OTHER INFORMATION: plasmid pKR1145
<220> FEATURE:
<221> NAME/KEY: misc_feature
<222> LOCATION: (4340)..(4340)
<223> OTHER INFORMATION: n is a, c, g, or t
```

<400> SEQUENCE: 38

| | | | | | |
|---|---|---|---|---|---|
| ggccgcgaca | caagtgtgag | agtactaaat | aaatgctttg | gttgtacgaa atcattacac | 60 |
| taaataaaat | aatcaaagct | tatatatgcc | ttccgctaag | gccgaatgca aagaaattgg | 120 |
| ttctttctcg | ttatcttttg | ccacttttac | tagtacgtat | taattactac ttaatcatct | 180 |
| ttgtttacgg | ctcattatat | ccggtctaga | ggatccaagg | ccgcgaagtt aaaagcaatg | 240 |
| ttgtcacttg | tcgtactaac | acatgatgtg | atagttatg | ctagctagct ataacataag | 300 |
| ctgtctctga | gtgtgttgta | tattaataaa | gatcatcact | ggtgaatggt gatcgtgtac | 360 |
| gtaccctact | agtaggcaa | tggaagcact | tagagtgtgc | tttgtgcatg gccttgcctc | 420 |
| tgttttgaga | cttttgtaat | gttttcgagt | ttaaatcttt | gcctttgcgt acgtgggcgg | 480 |
| atcccccggg | ctgcaggaat | tcactggccg | tcgttttaca | acgtcgtgac tgggaaaacc | 540 |
| ctggcgttac | ccaacttaat | cgccttgcag | cacatccccc | tttcgccagc tggcgtaata | 600 |
| gcgaagaggc | ccgcaccgat | cgcccttccc | aacagttgcg | cagcctgaat ggcgaatggc | 660 |
| gcctgatgcg | gtattttctc | cttacgcatc | tgtgcggtat | tcacaccgc atatggtgca | 720 |
| ctctcagtac | aatctgctct | gatgccgcat | agttaagcca | gccccgacac ccgccaacac | 780 |
| ccgctgacgc | gccctgacgg | gcttgtctgc | tcccggcatc | cgcttacaga caagctgtga | 840 |
| ccgtctccgg | gagctgcatg | tgtcagaggt | tttcaccgtc | atcaccgaaa cgcgcgagac | 900 |
| gaaagggcct | cgtgatacgc | ctatttttat | aggttaatgt | catgataata atggtttctt | 960 |
| agacgtcagg | tggcactttt | cggggaaatg | tgcgcggaac | ccctatttgt ttatttttct | 1020 |
| aaatacattc | aaatatgtat | ccgctcatga | gacaataacc | ctgataaatg cttcaataat | 1080 |
| attgaaaaag | gaagagtatg | agtattcaac | atttccgtgt | cgcccttatt cccttttttg | 1140 |
| cggcattttg | ccttcctgtt | tttgctcacc | cagaaacgct | ggtgaaagta aaagatgctg | 1200 |
| aagatcagtt | gggtgcacga | gtgggttaca | tcgaactgga | tctcaacagc ggtaagatcc | 1260 |
| ttgagagttt | tcgccccgaa | gaacgttttc | caatgatgag | cacttttaaa gttctgctat | 1320 |
| gtggcgcggt | attatcccgt | attgacgccg | ggcaagagca | actcggtcgc cgcatacact | 1380 |
| attctcagaa | tgacttggtt | gagtactcac | cagtcacaga | aaagcatctt acggatggca | 1440 |
| tgacagtaag | agaattatgc | agtgctgcca | taaccatgag | tgataacact gcggccaact | 1500 |
| tacttctgac | aacgatcgga | ggaccgaagg | agctaaccgc | ttttttgcac aacatgggg | 1560 |
| atcatgtaac | tcgccttgat | cgttgggaac | cggagctgaa | tgaagccata ccaaacgacg | 1620 |
| agcgtgacac | cacgatgcct | gtagcaatgg | caacaacgtt | gcgcaaacta ttaactggcg | 1680 |
| aactacttac | tctagcttcc | cggcaacaat | taatagactg | gatggaggcg gataaagttg | 1740 |

```
caggaccact tctgcgctcg gcccttccgg ctggctggtt tattgctgat aaatctggag   1800
ccggtgagcg tgggtctcgc ggtatcattg cagcactggg gccagatggt aagccctccc   1860
gtatcgtagt tatctacacg acggggagtc aggcaactat ggatgaacga aatagacaga   1920
tcgctgagat aggtgcctca ctgattaagc attggtaact gtcagaccaa gtttactcat   1980
atatacttta gattgattta aaacttcatt tttaatttaa aaggatctag gtgaagatcc   2040
tttttgataa tctcatgacc aaaatccctt aacgtgagtt ttcgttccac tgagcgtcag   2100
accccgtaga aaagatcaaa ggatcttctt gagatccttt ttttctgcgc gtaatctgct   2160
gcttgcaaac aaaaaaacca ccgctaccag cggtggtttg tttgccggat caagagctac   2220
caactctttt tccgaaggta actggcttca gcagagcgca gataccaaat actgtccttc   2280
tagtgtagcc gtagttaggc caccacttca agaactctgt agcaccgcct acatacctcg   2340
ctctgctaat cctgttacca gtggctgctg ccagtggcga taagtcgtgt cttaccgggt   2400
tggactcaag acgatagtta ccggataagg cgcagcggtc gggctgaacg ggggggttcgt   2460 gcacacagcc cagcttggag cgaacgacct acaccgaact gagataccta cagcgtgagc   2520
tatgagaaag cgccacgctt cccgaaggga gaaaggcgga caggtatccg gtaagcggca   2580
gggtcggaac aggagagcgc acgagggagc ttccagggg aaacgcctgg tatctttata   2640
gtcctgtcgg gtttcgccac ctctgacttg agcgtcgatt tttgtgatgc tcgtcagggg   2700
ggcggagcct atggaaaaac gccagcaacg cggccttttt acggttcctg gccttttgct   2760
ggccttttgc tcacatgttc tttcctgcgt tatcccctga ttctgtggat aaccgtatta   2820
ccgcctttga gtgagctgat accgctcgcc gcagccgaac gaccgagcgc agcgagtcag   2880
tgagcgagga agcggaagag cgcccaatac gcaaaccgcc tctccccgcg cgttggccga   2940
ttcattaatg cagctggcac gacaggtttc ccgactggaa agcgggcagt gagcgcaacg   3000
caattaatgt gagttagctc actcattagg caccccaggc tttacacttt atgcttccgg   3060
ctcgtatgtt gtgtggaatt gtgagcggat aacaatttca cacaggaaac agctatgacc   3120
atgattacgc caagcttgca tgcctgcagg tcgactcgac gtacgtcctc gaagagaagg   3180
gttaataaca catttttaa cattttaac acaaattta gttatttaaa aatttattaa   3240
aaaatttaaa ataagaagag gaactcttta aataaatcta acttacaaaa tttatgattt   3300
ttaataagtt ttcaccaata aaaatgtca taaaaatatg ttaaaagta tattatcaat   3360 attctcttta tgataaataa aaagaaaaaa aaaataaaag ttaagtgaaa atgagattga   3420
agtgacttta ggtgtgtata aatatatcaa ccccgccaac aatttattta atccaaatat   3480
attgaagtat attattccat agcctttatt tatttatata tttattatat aaaagcttta   3540
tttgttctag gttgttcatg aaatatttt ttggttttat ctccgttgta agaaaatcat   3600
gtgctttgtg tcgccactca ctattgcagc ttttcatgc attggtcaga ttgacggttg   3660
attgtatttt tgttttttat ggttttgtgt tatgacttaa gtcttcatct ctttatctct   3720
tcatcaggtt tgatggttac ctaatatggt ccatgggtac atgcatggtt aaattaggtg   3780
gccaactttg ttgtgaacga tagaattttt tttatattaa gtaaactatt tttatattat   3840 gaataataa taaaaaaat attttatcat tattaacaaa atcatattag ttaatttgtt   3900
aactctataa taaagaaat actgtaacat tcacattaca tggtaacatc tttccaccct   3960
ttcatttgtt ttttgtttga tgacttttt tcttgtttaa atttatttcc cttcttttaa   4020
atttggaata cattatcatc atatataaac taaaatacta aaacaggat tacacaaatg   4080 ataaataata acacaaatat ttataaatct agctgcaata tatttaaact agctatatcg   4140
```

```
atattgtaaa ataaaactag ctgcattgat actgataaaa aaatatcatg tgctttctgg    4200
actgatgatg cagtatactt ttgacattgc ctttatttta tttttcagaa aagctttctt    4260
agttctgggt tcttcattat ttgtttccca tctccattgt gaattgaatc atttgcttcg    4320
tgtcacaaat acaatttagn taggtacatg cattggtcag attcacggtt tattatgtca    4380
tgacttaagt tcatggtagt acattacctg ccacgcatgc attatattgg ttagatttga    4440
taggcaaatt tggttgtcaa caatataaat ataataatg tttttatatt acgaaataac    4500
agtgatcaaa acaaacagtt ttatctttat taacaagatt ttgttttgt ttgatgacgt    4560
tttttaatgt ttacgctttc ccccttcttt tgaatttaga cactttatc atcataaaat    4620
caaatactaa aaaaattaca tatttcataa ataataacac aaatatttt aaaaaatctg    4680
aaataataat gaacaatatt acatattatc acgaaaattc attaataaaa atattatata    4740
aataaaatgt aatagtagtt atatgtagga aaaaagtact gcacgcataa tatatacaaa    4800
aagattaaaa tgaactatta taaataataa cactaaatta atggtgaatc atatcaaaat    4860
aatgaaaaag taaataaaat ttgtaattaa cttctatatg tattacacac acaaataata    4920
aataatagta aaaaaaatta tgataaatat ttaccatctc ataagatatt taaaataatg    4980
ataaaaatat agattatttt ttatgcaact agctagccaa aaagagaaca cgggtatata    5040
taaaaagagt acctttaaat tctactgtac ttcctttatt cctgacgttt ttatatcaag    5100
tggacatacg tgaagatttt aattatcagt ctaaatattt cattagcact taatactttt    5160
ctgttttatt cctatcctat aagtagtccc gattctccca acattgctta ttcacacaac    5220
taactaagaa agtcttccat agcccccaa gcggccgcac catgtctcct aagcggcaag    5280
ctctgccaat cacaattgat ggcgcaactt atgatgtgtc tgcttgggtc aatcaccacc    5340
ctggaggagc tgacattatc gagaactatc gcaaccgcga tgcgaccgat gtcttcatgg    5400
tgatgcactc tcaagaagcc gtcgccaagt tgaagagaat gcctgttatg gagccttcct    5460
ctcctgacac acctgttgca cccaagccta agcgtgatga gccccaggag gatttccgca    5520
agttgcggga ggaattcatc tccaagggta tgttcgagac gagtttcctt tggtatttt    5580
acaagacttc aactaccgtc ggtttgatgg tccttccat cttgatgacc gtgtacacga    5640
attggtattt caccgctgct ttggttcttg gcgtgtgcta ccaacagcta ggctggttgt    5700
cccacgacta ttgccatcac caggttttca caaaccgcaa gattaacgac gctttcggtc    5760
tcttttcgg taacgtgatg cagggatact cacagacttg gtggaaggat aggcacaatg    5820
gtcaccatgc cgccaccaat gtggtcggcc atgacccaga tattgataac ctccccatcc    5880
tggcttggtc tcccgaagat gtcaagaggg ctactccttc gactcggaat ctcatcaagt    5940
accagcagta ctacttcatt cccaccattg catcccttag gttcatctgg tgcctccaat    6000
ccatcggcgg cgtcatgtcc tacaagagcg aggagaggaa cctgtactac aagcgccagt    6060
acactaagga ggcgattggt ctggccctcc actgggtgct caaggccact ttctattgca    6120
gtgccatgcc tagctttgcc accggtttgg gatgcttctt gatctccgag ctgctcggag    6180
gatttggcat tgccatcgtt gtgtttctga atcactatcc tttggacaag gttgaggaga    6240
ctgtctggga tgagcacggg ttcagcgcca gccagatcca cgagacgttg aacattaagc    6300
ccggccttct caccgattgg gtcttttggtg gtctcaacta ccagattgag caccacttgt    6360
ggcccaacat gcccaggcac aacctcacgg cagcttccct ggaggtgcag aagttgtgcg    6420
ccaagcacaa cctgccctac agggcccag ccatcatccc cggggttcag aaattggtca    6480
gcttcttagg cgagattgcc cagctggctg ctgtccctga atgagc    6526
```

-continued

```
<210> SEQ ID NO 39
<211> LENGTH: 11706
<212> TYPE: DNA
<213> ORGANISM: Artificial Sequence
<220> FEATURE:
<223> OTHER INFORMATION: plasmid pKR1151
<220> FEATURE:
<221> NAME/KEY: misc_feature
<222> LOCATION: (10531)..(10531)
<223> OTHER INFORMATION: n is a, c, g, or t

<400> SEQUENCE: 39
```

| | | | | | |
|---|---|---|---|---|---|
| gtacgagatc | cggccggcca | gatcctgcag | gagatccaag | cttttgatcc | atgcccttca | 60 |
| tttgccgctt | attaattaat | ttggtaacag | tccgtactaa | tcagttactt | atccttcccc | 120 |
| catcataatt | aatcttggta | gtctcgaatg | ccacaacact | gactagtctc | ttggatcata | 180 |
| agaaaaagcc | aaggaacaaa | agaagacaaa | acacaatgag | agtatccttt | gcatagcaat | 240 |
| gtctaagttc | ataaaattca | aacaaaaacg | caatcacaca | cagtggacat | cacttatcca | 300 |
| ctagctgatc | aggatcgccg | cgtcaagaaa | aaaaaactgg | accccaaaag | ccatgcacaa | 360 |
| caacacgtac | tcacaaaggt | gtcaatcgag | cagcccaaaa | cattcaccaa | ctcaacccat | 420 |
| catgagccct | cacatttgtt | gtttctaacc | caacctcaaa | ctcgtattct | cttccgccac | 480 |
| ctcattttg | tttatttcaa | cacccgtcaa | actgcatgcc | accccgtggc | caaatgtcca | 540 |
| tgcatgttaa | caagacctat | gactataaat | agctgcaatc | tcggcccagg | ttttcatcat | 600 |
| caagaaccag | ttcaatatcc | tagtacaccg | tattaaagaa | tttaagatat | actgcggccg | 660 |
| caccatggaa | gcagccaaag | aattggtttc | catcgtccaa | gaggagctcc | ccaaggtgga | 720 |
| ctatgcccag | cttttggcagg | atgccagcag | ctgtgaggtc | cttttacctct | cggtggcatt | 780 |
| cgtggcgatc | aagttcatgc | tgcgcccact | ggacctgaag | cgccaggcca | ccttgaagaa | 840 |
| gctgttcaca | gcatacaact | tcctcatgtc | gatctattcc | tttggctcct | tcctggccat | 900 |
| ggcctatgcc | ctatcagtaa | ctggcatcct | ctccggcgac | tgtgagacgg | cgttcaacaa | 960 |
| cgatgtgttc | aggatcacaa | ctcagctgtt | ctacctcagc | aagttcgtag | agtacatcga | 1020 |
| ctccttctac | cttcccctta | tggacaagcc | actgtcgttc | cttcagttct | tccatcattt | 1080 |
| gggggcccc | attgacatgt | ggctattcta | caaataccgc | aacgaaggag | tctggatctt | 1140 |
| tgtcctgttg | aatgggttca | ttcactggat | catgtacggt | tactattgga | cgcggctcat | 1200 |
| caagctgaac | ttccccatgc | ccaagaacct | gatcacctcc | atgcagatca | tccagttcaa | 1260 |
| tgtcgggttc | tacatcgtct | ggaagtaccg | caatgtgcca | tgctaccgcc | aggatgggat | 1320 |
| gcgcatgttt | gcctggatct | tcaactactg | gtatgtcggg | acggtcttgc | tgctgttcct | 1380 |
| caacttttac | gtgcagacgt | acatccggaa | gccgaggaag | aaccgaggga | agaaggagta | 1440 |
| gcggccgcaa | gtatgaacta | aaatgcatgt | aggtgtaaga | gctcatggag | agcatggaat | 1500 |
| attgtatccg | accatgtaac | agtataataa | ctgagctcca | tctcacttct | tctatgaata | 1560 |
| aacaaaggat | gttatgatat | attaacactc | tatctatgca | ccttattgtt | ctatgataaa | 1620 |
| tttcctctta | ttattataaa | tcatctgaat | cgtgacggct | tatggaatgc | ttcaaatagt | 1680 |
| acaaaaacaa | atgtgtacta | taagactttc | taaacaattc | taaccttagc | attgtgaacg | 1740 |
| agacataagt | gttaagaaga | cataacaatt | ataatgaag | aagtttgtct | ccatttatat | 1800 |
| attatatatt | acccacttat | gtattatatt | aggatgttaa | ggagacataa | caattataaa | 1860 |
| gagagaagtt | tgtatccatt | tatatattat | atactaccca | tttatatatt | atacttatcc | 1920 |
| acttatttaa | tgtctttata | aggtttgatc | catgatattt | ctaatatttt | agttgatatg | 1980 |

```
tatatgaaag ggtactattt gaactctctt actctgtata aaggttggat catccttaaa    2040
gtgggtctat ttaattttat tgcttcttac agataaaaaa aaaattatga gttggtttga    2100
taaaatattg aaggatttaa ataataata ataacatat aatatatgta tataaattta    2160
ttataatata acatttatct ataaaaaagt aaatattgtc ataaatctat acaatcgttt    2220
agccttgctg gacgaatctc aattatttaa acgagagtaa acatatttga cttttttggtt    2280 atttaacaaa ttattattta acactatatg aaatttttt ttttatcagc aaagaataaa    2340
attaaattaa gaaggacaat ggtgtcccaa tccttataca accaacttcc acaagaaagt    2400
caagtcagag acaacaaaaa aacaagcaaa ggaaattttt taatttgagt tgtcttgttt    2460
gctgcataat ttatgcagta aaacactaca cataacccctt ttagcagtag agcaatggtt    2520
gaccgtgtgc ttagcttctt ttattttatt tttttatcag caaagaataa ataaaataaa    2580
atgagacact tcagggatgt ttcaacaagc ttggcgcgcc gttctatagt gtcacctaaa    2640
tcgtatgtgt atgatacata aggttatgta ttaattgtag ccgcgttcta acgacaatat    2700
gtccatatgg tgcactctca gtacaatctg ctctgatgcc gcatagttaa gccagccccg    2760
acacccgcca cacccgctg acgcgccctg acgggcttgt ctgctcccgg catccgctta    2820
cagacaagct gtgaccgtct ccgggagctg catgtgtcag aggttttcac cgtcatcacc    2880
gaaacgcgcg agacgaaagg gcctcgtgat acgcctattt ttataggtta atgtcatgac    2940
caaaatccct taacgtgagt tttcgttcca ctgagcgtca gaccccgtag aaaagatcaa    3000
aggatcttct tgagatcctt ttttttctgcg cgtaatctgc tgcttgcaaa caaaaaaacc    3060
accgctacca gcggtggttt gtttgccgga tcaagagcta ccaactcttt ttccgaaggt    3120
aactggcttc agcagagcgc agataccaaa tactgtcctt ctagtgtagc cgtagttagg    3180
ccaccacttc aagaactctg tagcaccgcc tacatacctc gctctgctaa tcctgttacc    3240
agtggctgct gccagtggcg ataagtcgtg tcttaccggg ttggactcaa gacgatagtt    3300
accggataag gcgcagcggt cgggctgaac ggggggttcg tgcacacagc ccagcttgga    3360
gcgaacgacc tacaccgaac tgagatacct acagcgtgag cattgagaaa gcgccacgct    3420
tcccgaaggg agaaaggcgg acaggtatcc ggtaagcggc agggtcggaa caggagagcg    3480
cacgagggag cttccagggg gaaacgcctg gtatctttat agtcctgtcg ggtttcgcca    3540
cctctgactt gagcgtcgat ttttgtgatg ctcgtcaggg gggcggagcc tatgaaaaa    3600 cgccagcaac gcggcctttt tacggttcct ggccttttgc tggccttttg ctcacatgtt    3660
ctttcctgcg ttatccccctg attctgtgga taaccgtatt accgcctttg agtgagctga    3720
taccgctcgc cgcagccgaa cgaccgagcg cagcgagtca gtgagcgagg aagcggaaga    3780
gcgcccaata cgcaaaccgc ctctccccgc gcgttggccg attcattaat gcaggttgat    3840
cgattcgaca tcgatctagt aacatagatg acaccgcgcg cgataattta tcctagtttg    3900
cgcgctatat tttgttttct atcgcgtatt aaatgtataa ttgcgggact ctaatcataa    3960
aaacccatct cataaataac gtcatgcatt acatgttaat tattacatgc ttaacgtaat    4020
tcaacagaaa ttatatgata atcatcgcaa gaccggcaac aggattcaat cttaagaaac    4080
tttattgcca aatgtttgaa cgatctgctt cgacgcactc cttctttagg tacctcacta    4140
ttcctttgcc ctcggacgag tgctggggcg tcggtttcca ctatcggcga gtacttctac    4200
acagccatcg gtccagacgg ccgcgcttct gcgggcgatt tgtgtacgcc cgacagtccc    4260
ggctccggat cggacgattg cgtcgcatcg accctgcgcc caagctgcat catcgaaatt    4320
gccgtcaacc aagctctgat agagttggtc aagaccaatg cggagcatat acgcccggag    4380
```

| | |
|---|---|
| ccgcggcgat cctgcaagct ccggatgcct ccgctcgaag tagcgcgtct gctgctccat | 4440 |
| acaagccaac cacggcctcc agaagaagat gttggcgacc tcgtattggg aatccccgaa | 4500 |
| catcgcctcg ctccagtcaa tgaccgctgt tatgcggcca ttgtccgtca ggacattgtt | 4560 |
| ggagccgaaa tccgcgtgca cgaggtgccg gacttcgggg cagtcctcgg cccaaagcat | 4620 |
| cagctcatcg agagcctgcg cgacggacgc actgacggtg tcgtccatca cagtttgcca | 4680 |
| gtgatacaca tggggatcag caatcgcgca tatgaaatca cgccatgtag tgtattgacc | 4740 |
| gattccttgc ggtccgaatg ggccgaaccc gctcgtctgg ctaagatcgg ccgcagcgat | 4800 |
| cgcatccatg gcctccgcga ccggctgcag aacagcgggc agttcggttt caggcaggtc | 4860 |
| ttgcaacgtg cacccctgtg cacggcggga gatgcaatag gtcaggctct cgctgaattc | 4920 |
| cccaatgtca agcacttccg gaatcgggag cgcggccgat gcaaagtgcc gataaacata | 4980 |
| acgatctttg tagaaaccat cggcgcagct atttacccgc aggacatatc cacgccctcc | 5040 |
| tacatcgaag ctgaaagcac gagattcttc gccctccgag agctgcatca ggtcggagac | 5100 |
| gctgtcgaac ttttcgatca gaaacttctc gacagacgtc gcggtgagtt caggcttttt | 5160 |
| catggtttaa taagaagaga aaagagttct tttgttatgg ctgaagtaat agagaaatga | 5220 |
| gctcgagcgt gtcctctcca aatgaaatga acttccttat atagaggaag ggtcttgcga | 5280 |
| aggatagtgg gattgtgcgt catcccttac gtcagtggag atgtcacatc aatccacttg | 5340 |
| ctttgaagac gtggttggaa cgtcttcttt ttccacgatg ctcctcgtgg gtggggtcc | 5400 |
| atctttggga ccactgtcgg cagaggcatc ttgaatgata gccttttcctt tatcgcaatg | 5460 |
| atggcatttg taggagccac cttccttttc tactgtcctt tcgatgaagt gacagatagc | 5520 |
| tgggcaatgg aatccgagga ggtttcccga aattatcctt tgttgaaaag tctcaatagc | 5580 |
| cctttggtct tctgagactg tatctttgac attttggag tagaccagag tgtcgtgctc | 5640 |
| caccatgttg acgaagattt tcttcttgtc attgagtcgt aaaagactct gtatgaactg | 5700 |
| ttcgccagtc ttcacggcga gttctgttag atcctcgatt tgaatcttag actccatgca | 5760 |
| tggccttaga ttcagtagga actaccttt tagagactcc aatctctatt acttgccttg | 5820 |
| gtttatgaag caagccttga atcgtccata ctggaatagt acttctgatc ttgagaaata | 5880 |
| tgtctttctc tgtgttcttg atgcaattag tcctgaatct tttgactgca tctttaacct | 5940 |
| tcttgggaag gtatttgatc tcctggagat tgttactcgg gtagatcgtc ttgatgagac | 6000 |
| ctgctgcgta ggcctctcta accatctgtg ggtcagcatt ctttctgaaa ttgaagaggc | 6060 |
| taaccttctc attatcagtg gtgaacatag tgtcgtcacc ttcaccttcg aacttccttc | 6120 |
| ctagatcgta aagatagagg aaatcgtcca ttgtaatctc cggggcaaag gagatctctt | 6180 |
| ttggggctgg atcactgctg ggccttttgg ttcctagcgt gagccagtgg gcttttgct | 6240 |
| ttggtgggct tgttagggcc ttagcaaagc tcttgggctt gagttgagct tctcctttgg | 6300 |
| ggatgaagtt caacctgtct gttgctgac ttgttgtgta cgcgtcagct gctgctcttg | 6360 |
| cctctgtaat agtggcaaat tcttgtgtg caactccggg aacgccgttt gttgccgcct | 6420 |
| ttgtacaacc ccagtcatcg tatataccgg catgtggacc gttatacaca acgtagtagt | 6480 |
| tgatatgagg gtgttgaata cccgattctg ctctgagagg agcaactgtg ctgttaagct | 6540 |
| cagattttg tgggattgga attggatcga tctcgatccc gcgaaattaa tacgactcac | 6600 |
| tatagggaga ccacaacggt ttccctctag aaataatttt gtttaacttt aagaaggaga | 6660 |
| tatacccatg gaaaagcctg aactcaccgc gacgtctgtc gagaagtttc tgatcgaaaa | 6720 |
| gttcgacagc gtctccgacc tgatgcagct ctcggagggc gaagaatctc gtgctttcag | 6780 |

```
cttcgatgta ggagggcgtg gatatgtcct gcgggtaaat agctgcgccg atggtttcta    6840
caaagatcgt tatgtttatc ggcactttgc atcggccgcg ctcccgattc cggaagtgct    6900
tgacattggg gaattcagcg agagcctgac ctattgcatc tcccgccgtg cacagggtgt    6960
cacgttgcaa gacctgcctg aaaccgaact gcccgctgtt ctgcagccgg tcgcggaggc    7020
tatggatgcg atcgctgcgg ccgatcttag ccagacgagc gggttcggcc cattcggacc    7080
gcaaggaatc ggtcaataca ctacatggcg tgatttcata tgcgcgattg ctgatcccca    7140
tgtgtatcac tggcaaactg tgatggacga caccgtcagt gcgtccgtcg cgcaggctct    7200
cgatgagctg atgctttggg ccgaggactg ccccgaagtc cggcacctcg tgcacgcgga    7260
tttcggctcc aacaatgtcc tgacggacaa tggccgcata acagcggtca ttgactggag    7320
cgaggcgatg ttcggggatt cccaatacga ggtcgccaac atcttcttct ggaggccgtg    7380
gttggcttgt atggagcagc agacgcgcta cttcgagcgg aggcatccgg agcttgcagg    7440
atcgccgcgg ctccgggcgt atatgctccg cattggtctt gaccaactct atcagagctt    7500
ggttgacggc aatttcgatg atgcagcttg ggcgcagggt cgatgcgacg caatcgtccg    7560
atccggagcc gggactgtcg ggcgtacaca aatcgcccgc agaagcgcgg ccgtctggac    7620
cgatggctgt gtagaagtac tcgccgatag tggaaaccga cgccccagca ctcgtccgag    7680
ggcaaaggaa tagtgaggta cagcttggat cgatccggct gctaacaaag cccgaaagga    7740
agctgagttg gctgctgcca ccgctgagca ataactagca taaccccttg ggcctctaa    7800
acgggtcttg aggggttttt tgctgaaagg aggaactata tccggatgat cgggcgcgcc    7860
gtcgacggat ccgtacgcaa aggcaaagat ttaaactcga aaacattaca aaagtctcaa    7920
aacagaggca aggccatgca caaagcacac tctaagtgct tccattgcct actaagtagg    7980
gtacgtacac gatcaccatt caccagtgat gatctttatt aatatacaac acactcagag    8040
acagcttatg ttatagctag ctagcataaa ctatcacatc atgtgttagt acgacaagtg    8100
acaacattgc ttttaacttc gcggccttgg atcctctaga ccggatataa tgagccgtaa    8160
acaaagatga ttaagtagta attaatacgt actagtaaaa gtggcaaaag ataacgagaa    8220
agaaccaatt tctttgcatt cggccttagc ggaaggcata tataagcttt gattatttta    8280
tttagtgtaa tgatttcgta caaccaaagc atttatttag tactctcaca cttgtgtcgc    8340
ggccgctcat tcagggacag cagccagctg ggcaatctcg cctaagaagc tgaccaattt    8400
ctgaaccccg gggatgatgg ctggggccct gtagggcagg ttgtgcttgg cgcacaactt    8460
ctgcacctcc agggaagctg ccgtgaggtt gtgcctgggc atgttgggcc acaagtggtg    8520
ctcaatctgg tagttgagac caccaaagac ccaatcggtg agaaggccgg gcttaatgtt    8580
caacgtctcg tggatctggc tggcgctgaa cccgtgctca tcccagacag tctcctcaac    8640
cttgtccaaa ggatagtgat tcagaaacac aacgatggca atgccaaatc ctccgagcag    8700
ctcggagatc aagaagcatc ccaaaccggt ggcaaagcta ggcatggcac tgcaatagaa    8760
agtggccttg agcacccagt ggagggccag accaatcgcc tccttagtgt actggcgctt    8820
gtagtacagg ttcctctcct cgctcttgta ggacatgacg ccgccgatgg attggaggca    8880
ccagatgaac ctaagggatg caatggtggg aatgaagtag tactgctggt acttgatgag    8940
attccgagtc gaaggagtag ccctcttgac atcttcggga gaccaagcca ggatggggag    9000
gttatcaata tctgggtcat ggccgaccac attggtggcg gcatggtgac cattgtgcct    9060
atccttccac caagtctgtg agtatccctg catcacgtta ccgaaaaaga gaccgaaagc    9120
gtcgttaatc ttgcggtttg tgaaaacctg gtgatggcaa tagtcgtggg acaaccagcc    9180
```

```
tagctgttgg tagcacacgc caagaaccaa agcagcggtg aaataccaat tcgtgtacac   9240
ggtcatcaag atggaaagga ccatcaaacc gacggtagtt gaagtcttgt aaaaatacca   9300
aaggaaactc gtctcgaaca tacccttgga gatgaattcc tcccgcaact tgcggaaatc   9360
ctcctggggc tcatcacgct taggcttggg tgcaacaggt gtgtcaggag aggaaggctc   9420
cataacaggc attctcttca acttggcgac ggcttcttga gagtgcatca ccatgaagac   9480
atcggtcgca tcgcggttgc gatagttctc gataatgtca gctcctccag ggtggtgatt   9540
gacccaagca gacacatcat aagttgcgcc atcaattgtg attggcagag cttgccgctt   9600
aggagacatg gtgcggccgc ttgggggggct atggaagact ttcttagtta gttgtgtgaa   9660
taagcaatgt tgggagaatc gggactactt ataggatagg aataaaacag aaaagtatta   9720
agtgctaatg aaatatttag actgataatt aaaatcttca cgtatgtcca cttgatataa   9780
aaacgtcagg aataaaggaa gtacagtaga atttaaaggt actcttttta tatatacccg   9840
tgttctcttt ttggctagct agttgcataa aaaataatct atatttttat cattatttta   9900
aatatcttat gagatggtaa atatttatca taattttttt tactattatt tattatttgt   9960
gtgtgtaata catatagaag ttaattacaa atttttattta ctttttcatt attttgatat  10020
gattcaccat taatttagtg ttattatttta taatagttca ttttaatctt tttgtatata  10080
ttatgcgtgc agtactttttt tcctacatat aactactatt acatttt att tatataaat  10140
ttttattaat gaattttcgt gataatatgt aatattgttc attattattt cagattttt  10200
aaaaatattt gtgttattat ttatgaaata tgtaatttt ttagtatttg atttatgat   10260
gataaagtgt tctaaattca aagaaggggg gaaagcgtaa acattaaaaa acgtcatcaa  10320
acaaaaacaa aatcttgtta ataaagataa aactgtttgt tttgatcact gttatttcgt  10380
aatataaaaa cattatttat atttatattg ttgacaacca aatttgccta tcaaatctaa  10440
ccaatataat gcatgcgtgg caggtaatgt actaccatga acttaagtca tgacataata  10500
aaccgtgaat ctgaccaatg catgtaccta nctaaattgt atttgtgaca cgaagcaaat  10560
gattcaattc acaatggaga tgggaaacaa ataatgaaga acccagaact aagaaagctt  10620
ttctgaaaaa taaaataaag gcaatgtcaa aagtatactg catcatcagt ccagaaagca  10680
catgatattt ttttatcagt atcaatgcag ctagttttat tttacaatat cgatatagct  10740
agtttaaata tattgcagct agatttataa atatttgtgt tattatttat catttgtgta  10800
atcctgtttt tagtatttta gtttatatat gatgataatg tattccaaat ttaaagaag  10860
ggaaataaat ttaaacaaga aaaaagtca tcaaacaaaa aacaaatgaa agggtggaaa  10920
gatgttacca tgtaatgtga atgttacagt atttctttta ttatagagtt aacaaattaa  10980
ctaatatgat tttgttaata atgataaat attttttta tt attatttc ataatataaa   11040
aatagtttac ttaatataaa aaaaattcta tcgttcacaa caaagttggc cacctaattt  11100
aaccatgcat gtacccatgg accatattag gtaaccatca aacctgatga agagataaag  11160
agatgaagac ttaagtcata acacaaaacc ataaaaaaca aaatacaat caaccgtcaa  11220
tctgaccaat gcatgaaaaa gctgcaatag tgagtggcga cacaaagcac atgatttttct  11280
tacaacggag ataaaaccaa aaaatatttt catgaacaac ctagaacaaa taaagctttt  11340
atataataaa tatataaata aataaaggct atggaataat atacttcaat atatttggat  11400
taaataaatt gttggcgggg ttgatatatt tatacacacc taaagtcact tcaatctcat  11460
tttcacttaa cttttattttt ttttttcttt ttatttatca taaagagaat attgataata  11520
tacttttaa catattttta tgacattttt tattggtgaa aacttattaa aaatcataaa  11580
```

-continued

| ttttgtaagt tagatttatt taaagagttc ctcttcttat tttaaatttt ttaataaatt | 11640 |
| tttaaataac taaaatttgt gttaaaaatg ttaaaaaatg tgttattaac ccttctcttc | 11700 |
| gaggac | 11706 |

<210> SEQ ID NO 40
<211> LENGTH: 774
<212> TYPE: DNA
<213> ORGANISM: Artificial Sequence
<220> FEATURE:
<223> OTHER INFORMATION: DNA sequence of the codon-optimized Euglena anabaena delta-9 elongase gene (EaD9ES gene)

<400> SEQUENCE: 40

| atggaggctg ccaaggagct ggtctccatc gtccaggagg aacttcccaa ggtggactac | 60 |
| gcccagctct ggcaggacgc ctcctcttgc gaggttctgt acctctcggt cgctttcgtg | 120 |
| gccatcaagt tcatgcttcg acctctggac ctcaagcgac aagccaccct caaaaagctg | 180 |
| ttcaccgcat acaactttct catgtccatc tactcgttcg ctccttcct ggcgatggcc | 240 |
| tacgctctct ctgtcactgg tattcttccc ggcgattgtg agactgcctt caacaatgac | 300 |
| gtgttccgaa tcaccactca gctgttctac ctcagcaagt tcgtcgagta catcgactcc | 360 |
| ttctaccttc ccctcatgga caagcccttg tcgtttctgc agttctttca ccatctcgga | 420 |
| gctcccatcg acatgtggct gttctacaag tatcgaaacg aaggcgtctg gatctttgtt | 480 |
| ctgctcaacg gcttcattca ctggatcatg tacggttact attggacgcg actcatcaag | 540 |
| ctgaacttcc ctatgcccaa gaacctcatt acctccatgc aaattatcca gttcaacgtc | 600 |
| ggattctaca tcgtctggaa gtaccgaaac gtgccctgct accggcagga cggtatgcga | 660 |
| atgtttgcct ggatcttcaa ctactggtat gtcggcacgg tgctgcttct gttcctcaac | 720 |
| ttctacgtcc agacctacat tcggaagcct cgaaagaacc gaggcaaaaa ggag | 774 |

<210> SEQ ID NO 41
<211> LENGTH: 3497
<212> TYPE: DNA
<213> ORGANISM: Artificial Sequence
<220> FEATURE:
<223> OTHER INFORMATION: DNA sequence of the plasmid pEaD9ES gene

<400> SEQUENCE: 41

| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgagctcggt acctcgcgaa | 420 |
| tgcatctaga tccatggagg ctgccaagga gctggtctcc atcgtccagg aggaacttcc | 480 |
| caaggtggac tacgcccagc tctggcagga cgcctcctct tgcgaggttc tgtacctctc | 540 |
| ggtcgctttc gtggccatca agttcatgct tcgacctctg gacctcaagc gacaagccac | 600 |
| cctcaaaaag ctgttcaccg catacaactt tctcatgtcc atctactcgt tcgctccttc | 660 |
| cctggcgatg gcctacgctc tctctgtcac tggtattctt cccggcgatt gtgagactgc | 720 |
| cttcaacaat gacgtgttcc gaatcaccac tcagctgttc tacctcagca agttcgtcga | 780 |
| gtacatcgac tccttctacc ttcccctcat ggacaagccc ttgtcgtttc tgcagttctt | 840 |

```
tcaccatctc ggagctccca tcgacatgtg gctgttctac aagtatcgaa acgaaggcgt    900
ctggatcttt gttctgctca acggcttcat tcactggatc atgtacggtt actattggac    960
gcgactcatc aagctgaact ccctatgcc caagaacctc attacctcca tgcaaattat    1020
ccagttcaac gtcggattct acatcgtctg gaagtaccga acgtgccct gctaccggca    1080
ggacggtatg cgaatgtttg cctggatctt caactactgg tatgtcggca cggtgctgct    1140
tctgttcctc aacttctacg tccagaccta cattcggaag cctcgaaaga accgaggcaa    1200
aaaggagtaa gcggccgcat cggatcccgg gcccgtcgac tgcagaggcc tgcatgcaag    1260
cttggcgtaa tcatggtcat agctgttttcc tgtgtgaaat tgttatccgc tcacaattcc    1320
acacaacata cgagccggaa gcataaagtg taaagcctgg ggtgcctaat gagtgagcta    1380
actcacatta attgcgttgc gctcactgcc cgctttccag tcgggaaacc tgtcgtgcca    1440
gctgcattaa tgaatcggcc aacgcgcggg gagaggcggt ttgcgtattg ggcgctcttc    1500
cgcttcctcg ctcactgact cgctgcgctc ggtcgttcgg ctgcggcgag cggtatcagc    1560
tcactcaaag gcggtaatac ggttatccac agaatcaggg gataacgcag gaaagaacat    1620
gtgagcaaaa ggccagcaaa aggccaggaa ccgtaaaaag gccgcgttgc tggcgttttt    1680
ccataggctc cgcccccctg acgagcatca caaaaatcga cgctcaagtc agaggtggcg    1740
aaacccgaca ggactataaa gataccaggc gtttccccct ggaagctccc tcgtgcgctc    1800
tcctgttccg accctgccgc ttaccggata cctgtccgcc tttctccctt cgggaagcgt    1860
ggcgctttct catagctcac gctgtaggta tctcagttcg gtgtaggtcg ttcgctccaa    1920
gctgggctgt gtgcacgaac cccccgttca gcccgaccgc tgcgccttat ccggtaacta    1980
tcgtcttgag tccaacccgg taagacacga cttatcgcca ctggcagcag ccactggtaa    2040
caggattagc agagcgaggt atgtaggcgg tgctacagag ttcttgaagt ggtggcctaa    2100
ctacggctac actagaagaa cagtatttgg tatctgcgct ctgctgaagc cagttacctt    2160
cggaaaaaga gttggtagct cttgatccgg caaacaaacc accgctggta gcggtggttt    2220
ttttgtttgc aagcagcaga ttacgcgcag aaaaaaagga tctcaagaag atcctttgat    2280
cttttctacg gggtctgacg ctcagtggaa cgaaaactca cgttaaggga ttttggtcat    2340
gagattatca aaaaggatct tcacctagat ccttttaaat taaaaatgaa gttttaaatc    2400
aatctaaagt atatatgagt aaacttggtc tgacagttac caatgcttaa tcagtgaggc    2460
acctatctca gcgatctgtc tatttcgttc atccatagtt gcctgactcc ccgtcgtgta    2520
gataactacg atacgggagg gcttaccatc tggccccagt gctgcaatga taccgcgaga    2580
cccacgctca ccggctccag atttatcagc aataaaccag ccagccggaa gggccgagcg    2640
cagaagtggt cctgcaactt tatccgcctc catccagtct attaattgtt gccgggaagc    2700
tagagtaagt agttcgccag ttaatagttt gcgcaacgtt gttgccattg ctacaggcat    2760
cgtggtgtca cgctcgtcgt ttggtatggc ttcattcagc tccggttccc aacgatcaag    2820
gcgagttaca tgatccccca tgttgtgcaa aaaagcggtt agctccttcg gtcctccgat    2880
cgttgtcaga agtaagttgg ccgcagtgtt atcactcatg gttatggcag cactgcataa    2940
ttctcttact gtcatgccat ccgtaagatg cttttctgtg actggtgagt actcaaccaa    3000
gtcattctga gaatagtgta tgcggcgacc gagttgctct tgcccggcgt caatacggga    3060
taataccgcg ccacatagca gaactttaaa agtgctcatc attggaaaac gttcttcggg    3120
gcgaaaactc tcaaggatct taccgctgtt gagatccagt tcgatgtaac ccactcgtgc    3180
acccaactga tcttcagcat cttttacttt caccagcgtt tctgggtgag caaaaacagg    3240
```

| | | |
|---|---|---|
| aaggcaaaat gccgcaaaaa agggaataag ggcgacacgg aaatgttgaa tactcatact | 3300 |
| cttccttttt caatattatt gaagcattta tcagggttat tgtctcatga gcggatacat | 3360 |
| atttgaatgt atttagaaaa ataaacaaat aggggttccg cgcacatttc cccgaaaagt | 3420 |
| gccacctgac gtctaagaaa ccattattat catgacatta acctataaaa ataggcgtat | 3480 |
| cacgaggccc tttcgtc | 3497 |

<210> SEQ ID NO 42
<211> LENGTH: 15900
<212> TYPE: DNA
<213> ORGANISM: Artificial
<220> FEATURE:
<223> OTHER INFORMATION: pKR1191

<400> SEQUENCE: 42

| | | |
|---|---|---|
| cgcgccagat cctctagagt cgacctgcag gcatgcaagc ttggcgtaat catggtcata | 60 |
| gctgtttcct gtgtgaaatt gttatccgct cacaattcca cacaacatac gagccggaag | 120 |
| cataaagtgt aaagcctggg gtgcctaatg agtgagctaa ctcacattaa ttgcgttgcg | 180 |
| ctcactgccc gctttccagt cgggaaacct gtcgtgccag ctgcattaat gaatcggcca | 240 |
| acgcgcgggg agaggcggtt tgcgtattgg atcgatccct gaaagcgacg ttggatgtta | 300 |
| acatctacaa attgcctttt cttatcgacc atgtacgtaa gcgcttacgt ttttggtgga | 360 |
| cccttgagga aactggtagc tgttgtgggc ctgtggtctc aagatggatc attaatttcc | 420 |
| accttcacct acgatggggg gcatcgcacc ggtgagtaat attgtacggc taagagcgaa | 480 |
| tttggcctgt agacctcaat tgcgagcttt ctaatttcaa actattcggg cctaactttt | 540 |
| ggtgtgatga tgctgactgg caggatatat accgttgtaa tttgagctcg tgtgaataag | 600 |
| tcgctgtgta tgtttgtttg attgtttctg ttggagtgca gcccatttca ccggacaagt | 660 |
| cggctagatt gatttagccc tgatgaactg ccgaggggaa gccatcttga gcgcggaatg | 720 |
| ggaatggatt tcgttgtaca acgagacgac agaacaccca cgggaccgag cttcgcgagc | 780 |
| ttttgtatcc gtggcatcct tggtccgggc gatttgttca cgtccatgag gcgctctcca | 840 |
| aaggaacgca tattttccgg tgcaaccttt ccggttcttc ctctactcga cctcttgaag | 900 |
| tcccagcatg aatgttcgac cgctccgcaa gcggatcttt ggcgcaacca gccggtttcg | 960 |
| cacgtcgatt ctcgcgagcc tgcatacttt ggcaagattg ctgaatgacg ctgatgcttc | 1020 |
| atcgcaatct gcgataatgg ggtaagtatc cggtgaaggc cgcaggtcag gccgcctgag | 1080 |
| cactcagtgt cttggatgtc cagttccacg gcagctgttg ctcaagcctg ctgatcggag | 1140 |
| cgtccgcaag gtcggcgcgg acgtcggcaa gccaggcctg cggatcgatg ttattgagct | 1200 |
| tggcgctcat gatcagtgtc gccatgaacg ccgcacgttc agcacaacga tccgatccgg | 1260 |
| caaacagcca tgacttcctg ccgagtacat agcctctgag cgttcgttcg gcagcattgt | 1320 |
| tcgtcaggca aatcgggccg tcatcgagga atgacgtaat gccatccat cgcttgagca | 1380 |
| tgtaatttat cgcctcggcg acgggagaac tgcgcgacaa tttccccgc tcggtttcga | 1440 |
| gccaatcatg cagctcttcg gcgagtgacc ttgatcaggc caccgccacg accgcggaag | 1500 |
| acgaacagat gcctgcgcat cggatcgcgc ttcagcgtct cttgcaccat cagcgacaaa | 1560 |
| ccgggaaagc ctttgcgcat gtccgtactt atgtcgccac ttgggagggc ttcgtctacg | 1620 |
| tggccttcgt gatcgacgtc ttcgcccgtc gcattgtcgg atggcgggcg agccggacag | 1680 |
| cacatgcagg ctttgtcctc gatgccctcg aggaggctca tcatgatcgg cgtcccgctc | 1740 |
| atggcggcct agtgcatcac tcggatcgcg gtgttcaata cgtgtccttt cgctattccg | 1800 |

```
agcggttggc agaagcaggt atcgagccat ctatcggaag cgtcggcgac agcacgacaa   1860
cgccctcgca gaagcgatca acggtcttta caaggccgag gtcattcatc ggcgtggacc   1920
atggaggagc ttcgaagcgg tcgagttcgc taccttggaa tggatagact ggttcaacca   1980
cggcggcttt tgaagcccat cggcaatata ccgccagccg aagacgagga tcagtattac   2040
gccatgctgg acgaagcagc catgctgcg cattttaacg aaatggcctc cggcaaaccc   2100
ggtgcggttc acttgttgcg tgggaaagtt cacgggactc cgcgcacgag ccttcttcgt   2160
aatagccata tcgaccgaat tgacctgcag gggggggggg gaaagccacg ttgtgtctca   2220
aaatctctga tgttacattg cacaagataa aaatatatca tcatgaacaa taaaactgtc   2280
tgcttacata aacagtaata caaggggtgt tatgagccat attcaacggg aaacgtcttg   2340
ctcgaggccg cgattaaatt ccaacatgga tgctgattta tatgggtata aatgggctcg   2400
cgataatgtc gggcaatcag gtgcgacaat ctatcgattg tatgggaagc ccgatgcgcc   2460
agagttgttt ctgaaacatg gcaaaggtag cgttgccaat gatgttacag atgagatggt   2520
cagactaaac tggctgacgg aatttatgcc tcttccgacc atcaagcatt ttatccgtac   2580
tcctgatgat gcatggttac tcaccactgc gatccccggg aaaacagcat tccaggtatt   2640
agaagaatat cctgattcag gtgaaaatat tgttgatgcg ctggcagtgt tcctgcgccg   2700
gttgcattcg attcctgttt gtaattgtcc ttttaacagc gatcgcgtat ttcgtctcgc   2760
tcaggcgcaa tcacgaatga ataacggttt ggttgatgcg agtgattttg atgacgagcg   2820
taatggctgg cctgttgaac aagtctggaa agaaatgcat aagcttttgc cattctcacc   2880
ggattcagtc gtcactcatg gtgatttctc acttgataac cttattttg acgaggggaa   2940 attaataggt tgtattgatg ttggacgagt cggaatcgca gaccgatacc aggatcttgc   3000
catcctatgg aactgcctcg gtgagttttc tccttcatta cagaaacggc ttttttcaaaa   3060 atatggtatt gataatcctg atatgaataa attgcagttt catttgatgc tcgatgagtt   3120
tttctaatca gaattggtta attggttgta acactggcag agcattacgc tgacttgacg   3180
ggacggcggc tttgttgaat aaatcgaact tttgctgagt tgaaggatca gatcacgcat   3240
cttcccgaca acgcagaccg ttccgtggca aagcaaaagt tcaaaatcac caactggtcc   3300
acctacaaca aagctctcat caaccgtggc tccctcactt tctggctgga tgatggggcg   3360
attcaggcct ggtatgagtc agcaacacct tcttcacgag gcagacctca gcgcccccc   3420 ccccctgcag gtctttttcca atgatgagca cttttaaagt tctgctatgt ggcgcggtat   3480
tatcccgtgt tgacgccggg caagagcaac tcggtcgccg catacactat tctcagaatg   3540
acttggttga gtactcacca gtcacagaaa agcatcttac ggatggcatg acagtaagag   3600
aattatgcag tgctgccata accatgagtg ataacactgc ggccaactta cttctgacaa   3660
cgatcggagg accgaaggag ctaaccgctt ttttgcacaa catgggggat catgtaactc   3720
gccttgatcg ttgggaaccg gagctgaatg aagccatacc aaacgacgag cgtgacacca   3780
cgatgcctgt agcaatggca acaacgttgc gcaaactatt aactggcgaa ctacttactc   3840
tagcttcccg gcaacaatta atagactgga tgaggcgga taaagttgca ggaccacttc   3900
tgcgctcggc ccttccggct ggctggttta ttgctgataa atctggagcc ggtgagcgtg   3960
ggtctcgcgg tatcattgca gcactggggc cagatggtaa gccctcccgt atcgtagtta   4020
tctacacgac ggggagtcag gcaactatgg atgaacgaaa tagacagatc gctgagatag   4080
gtgcctcact gattaagcat tggtaactgt cagaccaagt ttactcatat atactttaga   4140
ttgatttaaa acttcatttt taatttaaaa ggatctaggt gaagatcctt tttgataatc   4200
```

```
tcatgaccaa atcccttaa cgtgagtttt cgttccactg agcgtcagac cccgtagaaa    4260
agatcaaagg atcttcttga gatccttttt ttctgcgcgt aatctgctgc ttgcaaacaa    4320
aaaaaccacc gctaccagcg gtggtttgtt tgccggatca agagctacca actcttttc    4380 cgaaggtaac tggcttcagc agagcgcaga taccaaatac tgtccttcta gtgtagccgt    4440
agttaggcca ccacttcaag aactctgtag caccgcctac atacctcgct ctgctaatcc    4500
tgttaccagt ggctgctgcc agtggcgata agtcgtgtct taccgggttg gactcaagac    4560
gatagttacc ggataaggcg cagcggtcgg gctgaacggg gggttcgtgc acacagccca    4620
gcttggagcg aacgacctac accgaactga gatacctaca gcgtgagcta tgagaaagcg    4680
ccacgcttcc cgaagggaga aaggcggaca ggtatccggt aagcggcagg gtcggaacag    4740
gagagcgcac gagggagctt ccaggggaaa acgcctggta tctttatagt cctgtcgggt    4800
ttcgccacct ctgacttgag cgtcgatttt tgtgatgctc gtcagggggg cggagcctat    4860
ggaaaaacgc cagcaacgcg gccttttac ggttcctggc cttttgctgg ccttttgctc    4920
acatgttctt cctgcgtta tcccctgatt ctgtggataa ccgtattacc gcctttgagt    4980
gagctgatac cgctcgccgc agccgaacga ccgagcgcag cgagtcagtg agcgaggaag    5040
cggaagagcg cctgatgcgg tattttctcc ttacgcatct gtgcggtatt tcacaccgca    5100
tatggtgcac tctcagtaca atctgctctg atgccgcata gttaagccag tatacactcc    5160
gctatcgcta cgtgactggg tcatggctgc gccccgacac ccgccaacac ccgctgacgc    5220
gccctgacgg gcttgtctgc tcccggcatc cgcttacaga caagctgtga ccgtctccgg    5280
gagctgcatg tgtcagaggt tttcaccgtc atcaccgaaa cgcgcgaggc agggtgcctt    5340
gatgtgggcg ccggcggtcg agtggcgacg gcgcggcttg tccgcgccct ggtagattgc    5400
ctggccgtag gccagccatt tttgagcggc cagcggccgc gataggccga cgcgaagcgg    5460
cggggcgtag ggagcgcagc gaccgaaggg taggcgcttt ttgcagctct tcggctgtgc    5520
gctggccaga cagttatgca caggccaggc gggttttaag agttttaata agttttaaag    5580
agttttaggc ggaaaaatcg ccttttttct cttttatatc agtcacttac atgtgtgacc    5640
ggttcccaat gtacggcttt gggttcccaa tgtacgggtt ccggttccca atgtacggct    5700
ttgggttccc aatgtacgtg ctatccacag gaaagagacc ttttcgacct ttttcccctg    5760
ctagggcaat ttgccctagc atctgctccg tacattagga accggcggat gcttcgccct    5820
cgatcaggtt gcggtagcgc atgactagga tcgggccagc ctgccccgcc tcctccttca    5880
aatcgtactc cggcaggtca tttgacccga tcagcttgcg cacggtgaaa cagaacttct    5940
tgaactctcc ggcgctgcca ctgcgttcgt agatcgtctt gaacaaccat ctggcttctg    6000
ccttgcctgc ggcgcggcgt gccaggcggt agagaaaacg gccgatgccg ggatcgatca    6060 aaagtaatc gggtgaacc gtcagcacgt ccgggttctt gccttctgtg atctcgcggt    6120
acatccaatc agctagctcg atctcgatgt actccggccg cccggtttcg ctctttacga    6180
tcttgtagcg gctaatcaag gcttcaccct cggataccgt caccaggcgg ccgttcttgg    6240
ccttcttcgt acgctgcatg gcaacgtgcg tggtgtttaa ccgaatgcag gtttctacca    6300
ggtcgtcttt ctgctttccg ccatcggctc gccggcagaa cttgagtacg tccgcaacgt    6360
gtggacggaa cacgcggccg ggcttgtctc ccttcccttc ccgtatcgg ttcatggatt    6420 cggttagatg ggaaaccgcc atcagtacca ggtcgtaatc ccacacactg gccatgccgg    6480
ccggccctgc ggaaacctct acgtgcccgt ctggaagctc gtagcggatc acctcgccag    6540
ctcgtcggtc acgcttcgac agacggaaaa cggccacgtc catgatgctg cgactatcgc    6600
```

```
gggtgcccac gtcatagagc atcggaacga aaaaatctgg ttgctcgtcg cccttgggcg   6660
gcttcctaat cgacggcgca ccggctgccg gcggttgccg ggattctttg cggattcgat   6720
cagcggccgc ttgccacgat tcaccggggc gtgcttctgc ctcgatgcgt tgccgctggg   6780
cggcctgcgc ggccttcaac ttctccacca ggtcatcacc cagcgccgcg ccgatttgta   6840
ccgggccgga tggtttgcga ccgctcacgc cgattcctcg gcttggggg ttccagtgcc    6900 attgcagggc cggcagacaa cccagccgct tacgcctggc caaccgcccg ttcctccaca   6960 catgggcat tccacggcgt cggtgcctgg ttgttcttga ttttccatgc cgcctccttt    7020
agccgctaaa attcatctac tcatttattc atttgctcat ttactctggt agctgcgcga   7080
tgtattcaga tagcagctcg gtaatggtct tgccttggcg taccgcgtac atcttcagct   7140
tggtgtgatc ctccgccggc aactgaaagt tgacccgctt catggctggc gtgtctgcca   7200
ggctggccaa cgttgcagcc ttgctgctgc gtgcgctcgg acggccggca cttagcgtgt   7260
ttgtgctttt gctcattttc tctttacctc attaactcaa atgagttttg atttaatttc   7320
agcggccagc gcctggacct cgcgggcagc gtcgccctcg ggttctgatt caagaacggt   7380
tgtgccggcg gcggcagtgc ctgggtagct cacgcgctgc gtgatacggg actcaagaat   7440
gggcagctcg tacccggcca gcgcctcggc aacctcaccg ccgatgcgcg tgcctttgat   7500
cgcccgcgac acgacaaagg ccgcttgtag ccttccatcc gtgacctcaa tgcgctgctt   7560
aaccagctcc accaggtcgg cggtggccca tatgtcgtaa gggcttggct gcaccggaat   7620
cagcacgaag tcgctgcct tgatcgcgga cacagccaag tccgccgcct ggggcgctcc    7680
gtcgatcact acgaagtcgc gccggccgat ggccttcacg tcgcggtcaa tcgtcgggcg   7740
gtcgatgccg acaacggtta gcggttgatc ttcccgcacg gccgcccaat cgcgggcact   7800
gccctgggga tcggaatcga ctaacagaac atcggcccg gcgagttgca gggcgcgggc    7860
tagatgggtt gcgatggtcg tcttgcctga cccgcctttc tggttaagta cagcgataac   7920
ttcatgcgtt cccttgcgta tttgtttatt tactcatcgc atcatatacg cagcgaccgc   7980
atgacgcaag ctgtttact caaatacaca tcaccttttt agacggcggc gctcggtttc     8040
ttcagcggcc aagctggccg gccaggccgc cagcttggca tcagacaaac cggccaggat   8100
ttcatgcagc cgcacggttg agacgtgcgc gggcggctcg aacacgtacc cggccgcgat   8160
catctccgcc tcgatctctt cggtaatgaa aaacggttcg tcctggccgt cctggtgcgg   8220
tttcatgctt gttcctcttg gcgttcattc tcggcggccg ccaggcgtc ggcctcggtc    8280 aatgcgtcct cacggaaggc accgcgccgc ctggcctcgg tgggcgtcac ttcctcgctg   8340
cgctcaagtg cgcggtacag ggtcgagcga tgcacgccaa gcagtgcagc cgcctctttc   8400
acggtgcggc cttcctggtc gatcagctcg cgggcgtgcg cgatctgtgc cggggtgagg   8460
gtagggcggg ggccaaactt cacgcctcgg gccttggcgg cctcgcgccc gctccgggtg   8520
cggtcgatga ttagggaacg ctcgaactcg gcaatgccgg cgaacacggt caacaccatg   8580
cggccggccg cgcgtggtggt gtcggcccac ggctctgcca ggctacgcag gcccgcgccg   8640
gcctcctgga tgcgctcggc aatgtccagt aggtcgcggg tgctgcgggc caggcggtct   8700
agcctggtca ctgtcacaac gtcgccaggg cgtaggtggt caagcatcct ggccagctcc   8760
gggcggtcgc gcctggtgcc ggtgatcttc tcggaaaaca gcttggtgca gccggccgcg   8820
tgcagttcgg cccgttggtt ggtcaagtcc tggtcgtcgg tgctgacgcg ggcatagccc   8880
agcaggccag cggcggcgct cttgttcatg gcgtaatgtc tccggttcta gtcgcaagta   8940
ttctacttta tgcgactaaa acacgcgaca agaaaacgcc aggaaaaggg cagggcggca   9000
```

```
gcctgtcgcg taacttagga cttgtgcgac atgtcgtttt cagaagacgg ctgcactgaa   9060
cgtcagaagc cgactgcact atagcagcgg aggggttgga ccacaggacg ggtgtggtcg   9120
ccatgatcgc gtagtcgata gtggctccaa gtagcgaagc gagcaggact gggcggcggc   9180
caaagcggtc ggacagtgct ccgagaacgg gtgcgcatag aaattgcatc aacgcatata   9240
gcgctagcag cacgccatag tgactggcga tgctgtcgga atggacgata tcccgcaaga   9300
ggcccggcag taccggcata accaagccta tgcctacagc atccagggtg acggtgccga   9360
ggatgacgat gagcgcattg ttagatttca tacacggtgc ctgactgcgt tagcaattta   9420
actgtgataa actaccgcat taaagctagc ttgcttggtc gttccgcgtg aacgtcggct   9480
cgattgtacc tgcgttcaaa tactttgcga tcgtgttgcg cgcctgcccg gtgcgtcggc   9540
tgatctcacg gatcgactgc ttctctcgca acgccatccg acggatgatg tttaaaagtc   9600
ccatgtggat cactccgttg ccccgtcgct caccgtgttg ggggaaggt gcacatggct    9660
cagttctcaa tggaaattat ctgcctaacc ggctcagttc tgcgtagaaa ccaacatgca   9720
agctccaccg ggtgcaaagc ggcagcggcg gcaggatata ttcaattgta aatggcttca   9780
tgtccgggaa atctacatgg atcagcaatg agtatgatgg tcaatatgga gaaaagaaa    9840
gagtaattac cattttttt tcaattcaaa aatgtagatg tccgcagcgt tattataaaa    9900
tgaaagtaca ttttgataaa acgacaaatt acgatccgtc gtatttatag gcgaaagcaa   9960
taaacaaatt attctaattc ggaaatcttt atttcgacgt gtctacattc acgtccaaat  10020
gggggcttag atgagaaact tcacgatcga tgccttgatt tcgccattcc cagatacccca 10080
tttcatcttc agattggtct gagattatgc gaaaatatac actcatatac ataaatactg  10140
acagtttgag ctaccaattc agtgtagccc attacctcac ataattcact caaatgctag  10200
gcagtctgtc aactcggcgt caatttgtcg gccactatac gatagttgcg caaattttca   10260
aagtcctggc ctaacatcac acctctgtcg gcggcgggtc ccatttgtga taaatccacc  10320
atatcgaatt aattcagact cctttgcccc agagatcaca atggacgact tcctctatct  10380
ctacgatcta gtcaggaagt tcgacggaga aggtgacgat accatgttca ccactgataa  10440
tgagaagatt agccttttca atttcagaaa gaatgctaac ccacagatgg ttagagaggc  10500
ttacgcagca ggtctcatca agacgatcta cccgagcaat aatctccagg agatcaaata  10560
ccttcccaag aaggttaaag atgcagtcaa aagattcagg actaactgca tcaagaacac  10620
agagaaagat atatttctca agatcagaag tactattcca gtatggacga ttcaaggctt  10680
gcttcacaaa ccaaggcaag taatagagat tggagtctct aaaaaggtag ttcccactga  10740
atcaaaggcc atggagtcaa agattcaaat agaggaccta acagaactcg ccgtaaagac  10800
tggcgaacag ttcatacaga gtctcttacg actcaatgac aagaagaaaa tcttcgtcaa  10860
catggtggag cacgacacgc ttgtctactc caaaaatatc aaagatacag tctcagaaga  10920
ccaaagggca attgagactt ttcaacaaag ggtaatatcc ggaaacctcc tcggattcca  10980
ttgcccagct atctgtcact ttattgtgaa gatagtggaa aaggaaggtg ctcctacaa   11040
atgccatcat tgcgataaag gaaaggccat cgttgaagat gcctctgccg acagtggtcc  11100
caaagatgga cccccaccca cgaggagcat cgtggaaaaa gaagacgttc caaccacgtc  11160
ttcaaagcaa gtggattgat gtgatatctc cactgacgta agggatgacg cacaatccca  11220
ctatccttcg caagacccctt cctctatata aggaagttca tttcatttgg agaggacacg  11280
ctgaaatcac cagtctccaa gcttgcgggg atcgtttcgc atgattgaac aagatggatt  11340
```

```
gcacgcaggt tctccggccg cttgggtgga gaggctattc ggctatgact gggcacaaca   11400
gacaatcggc tgctctgatg ccgccgtgtt ccggctgtca gcgcaggggc gcccggttct   11460
ttttgtcaag accgacctgt ccggtgccct gaatgaactg caggacgagg cagcgcggct   11520
atcgtggctg gccacgacgg gcgttccttg cgcagctgtg ctcgacgttg tcactgaagc   11580
gggaagggac tggctgctat tgggcgaagt gccggggcag gatctcctgt catctcacct   11640
tgctcctgcc gagaaagtat ccatcatggc tgatgcaatg cggcggctgc atacgcttga   11700
tccggctacc tgcccattcg accaccaagc gaaacatcgc atcgagcgag cacgtactcg   11760
gatggaagcc ggtcttgtcg atcaggatga tctggacgaa gagcatcagg ggctcgcgcc   11820
agccgaactg ttcgccaggc tcaaggcgcg catgcccgac ggcgaggatc tcgtcgtgac   11880
ccatggcgat gcctgcttgc cgaatatcat ggtggaaaat ggccgctttt ctggattcat   11940
cgactgtggc cggctgggtg tggcggaccg ctatcaggac atagcgttgg ctacccgtga   12000
tattgctgaa gagcttggcg gcgaatgggc tgaccgcttc ctcgtgcttt acggtatcgc   12060
cgctcccgat tcgcagcgca tcgccttcta tcgccttctt gacgagttct tctgagcggg   12120
actctggggt tcgaaatgac cgaccaagcg acgcccaacc tgccatcacg agatttcgat   12180
tccaccgccg ccttctatga aaggttgggc ttcggaatcg ttttccggga cgccggctgg   12240
atgatcctcc agcgcgggga tctcatgctg gagttcttcg cccacccccgg atcgatccaa   12300
cacttacgtt tgcaacgtcc aagagcaaat agaccacgaa cgccggaagg ttgccgcagc   12360
gtgtggattg cgtctcaatt ctctcttgca ggaatgcaat gatgaatatg atactgacta   12420
tgaaactttg agggaatact gcctagcacc gtcacctcat aacgtgcatc atgcatgccc   12480
tgacaacatg gaacatcgct attttctga agaattatgc tcgttggagg atgtcgcggc   12540
aattgcagct attgccaaca tcgaactacc cctcacgcat gcattcatca atattattca   12600
tgcggggaaa ggcaagatta atccaactgg caaatcatcc agcgtgattg gtaacttcag   12660
ttccagcgac ttgattcgtt ttggtgctac ccacgttttc aataaggacg agatggtgga   12720
gtaaagaagg agtgcgtcga agcagatcgt tcaaacattt ggcaataaag tttcttaaga   12780
ttgaatcctt ttgccggtct tgcgatgatt atcatataat ttctgttgaa ttacgttaag   12840
catgtaataa ttaacatgta atgcatgacg ttatttatga gatgggtttt tatgattaga   12900
gtcccgcaat tatacattta atacgcgata gaaaacaaaa tatagcgcgc aaactaggat   12960
aaattatcgc gcgcggtgtc atctatgtta ctagatcgat caaacttcgg tactgtgtaa   13020
tgacgatgag caatcgagag gctgactaac aaaaggtaca tcgcgatgga tcgatccatt   13080
cgccattcag gctgcgcaac tgttgggaag gcgatcggt gcgggcctct tcgctattac   13140
gccagctggc gaaaggggga tgtgctgcaa ggcgattaag ttgggtaacg ccagggtttt   13200
cccagtcacg acgttgtaaa acgacggcca gtgaattcct gcagcccggg ggatccgccc   13260
actcgaggcg cgccgtcgac ggatccgtac gagatccggc cggccagatc ctgcaggaga   13320
tccaagcttt tgatccatgc ccttcatttg ccgcttatta attaatttgg taacagtccg   13380
tactaatcag ttacttatcc ttcccccatc ataattaatc ttggtagtct cgaatgccac   13440
aacactgact agtctcttgg atcataagaa aaagccaagg aacaaaagaa gacaaaacac   13500
aatgagagta tcctttgcat agcaatgtct aagttcataa aattcaaaca aaacgcaat   13560
cacacacagt ggacatcact tatccactag ctgatcagga tcgccgcgtc aagaaaaaaa   13620
aactggaccc caaaagccat gcacaacaac acgtactcac aaaggtgtca atcgagcagc   13680
```

```
ccaaaacatt caccaactca acccatcatg agccctcaca tttgttgttt ctaacccaac    13740
ctcaaactcg tattctcttc cgccacctca tttttgttta tttcaacacc cgtcaaactg    13800
catgccaccc cgtggccaaa tgtccatgca tgttaacaag acctatgact ataaatagct    13860
gcaatctcgg cccaggtttt catcatcaag aaccagttca atatcctagt acaccgtatt    13920
aaagaattta agatatactg cggccgcacc atggaagcag ccaaagaatt ggtttccatc    13980
gtccaagagg agctccccaa ggtggactat gcccagcttt ggcaggatgc cagcagctgt    14040
gaggtccttt acctctcggt ggcattcgtg gcgatcaagt tcatgctgcg cccactggac    14100
ctgaagcgcc aggccacctt gaagaagctg ttcacagcat acaacttcct catgtcgatc    14160
tattcctttg gctccttcct ggccatggcc tatgccctat cagtaactgg catcctctcc    14220
ggcgactgtg agacggcgtt caacaacgat gtgttcagga tcacaactca gctgttctac    14280
ctcagcaagt tcgtagagta catcgactcc ttctaccttc cccttatgga caagccactg    14340
tcgttccttc agttcttcca tcatttgggg gcccccattg acatgtggct attctacaaa    14400
taccgcaacg aaggagtctg gatctttgtc ctgttgaatg ggttcattca ctggatcatg    14460
tacggttact attggacgcg gctcatcaag ctgaacttcc ccatgcccaa gaacctgatc    14520
acctccatgc agatcatcca gttcaatgtc gggttctaca tcgtctggaa gtaccgcaat    14580
gtgccatgct accgccagga tgggatgcgc atgtttgcct ggatcttcaa ctactggtat    14640
gtcgggacgg tcttgctgct gttcctcaac ttttacgtgc agacgtacat ccggaagccg    14700
aggaagaacc gagggaagaa ggagtagcgg ccgcaagtat gaactaaaat gcatgtaggt    14760
gtaagagctc atggagagca tggaatattg tatccgacca tgtaacagta taataactga    14820
gctccatctc acttcttcta tgaataaaca aaggatgtta tgatatatta acactctatc    14880
tatgcacctt attgttctat gataaatttc ctcttattat tataaatcat ctgaatcgtg    14940
acggcttatg gaatgcttca aatagtacaa aaacaaatgt gtactataag actttctaaa    15000
caattctaac cttagcattg tgaacgagac ataagtgtta agaagacata acaattataa    15060
tggaagaagt ttgtctccat ttatatatta tatattaccc acttatgtat tatattagga    15120
tgttaaggag acataacaat tataaagaga gaagtttgta tccatttata tattatatac    15180
tacccattta tatattatac ttatccactt atttaatgtc tttataaggt ttgatccatg    15240
atatttctaa tattttagtt gatatgtata tgaaagggta ctatttgaac tctcttactc    15300
tgtataaagg ttggatcatc cttaaagtgg gtctatttaa ttttattgct tcttacagat    15360
aaaaaaaaaa ttatgagttg gtttgataaa atattgaagg atttaaaata ataataaata    15420
acatataata tatgtatata aatttattat aatataacat ttatctataa aaagtaaat    15480 attgtcataa atctatacaa tcgtttagcc ttgctggacg aatctcaatt atttaaacga    15540
gagtaaacat atttgacttt ttggttattt aacaaattat tatttaacac tatatgaaat    15600 ttttttttt atcagcaaag aataaaatta aattaagaag acaatggtg tcccaatcct     15660 tatacaacca acttccacaa gaaagtcaag tcagagacaa caaaaaaaca agcaaaggaa    15720 atttttaat ttgagttgtc ttgtttgctg cataatttat gcagtaaaac actacacata     15780 accctttag cagtagagca atggttgacc gtgtgcttag cttctttat tttatttttt      15840 tatcagcaaa gaataaataa aataaaatga gacacttcag ggatgtttca acaagcttgg    15900
```

DELTA-9 ELONGASES AND THEIR USE IN MAKING POLYUNSATURATED FATTY ACIDS

This application claims the benefit of U.S. Provisional Application No. 60/911,925, filed Apr. 16, 2007, the entire content of which is hereby incorporated by reference.

FIELD OF THE INVENTION

This invention is in the field of biotechnology, in particular, this pertains to polynucleotide sequences encoding delta-9 elongases and the use of these elongases in making long-chain polyunsaturated fatty acids (PUFAs).

BACKGROUND OF THE INVENTION

The importance of PUFAs is undisputed. For example, certain PUFAs are important biological components of healthy cells and are recognized as: "essential" fatty acids that cannot be synthesized de novo in mammals and instead must be obtained either in the diet or derived by further elongation and desaturation of linoleic acid (LA; 18:2 ω-6) or α-linolenic acid (ALA; 18:3 ω-3); constituents of plasma membranes of cells, where they may be found in such forms as phospholipids or triacylglycerols; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain ω-3 PUFAs produces cardiovascular protective effects (Dyerberg et al., Amer. J. Clin. Nutr. 28:958-966 (1975); Dyerberg et al., Lancet. 2(8081):117-119 (1978); Shimokawa, H., World Rev. Nutr. Diet 88:100-108 (2001); von Schacky et al., World Rev. Nutr. Diet 88:90-99 (2001)). Numerous other studies document wide-ranging health benefits conferred by administration of omega-3 and/or omega-6 PUFAs against a variety of symptoms and diseases (e.g., asthma, psoriasis, eczema, diabetes, cancer).

Today, a variety of different hosts including plants, algae, fungi and yeast are being investigated as means for commercial PUFA production via numerous divergent efforts. Although the natural PUFA-producing abilities of the host organisms are sometimes essential to a given methodology, genetic engineering has also proven that the natural abilities of some hosts (even those natively limited to LA and ALA fatty acid production) can be substantially altered to result in high-level production of various long-chain omega-3/omega-6 PUFAs. Whether this effect is the result of natural abilities or recombinant technology, production of arachidonic acid (ARA; 20:4 ω-6), eicosapentaenoic acid (EPA; 20:5 ω-3) and docosahexaenoic acid (DHA; 22:6 ω-3) all require expression of either the delta-9 elongase/delta-8 desaturase pathway (which operates in some organisms, such as euglenoid species and which is characterized by the production of eicosadienoic acid (EDA; 20:2 ω-6) and/or eicosatrienoic acid (ETrA; 20:3 ω-3)) or the delta-6 desaturase/delta-6 elongase pathway (which is predominantly found in algae, mosses, fungi, nematodes and humans and which is characterized by the production of γ-linoleic acid (GLA; 18:3 ω-6) and/or stearidonic acid (STA; 18:4%-3)) (FIG. 6). A delta-6 elongase is also known as a $C_{18/20}$ elongase.

The delta-8 desaturase enzymes identified thus far have the ability to convert both EDA to dihomo-γ-linolenic acid (DGLA; 20:3) and ETrA to eicosatetraenoic acid (ETA; 20:4) (wherein ARA are EPA are subsequently synthesized from DGLA and ETA, respectively, following reaction with a delta-5 desaturase, while DHA synthesis requires subsequent expression of an additional $C_{20/22}$ elongase and a delta-4 desaturase).

Based on the role delta-8 desaturase enzymes play in the synthesis of e.g., ARA, EPA and DHA, there has been effort to identify and characterize these enzymes. Initial efforts on the isolation and characterization of delta-8 desaturases from Euglena gracilis; and, several sequence variations within the Euglena gracilis delta-8 desaturase have been reported (see, e.g., Wallis et al., Arch. Biochem. and Biophys. 365(2):307-316 (1999); PCT Publication No. WO 2000/34439; U.S. Pat. No. 6,825,017; PCT Publication No. WO 2004/057001). Also, Applicants'Assignee's co-pending applications having U.S. application Ser. Nos. 11/166,003 and 11/166,993 filed Jun. 24, 2005 (PCT Publication Nos. WO 2006/012325 and WO 2006/012326; both published Feb. 2, 2006) discloses amino acid and nucleic acid sequences for a Euglena gracilis delta-8 desaturase.

More recently, PCT Publication No. WO 2005/103253 (published Apr. 22, 2005) discloses amino acid and nucleic acid sequences for a delta-8 desaturase enzyme from Pavlova salina (see also U.S. Publication No. 2005/0273885). Sayanova et al. (FEES Lett. 580:1946-1952 (2006)) describes the isolation and characterization of a cDNA from the free living soil amoeba Acanthamoeba castellanii that, when expressed in Arabidopsis, encodes a $C_{20}$ delta-8 desaturase. Also, Applicants' Assignee's co-pending application having U.S. patent application Ser. No. 11/737,772 (filed Apr. 20, 2007) discloses amino acid and nucleic acid sequences for a delta-8 desaturase enzyme from Pavlova lutheri (CCMP459). U.S. patent application Ser. No. 11/876,115 (filed Oct. 22, 2007) discloses amino acid and nucleic acid sequences for a delta-8 desaturase enzyme from Tetruetreptia pomquetensis CCMP1491, Eutreptiella sp. CCMP389 and Eutreptiella cf_gymnastica CCMP1594.

Based on the utility of expressing delta-8 desaturases in conjunction with delta-9 elongases, there has also been effort to identify and characterize delta-9 elongases from various sources. Most delta-9 elongase enzymes identified so far have the ability to convert both LA to EDA and ALA to ETrA (wherein DGLA and ETA are subsequently synthesized from EDA and ETrA, respectively, following reaction with a Δ8 desaturase; ARA and EPA are subsequently synthesized from DGLA and ETA, respectively, following reaction with a Δ5 desaturase; and, DHA synthesis requires subsequent expression of an additional $C_{20/22}$ elongase and a Δ4 desaturase). A delta-9 elongase from Isochrysis galbana has been publicly available (described in GenBank Accession No. AAL37626, as well as PCT Publication No. WO 02/077213). Applicants' Assignee's co-pending application having U.S. application Ser. No. 11/601,563 (filed Nov. 16, 2006, which published May 24, 2007), discloses a delta-9 elongase from Eulgena gracilis. Applicants' Assignee's co-pending application having U.S. application Ser. No. 11/601,564 filed Nov. 16, 2006, discloses a delta-9 elongase from Eutreptiella sp. CCMP389.

Applicants' Assignee has a number of patent applications concerning the production of PUFAs in oleaginous yeasts (i.e., Yarrowia lipolytica), including: PCT Publication Nos. WO 2004/101757 and WO 2004/101753 (both published Nov. 25, 2004); U.S. application Ser. No. 11/265,761 (filed Nov. 2, 2005); U.S. application Ser. No. 11/264,784 (filed Nov. 1, 2005); and U.S. application Ser. No. 11/264,737 (filed Nov. 1, 2005).

Relatedly, PCT Publication No. WO 2004/071467 (published Aug. 26, 2004) concerns the production of PUFAs in plants, while PCT Publication No. WO 2004/071178 (published Aug. 26, 2004) concerns annexin promoters and their use in expression of transgenes in plants; both are Applicants' Assignee's copending applications.

SUMMARY OF THE INVENTION

The present invention concerns an isolated polynucleotide comprising:
(a) a nucleotide sequence encoding a polypeptide having delta-9 elongase activity, wherein the polypeptide has at least 80% amino acid identity, based on the Clustal V method of alignment, when compared to an amino acid sequence as set forth in SEQ ID NO:13 or SEQ ID NO:14;
(b) a nucleotide sequence encoding a polypeptide having delta-8 desaturase activity, wherein the nucleotide sequence has at least 80% sequence identity, based on the BLASTN method of alignment, when compared to a nucleotide sequence as set forth in SEQ ID NO:11 or SEQ ID NO:12;
(c) a nucleotide sequence encoding a polypeptide having delta-8 desaturase activity, wherein the nucleotide sequence hybridizes under stringent conditions to a nucleotide sequence as set forth in SEQ ID NO:11 or SEQ ID NO:12; or
(d) a complement of the nucleotide sequence of (a), (b) or (c), wherein the complement and the nucleotide sequence consist of the same number of nucleotides and are 100% complementary.

In a second embodiment, the invention concerns a recombinant DNA construct comprising any of the isolated polynucleotides of the invention operably linked to at least one regulatory sequence.

In a third embodiment, the invention concerns a plant cell comprising in its genome the recombinant DNA construct of the invention.

In a fourth embodiment, the invention concerns a method for transforming a plant cell, comprising transforming a plant cell with a recombinant construct of the invention or an isolated polynucleotide of the invention and selecting those plant cells transformed with the recombinant construct or the isolated polynucleotide.

In a fifth embodiment, the invention concerns transgenic seed comprising in its genome the recombinant construct of the invention or a transgenic seed obtained from a plant made by a method of the invention. Also of interest is oil or by-products obtained from such transgenic seeds.

In a sixth embodiment, the invention concerns a method for making long-chain polyunsaturated fatty acids in a plant cell comprising:
(a) transforming a plant cell with the recombinant construct of the invention; and
(b) selecting those transformed plant cells that make long-chain polyunsaturated fatty acids.

In a seventh embodiment, the invention concerns a method for producing at least one polyunsaturated fatty acid in an oilseed plant cell comprising:
(a) transforming an oilseed plant cell with a first recombinant DNA construct comprising an isolated polynucleotide encoding at least one delta-9 elongase polypeptide, operably linked to at least one regulatory sequence and at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase;
(b) regenerating an oilseed plant from the transformed cell of step (a); and
(c) selecting those seeds obtained from the plants of step (b) having an altered level of polyunsaturated fatty acids when compared to the level in seeds obtained from a nontransformed oilseed plant.

In an eighth embodiment, the invention concerns an oilseed plant comprising in its genome the recombinant construct of the invention. Suitable oilseed plants include, but are not limited to, soybean, *Brassica* species, sunflower, maize, cotton, flax and safflower.

In a ninth embodiment, the invention concerns an oilseed plant comprising:
(a) a first recombinant DNA construct comprising an isolated polynucleotide encoding at least one delta-9 elongase polypeptide, operably linked to at least one regulatory sequence; and
(b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase.

Also of interest are transgenic seeds obtained from such oilseed plants as well as oil or by-products obtained from these transgenic seeds. A preferred product is lecithin.

In a tenth embodiment, the invention concerns food or feed incorporating an oil or seed of the invention or food or feed comprising an ingredient derived from the processing of the seeds.

In an eleventh embodiment, the invention concerns progeny plants obtained from obtained from a plant made by the method of the invention or an oilseed plant of the invention.

BIOLOGICAL DEPOSITS

The following plasmid has been deposited with the American Type Culture Collection (ATCC), 10801 University Boulevard, Manassas, Va. 20110-2209, and bears the following designation, Accession Number and date of deposit (Table 1).

TABLE 1

| ATCC Deposit | | |
|---|---|---|
| Plasmid | Accession Number | Date of Deposit |
| pKR72 | PTA-6019 | May 28, 2004 |

BRIEF DESCRIPTION OF THE DRAWINGS AND SEQUENCE LISTINGS

The invention can be more fully understood from the following detailed description and the accompanying drawings and Sequence Listing, which form a part of this application.

FIG. 5 are the fatty acid profiles for *Yarrowia lipolytica* expressing pY173-pY174 (see Example 4).

FIGS. 9A and 9B shows a comparison of the nucleotide sequences of EaD9E (same as EaD9Elo) (SEQ ID NO:11) and EaD9ES (SEQ ID NO:40).

The sequence descriptions summarize the Sequences Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2):345-373 (1984).

FIG. 11 shows five events having the highest average EDA content (average of the 5 embryos analyzed) from approximately 30 events transformed with pKR1140 (SEQ ID NO:30; called Experiment MSE2129). Fatty acids are identified as 16:0 (palmitate), 18:0 (stearic acid), 18:1 (oleic acid), LA, ALA, EDA and ERA. Fatty acid compositions are expressed as a weight percent (wt. %) of total fatty acids. Elongation activity is expressed as % delta-9 elongation of C18 fatty acids (delta-9% Elong), calculated according to the following formula: ([product]/[substrate+product])*100. More specifically, the combined percent elongation for LA and ALA is determined as: ([EDA+ERA]/[LA+ALA+EDA+ERA])*100. This elongation is also referred to as the overall % elongation. The individual omega-6 delta-9 elongation (LA % Elong) was calculated as: ([EDA]/[LA+EDA])*100. Similarly, the individual omega-3 delta-9 elongation (ALA % Elong) was calculated as: ([ERA]/[ALA+ERA])*100. The ratio of delta-9 elongation for omega-6 versus omega-3 substrates (Ratio [LA/ALA] % Elong) was obtained by dividing the LA % delta-9 elongation by the ALA % delta-9 elongation.

FIG. 12 shows five events having the highest average DGLA content (average of the 5 embryos analyzed) from approximately 30 events transformed with pKR1151 (SEQ ID NO:39; called MSE2131). Fatty acids are identified as 16:0 (palmitate), 18:0 (stearic acid), 18:1 (oleic acid), LA, ALA, EDA, ERA, DGLA and ETA. Fatty acid compositions are expressed as a weight percent (wt. %) of total fatty acids. Elongation activity is expressed as % delta-9 elongation of C18 fatty acids (C18% delta-9 elong), calculated according to the following formula: ([product]/[substrate+product])*100. More specifically, the combined percent elongation for LA and ALA is determined as: ([DGLA+ETA+EDA+ERA]/[LA+ALA+DGLA+ETA+EDA+ERA])*100. The combined percent desaturation for EDA and ERA is shown as "C20% delta-8 desat", determined as: ([DGLA+ETA]/[DGLA+ETA+EDA+ERA])*100. This is also referred to as the overall % desaturation.

Figure 13:
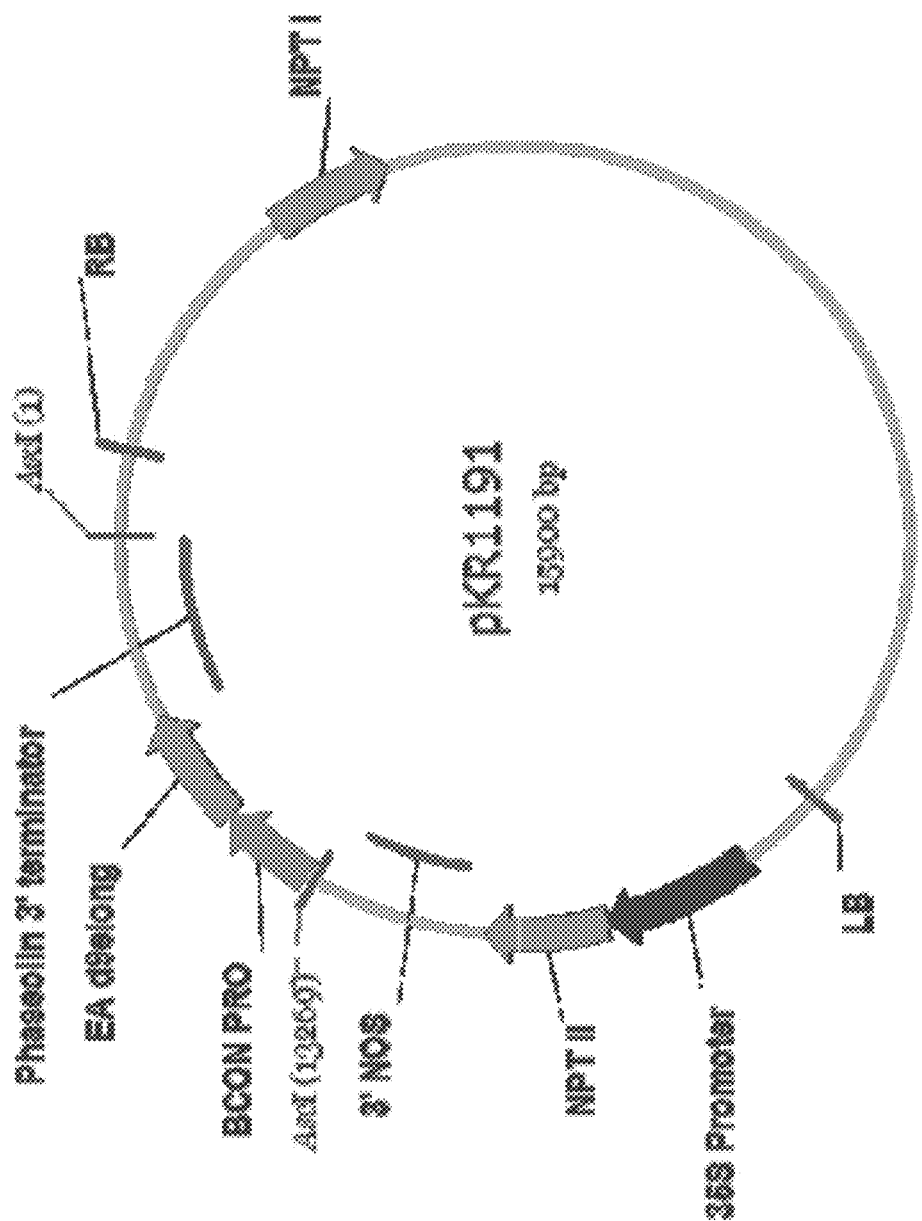

FIG. 13. shows a schematic depiction of pKR1191.

FIG. 14 shows the lipid profiles of T2 bulk seed for the 18 transformed events transformed with pKR1191. Fatty acids are identified as 16:0 (palmitate), 18:0 (stearic acid), 18:1 (oleic acid), LA, ALA, 20:0 (eicosanoic acid), 20:1 (eicosenoic acid), EDA and ERA. Fatty acid compositions are expressed as a weight percent (wt. %) of total fatty acids. The combined percent elongation for LA and ALA is shown as "delta-9% Elong", determined as: ([EDA+ERA]/[LA+ALA])*100. This is also referred to as the overall % elongation.

SEQ ID NO:1 is the nucleotide sequence of the *Euglena anabaena* delta-9 elongase cDNA (EaD9Elo1 cDNA).

SEQ ID NO:2 is the nucleotide sequence of the *Euglena anabaena* delta-9 elongase cDNA (EaD9Elo2 cDNA).

SEQ ID NO:3 is the nucleotide sequence of the *Euglena gracilis* delta-9 elongase coding sequence. (EgD9e).

SEQ ID NO:4 is the nucleotide sequence of the *Euglena gracilis* elongase sense oligonucleotide oEugEL1-1.

SEQ ID NO:5 is the nucleotide sequence of the *Euglena gracilis* elongase sense oligonucleotide oEugEL1-2.

SEQ ID NO:6 is the nucleotide sequence of plasmid pKR906.

SEQ ID NO:7 is the nucleotide sequence of the M13F universal primer.

SEQ ID NO:8 is the nucleotide sequence of the M13-28Rev primer.

SEQ ID NO:9 is the nucleotide sequence of plasmid pLF121-1.

SEQ ID NO:10 is the nucleotide sequence of plasmid pLF121-2.

SEQ ID NO:11 is the nucleotide sequence of the *Euglena anabaena* delta-9 elongase coding sequence (EaD8Des1 CDS).

SEQ ID NO:12 is the nucleotide sequence of the *Euglena anabaena* delta-9 elongase coding sequence (EaD8Des2 CDS).

SEQ ID NO:13 is the amino acid sequence of the *Euglena anabaena* delta-9 elongase (EaD9Elo1).

SEQ ID NO:14 is the amino acid sequence of the *Euglena anabaena* delta-9 elongase (EaD9Elo2).

SEQ ID NO:15 is the amino acid sequence of the *Isochrysis galbana* delta-9 elongase (IgD9e).

SEQ ID NO:16 is the amino acid sequence of the *Euglena gracilis* delta-9 elongase (EgD9e).

SEQ ID NO:17 is the nucleotide sequence of plasmid pDMW263.

SEQ ID NO:18 is the nucleotide sequence of plasmid pDMW237.

SEQ ID NO:19 is the nucleotide sequence of plasmid pY115.

SEQ ID NO:20 is the nucleotide sequence of primer oYFBA1.

SEQ ID NO:21 is the nucleotide sequence of primer oYFBA1-6.

SEQ ID NO:22 is the nucleotide sequence of plasmid pY158.

SEQ ID NO:23 is the nucleotide sequence of plasmid pY159.

SEQ ID NO:24 is the nucleotide sequence of plasmid pY173.

SEQ ID NO:25 is the nucleotide sequence of plasmid pY174.

SEQ ID NO:26 is the nucleotide sequence of primer oEAd9el1-1.

SEQ ID NO:27 is the nucleotide sequence of primer oEAd9el1-2.

SEQ ID NO:28 is the nucleotide sequence of plasmid pKR1137.

SEQ ID NO:29 is the nucleotide sequence of plasmid pKR72.

SEQ ID NO:30 is the nucleotide sequence of plasmid pKR1140.

SEQ ID NO:31 is the nucleotide sequence of *Tetruetreptia pomquetensis* CCMP1491 delta-8 desaturase coding sequence (TpomD8) (which is described in U.S. patent application Ser. No. 11/876,115 (filed Oct. 22, 2007).

SEQ ID NO:32 is the nucleotide sequence of the SMART IV oligonucleotide.

SEQ ID NO:33 is the nucleotide sequence of the Adaptor Primer from Invitrogen 3'-RACE kit.

SEQ ID NO:34 is the nucleotide sequence of primer Tpom-Not-5.

SEQ ID NO:35 is the nucleotide sequence of primer Tpom-Not-3.

SEQ ID NO:36 is the nucleotide sequence of plasmid pLF114-10.

SEQ ID NO:37 is the nucleotide sequence of plasmid pKR457.

SEQ ID NO:38 is the nucleotide sequence of plasmid pKR1145.

SEQ ID NO:39 is the nucleotide sequence of plasmid pKR1151.

SEQ ID NO:40 is the nucleotide sequence of the codon-optimized *Euglena anabaena* delta-9 elongase gene (EaD9ES).

SEQ ID NO:41 is the nucleotide sequence of plasmid pEaD9ES.

SEQ ID NO:42 is the nucleotide sequence of plasmid pKR1191

DETAILED DESCRIPTION OF THE INVENTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

The present invention relates to delta-9 elongase enzymes and nucleic acid for encoding the same isolated from *Euglena anabaena*. These are useful for, inter alia, for the manipulation of biochemical pathways for the production of PUFAs. Thus, the subject invention finds many applications.

PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolic progeny. For example, treatment with EPA can result not only in increased levels of EPA, but also downstream products of EPA such as eicosanoids (i.e., prostaglandins, leukotrienes, thromboxanes). Complex regulatory mechanisms can make it desirable to combine various PUFAs, or add different conjugates of PUFAs, in order to prevent, control or overcome such mechanisms to achieve the desired levels of specific PUFAs in an individual.

In the context of this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Triacylglycerols" are abbreviated TAGs.

The term "fatty acids" refers to long-chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in PCT Publication No. WO 2004/101757.

Fatty acids are described herein by a simple notation system of "X:Y", wherein X is number of carbon (C) atoms in the particular fatty acid and Y is the number of double bonds. The number following the fatty acid designation indicates the position of the double bond from the carboxyl end of the fatty acid with the "c" affix for the cis-configuration of the double bond (e.g., palmitic acid (16:0), stearic acid (18:0), oleic acid (18:1, 9c), petroselinic acid (18:1, 6c), LA (18:2, 9c,12c), GLA (18:3, 6c,9c,12c) and ALA (18:3, 9c,12c,15c)). Unless otherwise specified, 18:1, 18:2 and 18:3 refer to oleic, LA and ALA fatty acids, respectively. If not specifically written as otherwise, double bonds are assumed to be of the cis configuration. For instance, the double bonds in 18:2 (9,12) would be assumed to be in the cis configuration.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the table summarizes the common names of omega-3 and omega-6 fatty acids and their precursors, the abbreviations that will be used throughout the remainder of the specification, and each compounds' chemical name.

TABLE 2

Nomenclature of Polyunsaturated Fatty Acids and Precursors

| Common Name | Abbreviation | Chemical Name | Shorthand Notation |
|---|---|---|---|
| myristic | — | tetradecanoic | 14:0 |
| palmitic | PA | hexadecanoic | 16:0 |
| palmitoleic | — | 9-hexadecenoic | 16:1 |
| stearic | — | octadecanoic | 18:0 |
| oleic | — | cis-9-octadecenoic | 18:1 |
| linoleic | LA | cis-9,12-octadecadienoic | 18:2 ω-6 |
| gamma-linolenic | GLA | cis-6,9,12-octadecatrienoic | 18:3 ω-6 |
| eicosadienoic | EDA | cis-11,14-eicosadienoic | 20:2 ω-6 |
| dihomo-gamma-linolenic | DGLA | cis-8,11,14-eicosatrienoic | 20:3 ω-6 |
| sciadonic | SCI | cis-5,11,14-eicosatrienoic | 20:3b ω-6 |
| arachidonic | ARA | cis-5,8,11,14-eicosatetraenoic | 20:4 ω-6 |
| alpha-linolenic | ALA | cis-9,12,15-octadecatrienoic | 18:3 ω-3 |
| stearidonic | STA | cis-6,9,12,15-octadecatetraenoic | 18:4 ω-3 |

TABLE 2-continued

Nomenclature of Polyunsaturated Fatty Acids and Precursors

| Common Name | Abbreviation | Chemical Name | Shorthand Notation |
|---|---|---|---|
| eicosatrienoic | ETrA or ERA | cis-11,14,17-eicosatrienoic | 20:3 ω-3 |
| eicosatetraenoic | ETA | cis-8,11,14,17-eicosatetraenoic | 20:4 ω-3 |
| juniperonic | JUP | cis-5,11,14,17-eicosatrienoic | 20:4b ω-3 |
| eicosapentaenoic | EPA | cis-5,8,11,14,17-eicosapentaenoic | 20:5 ω-3 |
| docosapentaenoic | DPA | cis-7,10,13,16,19-docosapentaenoic | 22:5 ω-3 |
| docosahexaenoic | DHA | cis-4,7,10,13,16,19-docosahexaenoic | 22:6 ω-3 |

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to LA, EDA, GLA, DGLA, ARA, ALA, STA, ETrA, ETA, EPA, DPA and DHA. This process is well described in the literature (e.g., see PCT Publication No. WO 2006/052870). Simplistically, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzyme" refers to any of the following enzymes (and genes which encode said enzymes) associated with the biosynthesis of a PUFA, including: a delta-4 desaturase, a delta-5 desaturase, a delta-6 desaturase, a delta-12 desaturase, a delta-15 desaturase, a delta-17 desaturase, a delta-9 desaturase, a delta-8 desaturase, a delta-9 elongase, a $C_{14/18}$ elongase, a $C_{16/18}$ elongase, a $C_{18/20}$ elongase and/or a $C_{20/22}$ elongase.

Figure 1:
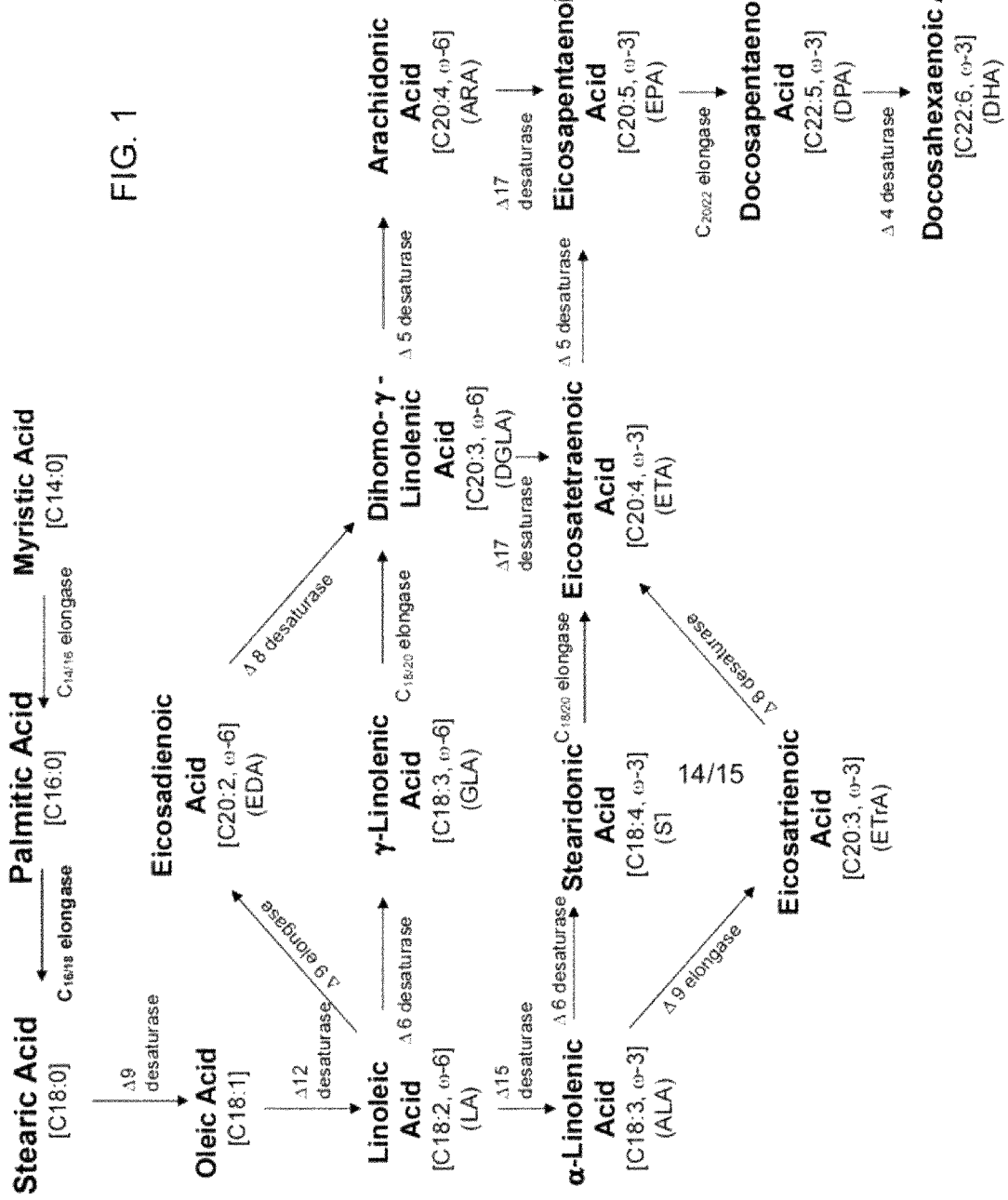
FIG. 1 is a representative omega-3 and omega-6 fatty acid pathway providing for the conversion of myristic acid through various intermediates to DHA.

The term "omega-3/omega-6 fatty acid biosynthetic pathway" refers to a set of genes which, when expressed under the appropriate conditions encode enzymes that catalyze the production of either or both omega-3 and omega-6 fatty acids. Typically the genes involved in the omega-3/omega-6 fatty acid biosynthetic pathway encode PUFA biosynthetic pathway enzymes. A representative pathway is illustrated in FIG. 1, providing for the conversion of myristic acid through various intermediates to DHA, which demonstrates how both omega-3 and omega-6 fatty acids may be produced from a common source. The pathway is naturally divided into two portions where one portion will generate omega-3 fatty acids and the other portion, omega-6 fatty acids.

The term "functional" as used herein in context with the omega-3/omega-6 fatty acid biosynthetic pathway means that some (or all of) the genes in the pathway express active enzymes, resulting in in vivo catalysis or substrate conversion. It should be understood that "omega-3/omega-6 fatty acid biosynthetic pathway" or "functional omega-3/omega-6 fatty acid biosynthetic pathway" does not imply that all the PUFA biosynthetic pathway enzyme genes are required, as a number of fatty acid products will only require the expression of a subset of the genes of this pathway.

The term "delta-9 elongase/delta-8 desaturase pathway" refers to a biosynthetic pathway for production of long-chain PUFAs. This pathway, at a minimum, comprises a delta-9 elongase and a delta-8 desaturase, thereby enabling biosynthesis of DGLA and/or ETA from LA and ALA, respectively. With expression of other desaturases and elongases, ARA, EPA, DPA and DHA may also be synthesized. This pathway may be advantageous in some embodiments, as the biosynthesis of GLA and/or STA is excluded.

The term "intermediate fatty acid" refers to any fatty acid produced in a fatty acid metabolic pathway that can be further converted to an intended product fatty acid in this pathway by the action of other metabolic pathway enzymes. For instance, when EPA is produced using the delta-9 elongase/delta-8 desaturase pathway, EDA, ETrA, DGLA, ETA and ARA can be produced and are considered "intermediate fatty acids" since these fatty acids can be further converted to EPA via action of other metabolic pathway enzymes.

The term "by-product fatty acid" refers to any fatty acid produced in a fatty acid metabolic pathway that is not the intended fatty acid product of the pathway nor an "intermediate fatty acid" of the pathway. For instance, when EPA is produced using the delta-9 elongase/delta-8 desaturase pathway, sciadonic acid (SCI) and juniperonic acid (JUP) also can be produced by the action of a delta-5 desaturase on either EDA or ETrA, respectively. They are considered to be "by-product fatty acids" since neither can be further converted to EPA by the action of other metabolic pathway enzymes.

The terms "triacylglycerol", "oil" and "TAGS" refer to neutral lipids composed of three fatty acyl residues esterified to a glycerol molecule (and such terms will be used interchangeably throughout the present disclosure herein). Such oils can contain long-chain PUFAs, as well as shorter saturated and unsaturated fatty acids and longer chain saturated fatty acids. Thus, "oil biosynthesis" generically refers to the synthesis of TAGs in the cell.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

The terms "conversion efficiency" and "percent substrate conversion" refer to the efficiency by which a particular enzyme (e.g., a elongase) can convert substrate to product. The conversion efficiency is measured according to the following formula: ([product]/[substrate product])*100, where 'product' includes the immediate product and all products in the pathway derived from it.

"Desaturase" is a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are delta-8 desaturases that will desaturate a fatty acid between the eighth and ninth carbon atom numbered from the carboxyl-terminal end of the molecule and that can, for example, catalyze the conversion of EDA to DGLA and/or ETrA to ETA. Other useful fatty acid desaturases include, for example: (1) delta-5 desaturases that catalyze the conversion of DGLA to ARA and/or ETA to EPA; (2) delta-6 desaturases that catalyze the conversion of LA to GLA and/or ALA to STA; (3) delta-4 desaturases that catalyze the conversion of DPA to DHA; (4) delta-12 desaturases that catalyze the conversion of oleic acid to LA; (5) delta-15 desaturases that catalyze the conversion of LA to ALA and/or GLA to STA; (6) delta-17 desaturases that catalyze the conversion of ARA to EPA and/or DGLA to ETA; and (7) delta-9 desaturases that catalyze the conversion of palmitic acid to palmitoleic acid (16:1) and/or stearic acid to oleic acid (18:1). In the art, delta-15 and delta-17 desaturases are also occasionally referred to as "omega-3 desaturases", "w-3 desaturases", and/or "ω-3 desaturases", based on their ability to convert omega-6 fatty acids into their omega-3 counterparts (e.g., conversion of LA into ALA and ARA into EPA, respectively). In some embodiments, it is most desirable to empirically determine the specificity of a particular fatty acid elongase by transforming a suitable host with the gene for the fatty acid elongase and determining its effect on the fatty acid profile of the host.

For the purposes herein, the terms "EaD9Elo1" or "EaD9E" refers to a delta-9 elongase enzyme (SEQ ID NO:13) isolated from *Euglena anabaena*, encoded by SEQ ID NO:11 herein. The term "EaD9Elo2" refers to a delta-9 elongase enzyme (SEQ ID NO:14) isolated from *Euglena anabaena*, encoded by SEQ ID NO:12 herein. Likewise, the term "EaD9ES" refers to a delta-9 elongase codon-optimized for expression in *Yarrowia lipolytica*.

For the purposes herein, the term "IgD9e" refers to a delta-9 elongase (SEQ ID NO:15) (NCBI Accession No. AAL37626 [GI 17226123], locus AAL37626, CDS AF390174; GenBank Accession No. AF390174) isolated from *Isochrysis galbana*. In contrast, the term "IgD9eS" refers to a synthetic (codon-optimized) delta-9 elongase derived from the DNA sequence of the *Isochrysis galbana* delta-9 elongase which can be used for expression in *Yarrowia lipolytica*.

Similarly for the purposes herein, the term "EgD9e" refers to a delta-9 elongase (SEQ ID NO:16) isolated from *Euglena gracilis*, encoded by SEQ ID NO:3. EgD9e is described in U.S. application Ser. No. 11/601,563 (filed Nov. 16, 2006, which published May 24, 2007).

Similarly, the term "EgD8" refers to a delta-8 desaturase enzyme isolated from *Euglena gracilis*. EgD8 is 100% identical and functionally equivalent to "Eg5", as described in PCT Publication Nos. WO 2006/012325 and WO 2006/012326 (SEQ ID NO:2 of U.S. Publication No. 20050287652-A1).

The term "elongase system" refers to a suite of four enzymes that are responsible for elongation of a fatty acid carbon chain to produce a fatty acid that is two carbons longer than the fatty acid substrate that the elongase system acts upon. More specifically, the process of elongation occurs in association with fatty acid synthase, whereby CoA is the acyl carrier (Lassner et al., *Plant Cell* 8:281-292 (1996)). In the first step, which has been found to be both substrate-specific and also rate-limiting, malonyl-CoA is condensed with a long-chain acyl-CoA to yield carbon dioxide ($CO_2$) and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongase systems are the conversion of GLA to DGLA, STA to ETA, LA to EDA, ALA to ETRA and EPA to DPA.

For the purposes herein, an enzyme catalyzing the first condensation reaction (i.e., conversion of malonyl-CoA and long-chain acyl-CoA to β-ketoacyl-CoA) will be referred to generically as an "elongase". In general, the substrate selectivity of elongases is somewhat broad but segregated by both chain length and the degree of unsaturation. Accordingly, elongases can have different specificities. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase will utilize a $C_{18}$ substrate (e.g., GLA, STA) and a $C_{20/22}$ elongase will utilize a $C_{20}$ substrate (e.g., EPA). Similarly, a "delta-9 elongase" may be able to catalyze the conversion of LA to EDA and/or ALA to ETrA. It is important to note that some elongases have broad specificity and thus a single enzyme may be capable of catalyzing several elongase reactions. Thus, for example, a delta-9 elongase may also act as a $C_{16/18}$ elongase, $C_{18/20}$ elongase and/or $C_{20/22}$ elongase and may have alternate, but not preferred, specificities for delta-5 and delta-6 fatty acids such as EPA and/or GLA, respectively.

As used herein, "nucleic acid" means a polynucleotide and includes single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deosycytidylate, "G" for guanylate or deoxyguanylate, "U" for uridlate, "T" for deosythymidylate, "R" for purines (A or G), "Y" for pyrimidiens (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for shod probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth et al., Anal. Biochem. 138:267-284 (1984): $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part 1, Chapter 2 "Overview of principles of hybridization and the strategy of nucleic acid probe assays", Elsevier, N.Y. (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, *CABIOS*, 5:151-153 (1989); Higgins, D. G. et al. (1992) *Comput. Appl. Biosci.* 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "genome" as it applies to a plant cells encompasses not only chromosomal DNA found within the nucleus, but organelle DNA found within subcellular components (e.g., mitochondrial, plastid) of the cell.

A "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same that plant is homozygous at that locus. If the alleles present at a given locus on a chromosome differ that plant is heterozygous at that locus.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B. *Biochemistry of Plants* 15:1-82 (1989).

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.* 3:225-236 (1995)).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. *Plant Cell* 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. Molecular Cloning; A Laboratory Manual; Cold Spring Harbor Laboratory: Cold Spring Harbor, N.Y. (1989). Transformation methods are well known to those skilled in the art and are described infra.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

The term "recombinant" refers to an artificial combination of two otherwise separated segments of sequence, e.g., by chemical synthesis or by the manipulation of isolated segments of nucleic acids by genetic engineering techniques.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host (i.e., to a discrete nucleic acid fragment into which a nucleic acid sequence or fragment can be moved.)

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., a mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

As used herein, "transgenic" refers to a plant or a cell which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (Vaucheret et al., Plant J. 16:651-659 (1998); Gura, Nature 404:804-808 (2000)). The overall efficiency of this phenomenon is low, and the extent of the RNA reduction is widely variable. More recent work has described the use of "hairpin" structures that incorporate all, or part, of an mRNA encoding sequence in a complementary orientation that results in a potential "stem-loop" structure for the expressed RNA (PCT Publication No. WO 99/53050, published Oct. 21, 1999; PCT Publication No. WO 02/00904, published Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083, published Aug. 20, 1998). Both of these co-suppressing phenomena have not been elucidated mechanistically, although genetic evidence has begun to unravel this complex situation (El-mayan et al., Plant Cell 10:1747-1757 (1998)).

The term "oleaginous" refers to those organisms that tend to store their energy source in the form of lipid (Weete, In: Fungal Lipid Biochemistry, 2nd Ed., Plenum, 1980). A class of plants identified as oleaginous are commonly referred to as "oilseed" plants. Examples of oilseed plants include, but are not limited to: soybean (*Glycine* and *Soja* sp.), flax (*Linum* sp.), rapeseed (*Brassica* sp.), maize, cotton, safflower (*Carthamus* sp.) and sunflower (*Helianthus* sp.).

Within oleaginous microorganisms the cellular oil or TAG content generally follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)). The term "oleaginous yeast" refers to those microorganisms classified as yeasts that make oil. It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces.*

The term "Euglenophyceae" refers to a group of unicellular colorless or photosynthetic flagellates ("euglenoids") found living in freshwater, marine, soil, and parasitic environments. The class is characterized by solitary unicells, wherein most are free-swimming and have two flagella (one of which may be nonemergent) arising from an anterior invagination known as a reservoir. Photosynthetic euglenoids contain one to many grass-green chloroplasts, which vary from minute disks to expanded plates or ribbons. Colorless euglenoids depend on osmotrophy or phagotrophy for nutrient assimilation. About 1000 species have been described and classified into about 40 genera and 6 orders. Examples of Euglenophyceae include, but are no means limited to, the following genera: *Euglena, Eutreptiella* and *Tetruetreptia*.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores.

"Progeny" comprises any subsequent generation of a plant.
An Overview: Microbial Biosynthesis of Fatty Acids and Triacylglycerols In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in PCT Publication No. WO 2004/101757. Palmitate is the precursor of longer-chain saturated and unsaturated fatty acid derivates, which are formed through the action of elongases and desaturases (FIG. 1).

TAGs (the primary storage unit for fatty acids) are formed by a series of reactions that involve: (1) the esterification of one molecule of acyl-CoA to glycerol-3-phosphate via an acyltransferase to produce lysophosphatidic acid; (2) the esterification of a second molecule of acyl-CoA via an acyltransferase to yield 1,2-diacylglycerol phosphate (commonly identified as phosphatidic acid); (3) removal of a phosphate by phosphatidic acid phosphatase to yield 1,2-diacylglycerol (DAG); and (4) the addition of a third fatty acid by the action of an acyltransferase to form TAG. A wide spectrum of fatty acids can be incorporated into TAGs, including saturated and unsaturated fatty acids and short-chain and long-chain fatty acids.
Biosynthesis of Omega Fatty Acids The metabolic process wherein oleic acid is converted to long chain omega-3/omega-6 fatty acids involves elongation of the carbon chain through the addition of carbon atoms and desaturation of the molecule through the addition of double bonds. This requires a series of special desaturation and elongation enzymes present in the endoplasmic reticulim membrane. However, as seen in FIG. 1 and as described below, there are often multiple alternate pathways for production of a specific long chain omega-3/omega-6 fatty acid.

Specifically, all pathways require the initial conversion of oleic acid to LA, the first of the omega-6 fatty acids, by a delta-12 desaturase. Then, using the "delta-9 elongase/ delta-8 desaturase pathway", long chain omega-6 fatty acids are formed as follows: (1) LA is converted to EDA by a delta-9 elongase; (2) EDA is converted to DGLA by a delta-8 desaturase; and (3) DGLA is converted to ARA by a delta-5 desaturase. Alternatively, the "delta-9 elongase/delta-8 desaturase pathway" can be utilized for formation of long chain omega-3 fatty acids as follows: (1) LA is converted to ALA, the first of the omega-3 fatty acids, by a delta-15 desaturase; (2) ALA is converted to ETrA by a delta-9 elongase; (3) ETrA is converted to ETA by a delta-8 desaturase; (4) ETA is converted to EPA by a delta-5 desaturase; (5) EPA is converted to DPA by a $C_{20/22}$ elongase; and (6) DPA is converted to DHA by a delta-4 desaturase. Optionally, omega-6 fatty acids may be converted to omega-3 fatty acids; for example, ETA and EPA are produced from DGLA and ARA, respectively, by delta-17 desaturase activity.

Alternate pathways for the biosynthesis of omega-3/omega-6 fatty acids utilize a delta-6 desaturase and $C_{18/20}$ elongase (also known as delta-6 elongase, the terms can be used interchangeably) (i.e., the "delta-6 desaturase/delta-6 elongase pathway"). More specifically, LA and ALA may be converted to GLA and STA, respectively, by a delta-6 desaturase; then, a $C_{18/20}$ elongase converts GLA to DGLA and/or STA to ETA.

It is contemplated that the particular functionalities required to be introduced into a specific host organism for production of omega-3/omega-6 fatty acids will depend on the host cell (and its native PUFA profile and/or desaturase/elongase profile), the availability of substrate, and the desired end product(s). For example, expression of the delta-9 elongase/delta-8 desaturase pathway may be preferred in some embodiments, as opposed to expression of the delta-6 desaturase/delta-6 elongase pathway, since PUFAs produced via the former pathway are devoid of GLA.

One skilled in the art will be able to identify various candidate genes encoding each of the enzymes desired for omega-3/omega-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: (1) the substrate specificity of the polypeptide; (2) whether the polypeptide or a component thereof is a rate-limiting enzyme; (3) whether the desaturase or elongase is essential for synthesis of a desired PUFA; and/or (4) co-factors required by the polypeptide. The expressed polypeptide preferably has parameters compatible with the biochemical environment of its location in the host cell (see PCT Publication No. WO 2004/101757 for additional details).

In additional embodiments, it will also be useful to consider the conversion efficiency of each particular desaturase and/or elongase. More specifically, since each enzyme rarely functions with 100% efficiency to convert substrate to product, the final lipid profile of unpurified oils produced in a host cell will typically be a mixture of various PUFAs consisting of the desired omega-3/omega-6 fatty acid, as well as various upstream intermediary PUFAs. Thus, consideration of each enzyme's conversion efficiency is also a variable when optimizing biosynthesis of a desired fatty acid that must be considered in light of the final desired lipid profile of the product.

With each of the considerations above in mind, candidate genes having the appropriate desaturase and elongase activities (e.g., delta-6 desaturases, $C_{18/20}$ elongases, delta-5 desaturases, delta-17 desaturases, delta-15 desaturases, delta-9 desaturases, delta-12 desaturases, $C_{14/16}$ elongases, $C_{16/18}$ elongases, delta-9 elongases, delta-8 desaturases, delta-4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Sequence Identification of Novel Delta-9 Elongases

In the present invention, nucleotide sequences encoding delta-9 elongases have been isolated from *Euglena anabaena* (designated herein as "EaD9Elo1" and "EaD9Elo2").

Thus, the present invention concerns an isolated polynucleotide comprising:
  (a) a nucleotide sequence encoding a polypeptide having delta-9 elongase activity, wherein the polypeptide has at least 80% amino acid identity, based on the Clustal V method of alignment, when compared to an amino acid sequence as set forth in SEQ ID NO:13 [EaD9Elo1] or SEQ ID NO:14 [EaD9Elo2];
  (b) a nucleotide sequence encoding a polypeptide having delta-8 desaturase activity, wherein the nucleotide sequence has at least 80% sequence identity, based on the BLASTN method of alignment, when compared to a nucleotide sequence as set forth in SEQ ID NO:11 [EaD9Elo1] or SEQ ID NO:12 [EaD9Elo2]; or,
  (c) a complement of the nucleotide sequence of (a) or (b), wherein the complement and the nucleotide sequence consist of the same number of nucleotides and are 100% complementary.

In still another aspect, this invention concerns an isolated polynucleotide comprising a nucleotide sequence encoding a polypeptide having delta-9 elongase activity, wherein the nucleotide sequence has at least 90% sequence identity, based on the BLASTN method of alignment, when compared to a nucleotide sequence as set forth in SEQ ID NO:11 or SEQ ID NO:12.

In alternate embodiments, the instant EaD9Elo1 and EaD9Elo1 sequences can be codon-optimized for expression in a particular host organism (see SEQ ID NO:40). As is well known in the art, this can be a useful means to further optimize the expression of the enzyme in the alternate host, since use of host-preferred codons can substantially enhance the expression of the foreign gene encoding the polypeptide. In general, host-preferred codons can be determined within a particular host species of interest by examining codon usage in proteins (preferably those expressed in the largest amount) and determining which codons are used with highest frequency. Then, the coding sequence for a polypeptide of interest having e.g., elongase activity can be synthesized in whole or in part using the codons preferred in the host species.

EaD9Elo1 and/or EaD9Elo2 could be codon-optimized for expression in *Yarrowia lipolytica*, as taught in PCT Publication No. WO 04/101757 and U.S. Pat. No. 7,125,672. In one embodiment, it may be desirable to modify a portion of the codons encoding EaD9Elo1 and/or EaD9Elo2 (as set forth in SEQ ID NOs:11 and 13, respectively) to enhance expression of the gene in a host organism including, but not limited to, a plant or plant part.

One skilled in the art would be able to use the teachings herein to create various other codon-optimized delta-9 elongase proteins suitable for optimal expression in alternate hosts, based on the wildtype EaD9Elo1 and/or EaD9Elo2 sequences. Accordingly, the instant invention relates to any codon-optimized delta-9 elongase protein that is derived from the wildtype EaD9Elo1 (i.e., encoded by SEQ ID NO:11) or the wildtype EaD9Elo2 (i.e., encoded by SEQ ID NO:12).

Identification and Isolation of Homologs

Any of the instant elongase sequences (i.e., EaD9Elo1 or EaD9Elo2) or portions thereof may be used to search for delta-9 elongase homologs in the same or other bacterial, algal, fungal, euglenoid or plant species using sequence analysis software. In general, such computer software matches similar sequences by assigning degrees of homology to various substitutions, deletions, and other modifications.

Alternatively, any of the instant elongase sequences or portions thereof may also be employed as hybridization reagents for the identification of delta-9 elongase homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the delta-9 elongase nucleic acid fragments described herein (or any homologs identified thereof) may be used to isolate genes encoding homologous proteins from the same or other bacterial, algal, fungal, euglenoid or plant species. Isolation of homologous genes using sequence-dependent protocols is well known in the art. Examples of sequence-dependent protocols include, but are not limited to: (1) methods of nucleic acid hybridization; (2) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor et al., *Proc. Acad. Sci. USA* 82:1074 (1985); or strand displacement amplification (SDA), Walker et al., *Proc. Natl. Acad. Sci. U.S.A.*, 89:392 (1992)]; and (3) methods of library construction and screening by complementation.

For example, genes encoding similar proteins or polypeptides to the delta-9 elongases described herein could be isolated directly by using all or a portion of the instant nucleic acid fragments as DNA hybridization probes to screen libraries from e.g., any desired yeast or fungus using methodology well known to those skilled in the art (wherein those organisms producing DGLA and/or ETA would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *PNAS USA* 86:5673 (1989); Loh et al., *Science* 243:217 (1989)).

In other embodiments, any of the delta-9 elongase nucleic acid fragments described herein (or any homologs identified thereof) may be used for creation of new and improved fatty acid elongases. As is well known in the art, in vitro mutagenesis and selection, chemical mutagenesis, "gene shuffling" methods or other means can be employed to obtain mutations of naturally occurring elongase genes. Alternatively, improved fatty acids may be synthesized by domain swapping, wherein a functional domain from any of the delta-9 elongase nucleic acid fragments described herein are exchanged with a functional domain in an alternate elongase gene to thereby result in a novel protein. As used herein, "domain" or "functional domain" refer to nucleic acid sequence(s) that are capable of eliciting a biological response in plants.

Methods for Production of Various Omega-3 and/or Omega-6 Fatty Acids

It is expected that introduction of chimeric genes encoding the delta-9 elongases described herein (i.e., EaD9Elo1 EaD9Elo2 or other mutant enzymes, codon-optimized enzymes or homologs thereof), under the control of the appropriate promoters will result in increased production of DGLA and/or ETA in the transformed host organism, respectively. As such, the present invention encompasses a method for the direct production of PUFAs comprising exposing a fatty acid substrate (i.e., LA and/or ALA) to the elongase enzymes described herein (e.g., EaD9Elo1 or EaD9Elo2), such that the substrate is converted to the desired fatty acid product (i.e., EDA and/or ETrA).

More specifically, it is an object of the present invention to provide a method for the production of EDA in a plant host cell (e.g. soybean), wherein the plant host cell comprises:
 (a) a recombinant construct encoding a delta-9 elongase polypeptide selected from the group consisting of SEQ ID NO:13 and SEQ ID NO:14; and,
 (b) a source of LA;
wherein the plant host cell is grown under conditions such that the delta-9 elongase is expressed and the LA is converted to EDA, and wherein the EDA is optionally recovered.

In alternate embodiments of the present invention, the delta-9 elongase may be used for the use of the enzyme for the conversion of ALA to ETrA. Accordingly the invention provides a method for the production of ETrA, wherein the plant host cell comprises:
 (a) a recombinant construct encoding a delta-9 elongase polypeptide selected from the group consisting of SEQ ID NO:13 and SEQ ID NO:14; and,
 (b) a source of ALA;
wherein the plant host cell is grown under conditions such that the delta-9 elongase is expressed and the ALA is converted to ETrA, and wherein the ETrA is optionally recovered.

Alternatively, each delta-9 elongase gene and its corresponding enzyme product described herein can be used indirectly for the production of various omega-6 and omega-3 PUFAs, including e.g., DGLA, ETA, ARA, EPA, DPA and/or DHA (see FIG. 1; see also PCT Publication No. WO 2004/101757). Indirect production of omega-3/omega-6 PUFAs occurs wherein the fatty acid substrate is converted indirectly into the desired fatty acid product, via means of an intermediate step(s) or pathway intermediate(s). Thus, it is contemplated that the delta-9 elongases described herein (i.e., EaD9Elo1, EaD9Elo2, or other mutant enzymes, codon-optimized enzymes or homologs thereof) may be expressed in conjunction with additional genes encoding enzymes of the PUFA biosynthetic pathway (e.g., delta-6 desaturases, $C_{18/20}$ elongases, delta-17 desaturases, delta-8 desaturases, delta-15 desaturases, delta-9 desaturases, delta-12 desaturases, $C_{14/16}$ elongases, $C_{16/18}$ elongases, delta-9 elongases, delta-5 desaturases, delta-4 desaturases, $C_{20/22}$ elongases) to result in higher levels of production of longer-chain omega-3/omega-6 fatty acids (e.g., ARA, EPA, DPA and DHA).

In preferred embodiments, the delta-9 elongases of the present invention will minimally be expressed in conjunction with a delta-8 desaturases (e.g., a delta-8 desaturase or a codon-optimized delta-8 desaturase). However, the particular genes included within a particular expression cassette will depend on the host cell (and its PUFA profile and/or desaturase/elongase profile), the availability of substrate and the desired end product(s).

The term "delta-6 desaturase/delta-6 elongase pathway" also refers to a biosynthetic pathway for production of long-chain PUFAs. This pathway, at a minimum, comprises a delta-6 desaturase and a delta-6 elongase, thereby enabling biosynthesis of DGLA and/or ETA from LA and ALA, respectively. With expression of other desaturases and elongases, ARA, EPA, DPA and DHA may also be synthesized. Occasionally, a delta-6 elongase may elongate fatty acids other than the intended fatty acid. For instance, delta-6 elongases generally convert GLA to DGLA but some delta-6 elongases may also convert unintended substrates such as LA or ALA to EDA or ETrA, respectively. In a delta-6 desaturase/delta-6 elongase pathway, EDA and ETrA would be considered "by-product fatty acids" as defined herein. Addition of a delta-8 desaturase to a delta-6 desaturase/delta-6 elongase pathway would provided a means to convert the "by-product fatty acids" EDA and ETrA back into the "intermediate fatty acids" (as defined previously) DGLA and ETA, respectively.

Plant Expression Systems, Cassettes and Vectors, and Transformation

In one embodiment, this invention concerns a recombinant construct comprising any one of the delta-9 elongase polynucleotides of the invention operably linked to at least one regulatory sequence suitable for expression in a plant. A promoter is a DNA sequence that directs cellular machinery of a plant to produce RNA from the contiguous coding sequence downstream (3') of the promoter. The promoter region influences the rate, developmental stage, and cell type in which the RNA transcript of the gene is made. The RNA transcript is processed to produce mRNA which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cell to cause termination of the RNA transcript and the addition of polyadenylate nucleotides to the 3' end of the RNA.

The origin of the promoter chosen to drive expression of the delta-9 elongase coding sequence is not important as long as it has sufficient transcriptional activity to accomplish the invention by expressing translatable mRNA for the desired nucleic acid fragments in the desired host tissue at the right time. Either heterologous or non-heterologous (i.e., endogenous) promoters can be used to practice the invention. For example, suitable promoters include, but are not limited to: the alpha prime subunit of beta conglycinin promoter, the Kunitz trypsin inhibitor 3 promoter, the annexin promoter, the glycinin Gy1 promoter, the beta subunit of beta conglycinin promoter, the P34/Gly Bd m 30K promoter, the albumin promoter, the Leg A1 promoter and the Leg A2 promoter.

The annexin, or P34, promoter is described in PCT Publication No. WO 2004/071178 (published Aug. 26, 2004). The level of activity of the annexin promoter is comparable to that of many known strong promoters, such as: (1) the CaMV 35S promoter (Atanassova et al., *Plant Mol. Biol.* 37:275-285 (1998); Battraw and Hall, *Plant Mol. Biol.* 15:527-538 (1990); Holtorf et al., *Plant Mol. Biol.* 29:637-646 (1995); Jefferson et al., *EMBO J.* 6:3901-3907 (1987); Wilmink et al., *Plant Mol. Biol.* 28:949-955 (1995)); (2) the *Arabidopsis* oleosin promoters (Plant et al., *Plant Mol. Biol.* 25:193-205 (1994); Li, Texas A&M University Ph.D. dissertation, pp. 107-128 (1997)); (3) the *Arabidopsis* ubiquitin extension protein promoters (Callis et al., *J Biol. Chem.* 265(21):12486-93 (1990)); (4) a tomato ubiquitin gene promoter (Rollfinke et al., *Gene.* 211(2):267-76 (1998)); (5) a soybean heat shock protein promoter (Schoffl et al., *Mol Gen Genet.* 217(2-3):246-53 (1989)); and, (6) a maize H3 histone gene promoter (Atanassova et al., *Plant Mol Biol.* 37(2):275-85 (1989)).

Another useful feature of the annexin promoter is its expression profile in developing seeds. The annexin promoter is most active in developing seeds at early stages (before 10 days after pollination) and is largely quiescent in later stages. The expression profile of the annexin promoter is different from that of many seed-specific promoters, e.g., seed storage protein promoters, which often provide highest activity in later stages of development (Chen et al., *Dev. Genet.* 10:112-122 (1989); Ellerstrom et al., *Plant Mol. Biol.* 32:1019-1027 (1996); Keddie et al., *Plant Mol. Biol.* 24:327-340 (1994); Plant et al., (supra); Li, (supra)). The annexin promoter has a more conventional expression profile but remains distinct from other known seed specific promoters. Thus, the annexin promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

Following identification of an appropriate promoter suitable for expression of a specific delta-9 elongase coding sequence, the promoter is then operably linked in a sense orientation using conventional means well known to those skilled in the art.

Standard recombinant DNA and molecular cloning techniques used herein are well known in the art and are described more fully in Sambrook, J. et al., In *Molecular Cloning: A Laboratory Manual;* 2nd ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In *Current Protocols in Molecular Biology*; John Wiley and Sons: New York, 1990 (hereinafter "Ausubel et al., 1990").

Once the recombinant construct has been made, it may then be introduced into a plant cell of choice by methods well known to those of ordinary skill in the art (e.g., transfection, transformation and electroporation). Oilseed plant cells are the preferred plant cells. The transformed plant cell is then cultured and regenerated under suitable conditions permitting expression of the long-chain PUFA which is then optionally recovered and purified.

The recombinant constructs of the invention may be introduced into one plant cell; or, alternatively, each construct may be introduced into separate plant cells.

Expression in a plant cell may be accomplished in a transient or stable fashion as is described above.

The desired long-chain PUFAs can be expressed in seed. Also within the scope of this invention are seeds or plant parts obtained from such transformed plants.

Plant parts include differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or a group of tissues that constitute a morphologically and functionally distinct part of a plant. The term "genome" refers to the following: (1) the entire complement of genetic material (genes and non-coding sequences) that is present in each cell of an organism, or virus or organelle; and/or (2) a complete set of chromosomes inherited as a (haploid) unit from one parent.

Thus, this invention also concerns a method for transforming a cell, comprising transforming a cell with the recombinant construct of the invention and selecting those cells transformed with the recombinant construct of the invention.

Also of interest is a method for producing a transformed plant comprising transforming a plant cell with the delta-9 elongase polynucleotides of the instant invention and regenerating a plant from the transformed plant cell.

Methods for transforming dicots (primarily by use of *Agrobacterium tumefaciens*) and obtaining transgenic plants have been published, among others, for: cotton (U.S. Pat. No. 5,004,863; U.S. Pat. No. 5,159,135); soybean (U.S. Pat. No. 5,569,834; U.S. Pat. No. 5,416,011); *Brassica* (U.S. Pat. No. 5,463,174); peanut (Cheng et al. *Plant Cell Rep.* 15:653-657 (1996); McKently et al. *Plant Cell Rep.* 14:699-703 (1995)); papaya (Ling, K. et al. *Bio/technology* 9:752-758 (1991)); and pea (Grant et al. *Plant Cell Rep.* 15:254-258 (1995)). For a review of other commonly used methods of plant transformation see Newell, C. A. (*Mol. Biotechnol.* 16:53-65 (2000)). One of these methods of transformation uses *Agrobacterium rhizogenes* (Tepfler, M. and Casse-Delbart, F. *Microbial. Sci.* 4:24-28 (1987)). Transformation of soybeans using direct delivery of DNA has been published using PEG fusion (PCT Publication No. WO 92/17598), electroporation (Chowrira, G. M. et al., *Mol. Biotechnol.* 3:17-23 (1995); Christou, P. et al., *Proc. Natl. Acad. Sci. U.S.A.* 84:3962-3966 (1987)), microinjection and particle bombardement (McCabe, D. E. et. al., *Bio/Technology* 6:923 (1988); Christou et al., *Plant Physiol.* 87:671-674 (1988)).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, In: Methods for Plant Molecular Biology, (Eds.), Academic: San Diego, Calif. (1988)). This regeneration and growth process typically includes the steps of selection of transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for: the construction, manipulation and isolation of macromolecules (e.g., DNA molecules, plasmids, etc.); the generation of recombinant DNA fragments and recombinant expression constructs; and, the screening and isolating of clones. See, for example: Sambrook et al., Molecular Cloning: A Laboratory Manual, Cold Spring Harbor: NY (1989); Maliga et al., Methods in Plant Molecular Biology, Cold Spring Harbor: NY (1995); Birren et al., Genome Analysis: Detecting Genes, Vol. 1, Cold Spring Harbor: NY (1998); Birren et al., Genome Analysis: Analyzing DNA, Vol. 2, Cold Spring Harbor: NY (1998); Plant Molecular Biology: A Laboratory Manual, eds. Clark, Springer: NY (1997).

Examples of oilseed plants include, but are not limited to: soybean, *Brassica* species, sunflower, maize, cotton, flax and safflower.

Examples of PUFAs having at least twenty carbon atoms and four or more carbon-carbon double bonds include, but are not limited to, omega-3 fatty acids such as EPA, DPA and DHA and the omega-6 fatty acid ARA. Seeds obtained from such plants are also within the scope of this invention as well as oil obtained from such seeds.

Thus, in one embodiment this invention concerns an oilseed plant comprising:
  (a) a first recombinant DNA construct comprising an isolated polynucleotide encoding a delta-9 elongase polypeptide, operably linked to at least one regulatory sequence; and,
  (b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-9 elongase, a delta-12 desaturase, a delta-15 desaturase, a delta-17 desaturase, a $C_{14/16}$ elongase, a $C_{16/18}$ elongase, a $C_{18/20}$ elongase and a $C_{20/22}$ elongase.

Additional desaturases are discussed, for example, in U.S. Pat. Nos. 6,075,183, 5,968,809, 6,136,574, 5,972,664, 6,051,754, 6,410,288 and PCT Publication Nos. WO 98/46763, WO 98/46764, WO 00/12720 and WO 00/40705.

The choice of combination of cassettes used depends in part on the PUFA profile and/or desaturase/elongase profile of the oilseed plant cells to be transformed and the long-chain PUFA which is to be expressed.

In another aspect, this invention concerns a method for making long-chain PUFAs in a plant cell comprising:
  (a) transforming a cell with the recombinant construct of the invention; and,
  (b) selecting those transformed cells that make long-chain PUFAs.

In still another aspect, this invention concerns a method for producing at least one PUFA in a soybean cell comprising:
  (a) transforming a soybean cell with a first recombinant DNA construct comprising:
    (i) an isolated polynucleotide encoding a delta-9 elongase polypeptide, operably linked to at least one regulatory sequence; and,
    (ii) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-9 elongase, a delta-12 desaturase, a delta-15 desaturase, a delta-17 desaturase, a $C_{14/16}$ elongase, a $C_{16/18}$ elongase, a $C_{18/20}$ elongase and a $C_{20/22}$ elongase;
  (b) regenerating a soybean plant from the transformed cell of step (a); and,
  (c) selecting those seeds obtained from the plants of step (b) having an altered level of PUFAs when compared to the level in seeds obtained from a nontransformed soybean plant.

In other preferred embodiments, the at least one additional recombinant DNA construct encodes a polypeptide having delta-9 elongase activity, e.g., the delta-9 elongase isolated or derived from *Isochrysis galbana* (GenBank Accession No. AF390174; IgD9e) or the delta-9 elongase isolated or derived from *Euglena gracilis*.

In other preferred embodiments, the at least one additional recombinant DNA construct encodes a polypeptide having delta-8 desaturase activity. For example, PCT Publication No. WO 2005/103253 (published Apr. 22, 2005) discloses amino acid and nucleic acid sequences for a delta-8 desaturase enzyme from *Pavlova salina* (see also U.S. Publication No. 2005/0273885). Sayanova et al. (*FEBS Lett.* 580:1946-1952 (2006)) describes the isolation and characterization of a cDNA from the free living soil amoeba *Acanthamoeba castellanii* that, when expressed in *Arabidopsis*, encodes a $C_{20}$ delta-8 desaturase. Also, Applicants' Assignee's co-pending application having U.S. patent application Ser. No. 11/737,772 (filed Apr. 20, 2007) discloses amino acid and nucleic acid sequences for a delta-8 desaturase enzyme from *Pavlova lutheri* (CCMP459). U.S. patent application Ser. No. 11/876,115 (filed Oct. 22, 2007) discloses amino acid and nucleic acid sequences for a delta-8 desaturase enzyme from *Tetruetreptia pomquetensis* CCMP1491, *Eutreptiella* sp. CCMP389 and *Eutreptiella cf_gymnastica* CCMP1594.

Microbial Expression Systems, Cassettes and Vectors, and Transformation

The delta-9 elongase genes and gene products described herein (i.e., EaD9Elo1, EaD9Elo2, or other mutant enzymes, codon-optimized enzymes or homologs thereof) may also be produced in heterologous microbial host cells, particularly in the cells of oleaginous yeasts (e.g., *Yarrowia lipolytica*).

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high-level expression of the encoded enzymes.

Vectors or DNA cassettes useful for the transformation of suitable microbial host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed microbial host cell, although it is to be understood that such control regions need not be derived from the genes native to the specific species chosen as a production host.

Initiation control regions or promoters which are useful to drive expression of the instant delta-9 elongase ORFS in the desired microbial host cell are numerous and familiar to those skilled in the art. Virtually any promoter capable of directing expression of these genes in the selected host cell is suitable for the present invention. Expression in a microbial host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species (e.g., see PCT Publication Nos. WO 2004/101757 and WO 2006/052870 for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, when the microbial host is a yeast cell, the termination region is derived from a yeast gene (particularly *Saccharomyces, Schizosaccharomyces, Candida, Yarrowia* or *Kluyveromyces*). The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included. Although not intended to be limiting, termination regions useful in the disclosure herein include: ~100 bp of the 3' region of the *Yarrowia lipolytica* extracellular protease (XPR; GenBank Accession No. M17741); the acyl-coA oxidase (Aco3: GenBank Accession No. AJ001301 and No. CAA04661; Pox3: GenBank Accession No. XP_503244) terminators; the Pex20 (GenBank Accession No. AF054613) terminator; the Pex16 (GenBank Accession No. U75433) terminator; the Lip1 (GenBank Accession No. Z50020) terminator; the Lip2 (GenBank Accession No. AJ012632) terminator; and the 3-oxoacyl-coA thiolase (OCT; GenBank Accession No. X69988) terminator.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the microbial host cell. More specifically, some of the molecular features that have been manipulated to control gene expression include: (1) the nature of the relevant transcriptional promoter and terminator sequences; (2) the number of copies of the cloned gene and whether the gene is plasmid-borne or integrated into the genome of the host cell; (3) the final cellular location of the synthesized foreign protein; (4) the efficiency of translation and correct folding of the protein in the host organism; (5) the intrinsic stability of the mRNA and protein of the cloned gene within the host cell; and (6) the codon usage within the cloned gene, such that its frequency approaches the frequency of preferred codon usage of the host cell. Each of these types of modifications are encompassed in the present invention, as means to further optimize expression of the delta-9 elongase described herein.

Once the DNA encoding a polypeptide suitable for expression in an appropriate microbial host cell (e.g., oleaginous yeast) has been obtained (e.g., a chimeric gene comprising a promoter, ORF and terminator), it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

The preferred method of expressing genes in *Yarrowia lipolytica* is by integration of linear DNA into the genome of the host; and, integration into multiple locations within the genome can be particularly useful when high level expression of genes are desired [e.g., in the Ura3 locus (GenBank Accession No. AJ306421), the Leu2 gene locus (GenBank Accession No. AF260230), the Lys5 gene (GenBank Accession No. M34929), the Aco2 gene locus (GenBank Accession No. AJ001300), the Pox3 gene locus (Pox3: GenBank Accession No. XP_503244); or, Aco3: GenBank Accession No. AJ001301), the delta-12 desaturase gene locus (PCT Publication No. WO2004/104167), the Lip1 gene locus (GenBank Accession No. Z50020) and/or the Lip2 gene locus (GenBank Accession No. AJ012632)].

Advantageously, the Ura3 gene can be used repeatedly in combination with 5-fluoroorotic acid (5-fluorouracil-6-carboxylic acid monohydrate; "5-FOA") selection (infra), to readily permit genetic modifications to be integrated into the *Yarrowia* genome in a facile manner.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a microbial host cell by any standard technique. These techniques include transformation (e.g., lithium acetate transformation [*Methods in Enzymology*, 194:186-187 (1991)]), protoplast fusion, bolistic impact, electroporation, microinjection, or any other method that introduces the gene of interest into the host cell. More specific teachings applicable for oleaginous yeasts (i.e., *Yarrowia lipolytica*) include U.S. Pat. No. 4,880,741 and U.S. Pat. No. 5,071,764 and Chen, D. C. et al. (*Appl. Microbial. Biotechnol.*, 48(2): 232-235 (1997)).

For convenience, a host cell that has been manipulated by any method to take up a DNA sequence (e.g., an expression cassette) will be referred to as "transformed" or "recombinant" herein. Thus, the term "transformed" and "recombinant" are used interchangeably herein. The transformed host will have at least one copy of the expression construct and may have two or more, depending upon whether the gene is integrated into the genome, amplified or is present on an extrachromosomal element having multiple copy numbers.

The transformed host cell can be identified by various selection techniques, as described in PCT Publication Nos. WO 2004/101757 and WO 2006/052870. Preferred selection methods for use herein are resistance to kanamycin, hygromycin and the amino glycoside G418, as well as ability to grow on media lacking uracil, leucine, lysine, tryptophan or histidine. In alternate embodiments, 5-FOA is used for selection of yeast Ura– mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of Ura⁻ mutant yeast strains (Bartel, P. L. and Fields, S., Yeast 2-Hybrid System, Oxford University: New York, v. 7, pp 109-147, 1997). More specifically, one can first knockout the native Ura3 gene to produce a strain having a Ura– phenotype, wherein selection occurs based on 5-FOA resistance. Then, a cluster of multiple chimeric genes and a new Ura3 gene can be integrated into a different locus of the *Yarrowia* genome to thereby produce a new strain having a Ura+ phenotype. Subsequent integration produces a new Ura3– strain (again identified using 5-FOA selection), when the introduced Ura3 gene is knocked out. Thus, the Ura3 gene (in combination with 5-FOA selection) can be used as a selection marker in multiple rounds of transformation.

Following transformation, substrates suitable for the instant delta-9 elongase (and, optionally other PUFA enzymes that are co-expressed within the host cell) may be produced by the host either naturally or transgenically, or they may be provided exogenously.

Microbial host cells for expression of the instant genes and nucleic acid fragments may include hosts that grow on a variety of feedstocks, including simple or complex carbohydrates, fatty acids, organic acids, oils and alcohols, and/or hydrocarbons over a wide range of temperature and pH values. Based on the needs of the Applicants' Assignee, the genes described in the instant invention will be expressed in an oleaginous yeast (and in particular *Yarrowia lipolytica*); however, it is contemplated that because transcription, translation and the protein biosynthetic apparatus is highly conserved, any bacteria, yeast, algae and/or fungus will be a suitable microbial host for expression of the present nucleic acid fragments.

Preferred microbial hosts, however, are oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C, tropicalis, C. utilis, Trichosporon pullans, T cutaneum, Rhodotorula glutinus, R. graminis,* and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM 8(7)1 (Papanikolaou S., and Aggelis G., *Bioresour. Technol.* 82(1):43-9 (2002)).

Historically, various strains of *Y. lipolytica* have been used for the manufacture and production of: isocitrate lyase; lipases; polyhydroxyalkanoates; citric acid; erythritol; 2-oxoglutaric acid; γ-decalactone; γ-dodecalatone; and pyruvic add. Specific teachings applicable for engineering ARA, EPA and DHA production in *Y. lipolytica* are provided in U.S. patent application Ser. No. 11/264,784 (WO 2006/055322), U.S. patent application Ser. No. 11/265,761 (WO 2006/052870) and U.S. patent application Ser. No. 11/264,737 (WO 2006/052871), respectively.

Other preferred microbial hosts include oleaginous bacteria, algae and other fungi; and, within this broad group of microbial hosts, of particular interest are microorganisms that synthesize omega-3/omega-6 fatty acids (or those that can be genetically engineered for this purpose [e.g., other yeast such as *Saccharomyces cerevisiae*]). Thus, for example, transformation of *Mortierella alpine* (which is commercially used for production of ARA) with any of the present delta-9 elongase genes under the control of inducible or regulated promoters could yield a transformant organism capable of synthesizing increased quantities of DGLA. The method of transformation of *M. alpina* is described by Mackenzie et al. (*Appl. Environ. Microbia*, 66:4655 (2000)). Similarly, methods for transformation of Thraustochytriales microorganisms are disclosed in U.S. Pat. No. 7,001,772.

Metabolic Engineering of Omega-3 and/or Omega-6 Fatty Acid Biosynthesis in Microbes Methods for manipulating biochemical pathways are well known to those skilled in the art; and, it is expected that numerous manipulations will be possible to maximize omega-3 and/or omega-6 fatty acid biosynthesis in oleaginous yeasts, and particularly, in *Yarrowia lipolytica*. This manipulation may require metabolic engineering directly within the PUFA biosynthetic pathway or additional coordinated manipulation of various other metabolic pathways.

In the case of manipulations within the PUFA biosynthetic pathway, it may be desirable to increase the production of LA to enable increased production of omega-6 and/or omega-3 fatty acids. Introducing and/or amplifying genes encoding delta-9 and/or delta-12 desaturases may accomplish this. To maximize production of omega-6 unsaturated fatty acids, it is well known to one skilled in the art that production is favored in a host microorganism that is substantially free of ALA; thus, preferably, the host is selected or obtained by removing or inhibiting delta-15 or omega-3 type desaturase activity that permits conversion of LA to ALA. Alternatively, it may be desirable to maximize production of omega-3 fatty acids (and minimize synthesis of omega-6 fatty acids). In this example, one could utilize a host microorganism wherein the delta-12 desaturase activity that permits conversion of oleic acid to LA is removed or inhibited; subsequently, appropriate expression cassettes would be introduced into the host, along with appropriate substrates (e.g., ALA) for conversion to omega-3 fatty acid derivatives of ALA (e.g., STA, ETrA, ETA, EPA, DPA, DHA).

In alternate embodiments, biochemical pathways competing with the omega-3 and/or omega-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase ARA, EPA or DHA (and associated techniques thereof) are presented in PCT Publication Nos. WO 2006/055322, WO 2006/052870 and WO 2006/052871, respectively, as are desirable manipulations in the TAG biosynthetic pathway and the TAG degradation pathway (and associated techniques thereof).

Within the context of the present invention, it may be useful to modulate the expression of the fatty acid biosynthetic pathway by any one of the strategies described above. For example, the present invention provides methods whereby genes encoding key enzymes in the delta-9 elongase/delta-8 desaturase biosynthetic pathway are introduced into oleaginous yeasts for the production of omega-3 and/or omega-6 fatty acids. It will be particularly useful to express the present the delta-9 elongase genes in oleaginous yeasts that do not naturally possess omega-3 and/or omega-6 fatty acid biosynthetic pathways and coordinate the expression of these genes, to maximize production of preferred PUFA products using various means for metabolic engineering of the host organism.

Microbial Fermentation Processes for PUFA Production

The transformed host cell is grown under conditions that optimize expression of chimeric desaturase genes and produce the greatest and the most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. *Yarrowia lipolytica* are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media should contain a suitable carbon source. Suitable carbon sources are taught in PCT Publication No. WO 2004/101757. Although it is contemplated that the source of carbon utilized may encompass a wide variety of carbon-containing sources, preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast (e.g., *Yarrowia lipolytica*). This approach is described in PCT Publication No. WO 2004/101757, as are various suitable fermentation process designs (i.e., batch, fed-batch and continuous) and considerations during growth.

Purification and Processing of PUFA Oils

PUFAs may be found in the host microorganisms and plants as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology*, 12(5/6): 463-491 (1992)). A brief review of downstream processing is also available by A. Singh and O. Ward (*Adv. Appl. Microbiol.*, 45:271-312 (1997)).

In general, means for the purification of PUFAs may include extraction with organic solvents, sonication, supercritical fluid extraction (e.g., using carbon dioxide), saponification and physical means such as presses, or combinations thereof. One is referred to the teachings of PCT Publication No. WO 2004/101757 for additional details. Methods of isolating seed oils are well known in the art: (Young et al., Processing of Fats and Oils, In *The Lipid Handbook*, Gunstone et al., eds., Chapter 5 pp 253-257; Chapman & Hall: London (1994)). For example, soybean oil is produced using a series of steps involving the extraction and purification of an edible oil product from the oil-bearing seed. Soybean oils and soybean byproducts are produced using the generalized steps shown in Table 3.

TABLE 3

Generalized Steps for Soybean Oil and Byproduct Production

| Process Step | Process | Impurities Removed and/or By-Products Obtained |
|---|---|---|
| #1 | soybean seed | |
| #2 | oil extraction | meal |
| #3 | degumming | lecithin |
| #4 | alkali or physical refining | gums, free fatty acids, pigments |
| #5 | water washing | soap |
| #6 | bleaching | color, soap, metal |
| #7 | (hydrogenation) | |
| #8 | (winterization) | stearine |
| #9 | deodorization | free fatty acids, tocopherols, sterols, volatiles |
| #10 | oil products | |

More specifically, soybean seeds are cleaned, tempered, dehulled and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the non hydrating, triglyceride fraction (soybean oil). The resulting lecithin gums may be further processed to make commercially important lecithin products used in a variety of food and industrial products as emulsification and release (i.e., antisticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, Practical Handbook of Soybean Processing and Utilization, The American Oil Chemists' Society and United Soybean Board (1995). Soybean oil is liquid at room temperature because it is relatively low in saturated fatty acids when compared with oils such as coconut, palm, palm kernel and cocoa butter.

Plant and microbial oils containing PUFAs that have been refined and/or purified can be hydrogenated, to thereby result in fats with various melting properties and textures. Many processed fats (including spreads, confectionary fats, hard butters, margarines, baking shortenings, etc.) require varying degrees of solidity at room temperature and can only be produced through alteration of the source oil's physical properties. This is most commonly achieved through catalytic hydrogenation.

Hydrogenation is a chemical reaction in which hydrogen is added to the unsaturated fatty acid double bonds with the aid of a catalyst such as nickel. For example, high oleic soybean oil contains unsaturated oleic, LA and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which in turn alter the composition of the final product. Operating conditions including pressure, temperature, catalyst type and concentration, agitation and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have become somewhat controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

PUFA-Containing Oils for Use in Foodstuffs

The market place currently supports a large variety of food and feed products, incorporating omega-3 and/or omega-6 fatty acids (particularly ARA, EPA and DHA). It is contemplated that the plant/seed oils, altered seeds and microbial oils of the invention comprising PUFAs will function in food and feed products to impart the health benefits of current formulations. Compared to other vegetable oils, the oils of the invention are believed to function similarly to other oils in food applications from a physical standpoint (for example, partially hydrogenated oils such as soybean oil are widely used as ingredients for soft spreads, margarine and shortenings for baking and frying).

Plant/seed oils, altered seeds and microbial oils containing omega-3 and/or omega-6 fatty acids as described herein will be suitable for use in a variety of food and feed products including, but not limited to: food analogs, meat products, cereal products, baked foods, snack foods and dairy products. Additionally, the present plant/seed oils, altered seeds and microbial oils may be used in formulations to impart health benefit in medical foods including medical nutritionals, dietary supplements, infant formula as well as pharmaceutical products. One of skill in the art of food processing and food formulation will understand how the amount and composition of the plant and microbial oils may be added to the food or feed product. Such an amount will be referred to herein as an "effective" amount and will depend on the food or feed product, the diet that the product is intended to supplement or the medical condition that the medical food or medical nutritional is intended to correct or treat.

Food analogs can be made using processes well known to those skilled in the art. There can be mentioned meat analogs, cheese analogs, milk analogs and the like. Meat analogs made from soybeans contain soy protein or tofu and other ingredients mixed together to simulate various kinds of meats. These meat alternatives are sold as frozen, canned or dried foods. Usually, they can be used the same way as the foods they replace. Meat alternatives made from soybeans are excellent sources of protein, iron and B vitamins. Examples of meat analogs include, but are not limited to: ham analogs, sausage analogs, bacon analogs, and the like.

Food analogs can be classified as imitation or substitutes depending on their functional and compositional characteristics. For example, an imitation cheese need only resemble the cheese it is designed to replace. However, a product can generally be called a substitute cheese only if it is nutritionally equivalent to the cheese it is replacing and meets the minimum compositional requirements for that cheese. Thus, substitute cheese will often have higher protein levels than imitation cheeses and be fortified with vitamins and minerals.

Milk analogs or nondairy food products include, but are not limited to, imitation milks and nondairy frozen desserts (e.g., those made from soybeans and/or soy protein products).

Meat products encompass a broad variety of products. In the United States "meat" includes "red meats" produced from cattle, hogs and sheep. In addition to the red meats there are poultry items which include chickens, turkeys, geese, guineas, ducks and the fish and shellfish. There is a wide assortment of seasoned and processed meat products: fresh, cured and fried, and cured and cooked. Sausages and hot dogs are examples of processed meat products. Thus, the term "meat products" as used herein includes, but is not limited to, processed meat products.

A cereal food product is a food product derived from the processing of a cereal grain. A cereal grain includes any plant from the grass family that yields an edible grain (seed). The most popular grains are barley, corn, millet, oats, quinoa, rice, rye, sorghum, triticale, wheat and wild rice. Examples of a cereal food product include, but are not limited to: whole grain, crushed grain, grits, flour, bran, germ, breakfast cereals, extruded foods, pastas, and the like.

A baked goods product comprises any of the cereal food products mentioned above and has been baked or processed in a manner comparable to baking (i.e., to dry or harden by subjecting to heat). Examples of a baked good product include, but are not limited to: bread, cakes, doughnuts, bars, pastas, bread crumbs, baked snacks, mini-biscuits, mini-crackers, mini-cookies, and mini-pretzels. As was mentioned above, oils of the invention can be used as an ingredient.

A snack food product comprises any of the above or below described food products.

A fried food product comprises any of the above or below described food products that has been fried.

A health food product is any food product that imparts a health benefit. Many oilseed-derived food products may be considered as health foods.

A beverage can be in a liquid or in a dry powdered form.

For example, there can be mentioned non-carbonated drinks such as fruit juices, fresh, frozen, canned or concentrate; flavored or plain milk drinks, etc. Adult and infant nutritional formulas are well known in the art and commercially available (e.g., Similac®, Ensure®, Jevity®, and Alimentum® from Ross Products Division, Abbott Laboratories).

Infant formulas are liquids or reconstituted powders fed to infants and young children. "Infant formula" is defined herein as an enteral nutritional product which can be substituted for human breast milk in feeding infants and typically is composed of a desired percentage of fat mixed with desired percentages of carbohydrates and proteins in an aqueous solution (e.g., see U.S. Pat. No. 4,670,285). Based on the worldwide composition studies, as well as levels specified by expert groups, average human breast milk typically contains about 0.20% to 0.40% of total fatty acids (assuming about 50% of calories from fat); and, generally the ratio of DHA to ARA would range from about 1:1 to 1:2 (see, e.g., formulations of Enfamil LIPIL™ (Mead Johnson & Company) and Similac Advance™ (Ross Products Division, Abbott Laboratories)). Infant formulas have a special role to play in the diets of infants because they are often the only source of nutrients for infants; and, although breast-feeding is still the best nourishment for infants, infant formula is a close enough second that babies not only survive but thrive.

A dairy product is a product derived from milk. A milk analog or nondairy product is derived from a source other than milk, for example, soymilk as was discussed above. These products include, but are not limited to: whole milk, skim milk, fermented milk products such as yogurt or sour milk, cream, butter, condensed milk, dehydrated milk, coffee whitener, coffee creamer, ice cream, cheese, etc.

Additional food products into which the PUFA-containing oils of the invention could be included are, for example, chewing gums, confections and frostings, gelatins and puddings, hard and soft candies, jams and jellies, white granulated sugar, sugar substitutes, sweet sauces, toppings and syrups, and dry-blended powder mixes.

PUFA-Containing Oils for Use in Health Food Products and Pharmaceuticals

A health food product is any food product that imparts a health benefit and include functional foods, medical foods, medical nutritionals and dietary supplements. Additionally, the plant/seed oils, altered seeds and microbial oils of the invention may be used in standard pharmaceutical compositions (e.g., the long-chain PUFA containing oils could readily be incorporated into the any of the above mentioned food products, to thereby produce a functional or medical food). More concentrated formulations comprising PUFAs include capsules, powders, tablets, softgels, gelcaps, liquid concentrates and emulsions which can be used as a dietary supplement in humans or animals other than humans.

PUFA-Containing Oils for Use in Animal Feeds

Animal feeds are generically defined herein as products intended for use as feed or for mixing in feed for animals other than humans. The plant/seed oils, altered seeds and microbial oils of the invention can be used as an ingredient in various animal feeds.

More specifically, although not limited therein, it is expected that the oils of the invention can be used within pet food products, ruminant and poultry food products and aquacultural food products. Pet food products are those products intended to be fed to a pet (e.g., dog, cat, bird, reptile, rodent). These products can include the cereal and health food products above, as well as meat and meat byproducts, soy protein products, grass and hay products (e.g., alfalfa, timothy, oat or brome grass, vegetables). Ruminant and poultry food products are those wherein the product is intended to be fed to an animal (e.g., turkeys, chickens, cattle, swine). As with the pet foods above, these products can include cereal and health food products, soy protein products, meat and meat byproducts, and grass and hay products as listed above. Aquacultural food products (or "aquafeeds") are those products intended to be used in aquafarming, i.e., which concerns the propagation, cultivation or farming of aquatic organisms and/or animals in fresh or marine waters.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The meaning of abbreviations is as follows: "sec" means second(s), "min" means minute(s), "h" means hour(s), "d"

means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

General Methods:

Transformation and Cultivation of Yarrowia lipolytica:

Yarrowia lipolytica strains with ATCC Accession Nos. #20362, #76982 and #90812 were purchased from the American Type Culture Collection (Rockville, Md.). Yarrowia lipolytica strains were typically grown at 28° C. on YPD agar (1% yeast extract, 2% bactopeptone, 2% glucose, 2% agar).

Transformation of Yarrowia lipolytica was performed according to the method of Chen, D. C. et al. (Appl. Microbial. Biotechnol. 48(2):232-235 (1997)), unless otherwise noted. Briefly, Yarrowia was streaked onto a YPD plate and grown at 30° C. for approximately 18 h. Several large loopfuls of cells were scraped from the plate and resuspended in 1 mL of transformation buffer, comprising: 2.25 mL of 50% PEG, average MW 3350; 0.125 mL of 2 M lithium acetate, pH 6.0; 0.125 mL of 2 M DTT; and 50 μg sheared salmon sperm DNA. Then, approximately 500 ng of linearized plasmid DNA was incubated in 100 μL of resuspended cells, and maintained at 39° C. for 1 h with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (Difco Laboratories, Detroit, Mich.) without ammonium sulfate or amino acids, 2% glucose, 0.1% proline, pH 6.1). Supplements of uracil were added as appropriate to a final concentration of 0.01% (thereby producing "MMU" selection media, prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (Difco Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Fatty Acid Analysis of Yarrowia lipolytica:

For fatty acid analysis, cells were collected by centrifugation and lipids were extracted as described in Bligh, E. G. & Dyer, W. J. (Can. J. Biochem. Physiol. 37:911-917 (1959)). Fatty acid methyl esters were prepared by transesterification of the lipid extract with sodium methoxide (Roughan, G. and Nishida I., Arch Biochem Biophys. 276(1):38-46 (1990)) and subsequently analyzed with a Hewlett-Packard 6890 GC fitted with a 30 m×0.25 mm (i.d.) HP-INNOWAX (Hewlett-Packard) column. The oven temperature was from 170° C. (25 min hold) to 185° C. at 3.5° C./min.

For direct base transesterification, Yarrowia culture (3 mL) was harvested, washed once in distilled water, and dried under vacuum in a Speed-Vac for 5-10 min. Sodium methoxide (100 μL of 1%) was added to the sample, and then the sample was vortexed and rocked for 20 min. After adding 3 drops of 1 M NaCl and 400 μL hexane, the sample was vortexed and spun. The upper layer was removed and analyzed by GC as described above.

Example 1

Synthesis of a cDNA Library from Euglena anabaena UTEX 373

The present Example describes the synthesis of a cDNA library from Euglena anabaena UTEX 373. This work included the generation of RNA, synthesis of cDNA, and generation of a cDNA library.

Growth of Euglena anabaena UTEX 373 and Preparation of RNA

Figure 8:
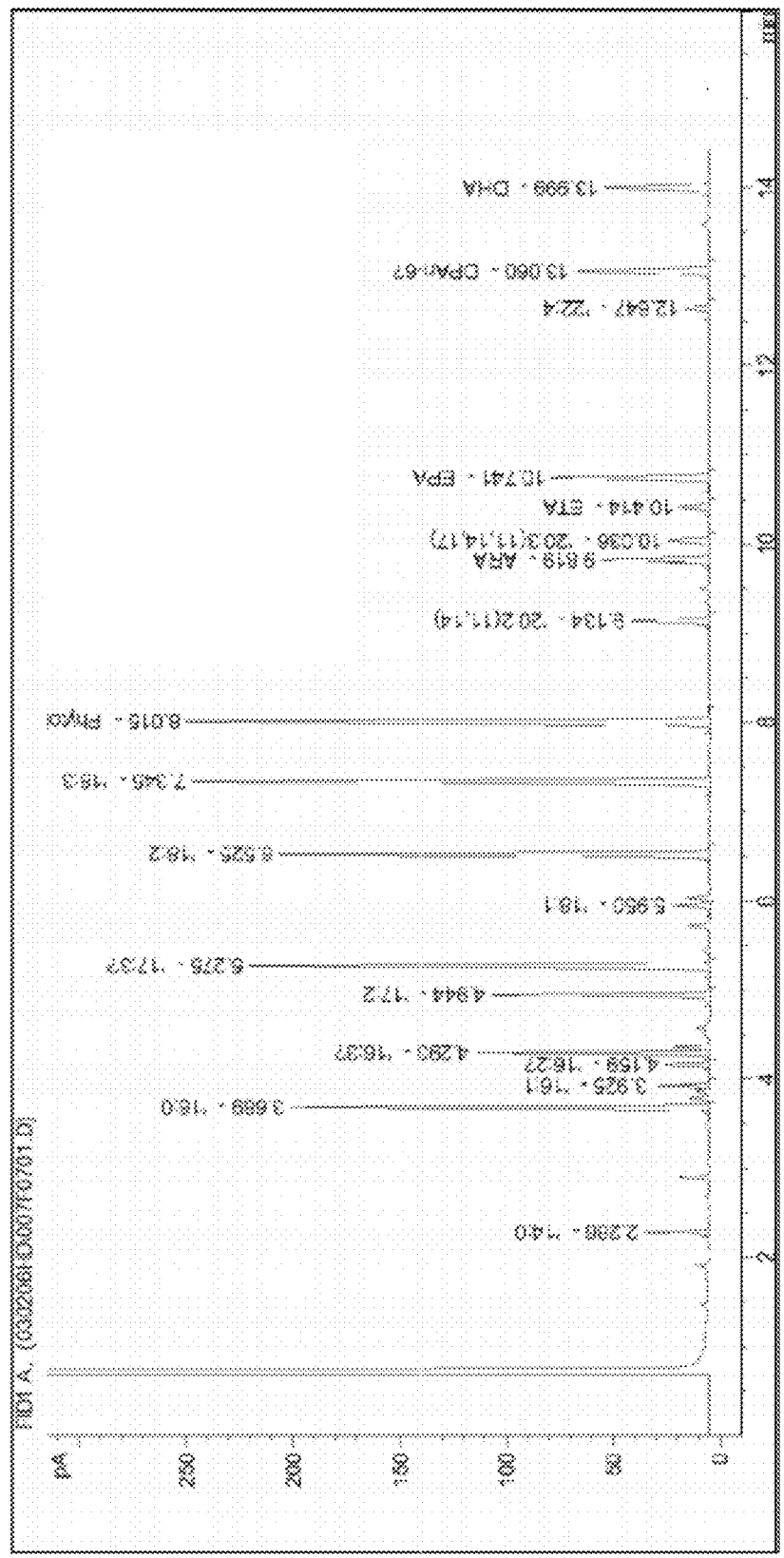
FIG. 8 shows a chromatogram of the lipid profile of an *Euglena anabaena* cell extract as described in the Examples.

Euglena anabaena UTEX 373 was obtained from Dr. Richard Triemer's lab at Michigan State University (East Lansing, Mich.). Approximately 2 mL of culture was removed for lipid analysis and centrifuged at 1,800×g for 5 min. The pellet was washed once with water and re-centrifuged. The resulting pellet was dried for 5 min under vacuum, resuspended in 100 μL of trimethylsulfonium hydroxide (TMSH) and incubated at room temperature for 15 min with shaking. After incubation, 0.5 mL of hexane was added and the vials were further incubated for 15 min at room temperature with shaking. Fatty acid methyl esters (5 μL injected from hexane layer) were separated and quantified using a Hewlett-Packard 6890 Gas Chromatograph fitted with an Omegawax 320 fused silica capillary column (Supelco Inc., Cat. No. 24152). The oven temperature was programmed to hold at 170° C. for 1.0 min, increase to 240° C. at 5° C./min and then hold for an additional 1.0 min. Carrier gas was supplied by a Whatman hydrogen generator. Retention times were compared to those for methyl esters of standards commercially available (Nu-Chek Prep, Inc. Cat. No. U-99-A) and the resulting chromatogram is shown in FIG. 8. The presence of EDA, ERA, EPA and DHA in the fatty acid profile, with the absence of GLA and STA, suggested that Euglena anabaena uses the delta-9 elongase/delta-8 desaturase pathway for LC-PUFA biosynthesis and would be a good source for LC-PUFA biosynthetic genes such as, but not limited to, delta-9 elongases.

The remaining 5 mL of an actively growing culture was transferred into 25 mL of AF-6 Medium (Watanabe & Hiroki, NIES-Collection List of Strains, 5$^{th}$ ed., National Institute for Environmental Studies, Tsukuba, 127 pp (2004)) in a 125 mL glass flask. Euglena anabaena cultures were grown at 22° C. with a 16 h light, 8 h dark cycle for 2 weeks with very gentle agitation.

After 2 weeks, the culture (25 mL) was transferred to 100 mL of AF-6 medium in a 500 mL glass bottle and the culture was grown for 1 month as described above. After this time, two 50 mL aliquots were transferred into two separate 500 mL glass bottles containing 250 mL of AF-6 medium and the cultures were grown for two months as described above (giving a total of ~600 mL of culture). After this, the cultures were pelleted by centrifugation at 1,800×g for 10 min, washed once with water and re-centrifuged. Total RNA was extracted from one of the resulting pellets using the RNA STAT-60™ reagent (TEL-TEST, Inc., Friendswood, Tex.) and following the manufacturer's protocol provided (use 5 mL of reagent, dissolved RNA in 0.5 mL of water). In this way, 340 μg of total RNA (680 μg/mL) was obtained from the pellet. The remaining pellet was frozen in liquid nitrogen and stored at −80° C. The mRNA was isolated from all 340 μg of total RNA using the mRNA Purification Kit (Amersham Biosciences, Piscataway, N.J.) following the manufacturer's protocol provided. In this way, 9.0 μg of mRNA was obtained.

Preparation of *Euglena anabaena* cDNA and Generation of cDNA Library eug1c

A cDNA library was generated using the Cloneminer™ cDNA Library Construction Kit (Cat. No. 18249-029, Invitrogen Corporation, Carlsbad, Calif.) and following the manufacturer's protocol provided (Version B, 25-0608). Using the non-radiolabeling method, cDNA was synthesized from 5.12 μg of mRNA (described above) using the Biotin-attB2-Oligo (dT) primer. After synthesis of the first and second strand, the attB1 adapter was added, ligated and the cDNA was size fractionated using column chromatography. DNA from fractions were concentrated, recombined into pDONR™222 and transformed into *E. coli* ElectroMAX™ DH10B™ T1 Phage-Resistant cells (Invitrogen Corporation). The *Euglena anabaena* library was named eug1c.

The cDNA library eug1c was plated onto LBKan plates (approx. 100,000 colonies), the colonies were scraped off and DNA was isolated using the QIAprep®Spin Miniprep Kit (Qiagen Inc., Valencia, Calif.) following the manufacturer's protocol. In this way, a plasmid DNA sub-library from eug1c was obtained.

Example 2

Isolation of the Full-length Delta-9 Elongases from *Euglena anabaena* UTEX 373

The present Example describes the identification of cDNAs (SEQ ID NOs:1 and 2) encoding delta-9 elongases from *Euglena anabaena* UTEX 373. This work included the generation of a probe derived from the *Euglena gracilis* delta-9 elongase (EgD9e; SEQ ID NO:3) and the hybridization of the probe to the cDNA library eug1c in order to identify delta-9 elongase homologs from *Euglena anabaena* UTEX 373.

*Euglena gracilis* Delta-9 Elongase (EgD9e):

A clone from the *Euglena* cDNA library (eeg1c), called eeg1c.pk001.n5f, containing the *Euglena gracilis* delta-9 elongase (EgD9e; SEQ ID NO:3; which is described in U.S. application Ser. No. 11/601,563 (filed Nov. 16, 2006, which published May 24, 2007) the contents of which are hereby incorporated by reference) was used as template to amplify EgD9e with oligonucleotide primers oEugEL1-1 (SEQ ID NO:4) and oEugEL1-2 (SEQ ID NO:5) using the VentR® DNA Polymerase (Cat. No. M0254S, New England Biolabs Inc., Beverly, Mass.) following the manufacturer's protocol. The resulting DNA fragment was cloned into the pCR-Blunt® cloning vector using the Zero Blunt® PCR Cloning Kit (Invitrogen Corporation), following the manufacturer's protocol, to produce pKR906 (SEQ ID NO:6).

Colony Lifts:

Approximately 17,000 clones of cDNA library eug1c were plated onto three large square (24 cm×24 cm) petri plates (Corning, Corning, N.Y.) each containing LB+50 μg/mL kanamycin agar media. Cells were grown overnight at 37° C. and plates were then cooled to room temperature.

Biodyne B 0.45 μm membrane (Cat. No. 60207, Pall Corporation, Pensacola, Fla.) was trimmed to approximately 22 cm×22 cm and the membrane was carefully layed on top of the agar to avoid air bubbles. After incubation for 2 min at room temperature, the membrane was marked for orientation, lifted off with tweezers and placed colony-side up on filter paper soaked with 0.5 M sodium hydroxide and 1.5 M sodium chloride. After denaturation for 4 min, the sodium hydroxide was neutralized by placing the membrane on filter paper soaked with 0.5 M Tris-HCL (pH 7.5) and 1.5 M sodium chloride for 4 min. This step was repeated and the membrane was rinsed briefly in 2×SSC buffer (20×SSC is 3M sodium chloride, 0.3 M sodium citrate; pH 7.0) and air dried on filter paper.

Hybridization:

Membranes were pre-hybridized at 65° C. in 200 mL hybridization solution for 2 h. Hybridization solution contained 6×SSPE (20×SSPE is 3 M sodium chloride, 0.2 M sodium phosphate, 20 mM EDTA; pH 7.4), 5×Denhardt's reagent (100×Denhardt's reagent is 2% (w/v) Ficoll, 2% (w/v) polyvinylpyrrolidone, 2% (w/v) acetylated bovine serum albumin), 0.5% sodium dodecyl sulfate (SDS), 100 μg/mL sheared salmon sperm DNA and 5% dextran sulfate.

A DNA probe was made using an agarose gel purified NcoI/NotI DNA fragment, containing the *Euglena gracilis* delta-9 elongase gene, from pKR906 (SEQ ID NO:6) labeled with $P^{32}$ dCTP using the RadPrime DNA Labeling System (Cat. No. 18428-011, Invitrogen, Carlsbad, Calif.) following the manufacture's instructions. Unincorporated $P^{32}$ dCTP was separated using a NICK column (Cat. No. 17-0855-02, Amersham Biosciences, Piscataway, N.J.) following the manufacturer's instructions. The probe was denatured for 5 min at 100° C., placed on ice for 3 min and half was added to the hybridization solution.

The membrane was hybridized with the probe overnight at 65° C. with gentle shaking and then washed the following day twice with 2×SSC containing 0.5% SDS (5 min each) and twice with 0.2×SSC containing 0.1% SDS (15 min each). After washing, hyperfilm (Cat. No. RPN30K, Amersham Biosciences, Piscataway, N.J.) was exposed to the membrane overnight at −80° C.

Based on alignment of plates with the exposed hyperfilm, positive colonies were picked using the blunt end of a Pasteur pipette into 1 mL of water and vortexed. Several dilutions were made and plated onto small round Petri dishes (82 mm) containing LB media plus 50 μg/mL kanamycin to obtain around 100 well isolated colonies on a single plate. Lifts were done as described above except NytranN membrane circles (Cat, No. 10416116, Schleicher & Schuell, Keene, N.H.) were used and hybridization was carried out in 100 mL using the remaining radiolabeled probe. In this way, positive clones were confirmed.

Individual positive clones were grown at 37° C. in LB+50 μg/mL kanamycin liquid media and plasmid was purified using the QIAprep° Spin Miniprep Kit (Qiagen Inc.) following the manufacturer's protocol.

DNA inserts were end-sequenced in 384-well plates, using vector-primed M13F universal primer (SEQ ID NO:7), M13rev-28 primer (SEQ ID NO:8) and the poly(A) tail-primed WobbleT oligonucleotides, with the ABI Big Dye version 3 Prism sequencing kit. For the sequencing reaction, 100-200 ng of template and 6.4 pmol of primer were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3700 automated sequencers. The WobbleT primer is an equimolar mix of 21mer poly(T)A, poly(T)C, and poly(T)G, used to sequence the 3' end of cDNA clones.

Sequences were aligned and compared using Sequencher™ (Version 4.2, Gene Codes Corporation, Ann Arbor, Mich.) and in this way, the clones could be categorized into one of two distinct groups based on insert sequence (called EaD9Elo1 and EaD9Elo2). Representative clones containing the cDNA for each class of sequence were chosen for further study and sequences for each representative plasmid (pLF121-1 and pLF121-2) are shown in SEQ ID NO:9 and SEQ ID NO:10, respectively. The sequence shown by a string of NNNN's represents a region of the polyA tail which was not sequenced. The coding sequences for EaD9Elo1 and EaD9Elo2 are shown in SEQ ID NO:11 and SEQ ID NO:12, respectively. The corresponding amino acid sequences for EaD9Elo1 and EaD9Elo2 are shown in SEQ ID NO:13 and SEQ ID NO:14, respectively.

Example 3

Primary Sequence Analysis of the Delta-9 Elongase Sequences of *Euglena anabaena* UTEX 373 (EaD9Elo1 and EaD9Elo2) and Comparison to a Delta-9 Elongase Sequence of *Euglena gracilis* (EgD9e)

The amino acid sequences for EaD9Elo1 (SEQ ID NO:13) and EaD9Elo2 (SEQ ID NO:14) were compared using the Clustal V method (Higgins, D. G. and Sharp, P. M., *Comput. Appl. Biosci.* 5:151-153 (1989); Higgins et al., *Comput. Appl. Biosci.* 8:189-191 (1992)) using the MegAlign™ v6.1 program of the LASERGENE bioinformatics computing suite (DNASTAR Inc., Madison, Wis.) with the default parameters for pairwise alignment (KTUPLE=1, GAP PENALTY=3, WINDOW=5 and DIAGONALS SAVED=5 and GAP LENGTH PENALTY=10).

Compared to a EaD9Elo1 (SEQ ID NO:13), EaD9Elo2 (SEQ ID NO:14) has 1 amino acid substitution (R254Q; based on numbering for EaD9Elo1).

The amino acid sequences for EaD9Elo1 (SEQ ID NO:13) and EaD9Elo2 (SEQ ID NO:14) were evaluated by BLASTP (Basic Local Alignment Search Tool; Altschul et al., *J. Mol. Biol.* 215:403-410 (1993)) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL and DDBJ databases) using default parameters with the filter turned off. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Both sequences yielded a pLog value of 38.70 (P value of 2e-39) versus the *Isochrysis galbana* long chain polyunsaturated fatty acid elongation enzyme (IgD9e; SEQ ID NO:15) (NCBI Accession No. AAL37626(GI 17226123), locus AAL37626, CDS AF390174; Qi et al., *FEBS Lett.* 510:159-165 (2002)) when compared to the "nr" database. BLAST scores and probabilities indicate that the instant nucleic acid fragments encode entire *Euglena anabaena* delta-9 fatty acid elongase.

The amino acid sequences for EaD9Elo1 (SEQ ID NO:13) and EaD9Elo2 (SEQ ID NO:14) were compared to the *Isochrysis galbana* long chain polyunsaturated fatty acid elongation enzyme (IgD9e; SEQ ID NO:15) and the *Euglena gracilis* delta-9 elongase amino acid sequence (EgD9e; SEQ ID NO:16; which is described in U.S. application Ser. No. 11/601,563 (filed Nov. 16, 2006, which published May 24, 2007) the contents of which are hereby incorporated by reference) using BlastP, Clustal V and the Jotun Hein methods of sequence comparison. The % identity against the IgD9e and EgD9e using each method is shown in Table 4 and Table 5, respectively.

Sequence percent identity calculations performed by the BlastP and Clustal V method as described above. Sequence percent identity calculations performed by the Jotun Hein method (Hein, J. J., *Meth. Enz.* 183:626-645 (1990)) were done using the MegAlign™ v6.1 program of the LASERGENE bioinformatics computing suite (DNASTAR Inc., Madison, Wis.) with the default parameters for pairwise alignment (KTUPLE=2).

TABLE 4

Sequence Comparison of EaD9Elo1 (SEQ ID NO: 13) and EaD9Elo2 (SEQ ID NO: 14) to IgD9e (SEQ ID NO: 15)

| Desaturase | % Identity to IgD9e by BLASTP | % Identity to IgD9e by the Jotun Hein Method | % Identity to IgD9e by the Clustal V Method |
|---|---|---|---|
| EaD9Elo1 (SEQ ID NO: 13) | 37% | 40.4% | 32.9% |
| EaD9Elo2 (SEQ ID NO: 14) | 37% | 41.2% | 32.9% |

TABLE 5

Sequence Comparison of EaD9Elo1 (SEQ ID NO: 13) and EaD9Elo2 (SEQ ID NO: 14) to EgD9e (SEQ ID NO: 16)

| Desaturase | % Identity to EgD9e by BLASTP | % Identity to EgD9e by the Jotun Hein Method | % Identity to EgD9e by the Clustal V Method |
|---|---|---|---|
| EaD9Elo1 (SEQ ID NO: 13) | 77% | 77.2% | 77.1% |
| EaD9Elo2 (SEQ ID NO: 14) | 77% | 77.2% | 77.1% |

Example 4

Functional Analysis of the Euglena Gracilis UTEX 373 Delta-9 Elongases in *Yarrowia lipolytica*

The present Example describes functional analysis of EaD9Elo1 (SEQ ID NO:13) and EaD9Elo2 (SEQ ID NO:14) in *Yarrowia lipolytica*. This work included the following steps: (1) Construction of Gateways-compatible *Yarrowia* expression vector pY159; (2) transfer of EaD9Elo1 (SEQ ID NO:13) and EaD9Elo2 (SEQ ID NO:14 into pY159 to produce pY173 and pY174; and, (3) comparison of lipid profiles within transformant organisms comprising pY173 and pY174.

Construction of Gateway®-Compatible *Yarrowia* Expression Vector pY159

Plasmid pY5-30 (which was previously described in PCT Publication No. WO 2005/003310 (the contents of which are hereby incorporated by reference), is a shuttle plasmid that can replicate both in *E. coli* and *Yarrowia lipolytica*. Plasmid pY5-30 contains the following: a *Yarrowia* autonomous replication sequence (ARS18); a ColE1 plasmid origin of replication; an ampicillin-resistance gene ($Amp^R$), for selection in *E. coli*; a *Yarrowia* LEU2 gene, for selection in *Yarrowia*; and a chimeric TEF::GUS::XPR gene. Plasmid pDMW263 (SEQ ID NO:17) was created from pY5-30, by replacing the TEF promoter with the *Yarrowia lipolytica* FBAINm promoter (PCT Publication No. WO 2005/049805) using techniques well known to one skilled in the art. Briefly, this promoter refers to a modified promoter which is located in the 5' upstream untranslated region in front of the 'ATG' translation initiation codon of the fructose-bisphosphate aldolase enzyme (E.C. 4.1.2.13) encoded by the fba1 gene and that is necessary for expression, plus a portion of 5' coding region that has an intron, wherein FBAINm has a 52 bp deletion between the ATG translation initiation codon and the intron of the FBAIN promoter (thereby including only 22 amino acids of the N-terminus) and a new translation consensus motif after the intron. Table 6 summarizes the components of pDMW263 (SEQ ID NO:17).

TABLE 6

Components of Plasmid pDMW263 (SEQ ID NO: 17)

| RE Sites and Nucleotides Within SEQ ID NO: 17 | Description of Fragment and Chimeric Gene Components |
|---|---|
| 4992-4296 SalI/SacII (8505-2014) | ARS18 sequence (GenBank Accession No. A17608) FBAINm::GUS::XPR, comprising: FBAINm: FBAINm promoter (WO2005/049805) GUS: *E. coli* gene encoding β-glucuronidase (Jefferson, R. A. *Nature*. 14: 342: 837-838 (1989) XPR: ~100 bp of the 3' region of the *Yarrowia* Xpr gene (GenBank Accession No. M17741) |
| 6303-8505 | *Yarrowia* Leu2 gene (GenBank Accession No. AF260230) |

Figure 2:
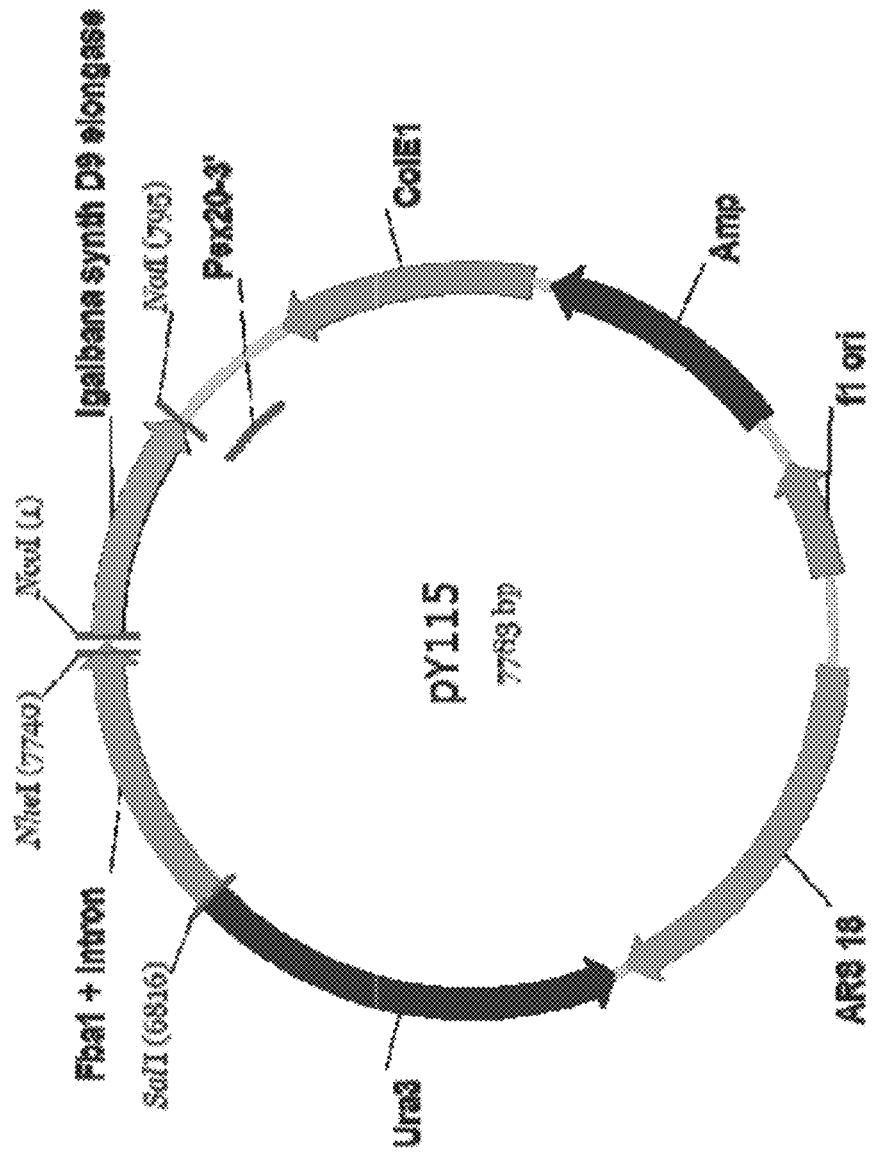
FIG. 2 is a map of plasmid pY115 (SEQ ID NO:19).

The NcoI/SalI DNA fragment from pDMW263 (SEQ ID NO:17), containing the *Yarrowia lipolytica* FBAINm promoter, was cloned into the NcoI/SalI DNA fragment of pDMW237 (SEQ ID NO:18), previously described in PCT Publication No. WO 2006/012325 (the contents of which are hereby incorporated by reference), containing a synthetic delta-9 elongase gene derived from *Isochrysis galbana* and codon-optimized for expression in *Yarrowia lipolytica* (IgD9eS), to produce pY115 (SEQ ID NO:19; FIG. 2). In FIG. 2, the modified FBAINm promoter is called FBA1+ Intron. It is also FBA1+Intron in other figures, as well as YAR FBA1 PRO+Intron and these terms are used interchangeably with FBAINm.

The FBAINm promoter was amplified from plasmid pY115 (SEQ ID NO:19), using PCR with oligonucleotide primers oYFBA1 (SEQ ID NO:20) and oYFBA1-6 (SEQ ID NO:21). Primer oYFBA1 (SEQ ID NO:20) was designed to introduce an BglII site at the 5' end of the promoter and primer oYFBA1-6 (SEQ ID NO:21) was designed to introduce a NotI site at the 3' end of the promoter while removing the NcoI site and thus, the ATG start codon. The resulting PCR fragment was digested with BglII and NotI and cloned into the BglII/NotI fragment of pY115, containing the vector backbone, to form pY158 (SEQ ID NO:22).

Figure 3:
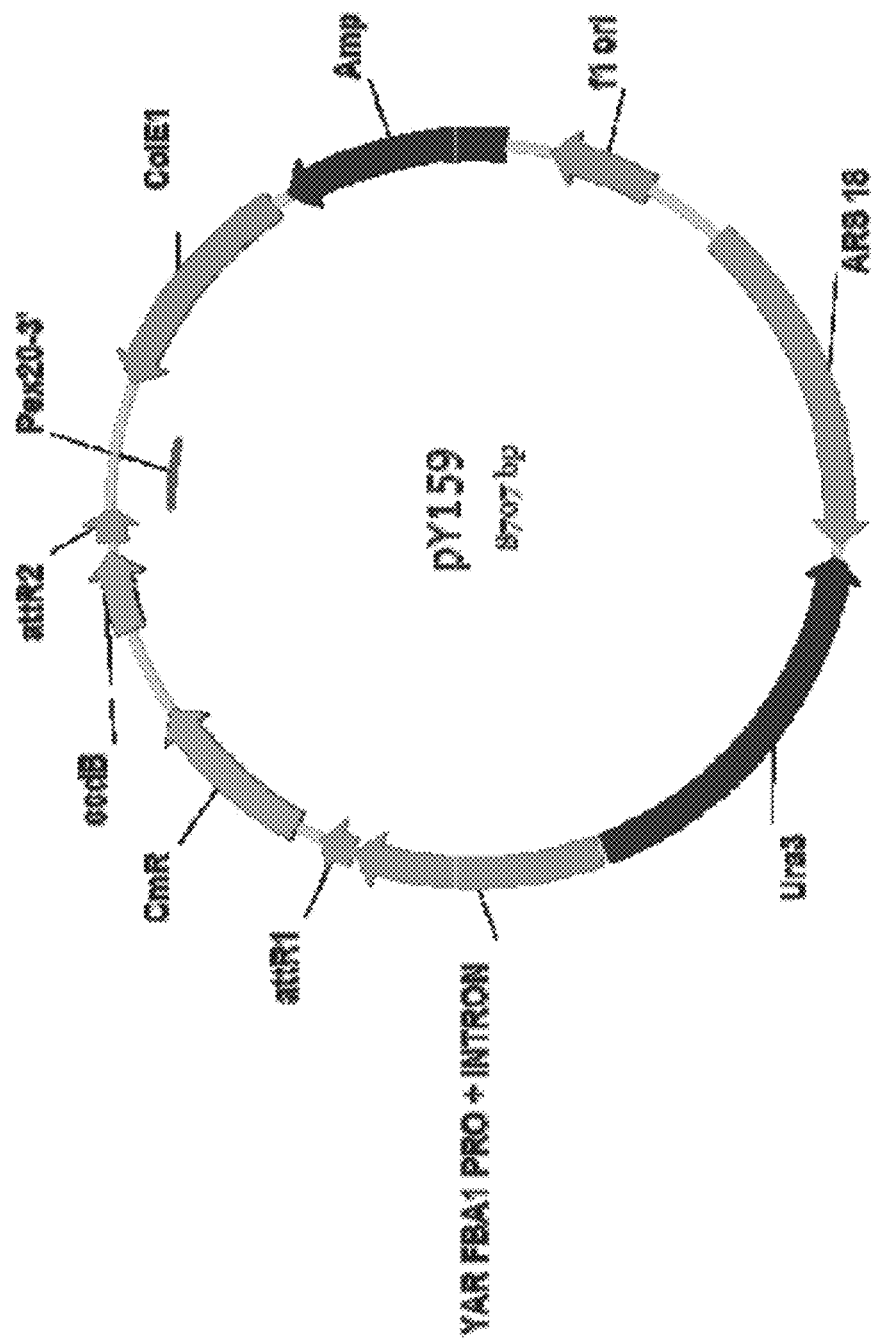
FIG. 3 is a map of plasmid pY159 (SEQ ID NO:23).

Plasmid pY158 (SEQ ID NO:22) was digested with NotI and the resulting DNA ends were filled. After filling to form blunt ends, the DNA fragments were treated with calf intestinal alkaline phosphatase and separated using agarose gel electrophoresis. The 6992 bp fragment containing the *Yarrowia lipolytica* FBAINm promoter was excised from the agarose gel and purified using the QIAquick® Gel Extraction Kit (Qiagen Inc., Valencia, Calif.) following the manufacturer's protocol. The purified 6992 bp fragment was ligated with cassette rfA using the Gateway Vector Conversion System (Cat. No. 11823-029, Invitrogen Corporation) following the manufacturer's protocol to form *Yarrowia lipolytica* Gateway® destination vector pY159 (SEQ ID NO:23; FIG. 3). Construction of *Yarrowia* Expression Vectors pY173 and pY174

Figure 4:
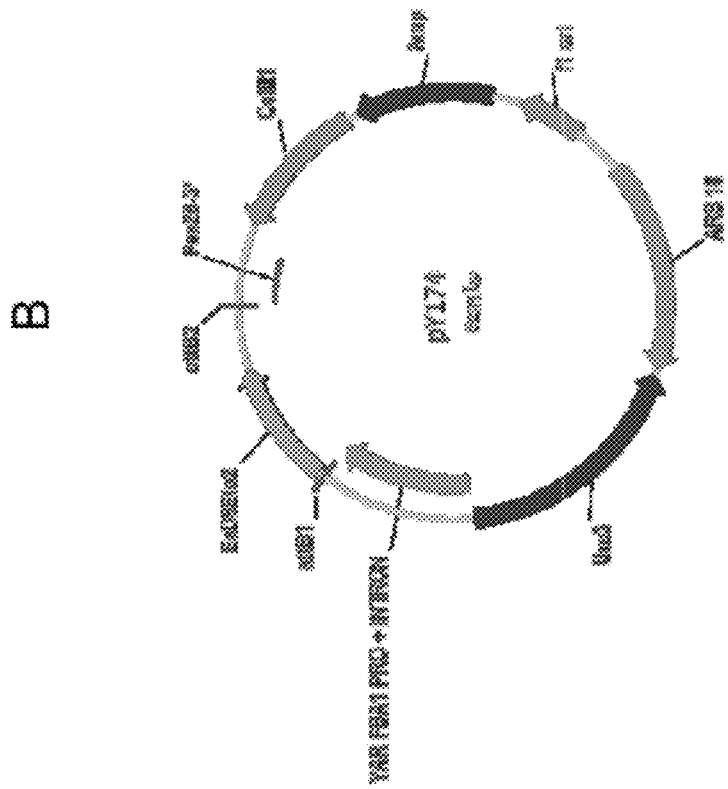
FIG. 4A is a map of plasmid pY173 (SEQ ID NO:24).
FIG. 4B is a map of plasmid pY174 (SEQ ID NO:25).
Figure 4:
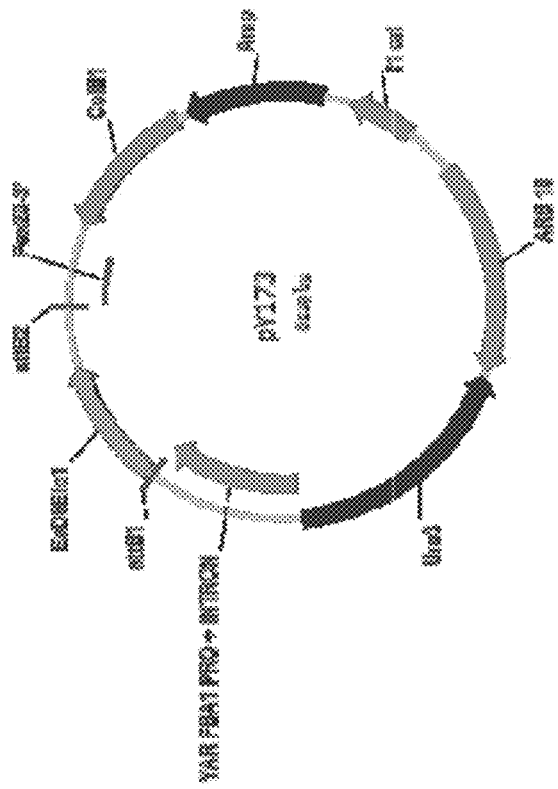
Figure 6:
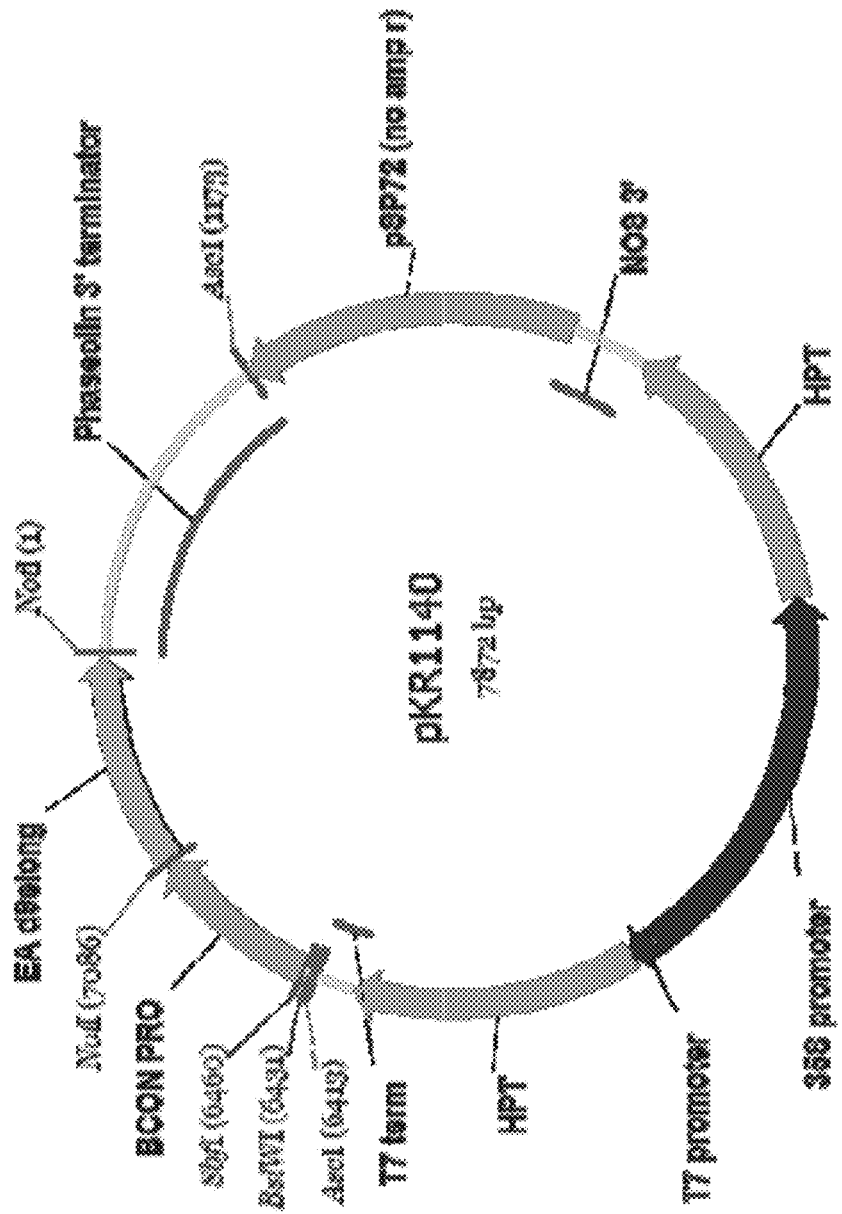
FIG. 6 is a map of pKR1140 (SEQ ID NO:30).

Using the Gateway® LR Clonase™ II enzyme mix (Cat. No. 11791-020, Invitrogen Corporation) and following the manufacturer's protocol, the cDNA inserts from pLF121-1 (SEQ ID NO:9) and pLF121-2 (SEQ ID NO:10) were transferred to pY159 (SEQ ID NO:23) to form pY173 (SEQ ID NO:24, FIG. 4A) and pY174 (SEQ ID NO:25; FIG. 4B), respectively.

Functional Analysis of EaD9Elo1 and EaD9Elo2 in *Yarrowia lipolytica*

Strain Y2224 was isolated in the following manner: *Yarrowia lipolytica* ATCC #20362 cells from a YPD agar plate (1% yeast extract, 2% bactopeptone, 2% glucose, 2% agar) were streaked onto a MM plate (75 mg/L each of uracil and uridine, 6.7 g/L YNB with ammonia sulfate, without amino acid, and 20 g/L glucose) containing 250 mg/L 5-FOA (Zymo Research). Plates were incubated at 28° C. and four of the resulting colonies were patched separately onto MM plates containing 200 mg/mL 5-FOA and MM plates lacking uracil and uridine to confirm uracil Ura3 auxotrophy.

Strain Y2224 was transformed with pY173 (SEQ ID NO:24, FIG. 4A) and pY174 (SEQ ID NO:25; FIG. 4B) as described in the General Methods.

Single colonies of transformant *Yarrowia lipolytica* containing pY173 and pY174 were grown in 3 mL minimal media lacking uraci at 30° C. for 16 h after which cells were centrifuged at 250 rpm to pellet. Cells were washed once with water, pelleted by centrifugation and air dried. Pellets were transesterified (Roughan, G. and Nishida, I., *Arch. Biochem. Biophys*. 276(1):38-46 (1990)) with 500 µL of 1% sodium methoxide for 30 min. at 50° C. after which 500 µL of 1M sodium chloride and 100 µL of heptane were added. After thorough mixing and centrifugation, fatty acid methyl esters (FAMEs) were analyzed by GC. FAMEs (5 µL injected from hexane layer) were separated and quantified using a Hewlett-Packard 6890 Gas Chromatograph fitted with an Omegawax 320 fused silica capillary column (Cat. No. 24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. Retention times were compared to those for methyl esters of standards commercially available (Nu-Chek Prep, Inc.).

The fatty acid profiles for *Yarrowia lipolytica* expressing pY173 and pY174 are shown in FIG. 5. Percent delta-9 elongation (delta-9% Elong) was calculated either by dividing the wt. % for EDA by the sum of the wt. % for EDA and LA and multiplying by 100 to express as a %. Average is indicated by Ave. followed by appropriate header.

Example 5

Construction of Soybean Expression Vector pKR1140 for Expression of *Euglena anabaena* UTEX 373 Delta-9 Elongase (EaD9Elo1)

The present Example describes construction of a soybean vector for expression of EaD9Elo1. This work included the following steps: (1) PCR amplification of EaD9Elo1 with appropriate restriction sites for cloning from plasmids described in Example 2; (2) cloning of the EaD9Elo1 PCR products into cloning vector pCR-Blunt® (Invitrogen Corporation) to produce pKR1137; (3) cloning EaD9Elo1 into soybean expression vector pKR72 to produce pKR1140.

In order to introduce NotI and NcoI restriction sites at the 5' end of the coding sequences and a NotI site at the 3' end of the coding sequences, EaD9Elo1 was PCR amplified. The coding sequence for EaD9Elo1 (SEQ ID NO:11) was amplified from pLF121-1 (SEQ ID NO:9) with oligonucleotide primers oEAd9el1-1 (SEQ ID NO:26) and oEAd9el1-2 (SEQ ID NO:27) using the Phusion™ High-Fidelity DNA Polymerase (Cat. No. F553S, Finnzymes Oy, Finland) following the manufacturer's protocol. The resulting DNA fragments were cloned into the pCR-Blunt® cloning vector using the Zero Blunt® PCR Cloning Kit (Invitrogen Corporation), following the manufacturer's protocol, to produce pKR1137 (SEQ ID NO:28).

A starting plasmid pKR72 (ATCC Accession No. PTA-6019; SEQ ID NO:29, 7085 bp sequence), a derivative of pKS123 which was previously described in PCT Publication No. WO 02/008269 (the contents of which are hereby incorporated by reference), contains the hygromycin B phosphotransferase gene (HPT) (Gritz, L. and Davies, J., Gene 25:179-188 (1983)), flanked by the T7 promoter and transcription terminator (T7prom/HPT/T7term cassette), and a bacterial origin of replication (ori) for selection and replication in bacteria (e.g., E. coli). In addition, pKR72 (SEQ ID NO:29) also contains HPT, flanked by the 35S promoter (Odell et al., Nature 313:810-812 (1985)) and NOS 3' transcription terminator (Depicker et al., J. Mol. Appl. Genet. 1:561-570 (1982)) (35S/HPT/NOS3' cassette) for selection in plants such as soybean. pKR72 (SEQ ID NO:29) also contains a NotI restriction site, flanked by the promoter for the α' subunit of β-conglycinin (Beachy et al., EMBO J. 4:3047-3053 (1985)) and the 3' transcription termination region of the phaseolin gene (Doyle et al., J. Biol. Chem. 261:9228-9238 (1986)), thus allowing for strong tissue-specific expression in the seeds of soybean of genes cloned into the NotI site.

EaD9Elo1 was released from pKR1137 (SEQ ID NO:28) by digestion with NotI and cloned into the NotI site of pKR72 (SEQ ID NO:29) to produce pKR1140 (SEQ ID NO:30).

Example 6

Construction of Soybean Expression Vector pKR1151 for Co-Expression of the *Tetruetreptia pomquetensis* CCMP1491 Delta-8 Desaturase (TpomD8) with a Delta-9 Elongase Derived from *Euglena anabaena* (EaD9Elo1)

The present Example describes construction of a soybean vector for co-expression of TpomD8 (SEQ ID NO:31; which is described in U.S. patent application Ser. No. 11/876,115 (filed Oct. 22, 2007)) with EaD9Elo1.

*Tetruetreptia pomquetensis* CCMP1491 Delta-8 Desaturase (TpomD8):

*Tetruetreptia pomquetensis* CCMP1491 cells (from 1 liter of culture) were purchased from the Provasoli-Guillard National Center for Culture of Marine Phytoplakton (CCMP) (Bigelow Laboratory for Ocean Sciences, West Boothbay Harbor, Me.). Total RNA was isolated using the trizol reagent (Invitrogen, Carlsbad, Calif.), according to the manufacturer's protocol. The cell pellet was resuspended in 0.75 mL of trizol reagent, mixed with 0.5 mL of 0.5 mm glass beads, and homogenized in a Biospec mini beadbeater (Bartlesville, Okla.) at the highest setting for 3 min. The mixture was centrifuged in an Eppendorf centrifuge for 30 sec at 14,000 rpm to remove debri and glass beads. Supernatant was extracted with 150 μL of 24:1 chloroform:isoamy alcohol. The upper aqueous phase was used for RNA isolation.

For RNA isolation, the aqueous phase was mixed with 0.375 mL of isopropyl alcohol and allowed to incubate at room temperature for 5 min. Precipitated RNA was collected by centrifugation at 8,000 rpm and 4° C. for 5 min. The pellet was washed once with 0.7 mL of 80% ethanol and air dried. Thus, 95 μg of total RNA was obtained from *Tetruetreptia pomquetensis* CCMP1491.

Total RNA (0.95 μg of total RNA in 1 μL) was used as template to synthesize double stranded cDNA. The Creator™ SMART™ cDNA Library Construction Kit from BD Bioscience Clontech (Palo Alto, Calif.) was used. Total RNA (1 μL) was mixed with 1 μL of SMART IV oligonucleotide (SEQ ID NO:32) 1 μL of the Adaptor Primer from Invitrogen 3'-RACE kit (SEQ ID NO:33) and 2 μL of water. The mixture was heated to 75° C. for 5 min and then cooled on ice for 5 min. To the mixture was added, 2 μL of 5× first strand buffer, 1 μL 20 mM DTT, 1 μL of dNTP mix (10 mM each of dATP, dCTP, dGTP and dTTP) and 1 μL of PowerScript reverse transcriptase. The sample was incubated at 42° C. for 1 h. The resulting first strand cDNAs were then used as template for amplification.

The *Tetruetreptia pomquetensis* CCMP1491 (TpomD8; SEQ ID NO:31) was amplified from the cDNA with oligonucleotide primers TpomNot-5 (SEQ ID NO:34) and TpomNot-3 (SEQ ID NO:35) using Taq polymerase (Invitrogen Corporation) following the manufacturer's protocol.

*Tetruetreptia pomquetensis* CCMP1491 cDNA (1 μL) was combined with 50 μmol of TpomNot-5 (SEQ ID NO:34), 50 μmol of TpomNot-3 (SEQ ID NO:35), 1 μL of PCR nucleotide mix (10 mM, Promega, Madison, Wis.), 5 μL of 10×PCR buffer (Invitrogen Corporation), 1.5 μL of MgCl$_2$ (50 mM, Invitrogen Corporation), 0.5 μL of Taq polymerase (Invitrogen Corporation) and water to 50 μL. The reaction conditions were 94° C. for 3 min followed by 35 cycles of 94° C. for 45 sec, 55° C. for 45 sec and 72° C. for 1 min. The PCR was finished at 72° C. for 7 min and then held at 4° C. The PCR reaction was analyzed by agarose gel electrophoresis on 5 μL and a DNA band with molecular weight around 1.3 kb was observed.

The remaining 45 μL of product was separated by agarose gel electrophoresis and the DNA purified using the Zymoclean™ Gel DNA Recovery Kit (Zymo Research, Orange, Calif.) following the manufacturer's protocol. The resulting DNA was cloned into the pGEM®-T Easy Vector (Promega) following the manufacturer's protocol to produce pLF114-10 (SEQ ID NO:36).

Vector pKR457 (SEQ ID NO:37), which was previously described in PCT Publication No. WO 2005/047479 (the contents of which are hereby incorporated by reference), contains a NotI site flanked by the Kunitz soybean Trypsin Inhibitor (KTi) promoter (Jofuku et al., Plant Cell 1:1079-1093 (1989)) and the KTi 3' termination region, the isolation of which is described in U.S. Pat. No. 6,372,965, followed by the soy albumin transcription terminator, which was previously described in PCT Publication No. WO 2004/071467 (Kti/NotI/Kti3'Salb3' cassette).

The NotI fragment of pLF114-10 (SEQ ID NO:36), containing the TpomD8 gene was cloned into the NotI site of pKR457 (SEQ ID NO:37), to produce pKR1145 (SEQ ID NO:38).

Figure 7:
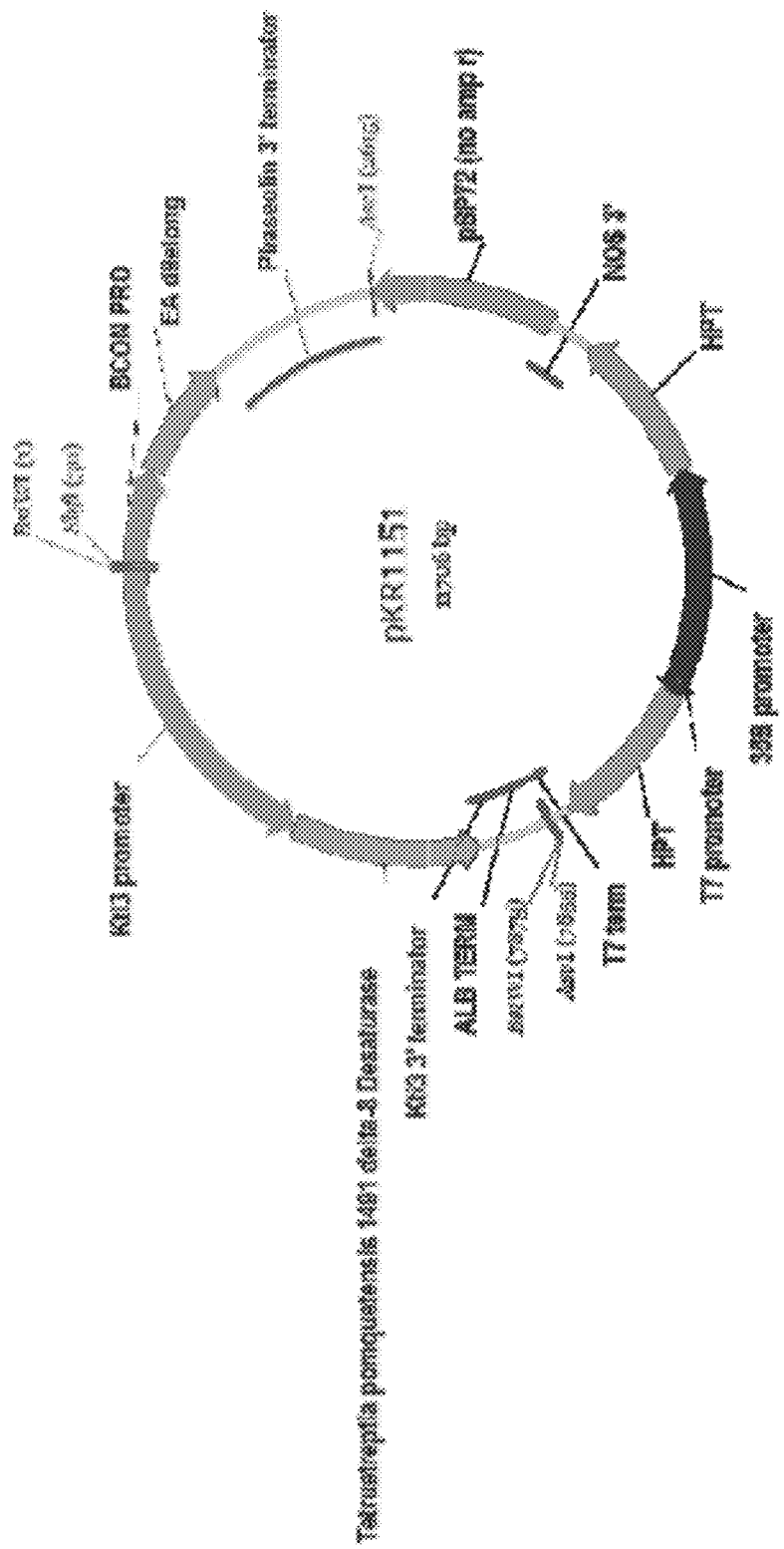
FIG. 7 is a map of pKR1151 (SEQ ID NO:39).

The BsiWI fragment from pKR1145 (SEQ ID NO:38), containing the TpomD8 gene, was cloned into the BsiWI site of pKR1140 (SEQ ID NO:30) to produce pKR1151 (SEQ ID NO:39; FIG. 7). the *Euglena anabaena* delta-9 elongase (EaD9Elo1) is called EA D9elong in FIG. 7.

Example 7

Production and Model System Transformation of Somatic Soybean Embryo Cultures with Soybean Expression Vectors and Plant Regeneration Culture Conditions:
Soybean embryogenic suspension cultures (cv. Jack) are maintained in 35 mL liquid medium SB196 (infra) on a rotary shaker, 150 rpm, 26° C. with cool white fluorescent lights on 16:8 hr day/night photoperiod at light intensity of 60-85 µE/m2/s. Cultures are subcultured every 7 days to two weeks by inoculating approximately 35 mg of tissue into 35 mL of fresh liquid SB196 (the preferred subculture interval is every 7 days).

Soybean embryogenic suspension cultures are transformed with the soybean expression plasmids by the method of particle gun bombardment (Klein et al., Nature 327:70 (1987)) using a DuPont Biolistic PDS1000/HE instrument (helium retrofit) for all transformations.

Soybean Embryogenic Suspension Culture Initiation:

Soybean cultures are initiated twice each month with 5-7 days between each initiation. Pods with immature seeds from available soybean plants are picked 45-55 days after planting. Seeds are removed from the pods and placed into a sterilized magenta box. The soybean seeds are sterilized by shaking them for 15 min in a 5% Clorox solution with 1 drop of Ivory soap (i.e., 95 mL of autoclaved distilled water plus 5 mL Clorox and 1 drop of soap, mixed well). Seeds are rinsed using 2 1-liter bottles of sterile distilled water and those less than 4 mm are placed on individual microscope slides. The small end of the seed is cut and the cotyledons pressed out of the seed coat. When cultures are being prepared for production transformation, cotyledons are transferred to plates containing SB1 medium (25-30 cotyledons per plate). Plates are wrapped with fiber tape and are maintained at 26° C. with cool white fluorescent lights on 16:8 h day/night photoperiod at light intensity of 60-80 µE/m2/s for eight weeks, with a media change after 4 weeks. When cultures are being prepared for model system experiments, cotyledons are transferred to plates containing SB199 medium (25-30 cotyledons per plate) for 2 weeks, and then transferred to SB1 for 2-4 weeks. Light and temperature conditions are the same as described above. After incubation on SB1 medium, secondary embryos are cut and placed into SB196 liquid media for 7 days.

Preparation of DNA for Bombardment:

Either an intact plasmid or a DNA plasmid fragment containing the genes of interest and the selectable marker gene are used for bombardment. Fragments from soybean expression plasmids are obtained by gel isolation of digested plasmids. In each case, 100 µg of plasmid DNA is used in 0.5 mL of the specific enzyme mix described below. Plasmids are digested with AscI (100 units) in NEBuffer 4 (20 mM Tris-acetate, 10 mM magnesium acetate, 50 mM potassium acetate, 1 mM dithiothreitol, pH 7.9), 100 µg/mL BSA, and 5 mM beta-mercaptoethanol at 37° C. for 1.5 hr. The resulting DNA fragments are separated by gel electrophoresis on 1% SeaPlaque GTG agarose (BioWhitaker Molecular Applications) and the DNA fragments containing gene cassettes are cut from the agarose gel. DNA is purified from the agarose using the GELase digesting enzyme following the manufacturer's protocol.

A 50 µL aliquot of sterile distilled water containing 3 mg of gold particles (3 mg gold) is added to 30 µL of a 10 ng/µL DNA solution (either intact plasmid or DNA fragment prepared as described herein), 25 µL 5M $CaCl_2$ and 20 µL of 0.1 M spermidine. The mixture is shaken 3 min on level 3 of a vortex shaker and spun for 10 sec in a bench microfuge. The supernatant is removed, followed by a wash with 400 µL 100% ethanol and another brief centrifugation. The 400 ul ethanol is removed and the pellet is resuspended in 40 µL of 100% ethanol. Five µL of DNA suspension is dispensed to each flying disk of the Biolistic PDS1000/HE instrument disk. Each 5 µL aliquot contains approximately 0.375 mg gold per bombardment (e.g., per disk).

For model system transformations, the protocol is identical except for a few minor changes (ie, 1 mg of gold particles is added to 5 µL of a 1 µg/µL DNA solution, 50 µL of a 2.5M $CaCl_2$ is used and the pellet is ultimately resuspended in 85 µL of 100% ethanol thus providing 0.058 mg of gold particles per bombardment).

Tissue Preparation and Bombardment with DNA:

Approximately 150-200 mg of seven day old embryogenic suspension cultures is placed in an empty, sterile 60×15 mm petri dish and the dish is covered with plastic mesh. The chamber is evacuated to a vacuum of 27-28 inches of mercury, and tissue is bombarded one or two shots per plate with membrane rupture pressure set at 1100 PSI. Tissue is placed approximately 3.5 inches from the retaining/stopping screen. Model system transformation conditions are identical except 100-150 mg of embryogenic tissue is used, rupture pressure is set at 650 PSI and tissue is place approximately 2.5 inches from the retaining screen.

Selection of Transformed Embryos:

Transformed embryos are selected either using hygromycin (when the hygromycin B phosphotransferase (HPT) gene is used as the selectable marker) or chlorsulfuron (when the acetolactate synthase (ALS) gene is used as the selectable marker).

Following bombardment, the tissue is placed into fresh SB196 media and cultured as described above. Six to eight days post-bombardment, the SB196 is exchanged with fresh SB196 containing either 30 mg/L hygromycin or 100 ng/mL chlorsulfuron, depending on the selectable marker used. The selection media is refreshed weekly. Four to six weeks post-selection, green, transformed tissue is observed growing from untransformed, necrotic embryogenic clusters.

Embryo Maturation:

For production transformations, isolated, green tissue is removed and inoculated into multiwell plates to generate new, clonally propagated, transformed embryogenic suspension cultures. Transformed embryogenic clusters are cultured for four-six weeks in multiwell plates at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 µE/m²s. After this time embryo clusters are removed to a solid agar media, SB166, for one-two weeks and then subcultured to SB103 medium for 3-4 weeks to mature embryos. After maturation on plates in SB103, individual embryos are removed from the clusters, dried and screened for alterations in their fatty acid compositions as described previously.

For model system transformations, embryos are matured in soybean histodifferentiation and maturation liquid medium (SHaM liquid media; Schmidt et al., Cell Biology and Morphogenesis 24:393 (2005)) using a modified procedure. Briefly, after 4 weeks of selection in SB196 as described above, embryo clusters are removed to 35 mL of SB228 (SHaM liquid media) in a 250 mL Erlenmeyer flask. Tissue is maintained in SHaM liquid media on a rotary shaker at 130 rpm and 26° C. with cool white fluorescent lights on a 16:8 hr day/night photoperiod at a light intensity of 60-85 µE/m2/s for 2 weeks as embryos mature. Embryos grown for 2 weeks in SHaM liquid media are equivalent in size and fatty acid content to embryos cultured on SB166/SB103 for 5-8 weeks.

After maturation in SHaM liquid media, individual embryos are removed from the clusters, dried and screened for alterations in their fatty acid compositions as described previously.

Media Recipes:

SB 196 - FN Lite Liquid Proliferation Medium (per liter)

| | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm |
| pH 5.8 | |

FN Lite Stock Solutions

| Stock Number | | 1000 mL | 500 mL |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 Solid Medium (per liter)

1 package MS salts (Gibco/BRL - Cat. No. 11117-066)
1 mL B5 vitamins 1000X stock
31.5 g glucose
2 mL 2,4-D (20 mg/L final concentration)
pH 5.7
8 g TC agar

SB199 Solid Medium (per liter)

1 package MS salts (Gibco/BRL - Cat. No. 11117-066)
1 mL B5 vitamins 1000X stock
30 g Sucrose
4 ml 2,4-D (40 mg/L final concentration)
pH 7.0
2 gm Gelrite

SB 166 Solid Medium (per liter)

1 package MS salts (Gibco/BRL - Cat. No. 11117-066)
1 mL B5 vitamins 1000X stock
60 g maltose
750 mg $MgCl_2$ hexahydrate
5 g activated charcoal
pH 5.7
2 g gelrite

SB 103 Solid Medium (per liter)

1 package MS salts (Gibco/BRL - Cat. No. 11117-066)
1 mL B5 vitamins 1000X stock
60 g maltose
750 mg MgCl2 hexahydrate
pH 5.7
2 g gelrite

SB 71-4 Solid Medium (per liter)

1 bottle Gamborg's B5 salts w/sucrose (Gibco/BRL - Cat. No. 21153-036)
pH 5.7
5 g TC agar

2,4-D Stock

Obtain premade from Phytotech Cat. No. D 295 - concentration 1 mg/mL

B5 Vitamins Stock (per 100 mL)

Store aliquots at −20° C.
10 g myo-inositol
100 mg nicotinic acid
100 mg pyridoxine HCl
1 g thiamine
If the solution does not dissolve quickly enough, apply a low level of heat via the hot stir plate.

SB 228- Soybean Histodifferentiation & Maturation (SHaM) (per liter)

| | |
|---|---|
| DDI $H_2O$ | 600 mL |
| FN-Lite Macro Salts for SHaM 10X | 100 mL |
| MS Micro Salts 1000x | 1 mL |
| MS FeEDTA 100x | 10 mL |
| CaCl 100x | 6.82 mL |
| B5 Vitamins 1000x | 1 mL |
| L-Methionine | 0.149 g |
| Sucrose | 30 g |
| Sorbitol | 30 g |
| Adjust volume to 900 mL | |
| pH 5.8 | |
| Autoclave | |
| Add to cooled media ($\leq 30°$ C.): | |
| *Glutamine (final concentration 30 mM) 4% | 110 mL |

*Note:
Final volume will be 1010 mL after glutamine addition.
Since glutamine degrades relatively rapidly, it may be preferable to add immediately prior to using media. Expiration 2 weeks after glutamine is added; base media can be kept longer w/o glutamine.

FN-lite Macro for SHAM 10X- Stock #1 (per liter)

| | |
|---|---|
| $(NH_4)2SO_4$ (ammonium sulfate) | 4.63 g |
| $KNO_3$ (potassium nitrate) | 28.3 g |
| $MgSO_4 * 7H_2O$ (magnesium sulfate heptahydrate) | 3.7 g |
| $KH_2PO_4$ (potassium phosphate, monobasic) | 1.85 g |
| Bring to volume | |
| Autoclave | |

MS Micro 1000X- Stock #2 (per 1 liter)

| | |
|---|---|
| $H_3BO_3$ (boric acid) | 6.2 g |
| $MnSO_4 * H_2O$ (manganese sulfate monohydrate) | 16.9 g |
| $ZnSO4 * 7H20$ (zinc sulfate heptahydrate) | 8.6 g |
| $Na_2MoO_4 * 2H20$ (sodium molybdate dihydrate) | 0.25 g |
| $CuSO_4 * 5H_20$ (copper sulfate pentahydrate) | 0.025 g |
| $CoCl_2 * 6H_20$ (cobalt chloride hexahydrate) | 0.025 g |
| KI (potassium iodide) | 0.8300 g |
| Bring to volume | |
| Autoclave | |

FeEDTA 100X- Stock #3 (per liter)

| | |
|---|---|
| $Na_2EDTA$* (sodium EDTA) | 3.73 g |
| $FeSO_4 * 7H_20$ (iron sulfate heptahydrate) | 2.78 g |
| Bring to Volume | |
| Solution is photosensitive. Bottle(s) should be wrapped in foil to omit light | |
| Autoclave | |

*EDTA must be completely dissolved before adding iron.

-continued

Ca 100X- Stock #4 (per liter)

| | |
|---|---|
| CaCl₂ * 2H₂0 (calcium chloride dihydrate) | 44 g |
| Bring to Volume | |
| Autoclave | |

B5 Vitamin 1000X- Stock #5 (per liter)

| | |
|---|---|
| Thiamine * HCl | 10 g |
| Nicotinic Acid | 1 g |
| Pyridoxine * HCl | 1 g |
| Myo-Inositol | 100 g |
| Bring to Volume | |
| Store frozen | |

4% Glutamine- Stock #6 (per liter)

| | |
|---|---|
| DDI water heated to 30° C. | 900 mL |
| L-Glutamine | 40 g |
| Gradually add while stirring and applying low heat. | |
| Do not exceed 35° C. | |
| Bring to Volume | |
| Filter Sterilize | |
| Store frozen* | |

*Note:
Warm thawed stock in 31° C. bath to fully dissolve crystals.

Regeneration of Soybean Somatic Embryos into Plants:

In order to obtain whole plants from embryogenic suspension cultures, the tissue must be regenerated. Embyros are matured as described in above. After subculturing on medium SB103 for 3 weeks, individual embryos can be removed from the clusters and screened for alterations in their fatty acid compositions as described in Example 7. It should be noted that any detectable phenotype, resulting from the expression of the genes of interest, could be screened at this stage. This would include, but not be limited to, alterations in fatty acid profile, protein profile and content, carbohydrate content, growth rate, viability, or the ability to develop normally into a soybean plant.

Matured individual embryos are desiccated by placing them into an empty, small petri dish (35×10 mm) for approximately 4 to 7 days. The plates are sealed with fiber tape (creating a small humidity chamber). Desiccated embryos are planted into SB71-4 medium where they are left to germinate under the same culture conditions described above. Germinated plantlets are removed from germination medium and rinsed thoroughly with water and then are planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot. After 10 to 16 weeks, mature seeds are harvested, chipped and analyzed for fatty acids.

Example 8

Fatty Acid Analysis of Transgenic Somatic Soybean Embryos

Mature somatic soybean embryos are a good model for zygotic embryos. While in the globular embryo state in liquid culture, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α'-subunit of β-conglycinin, kunitz trypsin inhibitor 3, and seed lectin are essentially absent. Upon transfer to hormone-free media to allow differentiation to the maturing somatic embryo state, triacylglycerol becomes the most abundant lipid class. As well, mRNAs for α'-subunit of β-conglycinin, kunitz trypsin inhibitor 3 and seed lectin become very abundant messages in the total mRNA population. On this basis, the somatic soybean embryo system behaves very similarly to maturing zygotic soybean embryos in vivo, and is thus a good and rapid model system for analyzing the phenotypic effects of modifying the expression of genes in the fatty acid biosynthesis pathway (see PCT Publication No. WO 2002/00904, Example 3). Most importantly, the model system is also predictive of the fatty acid composition of seeds from plants derived from transgenic embryos.

A subset of soybean embryos for each event generated from either production transformation or model system transformation (as described in Example 6) are harvested in the following way. Embryos (5-10 embryos) from each event are picked into glass GC vials and fatty acid methyl esters are prepared by transesterification. For transesterification, 50 μL of trimethylsulfonium hydroxide (TMSH) and 0.5 mL of hexane is added to the embryos in glass vials and incubated for 30 min at room temperature while shaking. Fatty acid methyl esters (5 μL injected from hexane layer) are separated and quantified using a Hewlett-Packard 6890 Gas Chromatograph fitted with an Omegawax 320 fused silica capillary column (Cat. No. 24152, Supelco Inc.). The oven temperature is programmed to hold at 220° C. for 2.6 min, increase to 240° C. at 20° C./min and then hold for an additional 2.4 min. Carrier gas is supplied by a Whatman hydrogen generator. Retention times are compared to those for methyl esters of standards commercially available (Nu-Chek Prep, Inc.). Events having good phenotype can be re-analyzed by GC using identical conditions except the oven temperature is held at 150° C. for 1 min and then increased to 240° C. at 5° C.

Example 9

Construction of Alternate Soybean Expression Vectors for Expression of *Euglena anabaena* UTEX 373 Delta-9 Elongase (EaD9Elo1)

In addition to the genes, promoters, terminators and gene cassettes described herein, one skilled in the art can appreciate that other promoter/gene/terminator cassette combinations can be synthesized in a way similar to, but not limited to, that described herein for expression of EaD9Elo1. Similarly, it may be desirable to express other PUFA genes (such as those described below in Table 9), for co-expression with any of the delta-9 elongases of the present invention.

For instance, PCT Publication Nos. WO 2004/071467 and WO 2004/071178 describe the isolation of a number of promoter and transcription terminator sequences for use in embryo-specific expression in soybean. Furthermore, PCT Publication Nos. WO 2004/071467, WO 20051047479 and WO 2006/012325 describe the synthesis of multiple promoter/gene/terminator cassette combinations by ligating individual promoters, genes and transcription terminators together in unique combinations. Generally, a NotI site flanked by the suitable promoter (such as those listed in, but not limited to, Table 7) and a transcription terminator (such as those listed in, but not limited to, Table 8) is used to clone the desired gene. NotI sites can be added to a gene of interest such as those listed in, but not limited to, Table 9 using PCR amplification with oligonucleotides designed to introduce NotI sites at the 5' and 3' ends of the gene. The resulting PCR product is then digested with NotI and cloned into a suitable promoter/NotI/terminator cassette.

In addition, PCT Publication Nos. WO 2004/071467, WO 2005/047479 and WO 2006/012325 describe the further linking together of individual gene cassettes in unique combinations, along with suitable selectable marker cassettes, in order to obtain the desired phenotypic expression. Although this is done mainly using different restriction enzymes sites, one skilled in the art can appreciate that a number of techniques can be utilized to achieve the desired promoter/gene/transcription terminator combination. In so doing, any combination of embryo-specific promoter/gene/transcription terminator cassettes can be achieved. One skilled in the art can also appreciate that these cassettes can be located on individual DNA fragments or on multiple fragments where co-expression of genes is the outcome of co-transformation of multiple DNA fragments.

TABLE 7

Seed-specific Promoters

| Promoter | Organism | Promoter Reference |
|---|---|---|
| β-conglycinin α'-subunit | soybean | Beachy et al., EMBO J. 4: 3047-3053 (1985) |
| kunitz trypsin inhibitor | soybean | Jofuku et al., Plant Cell 1: 1079-1093 (1989) |
| Annexin | soybean | WO 2004/071467 |
| glycinin Gy1 | soybean | WO 2004/071467 |
| albumin 2S | soybean | U.S. Pat. No. 6,177,613 |
| legumin A1 | pea | Rerie et al., Mol. Gen. Genet. 225: 148-157 (1991) |
| β-conglycinin β-subunit | soybean | WO 2004/071467 |
| BD30 (also called P34) | soybean | WO 2004/071467 |
| legumin A2 | pea | Rerie et al., Mol. Gen. Genet. 225: 148-157 (1991) |

TABLE 8

Transcription Terminators

| Transcription Terminator | Organism | Reference |
|---|---|---|
| phaseolin 3' | bean | WO 2004/071467 |
| kunitz trypsin inhibitor 3' | soybean | WO 2004/071467 |
| BD30 (also called P34) 3' | soybean | WO 2004/071467 |
| legumin A2 3' | pea | WO 2004/071467 |
| albumin 2S 3' | soybean | WO 2004/071467 |

TABLE 9

PUFA Biosynthetic Pathway Genes

| Gene | Organism | Reference |
|---|---|---|
| delta-6 desaturase | Saprolegnia diclina | WO 2002/081668 |
| delta-6 desaturase | Mortierella alpina | U.S. Pat. No. 5,968,809 |
| elongase | Mortierella alpina | WO 2000/12720 U.S. Pat. No. 6,403,349 |
| delta-5 desaturase | Mortierella alpina | U.S. Pat. No. 6,075,183 |
| delta-5 desaturase | Saprolegnia diclina | WO 2002/081668 |
| delta-5 desaturase | Peridinium sp. | U.S. Pat. application No. 11/748,637 |
| delta-5 desaturase | Euglena gracilis | U.S. Pat. application No. 11/748,629 |
| delta-15 desaturase | Fusarium moniliforme | WO 2005/047479 |
| delta-17 desaturase | Saprolegnia diclina | WO 2002/081668 |

TABLE 9-continued

PUFA Biosynthetic Pathway Genes

| Gene | Organism | Reference |
|---|---|---|
| elongase | Thraustochytrium aureum | WO 2002/08401 U.S. Pat. No. 6,677,145 |
| elongase | Pavlova sp. | Pereira et al., Biochem. J. 384: 357-366 (2004) |
| delta-4 desaturase | Schizochytrium aggregatum | WO 2002/090493 U.S. Pat. No. 7,045,683 |
| delta-4 desaturase | Isochrysis galbana | WO 2002/090493 U.S. Pat. No. 7,045,683 |
| delta-4 desaturase | Thraustochytrium aureum | WO 2002/090493 U.S. Pat. No. 7,045,683 |
| delta-4 desaturase | Euglena gracilis | U.S. Pat. application No. 10/552,127 |
| delta-9 elongase | Isochrysis galbana | WO 2002/077213 |
| delta-9 elongase | Euglena gracilis | U.S. Pat. application No. 11/601,563 |
| delta-9 elongase | Eutreptiella sp. CCMP389 | U.S. Pat. application No. 11/601,564 |
| delta-8 desaturase | Euglena gracilis | WO 2000/34439 U.S. Pat. No. 6,825,017 WO 2004/057001 WO 2006/012325 |
| delta-8 desaturase | Acanthamoeba castellanii | Sayanova et al., FEBS Lett. 580: 1946-1952 (2006) |
| delta-8 desaturase | Pavlova salina | WO 2005/103253 |
| delta-8 desaturase | Pavlova lutheri | U.S. Pat. application No. 11/737,772 |
| delta-8 desaturase | Tetruetreptia pomquetensis CCMP1491 | U.S. Pat. application No. 11/876,115 |
| delta-8 desaturase | Eutreptiella sp. CCMP389 | U.S. Pat. application No. 11/876,115 |
| delta-8 desaturase | Eutreptiella cf_gymnastica CCMP1594 | U.S. Pat. application No. 11/876,115 |

Example 10

Synthesis of a Codon-Optimized Delta-9 Elongase Gene for Yarrowia lipolytica (EaD9ES)

Figure 9A:
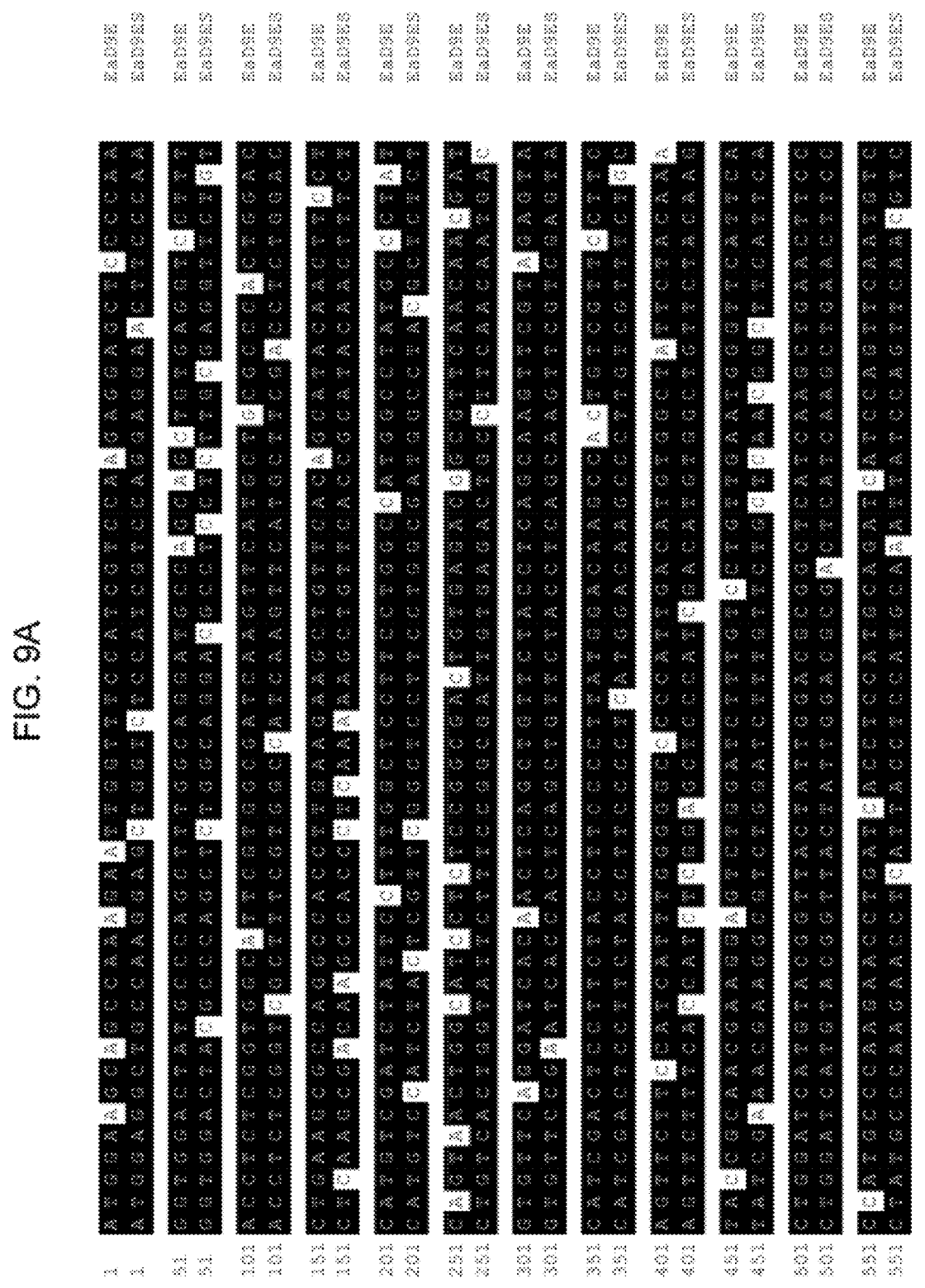
Figure 9B:
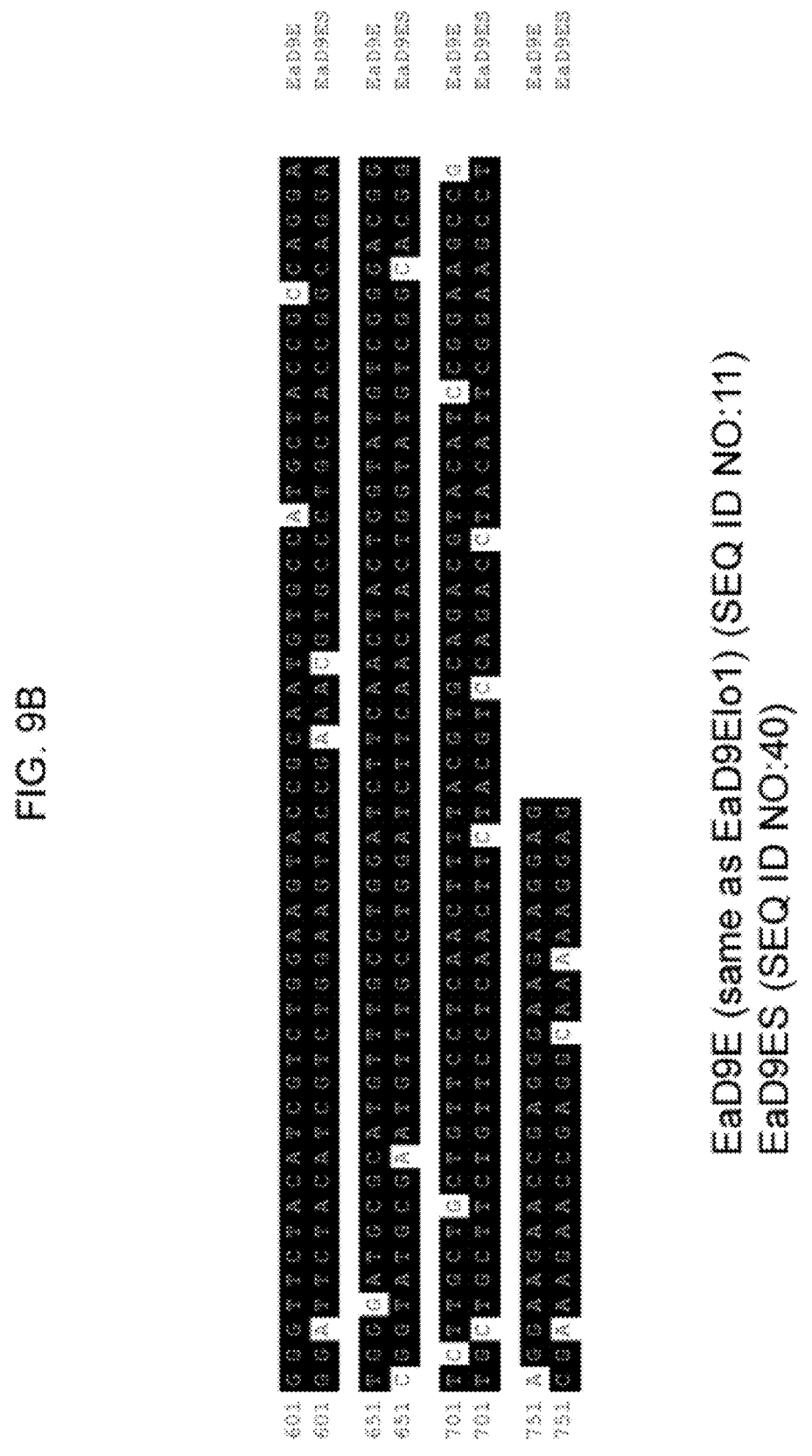
Figure 10:
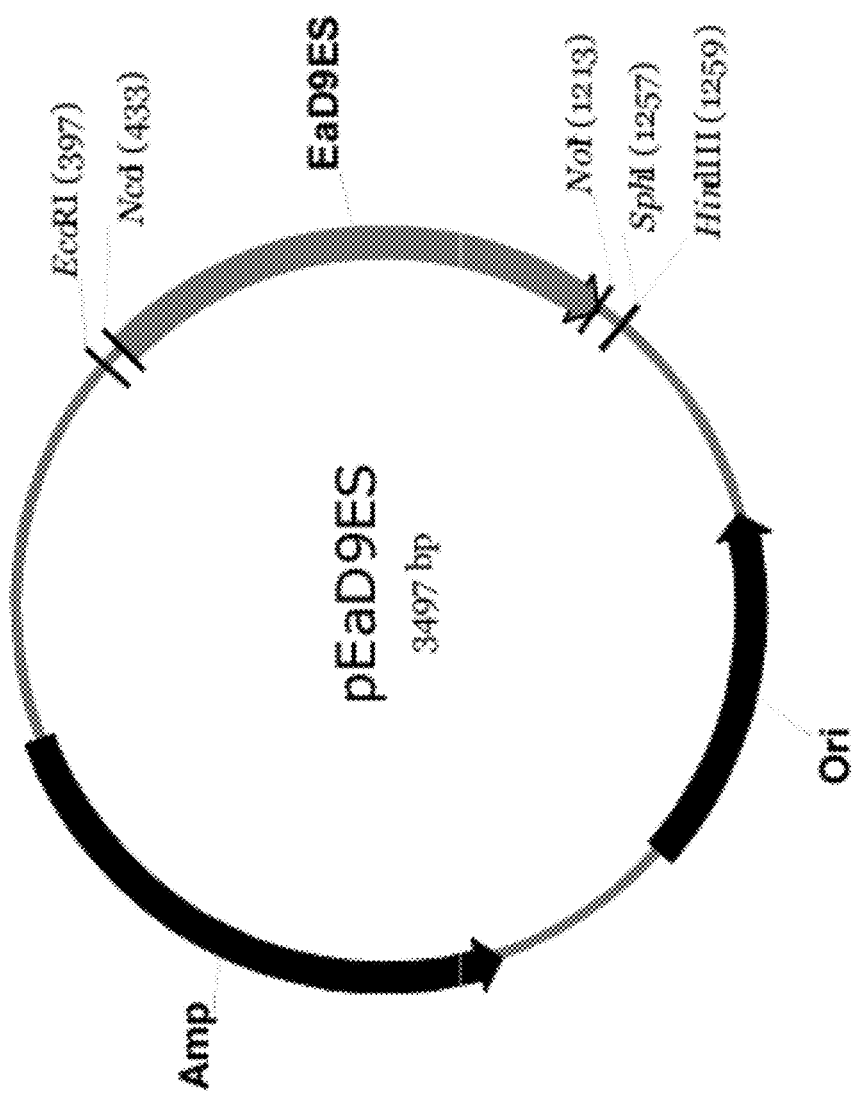
FIG. 10 is map of plasmid pEaD9ES (SEQ ID NO:41).

The codon usage of the delta-9 elongase gene (EaD9Elo1; SEQ ID NO:11) of Euglena anabaena was optimized for expression in Yarrowia lipolytica, in a manner similar to that described in PCT Publication No. WO 2004/101753. Specifically, a codon-optimized delta-9 elongase gene (designated "EaD9ES", SEQ ID NO:40) was designed based on the coding sequence of EaD9E (SEQ ID NO:11), according to the Yarrowia codon usage pattern (PCT Publication No. WO 2004/101753), the consensus sequence around the 'ATG' translation initiation codon, and the general rules of RNA stability (Guhaniyogi, G. and J. Brewer, Gene, 265(1-2):11-23 (2001)). In addition to modification of the translation initiation site, 106 bp of the 774 bp coding region were modified (13.7%) and 98 codons were optimized (38.0%). The GC content (52.1%) was about the same between the wild type gene (i.e., EaD9Elo1) and the synthetic gene (i.e., EaD9ES). A NcoI site and NotI sites were incorporated around the translation initiation codon and after the stop codon of EaD9ES (SEQ ID NO:40), respectively. FIGS. 9A and 9B shows a comparison of the nucleotide sequences of EaD9E (same as EaD9Elo1) (SEQ ID NO:11) and EaD9ES (SEQ ID NO:40). The codon optimized EaD9ES gene did not change any amino acid sequence of EaD9Elo1 (SEQ ID NO:13). The designed EaD9ES gene was synthesized by GenScript Corporation (Piscataway, N.J.) and cloned into pUC57 (GenBank Accession No. Y14837) to generate pEaD9ES (SEQ ID NO:41; FIG. 10).

Based on the teachings herein concerning vector construction and suitable promoter and terminators for use in *Yarrowia lipolytica*, one of skill in the art will be able to construct additional plasmids suitable for expression of EaD9ES (SEQ ID NO:40).

Example 11

Functional Analyses of *Euglena anabaena* Delta-9 Elongase in Soy

The present example describes the transformation and expression in soybean somatic embryos of either pKR1140 (SEQ ID NO:30; Example 5), comprising EaD9Elo1 or pKR1151 (SEQ ID NO:39; Example 6), comprising EaD9Elo1 and TpomD8.

Soybean embryogenic suspension culture (cv. Jack) was transformed with each of the vectors above and embryos were matured in soybean histodifferentiation and maturation liquid medium (SHaM liquid media; Schmidt et al., *Cell Biology and Morphogenesis*, 24:393 (2005)) as described in Example 7 and previously described in PCT Publication No. WO 2007/136877, published Nov. 29, 2007 (the contents of which are hereby incorporated by reference).

After maturation in SHaM liquid media a subset of transformed soybean embryos (i.e., 5-6 embryos per event) were harvested and analyzed as described herein.

In this way, approximately 30 events transformed with either pKR1140 (SEQ ID NO:30; called Experiment MSE2129) or pKR1151 (SEQ ID NO:39; called MSE2131) were analyzed and the five events having the highest average EDA or DGLA content (average of the 5 embryos analyzed) are shown in FIG. 11 or 12, respectively.

In FIG. 11, fatty acids are identified as 16:0 (palmitate), 18:0 (stearic acid), 18:1 (oleic acid), LA, ALA, EDA and ERA. Fatty acid compositions are expressed as a weight percent (wt. %) of total fatty acids. In FIG. 11, elongation activity is expressed as % delta-9 elongation of C18 fatty acids (delta-9% Elong), calculated according to the following formula: ([product]/[substrate+product])*100. More specifically, the combined percent elongation for LA and ALA is determined as: ([EDA+ERA]/[LA+ALA+EDA+ERA])*100. This elongation is also referred to as the overall % elongation. The individual omega-6 delta-9 elongation (LA % Elong) was calculated as: ([EDA]/[LA+EDA])*100. Similarly, the individual omega-3 delta-9 elongation (ALA % Elong) was calculated as: ([ERA]/[ALA+ERA])*100. The ratio of delta-9 elongation for omega-6 versus omega-3 substrates (Ratio [LA/ALA] % Elong) was obtained by dividing the LA % delta-9 elongation by the ALA % delta-9 elongation.

In FIG. 12, fatty acids are identified as 16:0 (palmitate), 18:0 (stearic acid), 18:1 (oleic acid), LA, ALA, EDA, ERA, DGLA and ETA. Fatty acid compositions are expressed as a weight percent (wt. %) of total fatty acids. In FIG. 12, elongation activity is expressed as % delta-9 elongation of C18 fatty acids (C18% delta-9 elong), calculated according to the following formula: ([product]/[substrate+product])*100. More specifically, the combined percent elongation for LA and ALA is determined as: ([DGLA+ETA+EDA+ERA]/ [LA+ALA+DGLA+ETA+EDA+ERA])*100. In FIG. 12, the combined percent desaturation for EDA and ERA is shown as "C20% delta-8 desat", determined as: ([DGLA+ETA]/ [DGLA+ETA+EDA+ERA])*100. This is also referred to as the overall % desaturation.

In summary of FIG. 11, the *Euglena anabeana* delta-9 elongase functioned in soybean to convert both LA and ALA to EDA and ERA, respectively. The line with the highest average EDA content (i.e., 2129-2-6) had embryos with an average EDA content of 26.7% and an average ERA content of 4.4%. The highest EDA and ERA content for an individual embryo from this line was 30.5% and 4.3%, respectively. The highest average overall % delta-9 elongation (i.e. 2129-2-2) was 47.9% with the highest overall % delta-9 elongation for an individual embryo being 53.3%. When broken down into % delta-9 elongation for the omega-6 and omega-3 substrates, the highest average % delta-9 elongation (i.e. 2129-2-2) was 47.3% and 49.9% for LA and ALA, respectively. The highest % delta-9 elongation for an individual embryo in this event was 52.2% and 56.8% for LA and ALA, respectively. In this example, the *Euglena anabaena* delta-9 elongase had no preference for ALA over LA, with the average desaturation ratio ranging from 0.9 to 1.1.

In summary of FIG. 12, the *Euglena anabeana* delta-9 elongase functioned in soybean, along with the TpomD8, to convert both LA and ALA to DGLA and ETA, respectively. The line with the highest average DGLA content (i.e., 2131-2-24) had embryos with an average DGLA content of 23.8% and an average ERA content of 7.2%. The highest DGLA and ETA content for an individual embryo from this line was 26.8% and 8.0%, respectively. The highest average overall % delta-9 elongation for this event was 63.2% with the highest overall % delta-9 elongation for an individual embryo being 65.7%.

Example 12

Functional Analysis of *Arabidopsis* Seed Transformed with pKR1191 for Expression of *Euglena anabaena* delta-9 elongase in *Arabidopsis*

The present example describes the synthesis of *Arabidopsis* expression plasmid pKR1191, comprising EaD9Elo1, and its transformation and expression in *Arabidopsis* seed.
Construction of pKR1191

The AscI fragment of pKR1140 (SEQ ID NO:30; Example 5), containing the EaD9Elo1, was cloned into the AscI site of pKR92 (which was previously described in WO2007/061845 published on May 31, 2007 to produce pKR1191 (SEQ ID NO:42). A schematic depiction of pKR1191 is shown in FIG. 13. In FIG. 13, EaD9Elo1 is called EA D9elong but they are identical. In this way, EaD9Elo1 was expressed in *Arabidopsis* under control of the soybean beta-conglycinin promoter. The soybean beta-conglycinin promoter functions as a strong, seed-specific promoter in *Arabidopsis*.
Functional Analysis of EaD9Elo1 in *Arabidopsis* Seed A fad3/fae1 double mutant (Smith et al., *Planta* 217:507-516 (2003)) of *Arabidopsis* produces seed where the ALA and 20:1 fatty acid content is less than 2.0%. The fad3/fae1 double mutant *Arabidopsis* plants were transformed with pKR1191 (SEQ ID NO:42), and plants were grown, maintained and seed was harvested as previously described in WO 2007/061845 (the contents of which are hereby incorporated by reference).

Segregating T2 seed was obtained from 18 individual events for each and bulk T2 seed lipid profiles for each event were obtained by transesterification with TMSH as described in herein with the following modifications. For each event, a small scoopful of seeds (approximately 25-50 seed each scoopful) was crushed in 50 μL of TMSH in a 1.5 mL eppendorf tube. After shaking in TMSH for 15 min., 400 μL of heptane was added and the tubes were vortexed well, shaken for an additional 15 min and centrifuged at 13,000×g for 1 min. After shaking, the heptane layer was removed into glass GC vials and the fatty acid methyl esters were analyzed as described in herein.

The lipid profiles of T2 bulk seed for the 18 transformed events is shown in FIG. 14. Fatty acids are identified as 16:0 (palmitate), 18:0 (stearic acid), 18:1 (oleic acid), LA, ALA, 20:0 (eicosanoic acid), 20:1 (eicosenoic acid), EDA and ERA; and, fatty acid compositions listed in FIG. 14 are expressed as a weight percent (wt. %) of total fatty acids. In FIG. 14, the combined percent elongation for LA and ALA is shown as "delta-9% Elong", determined as: ([EDA+ERA]/[LA+ALA])*100. This is also referred to as the overall % elongation.

In summary of FIG. 14, the event with the highest EDA content (i.e. ff1191-16) in bulk T2 seed analysis contained 32.9% EDA and 1.6% ERA. In this event, The delta-9% Elong was 50.9%, calculated as described above. Because bulk analysis of T2 seed (still segregating for the phenotype and thus having some wild-type seed) was performed, it is likely that individual seed within an event that are homozygous for the EaD9Elo1 gene will have higher EDA and ERA contents and thus higher overall % elongation.

What is claimed is:

1. An isolated polypeptide having delta-9 elongase activity and comprising an amino acid sequence having at least 85% sequence identity, based on the Clustal V method of alignment, when compared to the amino acid sequence set forth in either SEQ ID NO:13 or SEQ ID NO:14.

2. The isolated polypeptide of claim 1 wherein the amino acid sequence has at least 90% sequence identity, based on the Clustal V method of alignment, when compared to the amino acid sequence as set forth in either SEQ ID NO:13 or SEQ ID NO:14.

3. The isolated polypeptide of claim 2 wherein the amino acid sequence has at least 95% sequence identity, based on the Clustal V method of alignment, when compared to the amino acid sequence as set forth in either SEQ ID NO:13 or SEQ ID NO:14.

4. The isolated polypeptide of claim 3, wherein the amino acid sequence of the polypeptide comprises the amino acid sequence as set forth in either SEQ ID NO:13 or SEQ ID NO:14.

* * * * *